US009451938B2

(12) United States Patent
Overes et al.

(10) Patent No.: US 9,451,938 B2
(45) Date of Patent: Sep. 27, 2016

(54) INSERTION INSTRUMENT FOR ANCHOR ASSEMBLY

(75) Inventors: Tom Overes, Langendorf (CH); James Talbot, West Chester, PA (US); Daniel Vennard, West Chester, PA (US); Kevin Henrichsen, West Chester, PA (US); Jamie Manos, West Chester, PA (US); Scott Larsen, West Chester, PA (US); Wamis Singhatat, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 37 days.

(21) Appl. No.: 13/172,619

(22) Filed: Jun. 29, 2011

(65) Prior Publication Data

US 2012/0004669 A1 Jan. 5, 2012

Related U.S. Application Data

(63) Continuation-in-part of application No. 13/095,192, filed on Apr. 27, 2011, now Pat. No. 9,173,645.

(60) Provisional application No. 61/328,251, filed on Apr. 27, 2010, provisional application No. 61/398,699, filed on Jun. 29, 2010, provisional application No. 61/432,755, filed on Jan. 14, 2011, provisional application No. 61/461,490, filed on Jan. 18, 2011, provisional application No. 61/443,142, filed on Feb. 15, 2011.

(51) Int. Cl.
*A61B 17/10* (2006.01)
*A61B 17/00* (2006.01)
(Continued)

(52) U.S. Cl.
CPC ....... *A61B 17/0057* (2013.01); *A61B 17/0401* (2013.01); *A61B 17/0467* (2013.01); *A61B 17/0469* (2013.01); *A61B 17/0482* (2013.01); *A61B 17/0483* (2013.01); *A61B 17/0487* (2013.01); *A61B 17/842* (2013.01); *A61B 2017/00477* (2013.01); *A61B 2017/00623* (2013.01); *A61B 2017/00663* (2013.01);
(Continued)

(58) Field of Classification Search
CPC .............. A61B 2017/0419; A61B 2017/0417; A61B 2017/0409; A61B 17/0401; A61B 17/0057
USPC .......................... 606/151, 153, 157, 139, 232
See application file for complete search history.

(56) References Cited

U.S. PATENT DOCUMENTS

| 233,475 A | 10/1880 | Cook et al. |
| 261,501 A | 7/1882 | Vanermark |

(Continued)

FOREIGN PATENT DOCUMENTS

| CN | 101056587 | 10/2007 |
| DE | 4207854 | 9/1993 |

(Continued)

OTHER PUBLICATIONS

U.S. Appl. No. 60/113,548, filed Dec. 23, 1998, Schwartz.
(Continued)

*Primary Examiner* — Gregory Anderson
*Assistant Examiner* — Christina Lauer
(74) *Attorney, Agent, or Firm* — Baker & Hostetler LLP

(57) ABSTRACT

An insertion instrument is configured to eject a pair of anchor bodies across an anatomical gap so as to approximate the gap. The insertion instrument can include a single cannula that retains the pair of anchor bodies in a stacked relationship, or a pair of adjacent cannulas that each retain respective anchor bodies. The insertion instrument can be actuated so as to eject the anchor bodies into respective target anatomical locations.

88 Claims, 83 Drawing Sheets

(51) Int. Cl.
  *A61B 17/04* (2006.01)
  *A61B 17/84* (2006.01)
  *A61B 17/06* (2006.01)
  *A61B 17/29* (2006.01)

(52) U.S. Cl.
  CPC  *A61B2017/0406* (2013.01); *A61B 2017/0409* (2013.01); *A61B 2017/0414* (2013.01); *A61B 2017/0417* (2013.01); *A61B 2017/0419* (2013.01); *A61B 2017/0464* (2013.01); *A61B 2017/0475* (2013.01); *A61B 2017/0477* (2013.01); *A61B 2017/0496* (2013.01); *A61B 2017/06042* (2013.01); *A61B 2017/06052* (2013.01); *A61B 2017/06176* (2013.01); *A61B 2017/292* (2013.01); *A61B 2017/2917* (2013.01)

(56) References Cited

U.S. PATENT DOCUMENTS

| | | | |
|---|---|---|---|
| 330,087 | A | 11/1885 | Binns |
| 400,743 | A | 4/1889 | Brown |
| 2,490,364 | A | 12/1949 | Livingston |
| 3,580,256 | A | 5/1971 | Wilkinson |
| 3,867,728 | A | 2/1975 | Stubstad et al. |
| 3,908,677 | A | 9/1975 | Beach |
| 3,987,806 | A | 10/1976 | Gilbert |
| 4,006,747 | A | 2/1977 | Kronenthal et al. |
| 4,235,238 | A * | 11/1980 | Ogiu et al. ............ 606/145 |
| 4,669,473 | A | 6/1987 | Richards et al. |
| 4,741,330 | A | 5/1988 | Hayhurst |
| 4,778,990 | A | 10/1988 | Laughlin |
| 4,994,028 | A | 2/1991 | Leonard et al. |
| 5,021,059 | A | 6/1991 | Kensey et al. |
| 5,041,129 | A | 8/1991 | Hayhurst et al. |
| 5,053,046 | A | 10/1991 | Janese |
| 5,062,344 | A | 11/1991 | Gerker |
| 5,120,596 | A | 6/1992 | Yamada |
| 5,156,616 | A | 10/1992 | Meadows et al. |
| 5,269,809 | A | 12/1993 | Hayhurst et al. |
| 5,281,238 | A | 1/1994 | Chin et al. |
| 5,403,348 | A | 4/1995 | Bonutti |
| 5,417,691 | A | 5/1995 | Hayhurst |
| 5,464,426 | A | 11/1995 | Bonutti |
| 5,478,353 | A | 12/1995 | Yoon |
| 5,507,754 | A * | 4/1996 | Green et al. ............ 606/139 |
| 5,522,846 | A | 6/1996 | Bonutti |
| 5,527,343 | A | 6/1996 | Bonutti |
| 5,540,703 | A | 7/1996 | Barker et al. |
| 5,549,630 | A | 8/1996 | Bonutti |
| 5,562,684 | A | 10/1996 | Kammerer |
| 5,562,736 | A | 10/1996 | Ray et al. |
| 5,571,189 | A | 11/1996 | Kuslich |
| 5,584,862 | A | 12/1996 | Bonutti |
| 5,601,557 | A | 2/1997 | Hayhurst |
| 5,626,614 | A | 5/1997 | Hart |
| 5,628,756 | A | 5/1997 | Barker, Jr. et al. |
| 5,643,319 | A | 7/1997 | Green et al. |
| 5,649,945 | A | 7/1997 | Ray et al. |
| 5,699,657 | A | 12/1997 | Paulson |
| 5,702,462 | A | 12/1997 | Oberlander |
| 5,728,109 | A | 3/1998 | Schulze et al. |
| 5,733,306 | A | 3/1998 | Bonutti |
| 5,824,093 | A | 10/1998 | Ray et al. |
| 5,906,626 | A | 5/1999 | Carrillo |
| 5,941,900 | A | 8/1999 | Bonutti |
| 5,944,739 | A | 8/1999 | Zlock et al. |
| 5,951,590 | A | 9/1999 | Goldfarb |
| 5,957,953 | A | 9/1999 | DiPoto et al. |
| 5,970,697 | A | 10/1999 | Jacobs et al. |
| 5,989,252 | A | 11/1999 | Fumex |
| 6,056,773 | A | 5/2000 | Bonutti |
| 6,068,648 | A | 5/2000 | Cole |
| 6,077,292 | A | 6/2000 | Bonutti |
| 6,110,183 | A * | 8/2000 | Cope ............ 606/139 |
| 6,113,611 | A | 9/2000 | Allen et al. |
| 6,146,422 | A | 11/2000 | Lawson |
| 6,179,860 | B1 | 1/2001 | Fulton et al. |
| 6,187,048 | B1 | 2/2001 | Milner et al. |
| 6,209,550 | B1 | 4/2001 | Powell |
| 6,224,630 | B1 | 5/2001 | Bao et al. |
| 6,245,107 | B1 | 6/2001 | Ferree |
| 6,287,325 | B1 | 9/2001 | Bonutti |
| 6,296,659 | B1 | 10/2001 | Foerster |
| 6,306,159 | B1 | 10/2001 | Schwartz et al. |
| 6,325,816 | B1 | 12/2001 | Fulton et al. |
| 6,409,742 | B1 | 6/2002 | Fulton et al. |
| 6,432,123 | B2 | 8/2002 | Schwartz et al. |
| 6,482,235 | B1 | 11/2002 | Lambrecht et al. |
| 6,508,839 | B1 | 1/2003 | Lambrecht et al. |
| 6,511,498 | B1 | 1/2003 | Fumex |
| 6,530,933 | B1 | 3/2003 | Yeung et al. |
| 6,579,291 | B1 | 6/2003 | Keith et al. |
| 6,592,625 | B2 | 7/2003 | Cauthen |
| 6,656,182 | B1 | 12/2003 | Hayhurst |
| 6,689,125 | B1 | 2/2004 | Keith et al. |
| 6,719,797 | B1 | 4/2004 | Ferree |
| 6,758,855 | B2 | 7/2004 | Fulton et al. |
| 6,964,674 | B1 | 11/2005 | Matsuura et al. |
| 6,972,027 | B2 | 12/2005 | Fallin et al. |
| 6,984,247 | B2 | 1/2006 | Cauthen |
| 6,986,775 | B2 | 1/2006 | Morales et al. |
| 6,991,643 | B2 | 1/2006 | Saadat |
| 6,997,956 | B2 | 2/2006 | Cauthen |
| 7,004,970 | B2 | 2/2006 | Cauthen, III et al. |
| 7,033,393 | B2 | 4/2006 | Gainor et al. |
| 7,033,395 | B2 | 4/2006 | Cauthen |
| 7,041,052 | B2 | 5/2006 | Saadat et al. |
| 7,048,754 | B2 | 5/2006 | Martin et al. |
| 7,052,516 | B2 | 5/2006 | Cauthen et al. |
| 7,128,708 | B2 | 10/2006 | Saadat et al. |
| 7,153,312 | B1 | 12/2006 | Torrie et al. |
| 7,189,235 | B2 | 3/2007 | Cauthen |
| 7,285,124 | B2 | 10/2007 | Foerster |
| 7,303,575 | B2 | 12/2007 | Ogle |
| 7,326,221 | B2 * | 2/2008 | Sakamoto ............ A61B 17/0469 606/139 |
| 7,329,279 | B2 | 2/2008 | Haug et al. |
| 7,335,221 | B2 | 2/2008 | Collier et al. |
| 7,347,863 | B2 | 3/2008 | Rothe et al. |
| 7,390,332 | B2 | 6/2008 | Selvitelli et al. |
| 7,468,074 | B2 | 12/2008 | Caborn et al. |
| 7,491,212 | B2 | 2/2009 | Sikora et al. |
| 7,494,496 | B2 | 2/2009 | Swain et al. |
| 7,601,165 | B2 | 10/2009 | Stone |
| 7,615,076 | B2 | 11/2009 | Cauthen, III et al. |
| 7,621,925 | B2 | 11/2009 | Saadat et al. |
| 7,651,509 | B2 | 1/2010 | Bojarski et al. |
| 7,658,750 | B2 | 2/2010 | Li |
| 7,666,193 | B2 | 2/2010 | Starksen et al. |
| 7,670,379 | B2 | 3/2010 | Cauthen |
| 7,670,380 | B2 | 3/2010 | Cauthen, III |
| 7,678,135 | B2 | 3/2010 | Maahs et al. |
| 7,731,732 | B2 | 6/2010 | Ken |
| 7,736,379 | B2 | 6/2010 | Ewers et al. |
| 7,749,250 | B2 | 7/2010 | Stone et al. |
| 7,749,273 | B2 | 7/2010 | Cauthen, III et al. |
| 7,753,941 | B2 | 7/2010 | Keith et al. |
| 7,776,096 | B2 | 8/2010 | Cauthen |
| 7,828,850 | B2 | 11/2010 | Cauthen, III et al. |
| 7,846,208 | B2 | 12/2010 | Cauthen, III et al. |
| 7,857,830 | B2 | 12/2010 | Stone et al. |
| 7,905,904 | B2 | 3/2011 | Stone et al. |
| 7,905,923 | B2 | 3/2011 | Keith et al. |
| 7,909,851 | B2 | 3/2011 | Stone et al. |
| 7,909,879 | B2 | 3/2011 | Cauthen |
| 7,922,768 | B2 | 4/2011 | Cauthen, III et al. |
| 7,935,147 | B2 | 5/2011 | Wales |
| 7,951,201 | B2 | 5/2011 | Cauthen et al. |
| 7,959,650 | B2 | 6/2011 | Kaiser et al. |
| 7,963,992 | B2 | 6/2011 | Cauthen et al. |
| 7,985,257 | B2 | 7/2011 | Cauthen et al. |
| 7,993,405 | B2 | 8/2011 | Cauthen et al. |

(56) References Cited

U.S. PATENT DOCUMENTS

| | | |
|---|---|---|
| 8,034,112 B2 | 10/2011 | Cauthen et al. |
| 8,048,160 B2 | 11/2011 | Cauthen |
| 8,083,768 B2 | 12/2011 | Ginn et al. |
| 8,088,130 B2 | 1/2012 | Kaiser et al. |
| 8,088,165 B2 | 1/2012 | Cauthen et al. |
| 8,100,914 B2 | 1/2012 | Cauthen et al. |
| 8,118,836 B2 | 2/2012 | Denham et al. |
| 8,128,640 B2 | 3/2012 | Harris et al. |
| 8,128,658 B2 | 3/2012 | Kaiser et al. |
| 8,128,698 B2 | 3/2012 | Bentley et al. |
| 8,137,382 B2 | 3/2012 | Denham et al. |
| 8,216,253 B2 | 7/2012 | Saadat et al. |
| 8,216,260 B2 | 7/2012 | Lam et al. |
| 8,298,291 B2 * | 10/2012 | Ewers et al. ............... 623/23.72 |
| 8,814,903 B2 | 8/2014 | Sengun et al. |
| 8,828,053 B2 | 9/2014 | DeMatteo et al. |
| 8,920,436 B2 | 12/2014 | Lam et al. |
| 8,926,634 B2 | 1/2015 | Rothe et al. |
| 2002/0029782 A1 | 3/2002 | Linderoth |
| 2002/0065536 A1 | 5/2002 | Hart et al. |
| 2002/0115999 A1 | 8/2002 | McDevitt et al. |
| 2002/0143359 A1 | 10/2002 | Fulton et al. |
| 2002/0188301 A1 | 12/2002 | Dallara et al. |
| 2003/0167071 A1 | 9/2003 | Martin et al. |
| 2004/0097980 A1 | 5/2004 | Ferree |
| 2004/0153074 A1 | 8/2004 | Bojarski et al. |
| 2004/0162618 A1 | 8/2004 | Mujwid et al. |
| 2004/0225183 A1 * | 11/2004 | Michlitsch et al. .......... 600/106 |
| 2004/0243171 A1 | 12/2004 | Fulton et al. |
| 2005/0080422 A1 | 4/2005 | Otte et al. |
| 2005/0228448 A1 | 10/2005 | Li |
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0277966 A1 | 12/2005 | Ewers et al. |
| 2005/0277981 A1 | 12/2005 | Maahs et al. |
| 2005/0283192 A1 | 12/2005 | Torrie et al. |
| 2005/0283246 A1 | 12/2005 | Cauthen, III et al. |
| 2006/0064126 A1 | 3/2006 | Fallin et al. |
| 2006/0178680 A1 | 8/2006 | Nelson et al. |
| 2006/0190042 A1 | 8/2006 | Stone et al. |
| 2006/0259076 A1 | 11/2006 | Burkhart et al. |
| 2006/0265008 A1 | 11/2006 | Maruyama et al. |
| 2007/0010857 A1 * | 1/2007 | Sugimoto et al. ............ 606/232 |
| 2007/0027476 A1 | 2/2007 | Harris et al. |
| 2007/0073320 A1 | 3/2007 | Mikkaichi et al. |
| 2007/0083236 A1 | 4/2007 | Sikora et al. |
| 2007/0100348 A1 | 5/2007 | Cauthen, III et al. |
| 2007/0129804 A1 | 6/2007 | Bentley et al. |
| 2007/0142846 A1 | 6/2007 | Catanese |
| 2007/0156245 A1 | 7/2007 | Cauthen, III et al. |
| 2007/0162054 A1 | 7/2007 | Horaguchi |
| 2007/0162120 A1 | 7/2007 | Bouffier |
| 2007/0185532 A1 * | 8/2007 | Stone et al. .................. 606/232 |
| 2007/0255285 A1 | 11/2007 | Trieu |
| 2007/0276433 A1 | 11/2007 | Huss |
| 2008/0009888 A1 | 1/2008 | Ewers et al. |
| 2008/0015635 A1 | 1/2008 | Olsen et al. |
| 2008/0015636 A1 | 1/2008 | Olsen et al. |
| 2008/0033487 A1 | 2/2008 | Schwartz et al. |
| 2008/0086155 A1 | 4/2008 | Rothe et al. |
| 2008/0097484 A1 | 4/2008 | Lim et al. |
| 2008/0097522 A1 | 4/2008 | Chopra |
| 2008/0140092 A1 | 6/2008 | Stone et al. |
| 2008/0140093 A1 | 6/2008 | Stone et al. |
| 2008/0147086 A1 | 6/2008 | Pfister et al. |
| 2008/0147102 A1 | 6/2008 | Rotella et al. |
| 2008/0167658 A1 | 7/2008 | Kerr et al. |
| 2008/0177302 A1 | 7/2008 | Shumas |
| 2008/0177304 A1 | 7/2008 | Westra et al. |
| 2008/0188893 A1 | 8/2008 | Selvitelli et al. |
| 2008/0195145 A1 | 8/2008 | Bonutti et al. |
| 2008/0200930 A1 | 8/2008 | Saadat et al. |
| 2008/0208225 A1 | 8/2008 | Seibold et al. |
| 2008/0208226 A1 | 8/2008 | Seibold et al. |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0243151 A1 | 10/2008 | Binmoeller et al. |
| 2008/0269781 A1 | 10/2008 | Funamura et al. |
| 2008/0281355 A1 | 11/2008 | Mayer et al. |
| 2008/0312689 A1 | 12/2008 | Denham et al. |
| 2008/0319524 A1 | 12/2008 | Yachia et al. |
| 2009/0018561 A1 | 1/2009 | Schwartz et al. |
| 2009/0030522 A1 | 1/2009 | Cauthen, III et al. |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0062846 A1 | 3/2009 | Ken |
| 2009/0062847 A1 | 3/2009 | Ken |
| 2009/0062848 A1 * | 3/2009 | Ken ........................... 606/213 |
| 2009/0062850 A1 | 3/2009 | Ken |
| 2009/0062854 A1 | 3/2009 | Kaiser et al. |
| 2009/0069823 A1 | 3/2009 | Foerster et al. |
| 2009/0076547 A1 | 3/2009 | Sugimoto et al. |
| 2009/0082805 A1 | 3/2009 | Kaiser et al. |
| 2009/0157184 A1 | 6/2009 | Cauthen, III et al. |
| 2009/0228042 A1 | 9/2009 | Koogle et al. |
| 2009/0259260 A1 | 10/2009 | Bentley et al. |
| 2009/0306711 A1 | 12/2009 | Stone et al. |
| 2010/0049212 A1 | 2/2010 | Caborn et al. |
| 2010/0069923 A1 | 3/2010 | Nguyen et al. |
| 2010/0094337 A1 | 4/2010 | Maiorino |
| 2010/0094425 A1 | 4/2010 | Bentley et al. |
| 2010/0121376 A1 | 5/2010 | Li |
| 2010/0292731 A1 | 11/2010 | Gittings et al. |
| 2011/0022083 A1 * | 1/2011 | DiMatteo et al. ............. 606/228 |
| 2011/0022084 A1 | 1/2011 | Sengun et al. |
| 2011/0077667 A1 | 3/2011 | Singhatat et al. |
| 2011/0082472 A1 | 4/2011 | Harris et al. |
| 2011/0172701 A1 | 7/2011 | Wales et al. |
| 2011/0270278 A1 | 11/2011 | Overes et al. |
| 2012/0004669 A1 | 1/2012 | Overes et al. |
| 2012/0035654 A1 | 2/2012 | Belson |
| 2012/0046693 A1 | 2/2012 | Denham et al. |
| 2012/0053630 A1 | 3/2012 | Denham et al. |
| 2012/0109156 A1 | 5/2012 | Overes et al. |
| 2012/0130422 A1 | 5/2012 | Hootstein |
| 2012/0143215 A1 | 6/2012 | Corrao et al. |
| 2012/0150223 A1 | 6/2012 | Manos et al. |
| 2013/0110165 A1 | 5/2013 | Burkhart et al. |
| 2014/0336703 A1 | 11/2014 | Sengun et al. |
| 2015/0038992 A1 | 2/2015 | DiMatteo et al. |

FOREIGN PATENT DOCUMENTS

| | | |
|---|---|---|
| EP | 0834281 | 4/1998 |
| EP | 0838197 | 4/1998 |
| EP | 1938760 | 7/2008 |
| EP | 1964520 | 9/2008 |
| EP | 2238944 | 10/2010 |
| EP | 2663240 | 11/2013 |
| EP | 2663242 | 11/2013 |
| WO | WO 92/11810 | 7/1992 |
| WO | WO 99/22648 | 5/1999 |
| WO | WO 03/096910 | 11/2003 |
| WO | WO 2004/071307 | 8/2004 |
| WO | WO 2005/011463 | 2/2005 |
| WO | WO 2005/065553 | 7/2005 |
| WO | WO 2006/039296 | 4/2006 |
| WO | WO 2006/117398 | 11/2006 |
| WO | WO 2007/005394 | 1/2007 |
| WO | WO 2008/010738 | 1/2008 |
| WO | WO 2008/048667 | 4/2008 |
| WO | WO 2009/126781 | 10/2009 |
| WO | WO 2009/146402 | 12/2009 |

(56) References Cited

FOREIGN PATENT DOCUMENTS

| WO | WO 2010/088561 | 8/2010 |
|---|---|---|
| WO | WO 2011/137159 | 11/2011 |
| WO | WO 2012/006161 | 1/2012 |
| WO | WO 2012/096706 | 7/2012 |
| WO | WO 2012/096707 | 7/2012 |

OTHER PUBLICATIONS

U.S. Appl. No. 60/148,913, filed Aug. 13, 1999, Ferree.
U.S. Appl. No. 60/149,490, filed Aug. 18, 1999, Lambrecht.
U.S. Appl. No. 60/154,969, filed Sep. 20, 1999, Matsuura.
U.S. Appl. No. 60/161,085, filed Oct. 25, 1999, Lambrecht.
U.S. Appl. No. 09/453,120, filed Dec. 2, 1999, Torrie.
U.S. Appl. No. 60/263,343, filed Jan. 22, 2011, Keith.
Ahlgren et al., "Anular incision technique on the strength and multidirectional flexibility of the healing intervertebral disc," Spine, Apr. 15, 1994, 19(8), 948-954.
Ahlgren et al., "Effect of anular repair on the healing strength of the intervertebral disc: a sheep model," Spine, Sep. 1, 2000, 25(17), 2165-2170.
Arthrex, Inc., "Arthroscopic Meniscal Repair using the Meniscal Cinch: Surgical Technique," www.arthrex.com, © 2008, 6 pages.
Barrett et al., "T-Fix endoscopic meniscal repair: technique and approach to different types of tears," Arthroscopy: The Journal of Arthroscopic and Related Surgery, Apr. 1995, 11(2), 245-251.
Burg et al., "Modulation of Surface and Bulk Properties of Biomedical Polymers," Annals of the New York Academy of Sciences, Dec. 1997, 831, 217-222.
Caborn, D., "Meniscal Repair with the Fast T-Fix Suture System," Smith & Nephew Technique Plus Illustrated Guide, Mar. 2002, 10 pages.
Cauthen, J., "Annulotomy Study Table", Feb. 8, 1999, 1 page.
Cauthen, J., "Microsurgical Annular Reconstruction (Annuloplasty) Following Lumbar Microdiscectomy: A New Technique," Draft Abstract, Sep. 4, 1998, 4 pages.
Cauthen, J., "Microsurgical Annular Reconstruction (Annuloplasty) Following Lumbar Microdiscectomy: A New Technique," Abstract, AANS CNS Section on Disorders of the Spine and Peripheral Nerves Annual Meeting, 1999, 2 pages.
Cauthen,"Microsurgical Annular Reconstruction (Annuloplasty) Following Lumbar Microdiscectomy: Preliminary Report of a New Technique", CNS Boston Massachusetts, Spine & Peripheral Nerves Section (abstract only), http://abstracts.neurosurgeon.org/view.php?id=2790, accessed Oct. 6, 2010, 1999, 1 page.
Cobey, M., "Arthroplasties using compressed ivalon sponge ("intramedic sponge") long-term follow-up studies in 109 cases," Clinical Orthopaedics and Related Research, Sep.-Oct. 1967, 54, 139-144.
Coen et al., "An anatomic evaluation of T-Fix suture device placement for arthroscopic all-inside meniscal repair," Arthroscopy: The Journal of Arthroscopic and Related Surgery, Apr. 1999, 15(3), 275-280.
Dodge, Jr. et al., "Use of Polyvinyl Sponge in Neurosurgery," Journal of Neurosurgery, May 1954, 11(3), 258-261.
Edgerton et al., "Augmentation Mammaplasty: Psychiatric Implications and Surgical Indications," Plastic & Reconstructive Surgery, Apr. 1958, 21(4), 279-305.
Hampton et al., "Healing Potential of the Anulus Fibrosus," Spine, Apr. 1989, 14(4), 398-401.
International Patent Application No. PCT/US2011/034084: International Search Report and Written Opinion dated Jul. 1, 2011, 5 pages.
International Patent Application No. PCT/US2011/042384: International Search Report and Written Opinion dated Feb. 6, 2012, 26 pages.
International Patent Application No. PCT/US2011/058065: International Search Report and Written Opinion dated Apr. 5, 2012, 23 pages.

International Patent Application No. PCT/US2011/058071: International Search Report and Written Opinion dated Feb. 6, 2012, 14 pages.
Kambin et al., "Development of degenerative spondylosis of the lumbar spine after partial discectomy. Comparison of laminotomy, discectomy, and posterolateral discectomy," Spine, Mar. 1, 1995, 20(5), 599-607.
Kotilainen et al., "Microsurgical treatment of lumbar disc herniation: Follow-up of 237 patients," Acta Neurochirurgica, 1993, 120(3-4) 143-149.
Kroschwitz, J. I., "Concise Encyclopedia of Polymer Science and Engineering: Vinyl Alcohol Polymers," Wiley & Sons, 1990, 1233-1236.
Kusaka et al., "The Effect of Annulus Fibrosus Perforation on the Intradiscal Matrix Strain of the Axially Loaded Intervertebral Disc," Transactions of the 44$^{th}$ Annual Meeting, Orthopaedic Research Society, Mar. 16-19, 1998, New Orleans, Louisiana, 23(1), p. 190-32 (Abstract).
Lehmann et al., "Refinements in technique for open lumbar discectomy," International Society for the Study of the Lumbar Spine, 1997, 2 pages.
Liu et al., "Morphologic Characterization of Polyvinyl Sponge (Ivalon) Breast Prosthesis," Archives of Pathol. & Lab. Medicine, Sep. 1996, 120(9), 876-878.
Malemud, C. J., "The Role of Growth Factors in Cartilage Metabolism," Rheum. Dis. Clin. North Am., Aug. 1993, 19(3), 569-580.
Ordway et al., "Failure Properties of a Hydrogel Nucleus in the Intervertebral Disc," North American Spine Society, Oct. 22-25, 1997, 168-169.
Osti et al., "1990 Volvo Award in Experimental Studies: Anulus Tears and Intervertebral Disc Degeneration: An Experimental Study Using an Animal Model," Spine, Aug. 1990, 15(8), 762-767.
Osti et al., "Annular Tears and Disc Degeneration in the Lumbar Spine. A post-mortem study of 135 discs," The Journal of Bone and Joint Surgery, Sep. 1992, 74(5), 678-682.
Panjabi et al., "Intrinsic Disc Pressure as a Measure of Integrity of the Lumbar Spine," Spine, Aug. 1988, 13(8), 913-917.
Peters et al., "Ivalon Breast Prostheses: Evaluation 19 Years after Implantation," Plastic and Reconstructive Surgery, Apr. 1981, 67(4), 514-518.
PR Newswire, "Smith & Nephew Launches Fast-Fix™ AB Meniscal Repair System," http://www.prnewswire.com/news-releases/smith--nephew-launches-fast-fixtm-ab-menis . . . , Accessed Aug. 23, 2010, 1 page.
Ray, C. D., "Prosthetic Disc Nucleus Implants: Update," North American Spine Society 13$^{th}$ Annual Meeting, 1999, 252-253.
Sgaglione et al., "All-Inside Meniscal Repair with the Ultra Fast-Fix™ Meniscal Repair System," Smith & Nephew Knee Series Technique Guide, Feb. 2008, 12 pages.
Silver et al., "Cartilage Wound Healing: An Overview," Otolaryngol. Clin. North Am., Oct. 1995, 28(5), 847-863.
Smith & Nephew Endoscopy, "Endoscopic Meniscal Repair Using the T-Fix™," Smith & Nephew, May 1996, 16 pages.
Smith & Nephew Endoscopy, "Fast-Fix Meniscal Repair System: Technique Information," http://endo.smith-nephew.com/no/node.asp?Nodeld=3045, Accessed Apr. 26, 2011, 3 pages.
Southwick et al., "Prosthetic Replacement of Chest-Wall Defects: An Experimental and Clinical Study", A. M. A. Archives of Surgery, 1956, 72, 901-907.
Unipoint Industries, Inc., "Polyvinyl Alcohol Foam for Surgical and Industrial Use: Data Sheets," Jul. 15, 1989, 6 pages.
Urbaniak et al., "Replacement of intervertebral discs in chimpanzees by silicone-dacron implants: a preliminary report," J. Biomed. Mater. Res. Symposium, May 1973, 7(4), 165-186.
Wageck et al., "Arthroscopic meniscal suture with the "double-loop technique"," Arthroscopy: The Journal of Arthroscopic and Related Surgery, Feb. 1997, 13(1), 120-123.
Yasargil, M. G., "Microsurgical Operation of Herniated Lumbar Disc," Advances in Neurosurgery, Lumbar Disc Adult Hydrocephalus, Springer-Verlag, 1977, 4(81), p. 81.
International Patent Application No. PCT/US05/34495: International Search Report dated Apr. 4, 2007, 2 pages.

(56) References Cited

OTHER PUBLICATIONS

Snyder, S.J., "Shoulder Arthroscopy: Arthroscopic Treatment of the Acromioclavicular Joint", Chapter 13, 2nd Edition, 2003, 167-183.
U.S. Appl. No. 60/160,710, filed Oct. 20, 1999, Cauthen.
U.S. Appl. No. 09/484,706, filed Jan. 18, 2000, Cauthen.
U.S. Appl. No. 12/509,112: Non-Final Office Action, dated Jul. 12, 2012, 8 pages.
U.S. Appl. No. 12/509,112: Restriction Requirement, dated Nov. 17, 2011, 8 pages.
U.S. Appl. No. 12/509,112: Restriction Requirement, dated Apr. 10, 2012, 6 pages.
U.S. Appl. No. 13/095,192: Restriction Requirement, dated Sep. 6, 2012, 10 pages.
European Search Report for Application No. 10251328.0 dated Oct. 29, 2010.
European Search Report for Application No. 05802651.9 dated Aug. 31, 2009, 7 pages.
Brinckmann et al., "A laboratory model of lumbar disc protrusion", Fissure and Fragment Institut fur Experimentelle Biomechanik, Universitat, Munster, German, Spine (Phila., PA 1976) Jan. 15, 1994, 19(2): 228-235.
Maroon et al., "Microdiscectomy versus Chemonucleolysis", Neurosurgery, vol. 16(5), 644-649, May 1985.
Mitek Brochure, Rapid Loc, "Surgical Technique Guide for Repair of Meniscal Tears", 2001, 6 pages.
Biomet Maxfire Technique Guide, Meniscal Repair, 1994, 16 pages.
Cayenne Medical, Crossfix Meniscal Repair System, Surgical Technique Guide, Jul. 2009, 4 pages.
Hoffman et al., "Arthroscopic shoulder stablilization using Mitek anchors", Knee Surg., Sports Traumatol., Arthroscopy, Mar. 1995, vol. 3, Issue 1, 50-54.
Klinger, "Proceedings of the 1976 Meeting of the Deutsche Gesellschaft fur Neurochirurgica in Berlin", Acta Neurochirurgica, Sep. 1977, vol. 36, Issue 3-4, 265-294.
Mayer et al., "Percutaneous Endoscopic Lumbar Discectomy (PELD)", Neurosurg., Rev., Jun. 1993, 115-120.
Mayer et al., "Endoscopic Discectomy in Pediatric and Juvenile Lumbar Disc Herniation's", Journal of the Pediatric Orthopaedics, Part B, Jan. 1996, 3943.
Abstracts of the 7$^{th}$ Annual Meeting of the Japanese Society of Micosurgery, Oct. 1980, Niigata, Japan, 8 pages.
Vuono-Hawkins et al., "Mechanical Evaluation of a Canine Intervertebral Disc Spacer: In Situ and In Vivo Studies", Journal of Orthopaedic Research, Jan. 1994, 119-127.
U.S. Appl. No. 61/328,251, filed Apr. 27, 2010, Overes.
U.S. Appl. No. 61/398,699, filed Jun. 29, 2010, Overes et al.
U.S. Appl. No. 61/432,755, filed Jan. 14, 2010, Henrichsen et al.
U.S. Appl. No. 61/443,142, filed Feb. 15, 2011, Henrichsen et al.
U.S. Appl. No. 61/461,490, filed Jan. 18, 2011, Henrichsen et al.

\* cited by examiner

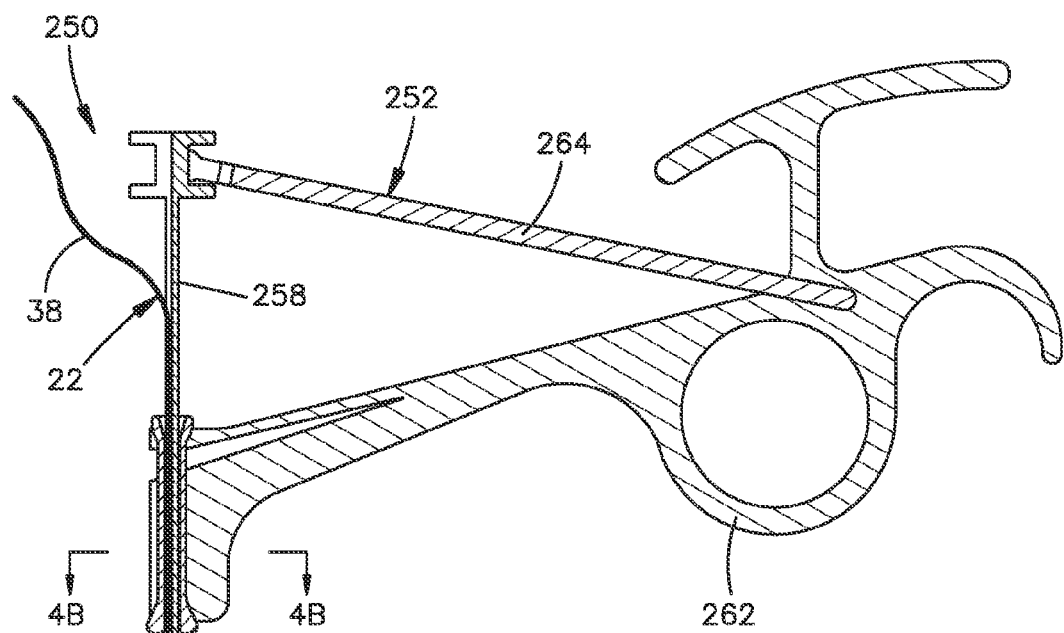
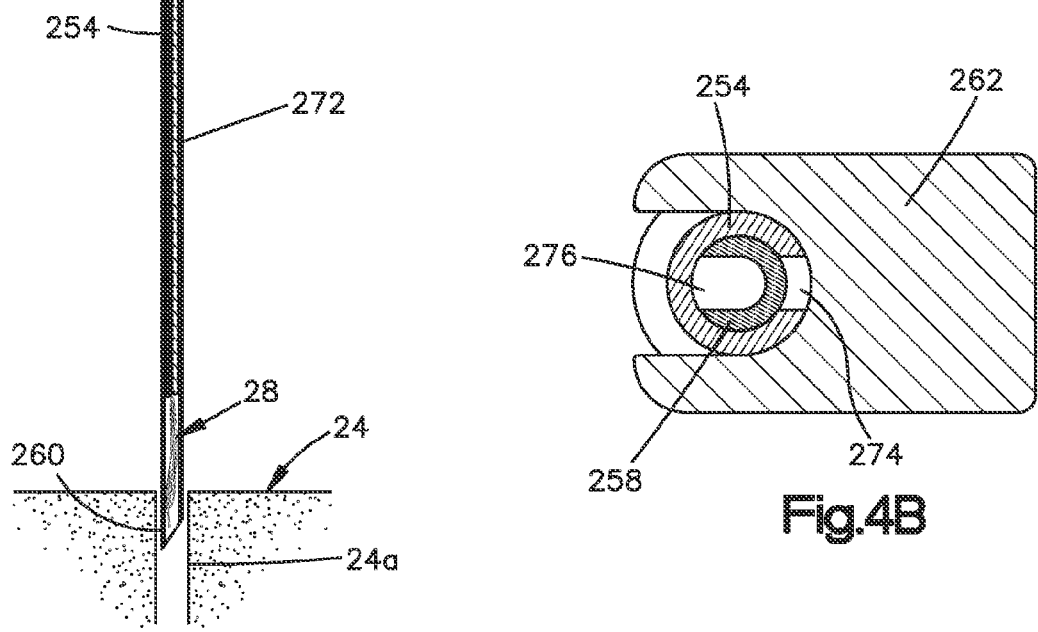
Fig.4A
Fig.4B

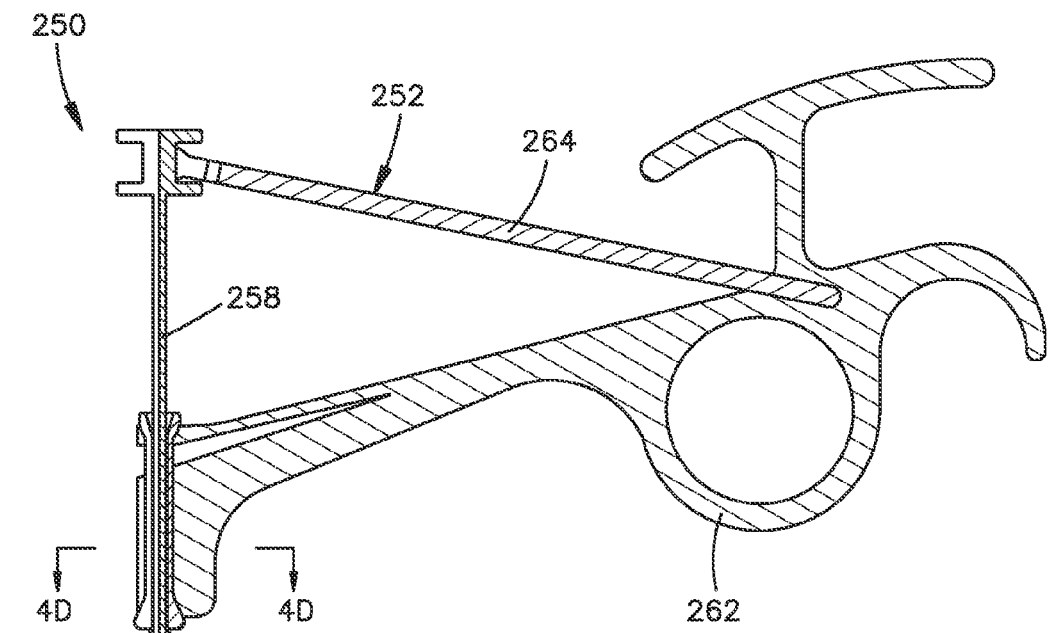
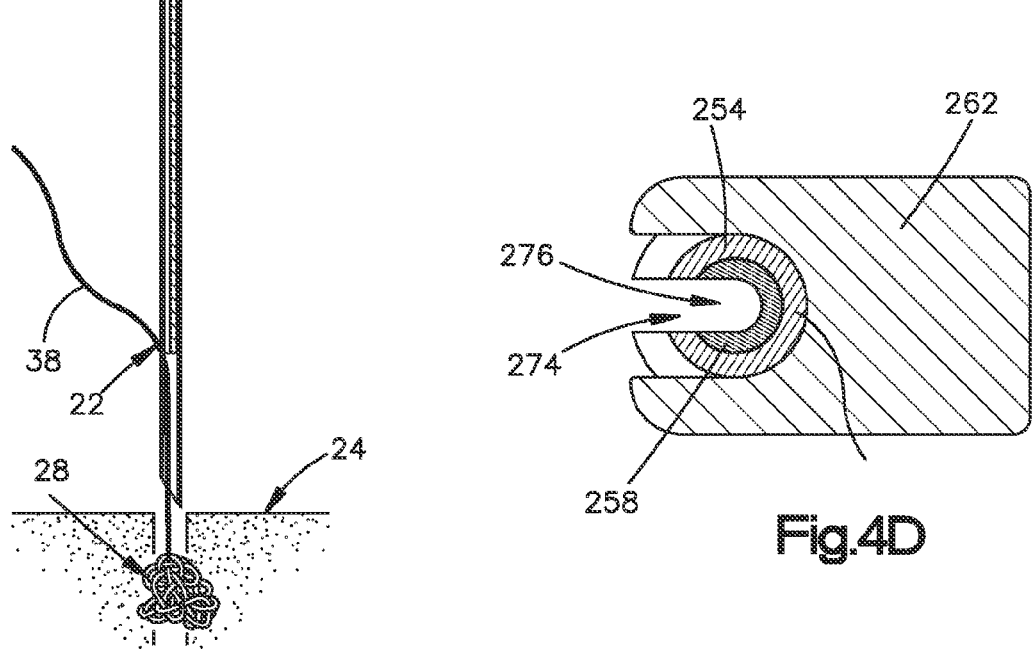

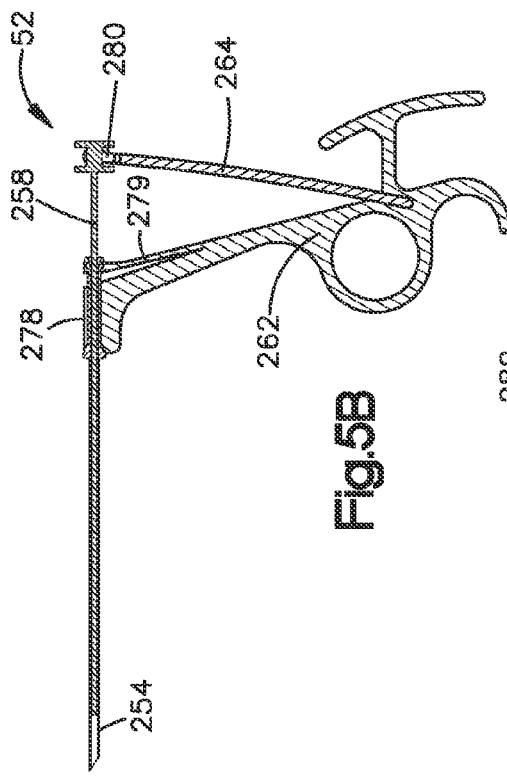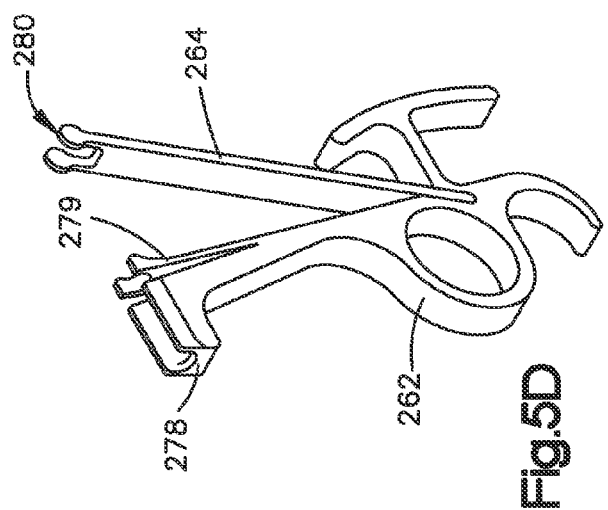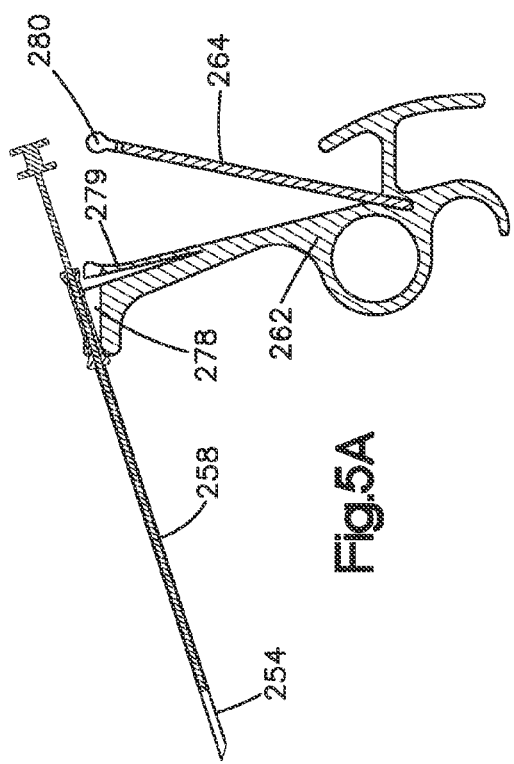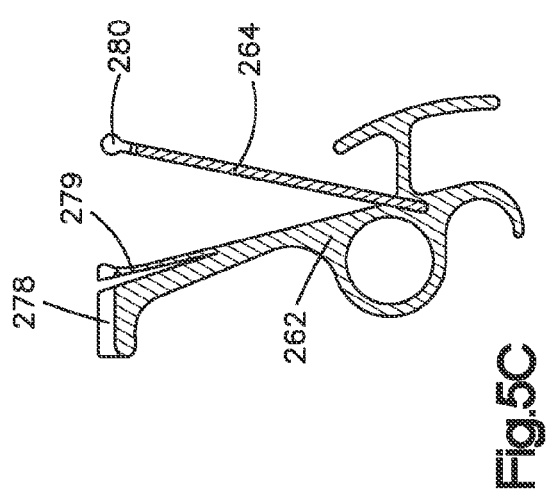

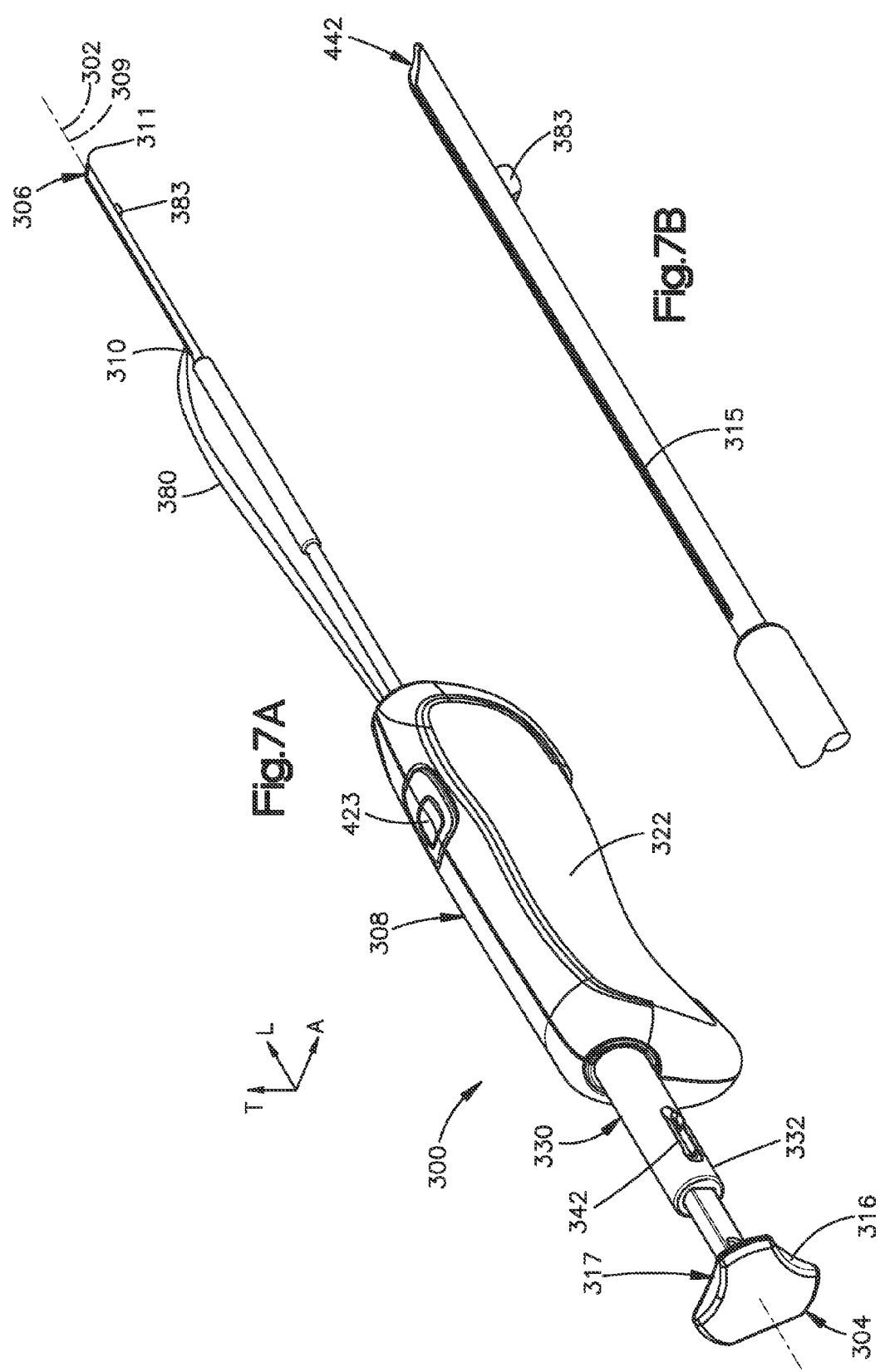

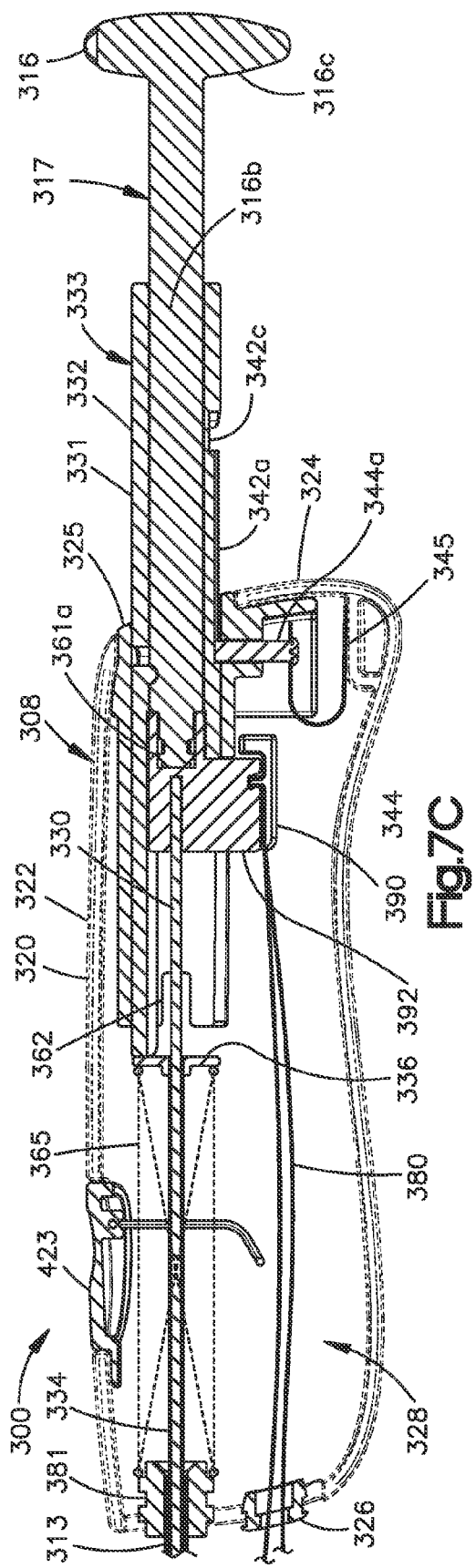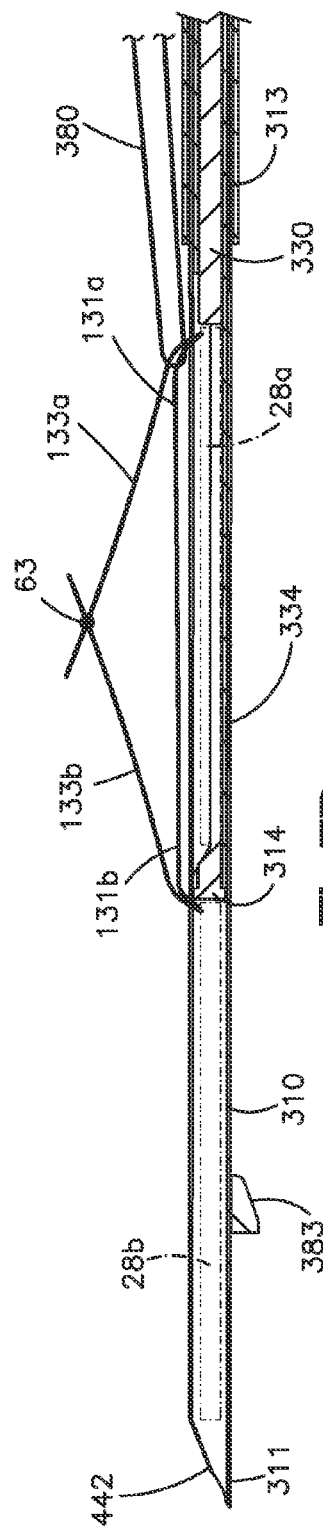

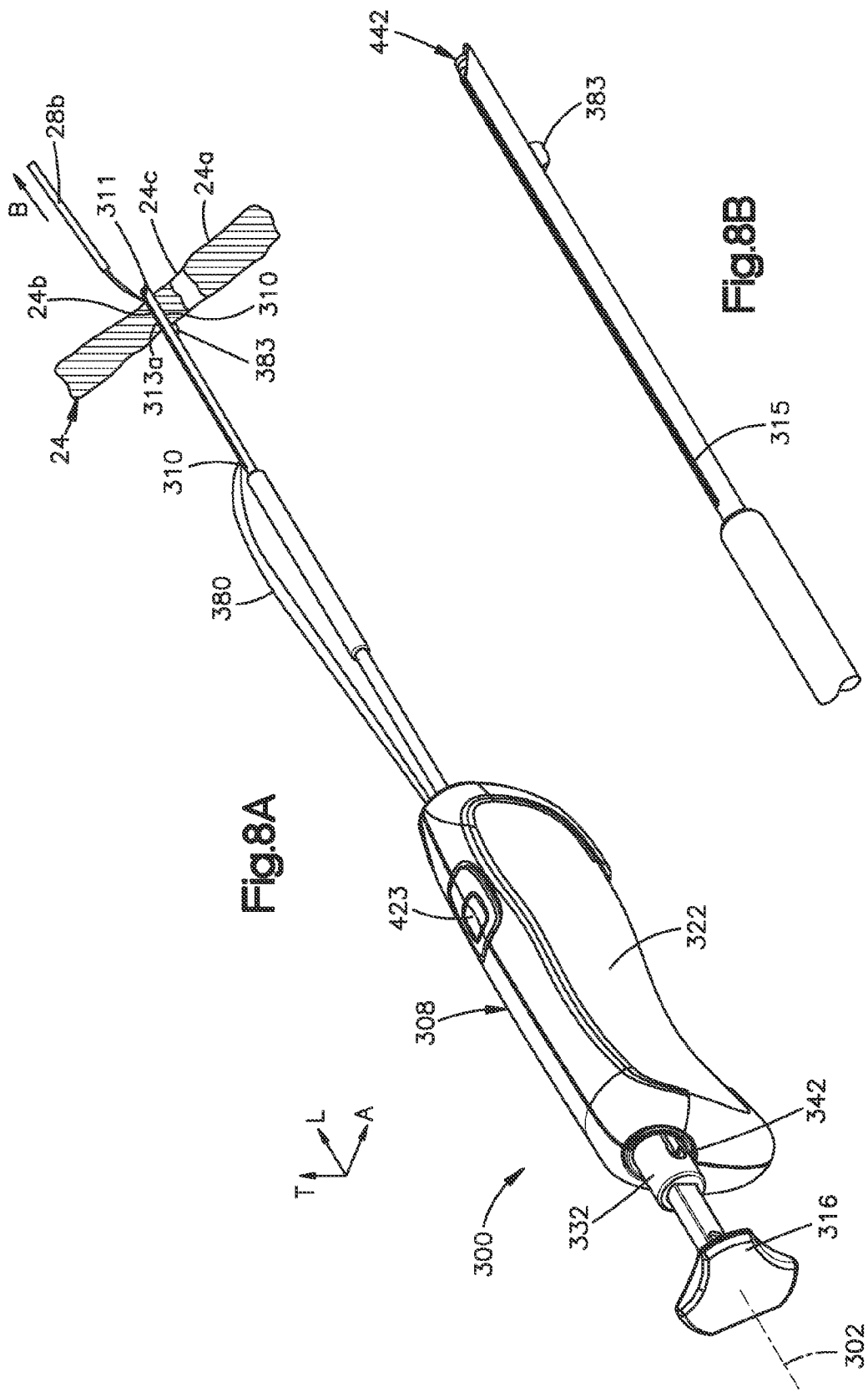

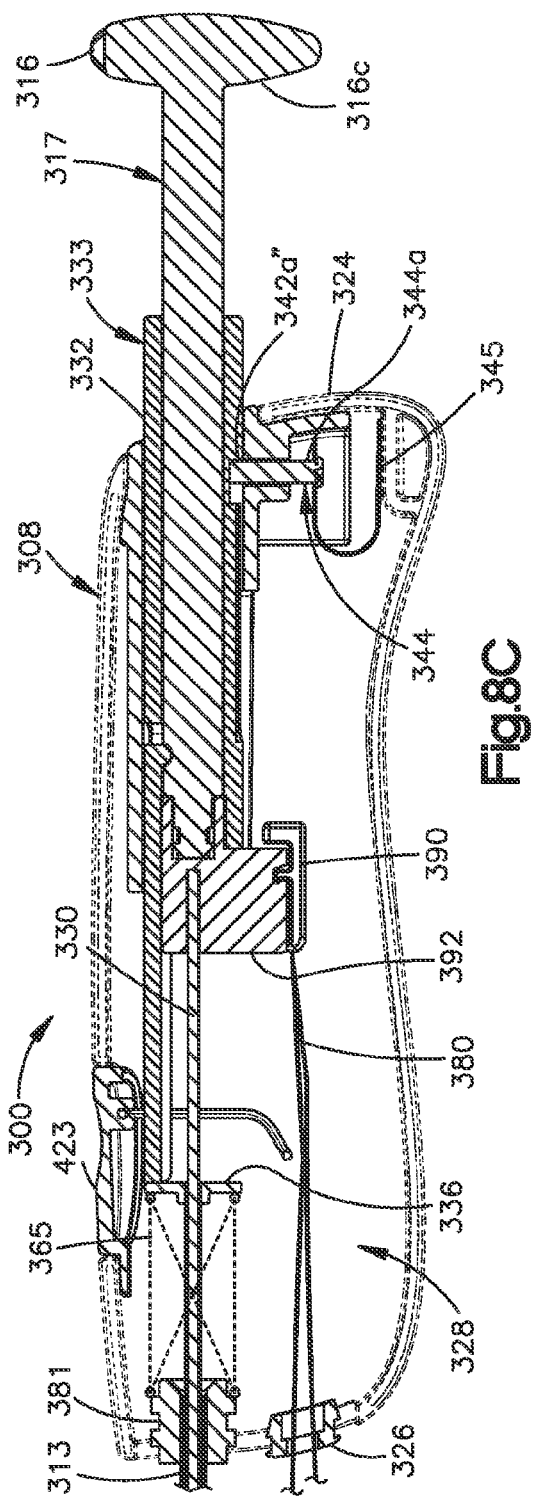
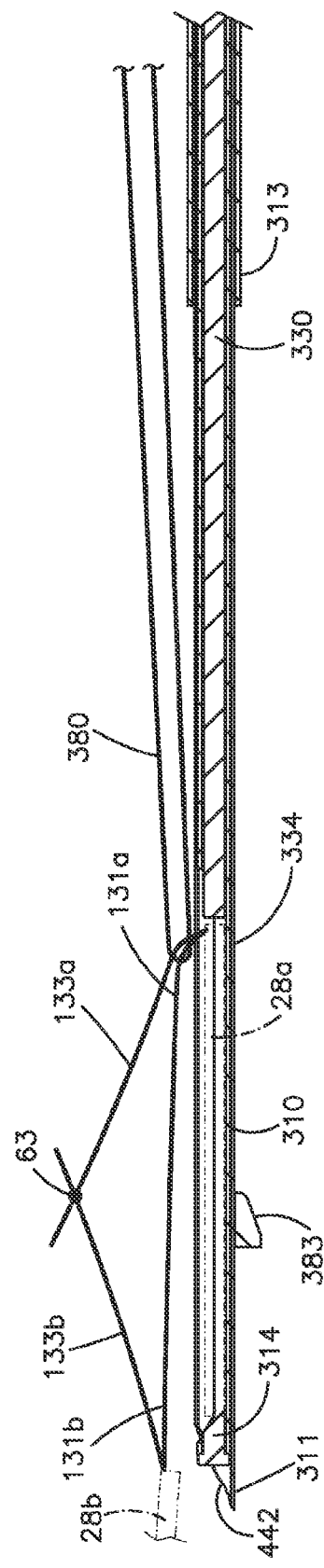
Fig.8C
Fig.8D

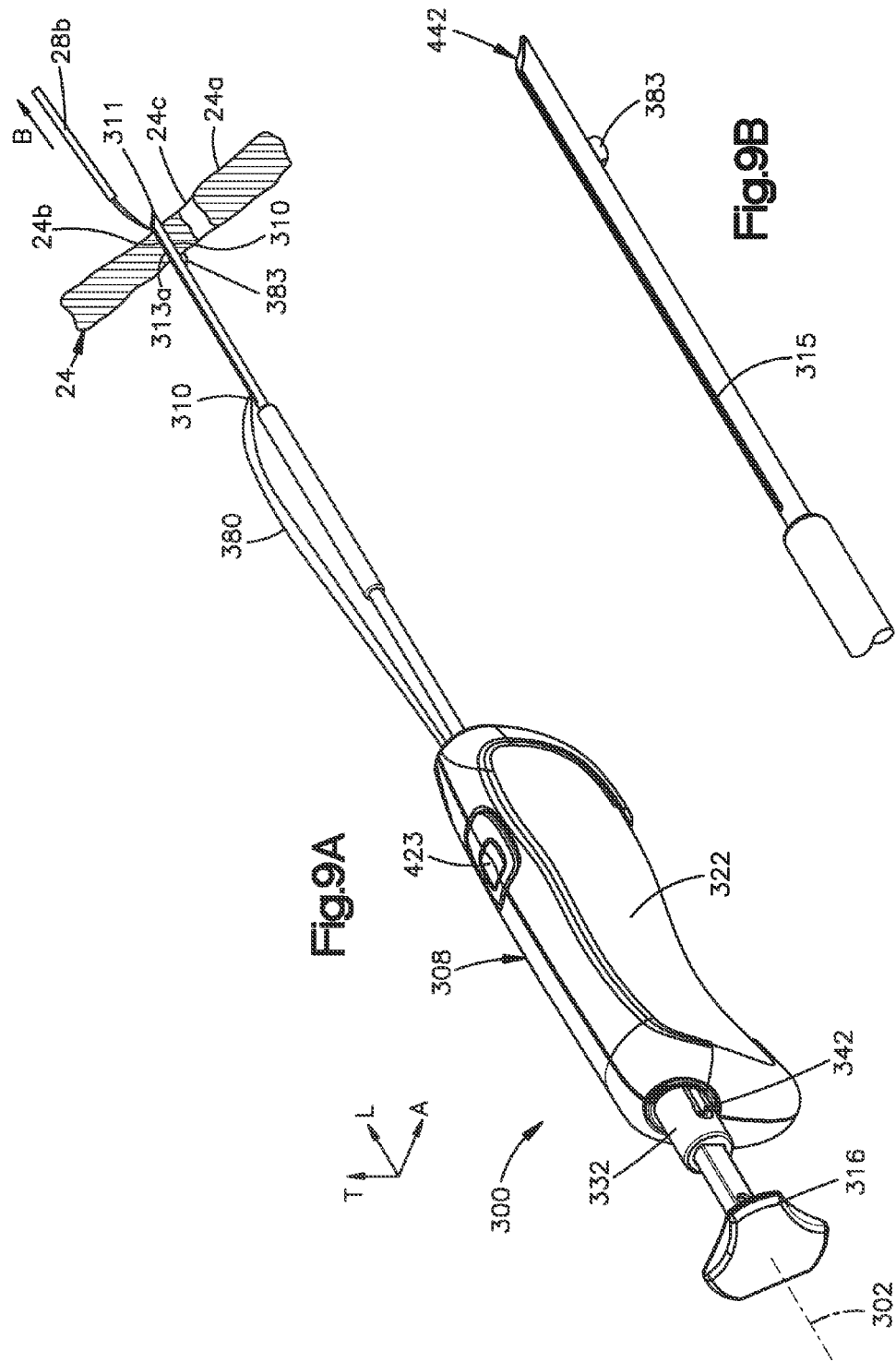

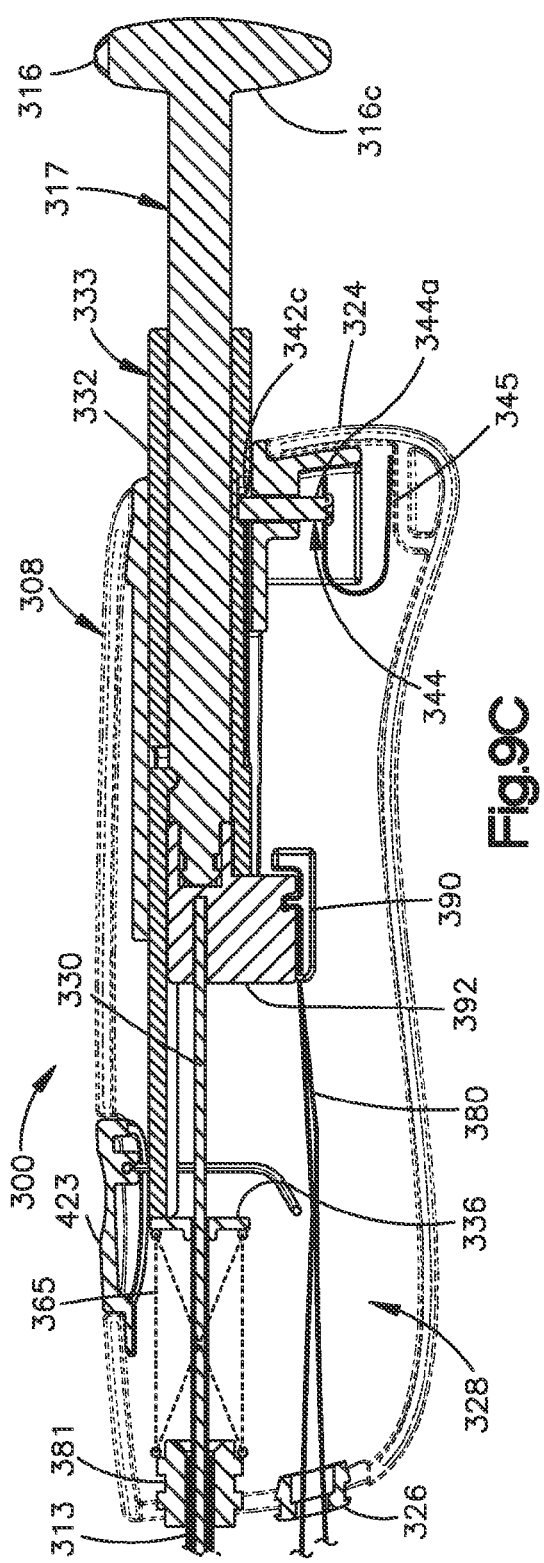
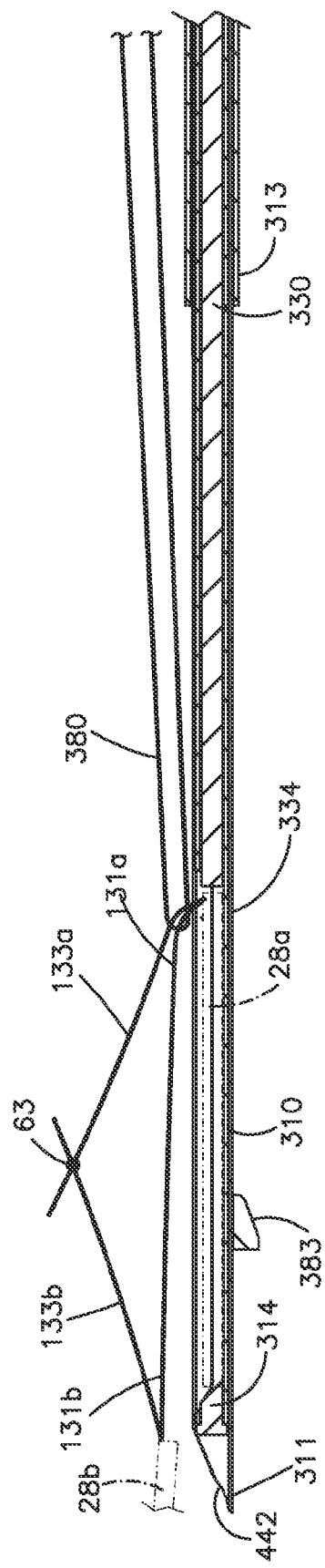
Fig.9C
Fig.9D

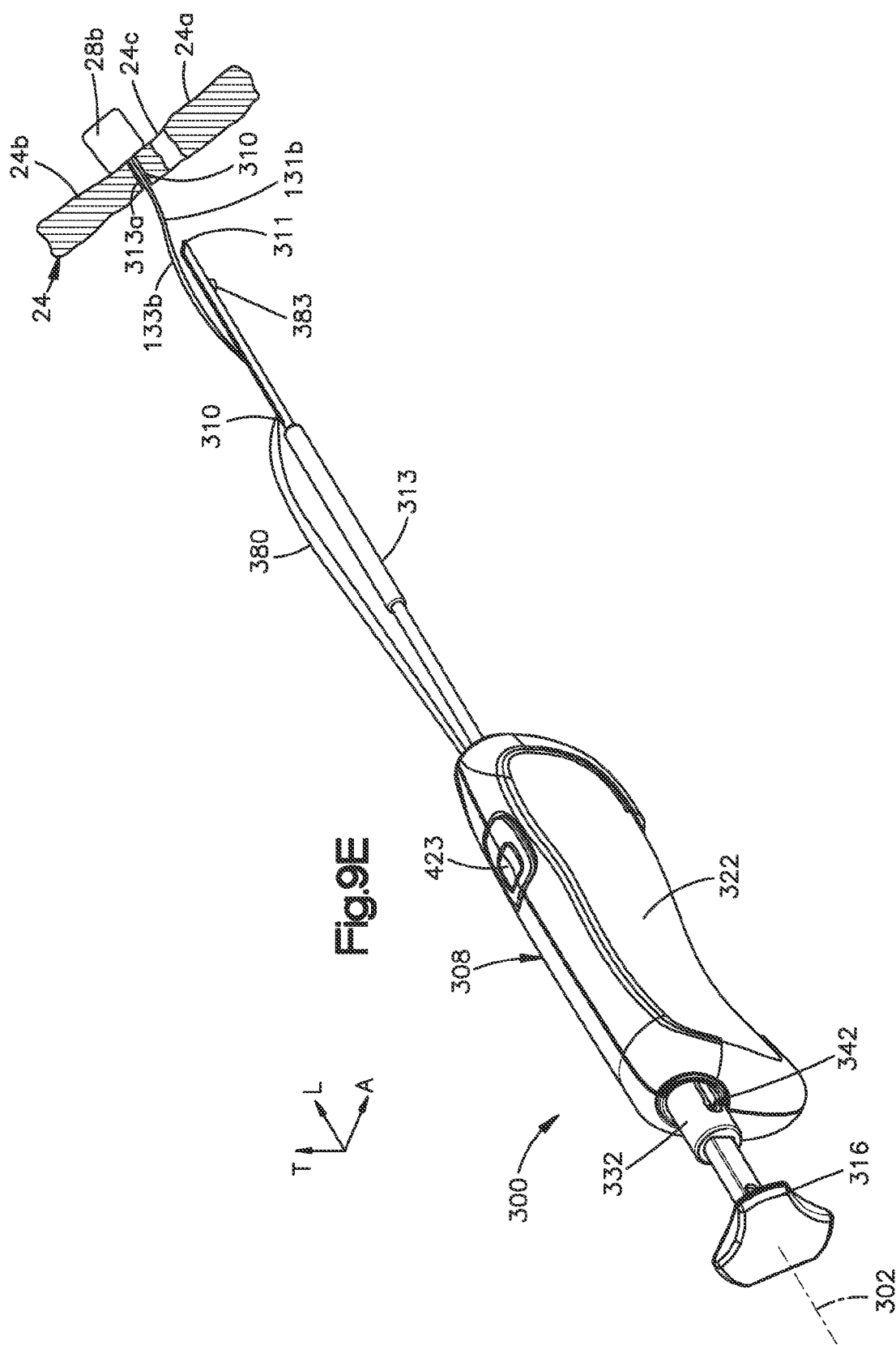

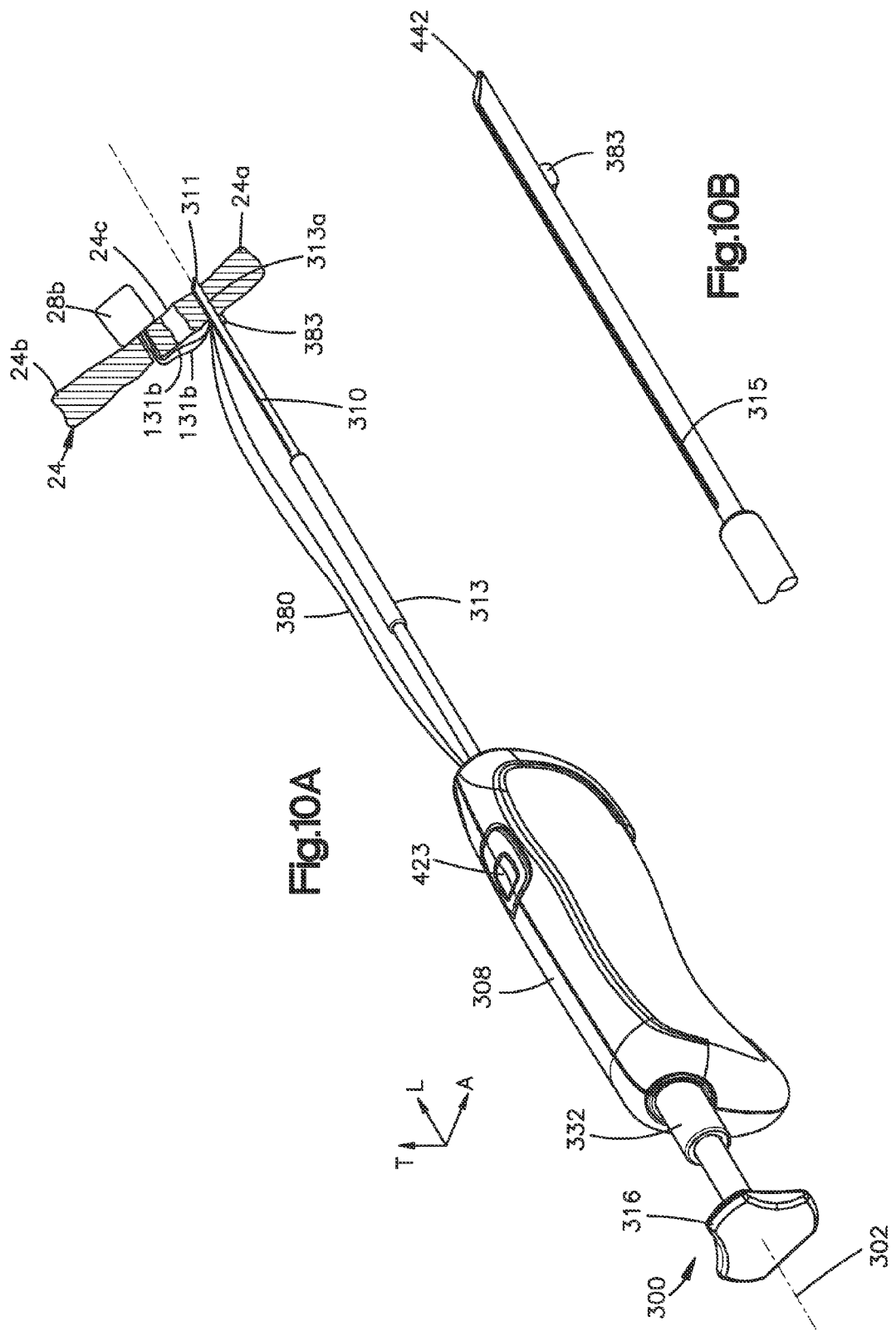

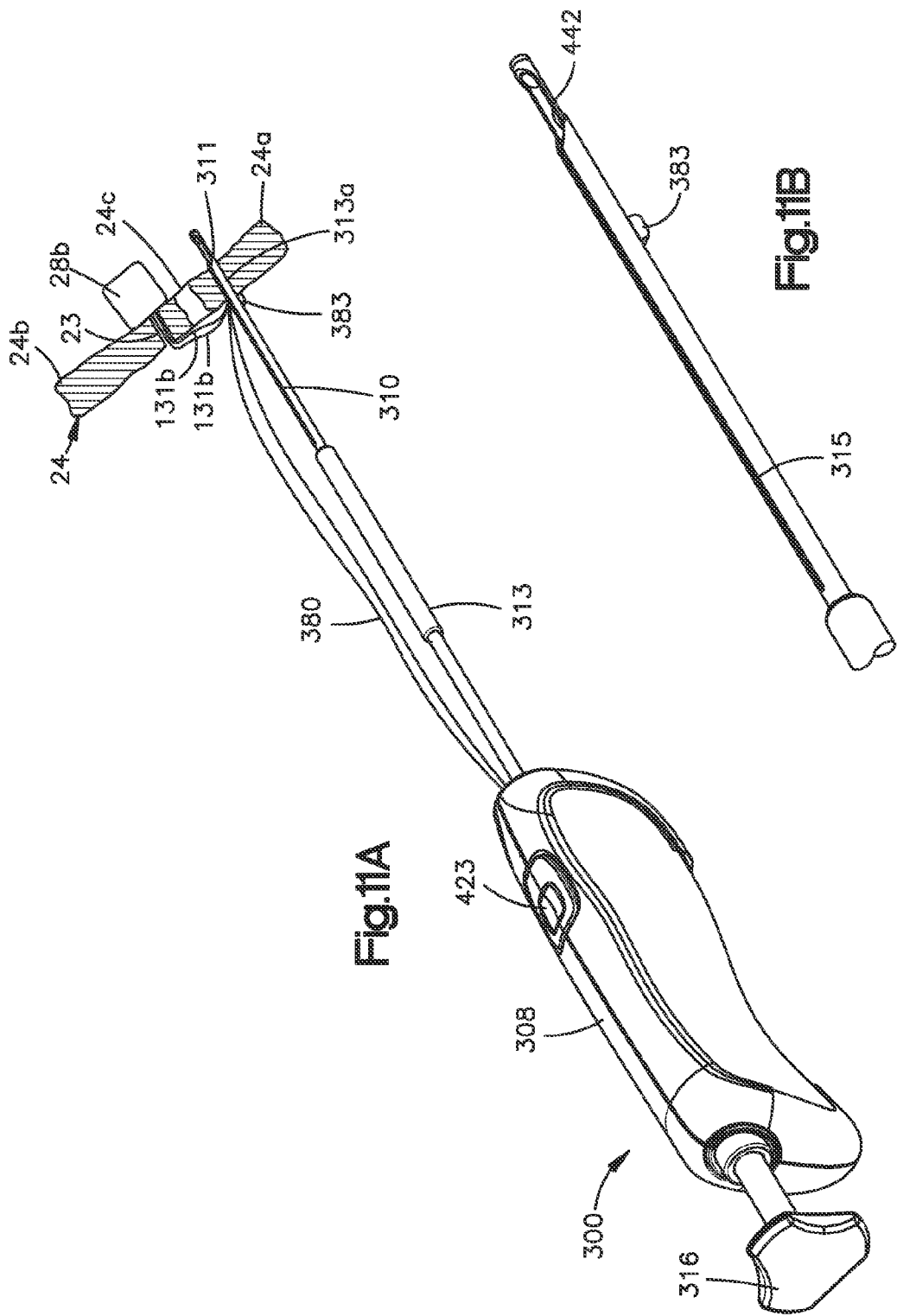

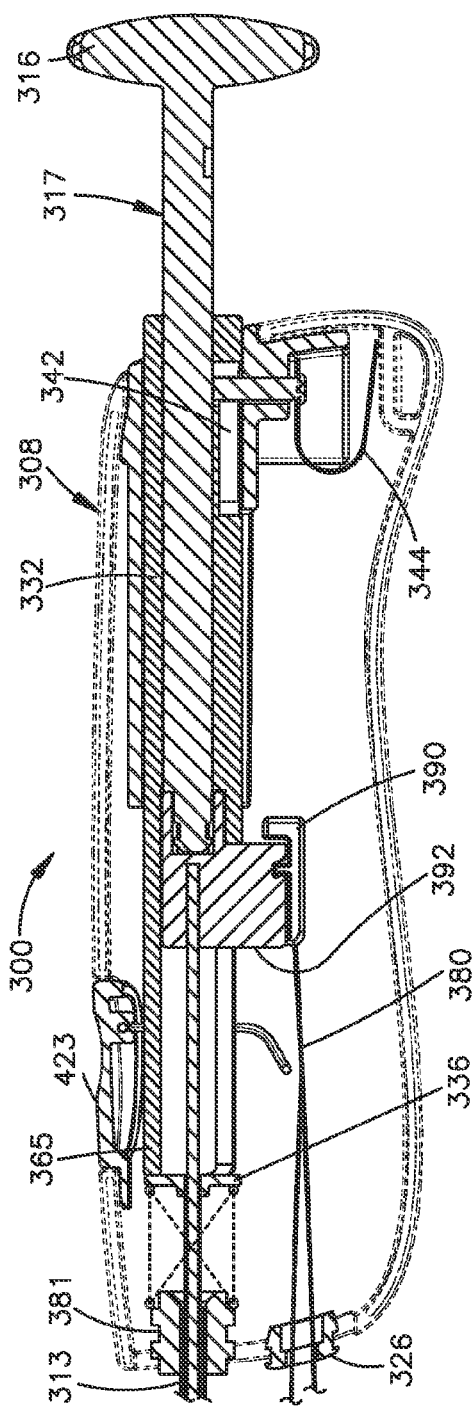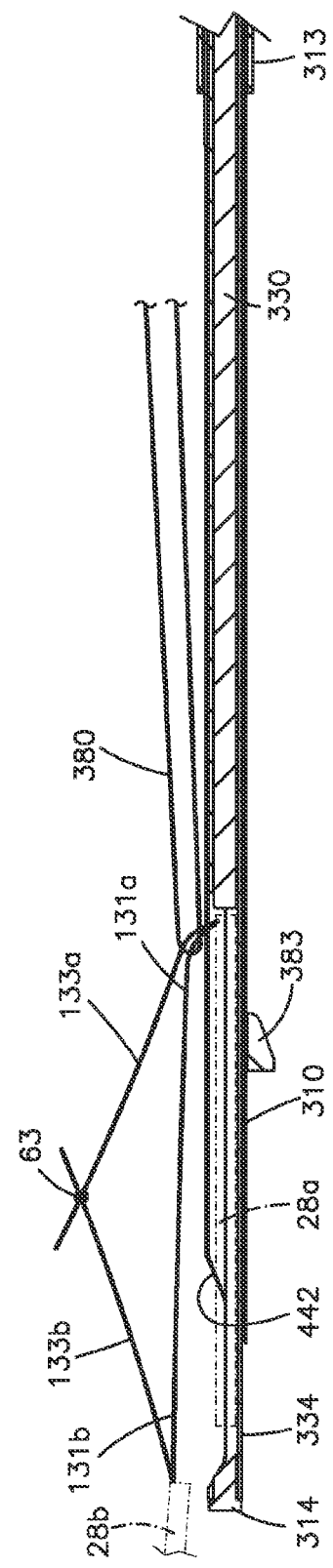
Fig.11C
Fig.11D

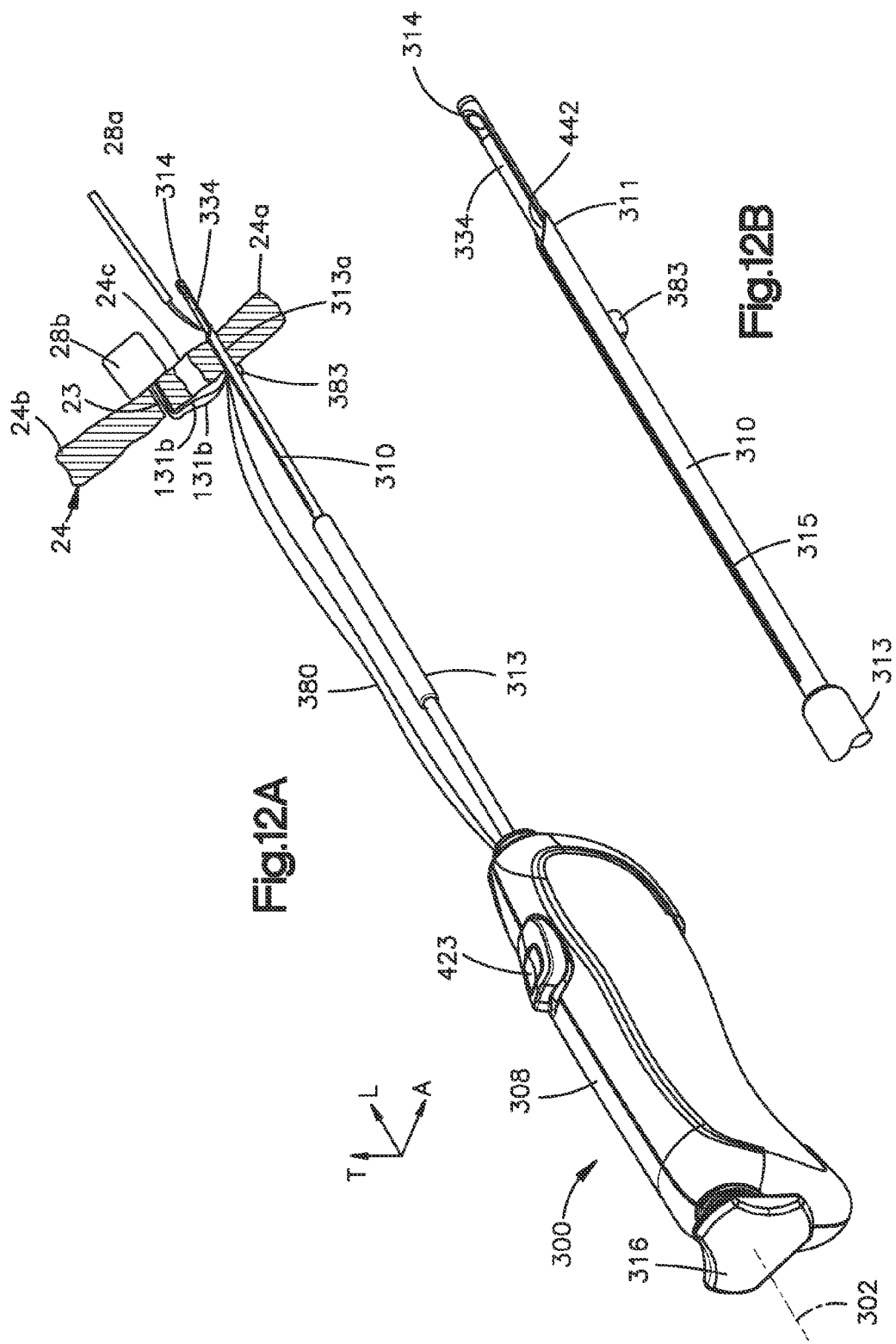

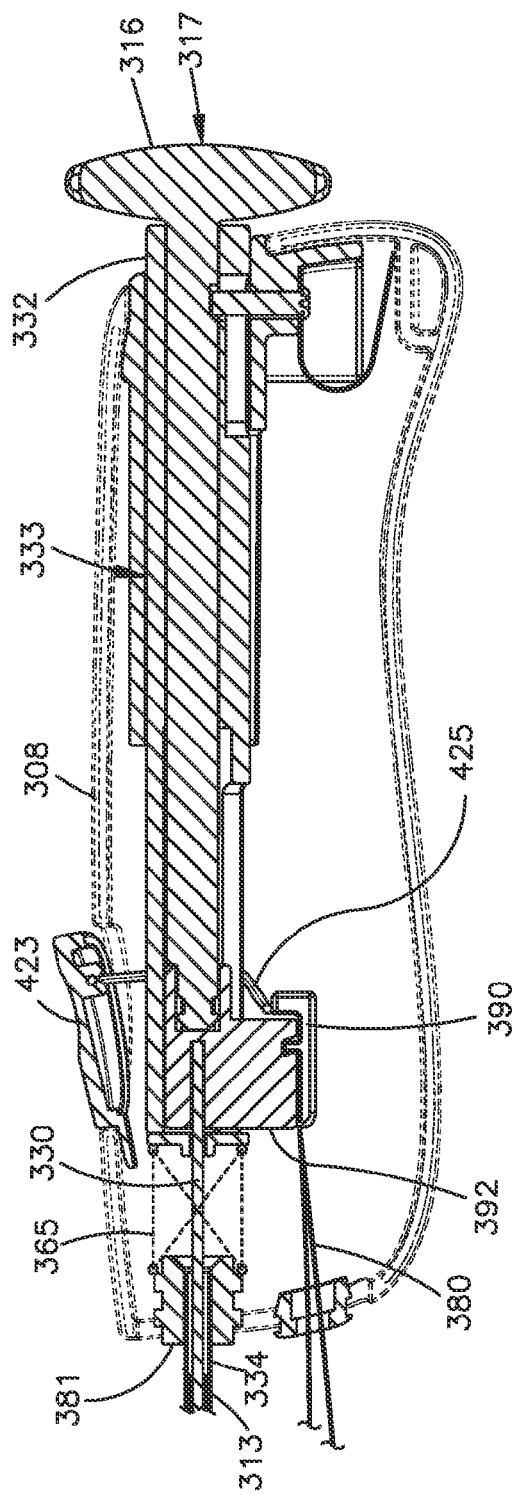
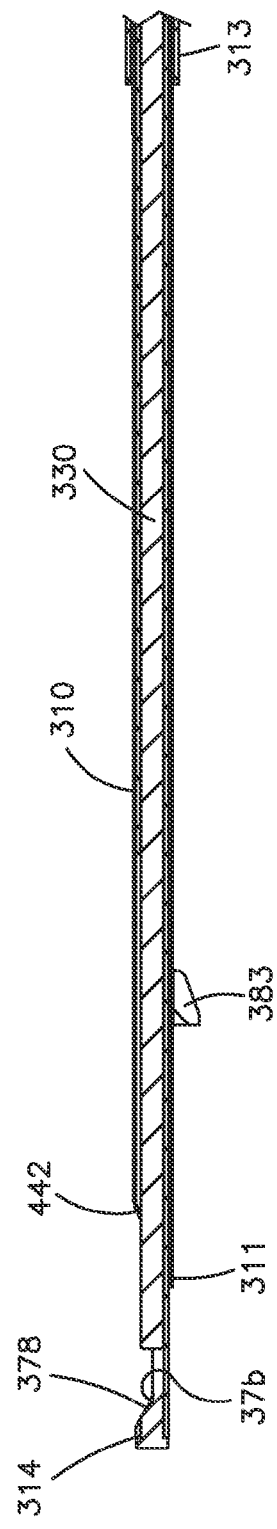
Fig.12C
Fig.12D

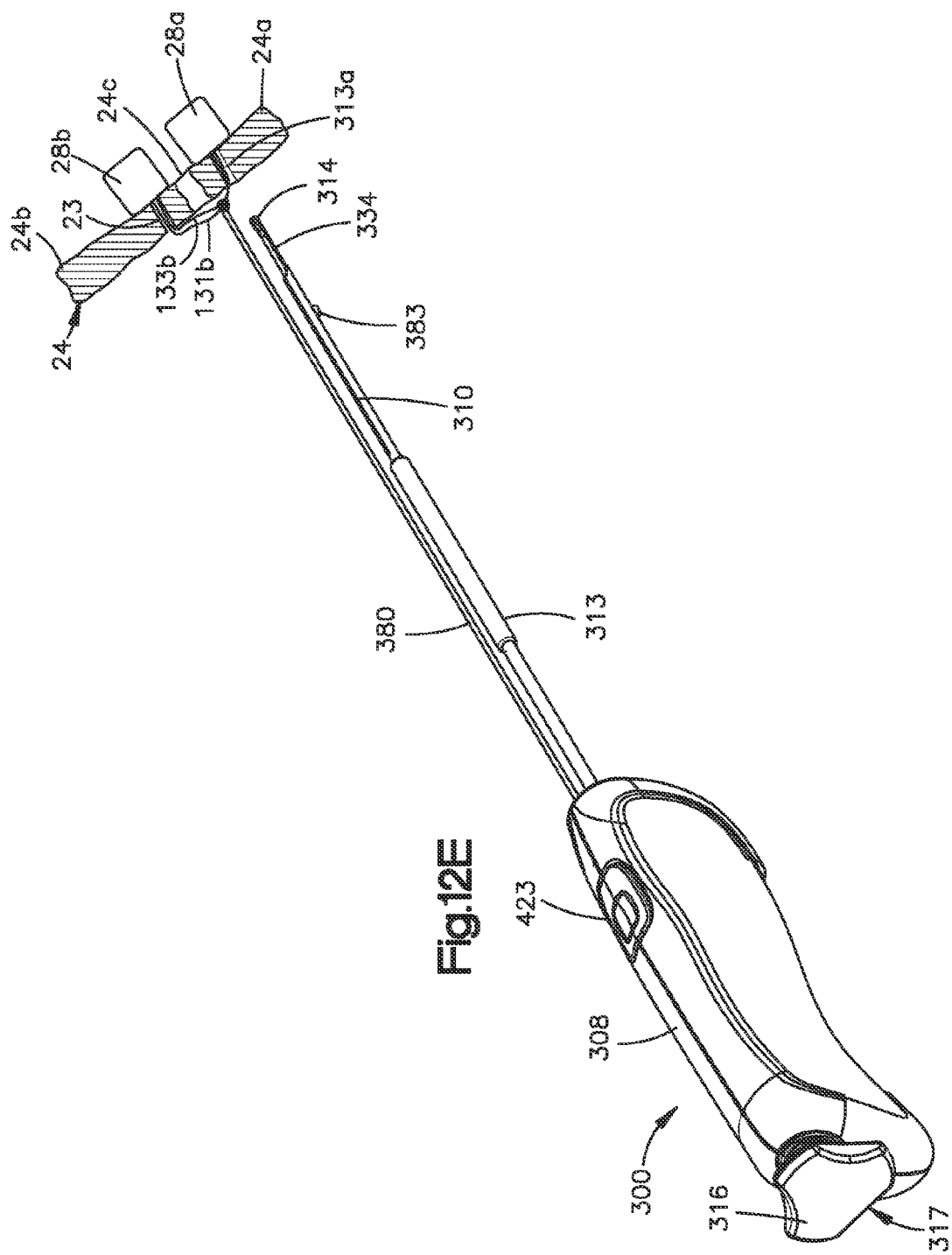

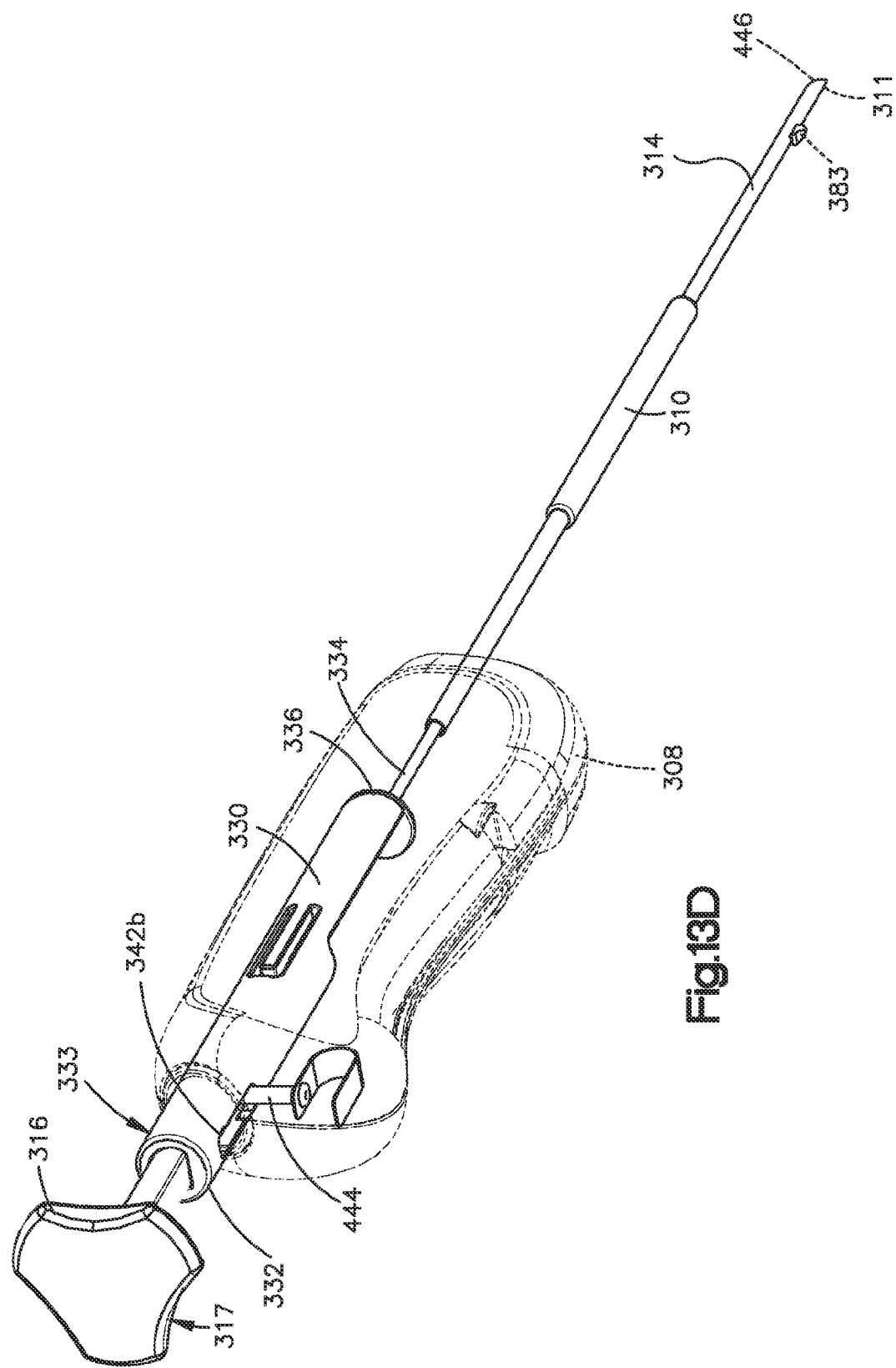

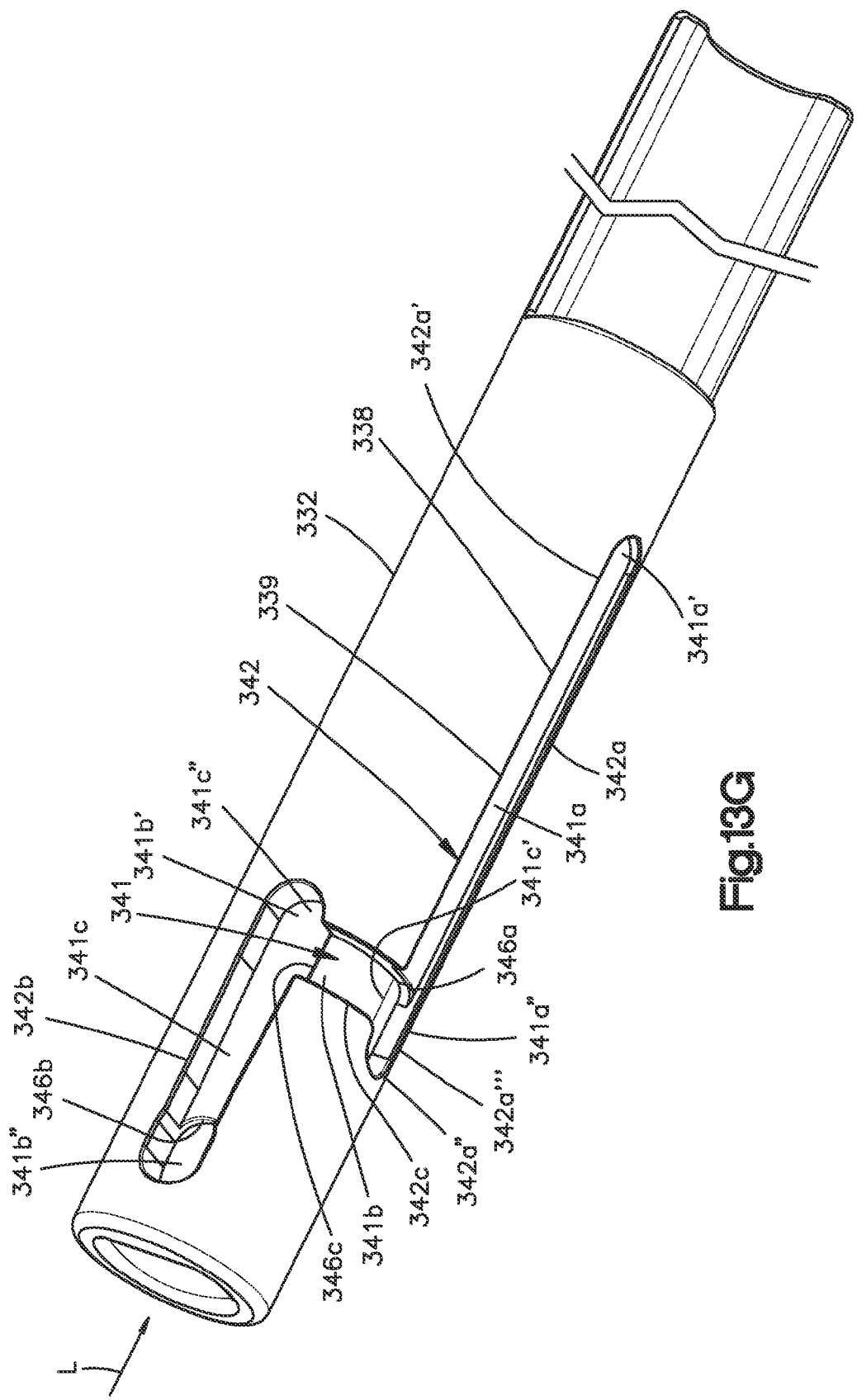

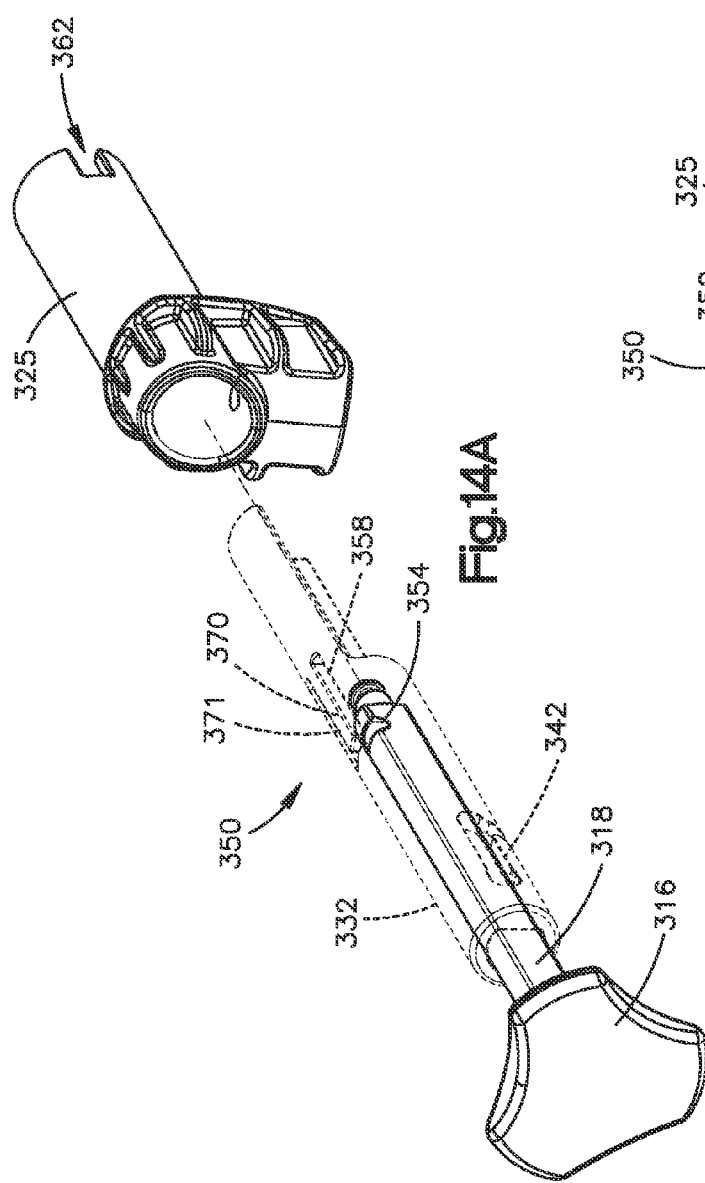
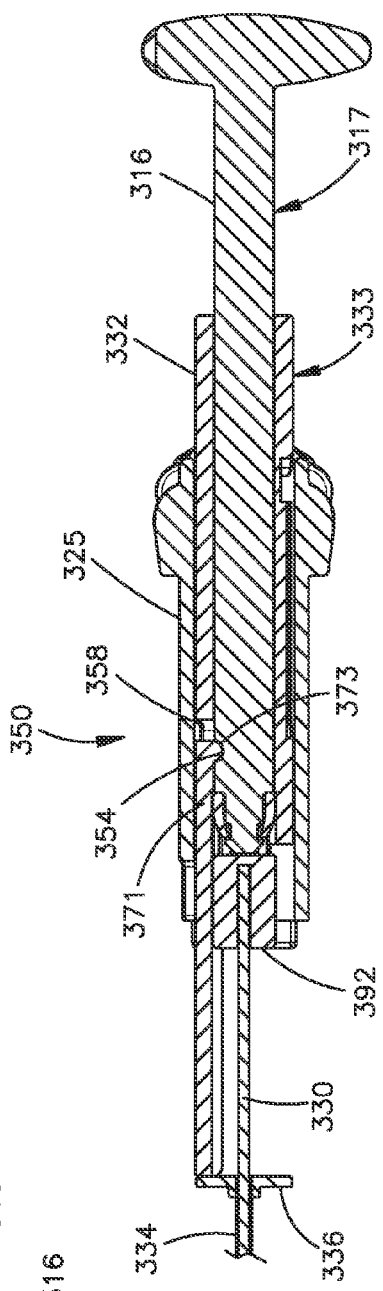
Fig.14A
Fig.14B

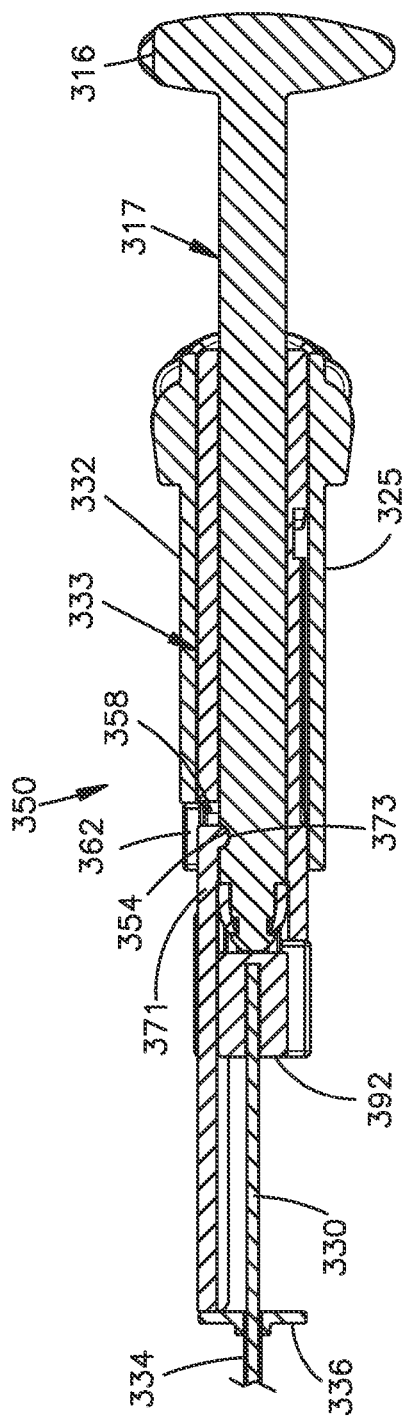
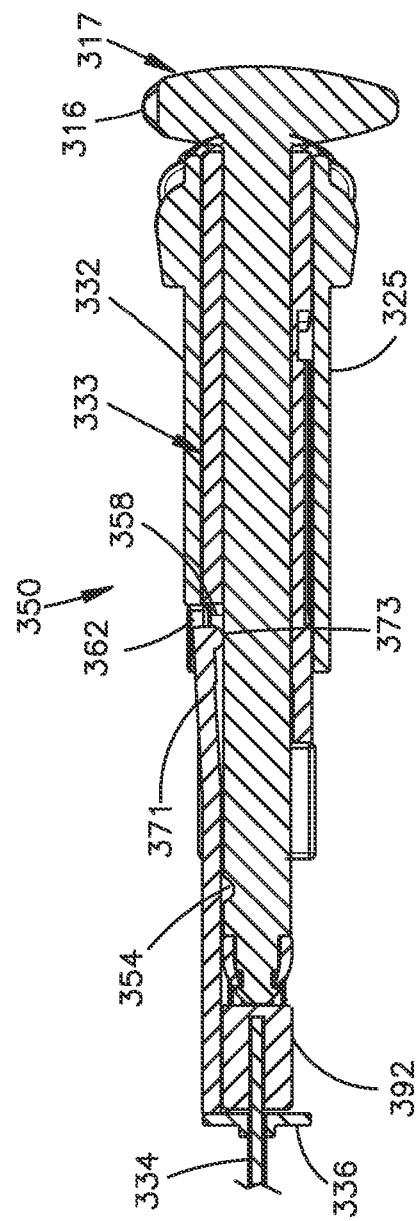

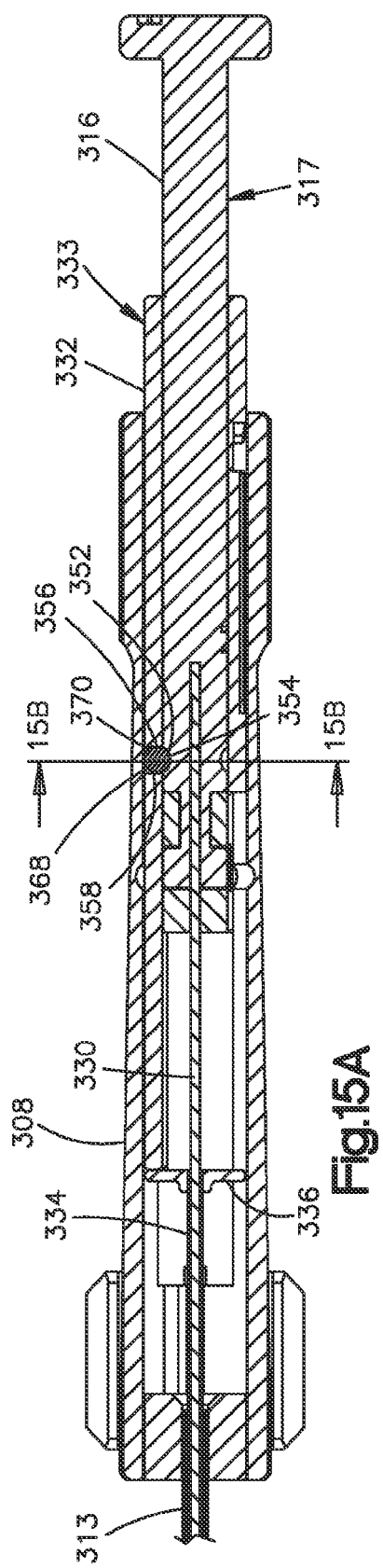
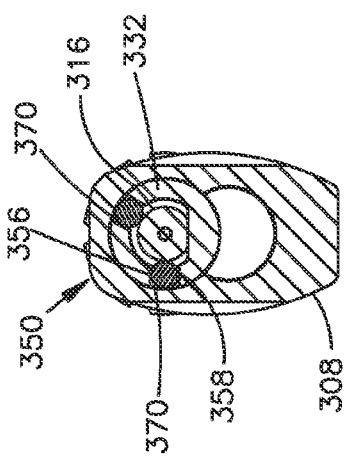
Fig.15A
Fig.15B

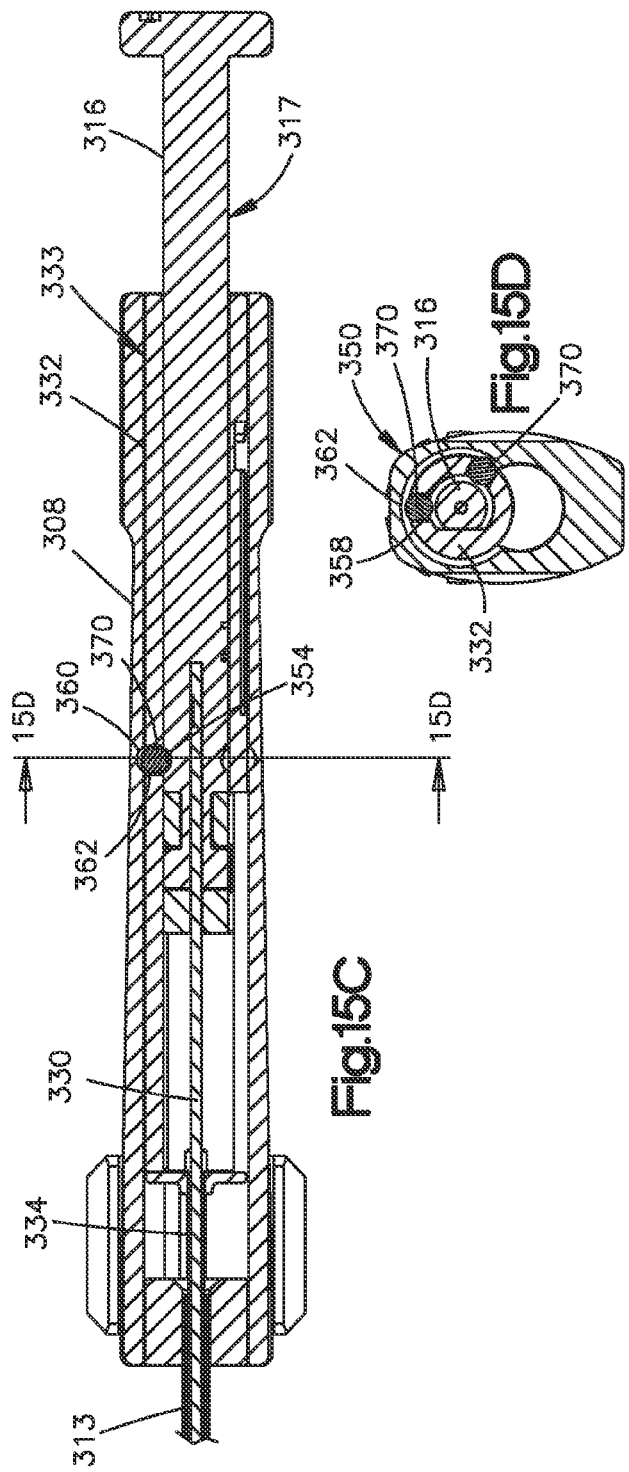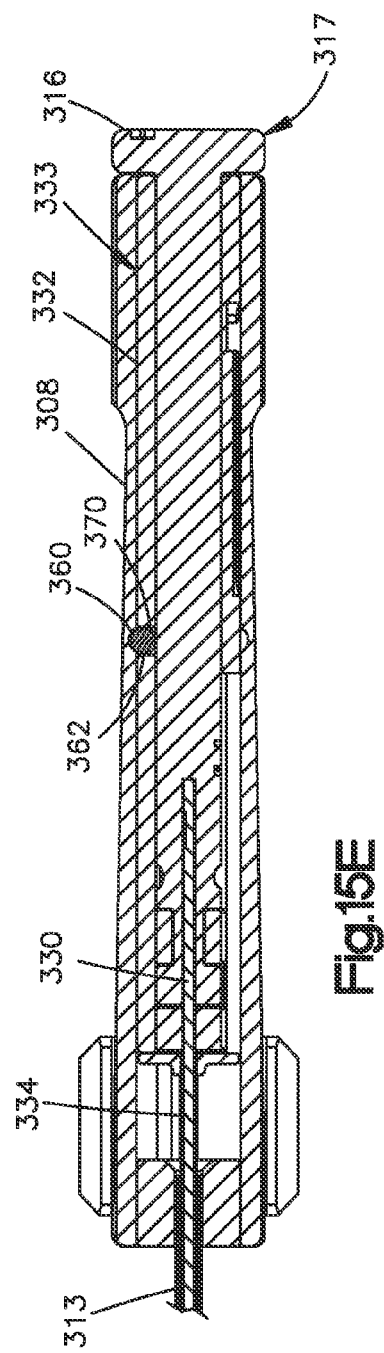

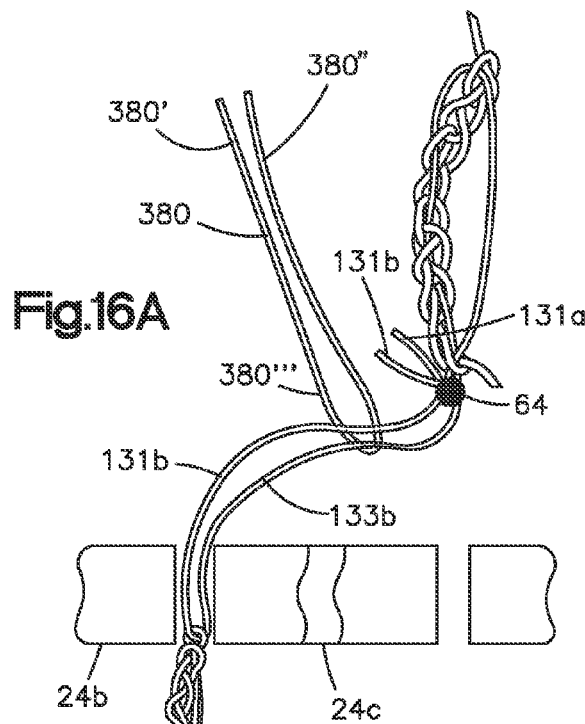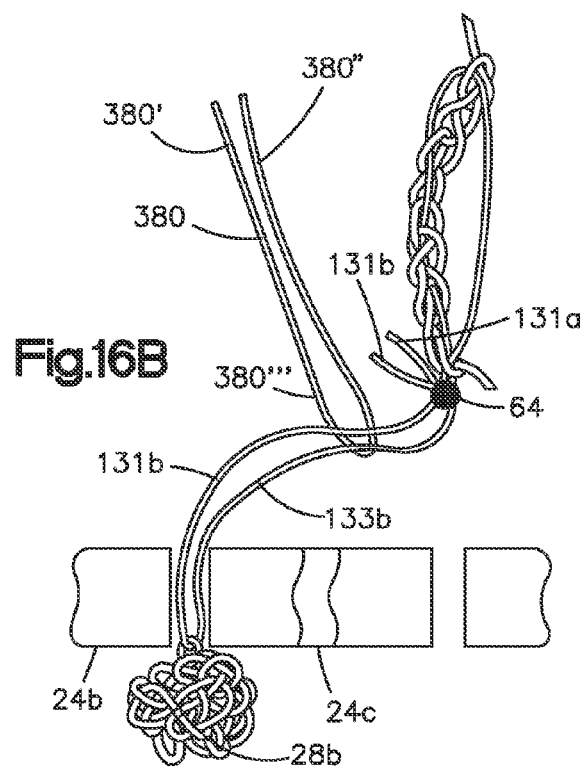

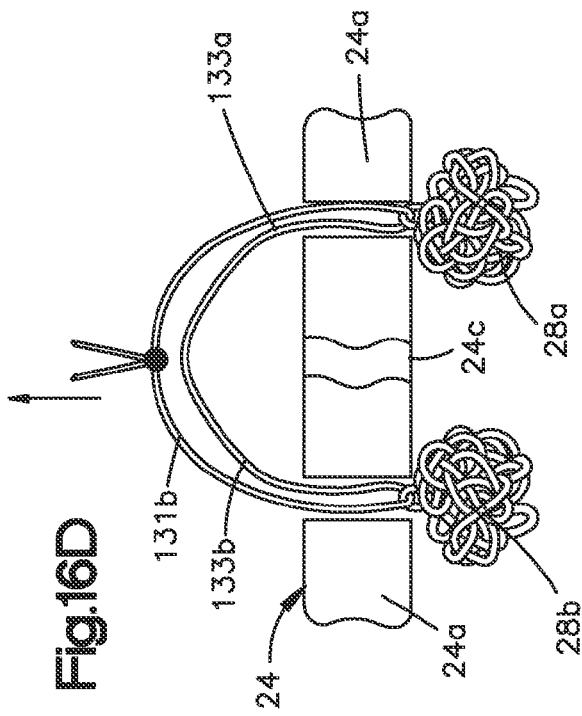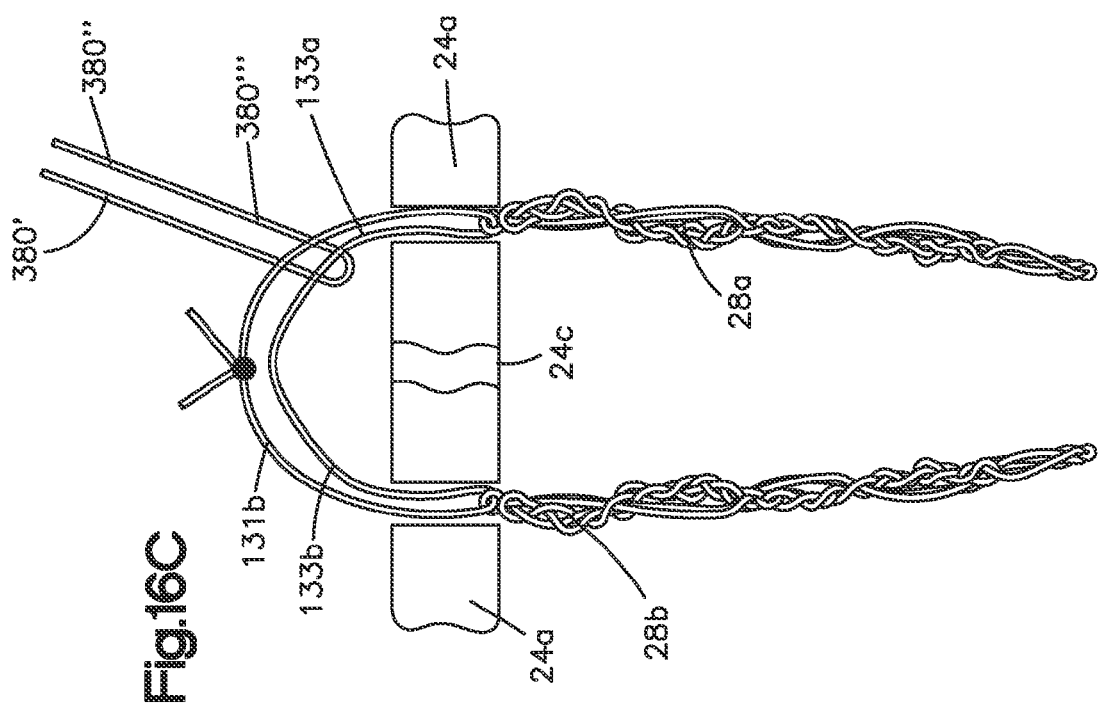

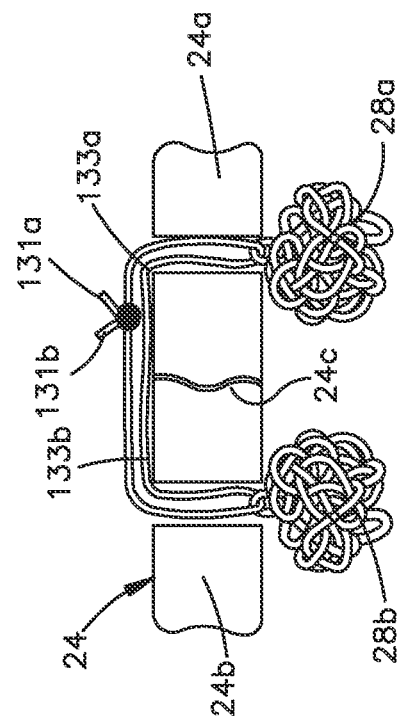
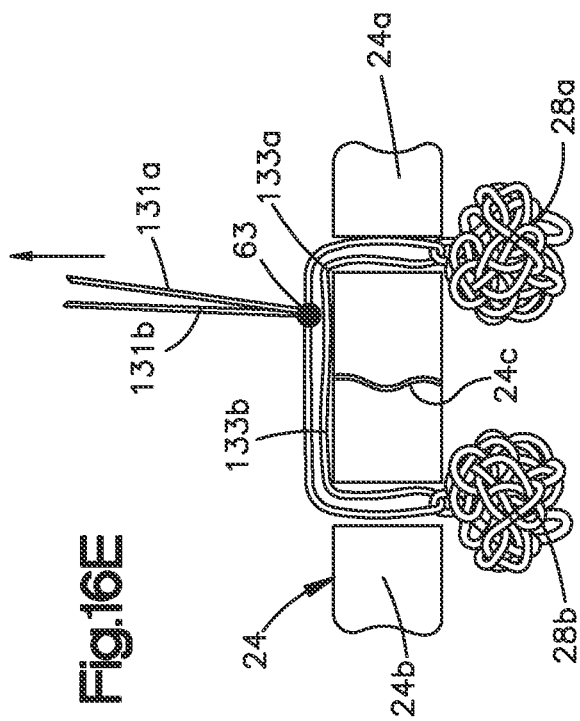

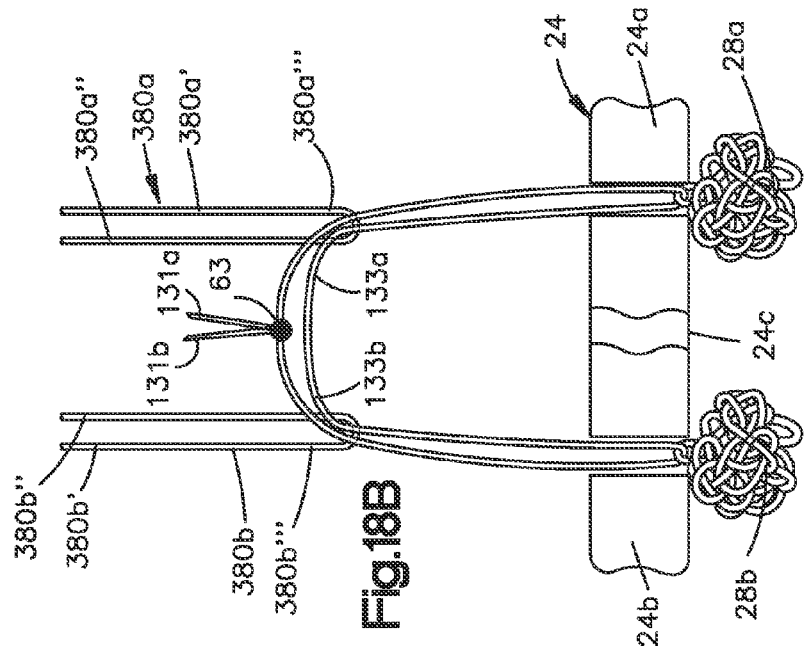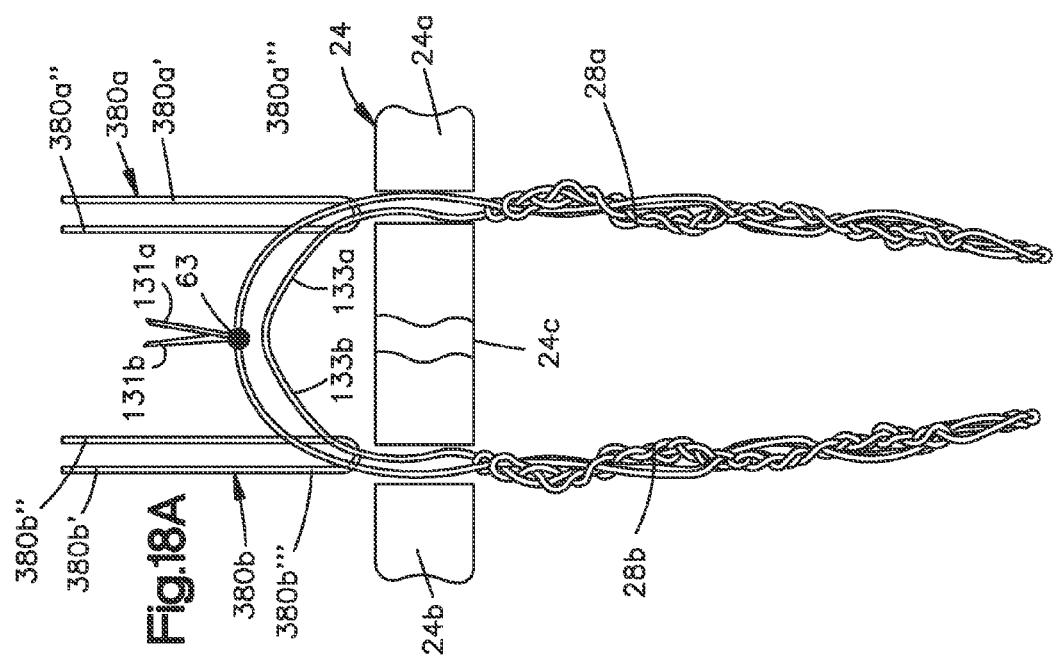

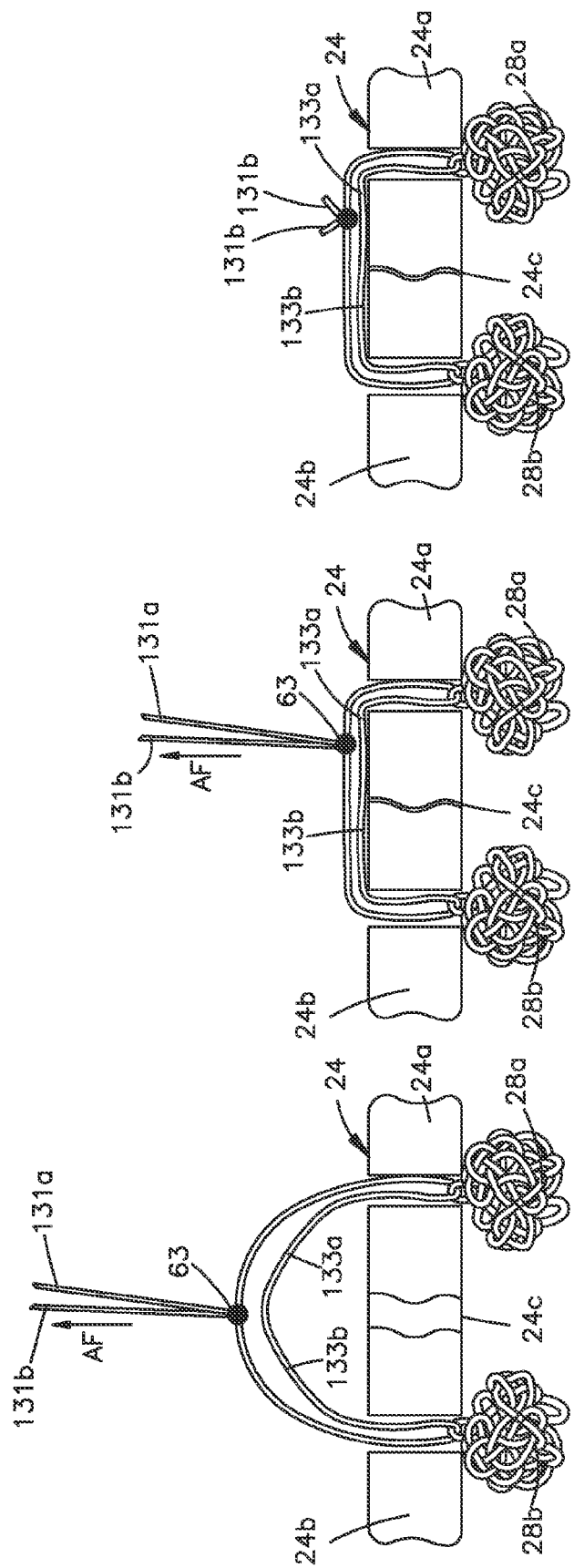

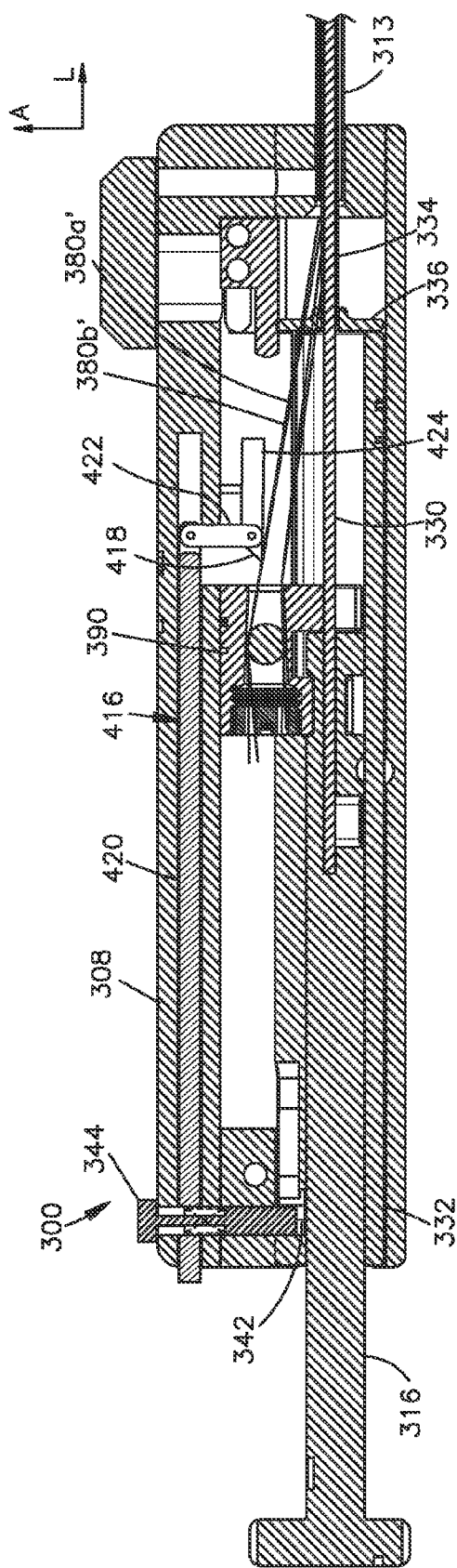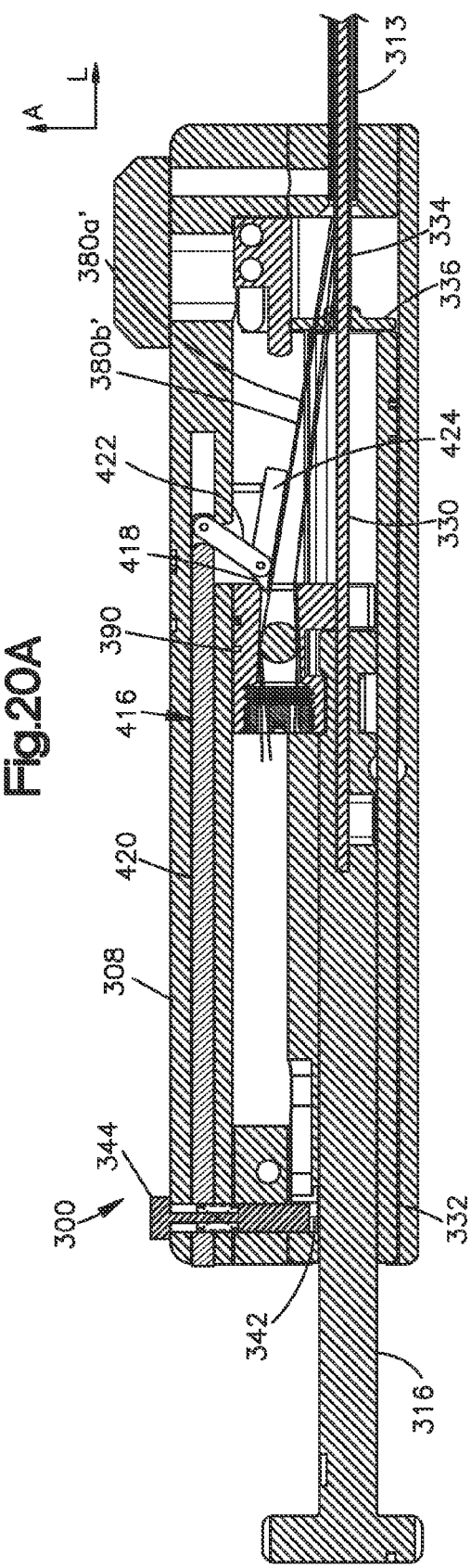
Fig.20A
Fig.20B

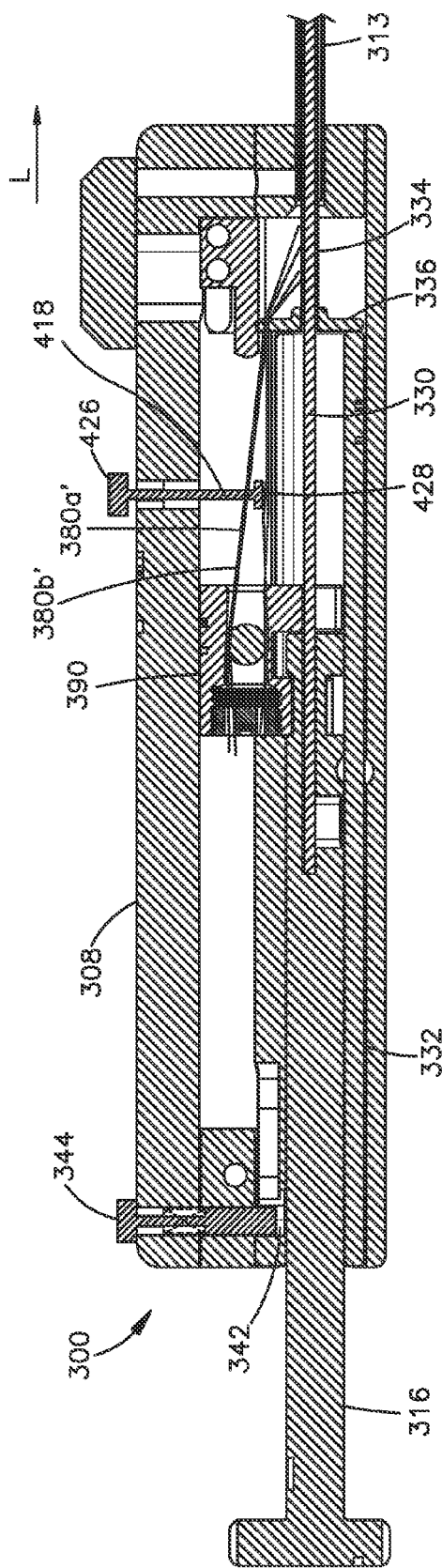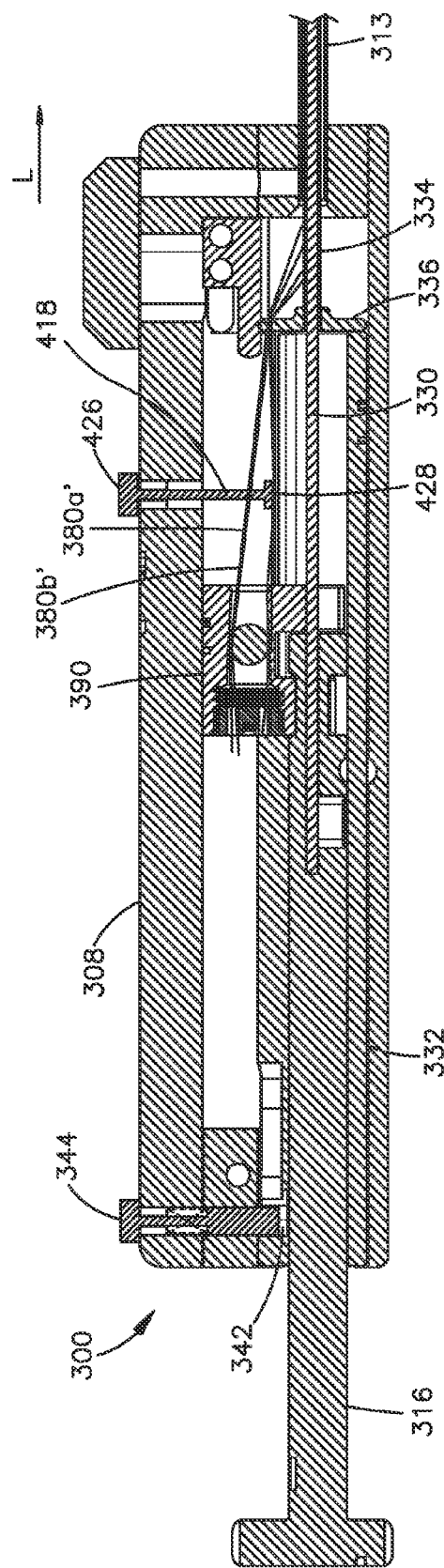

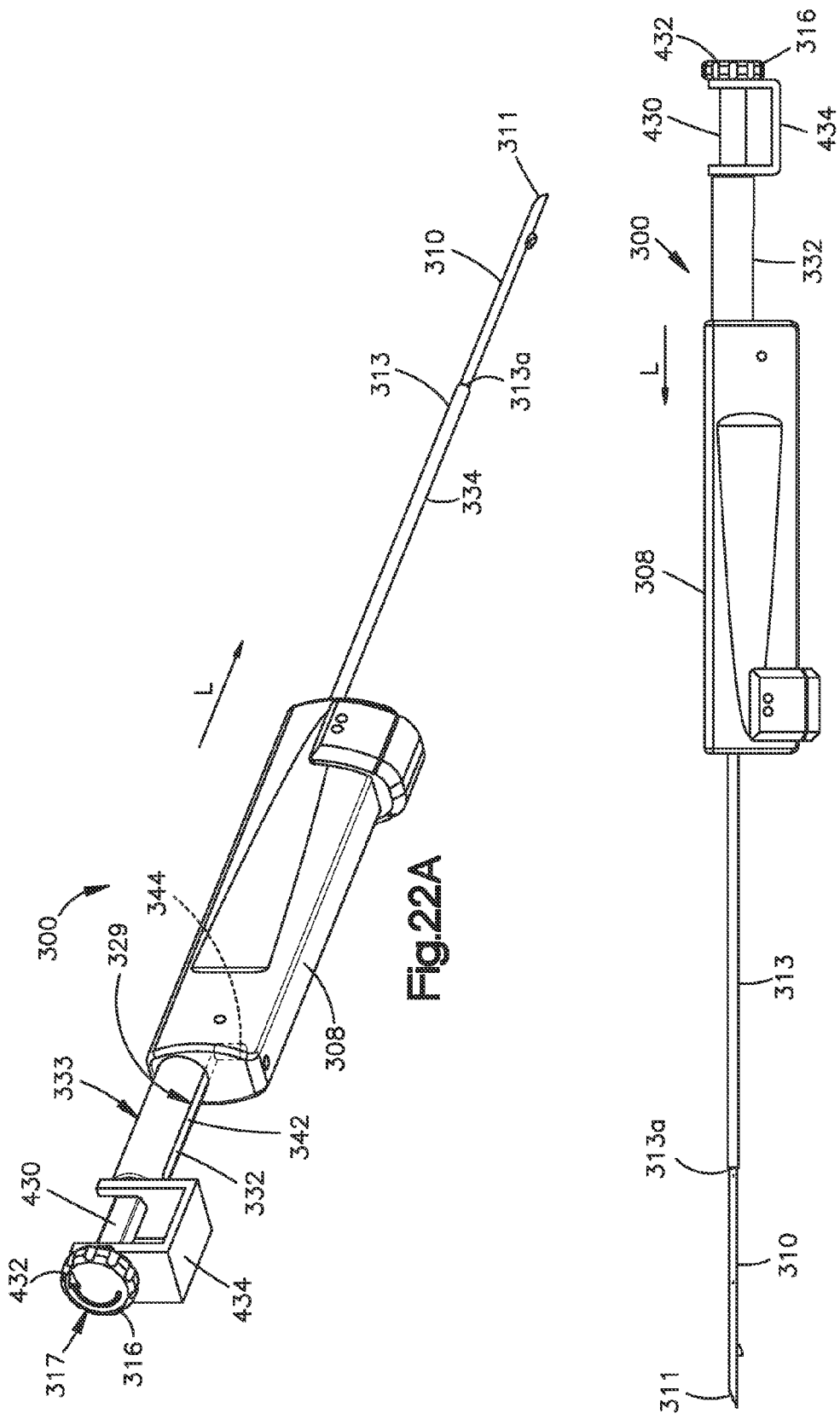

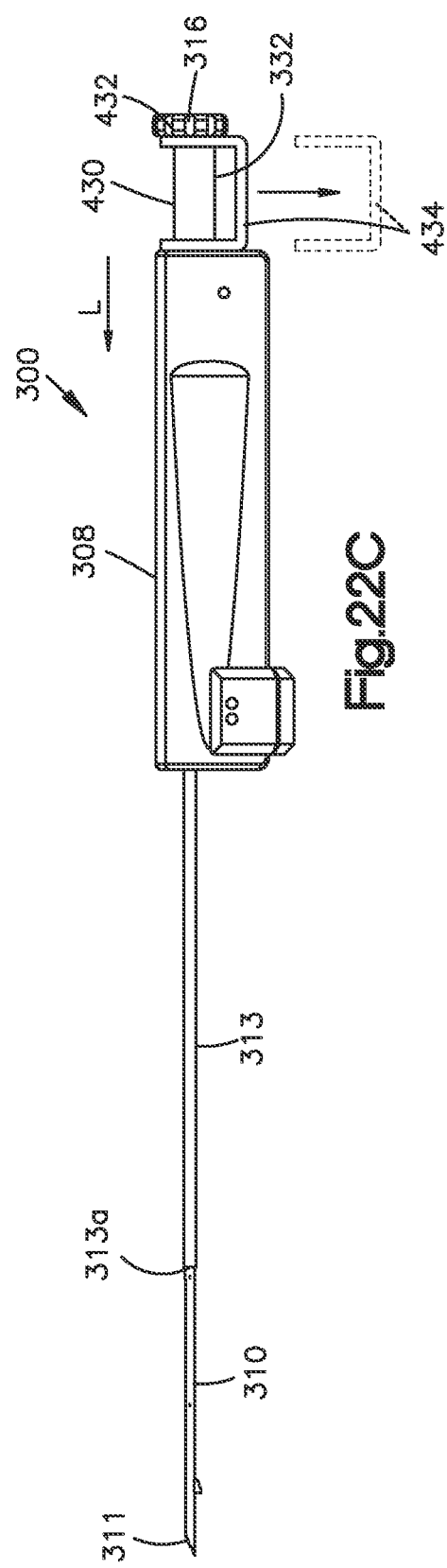
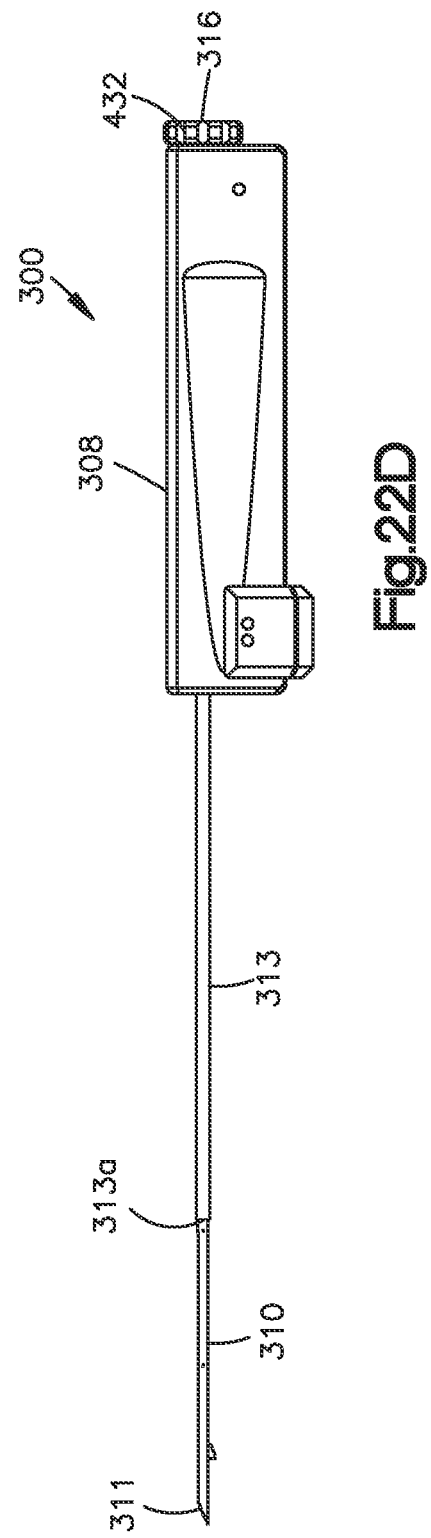
Fig.22C
Fig.22D

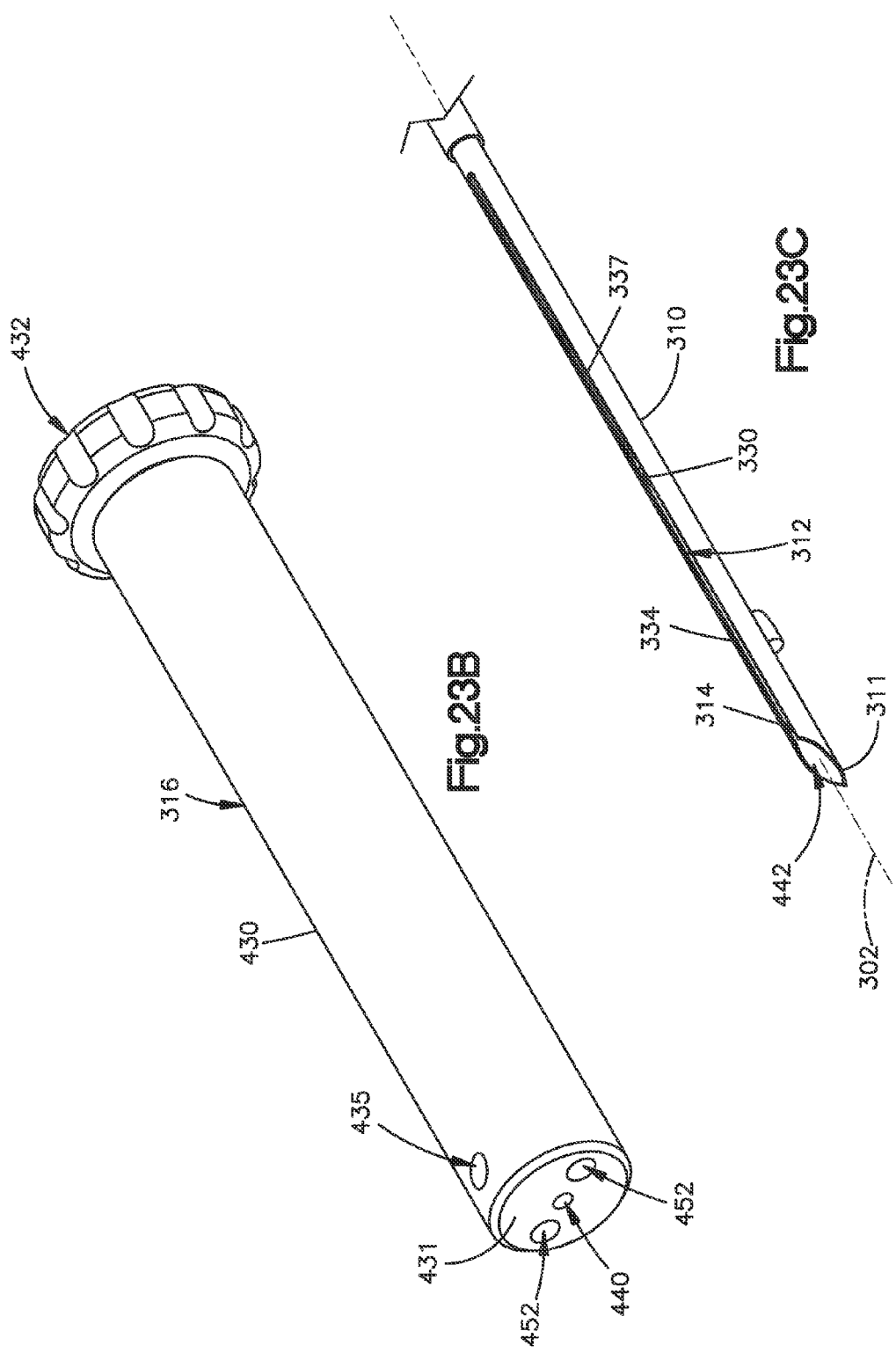

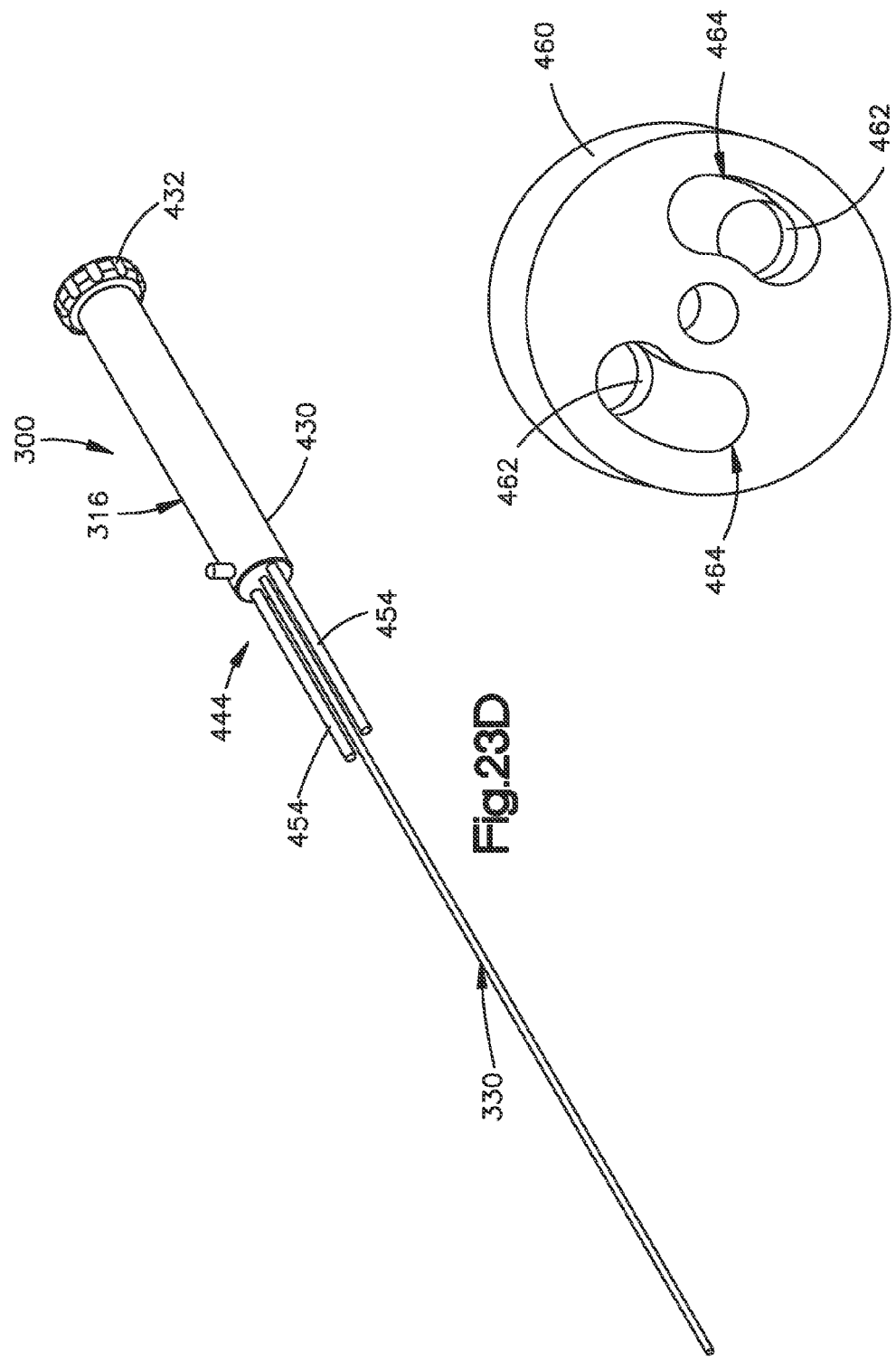

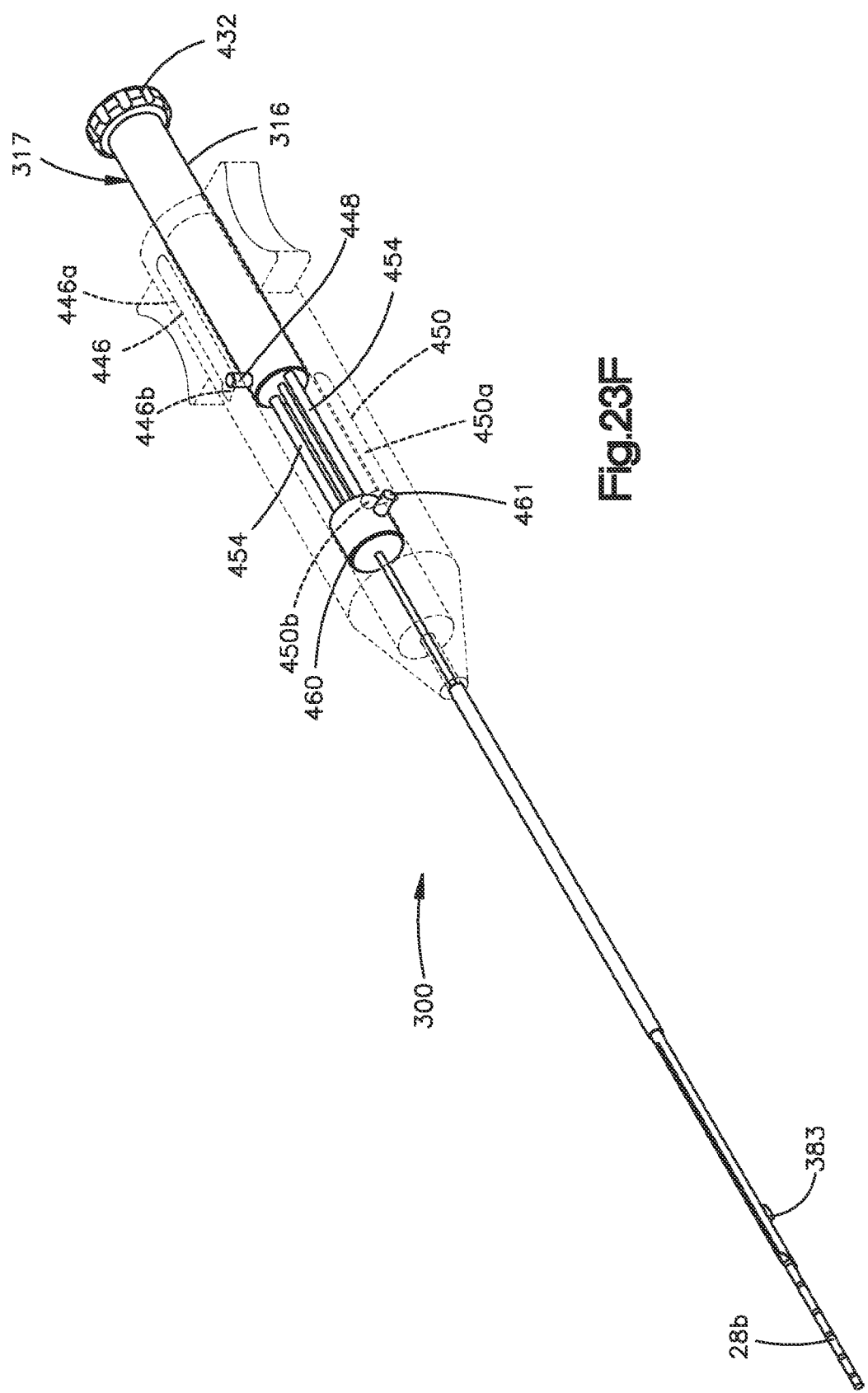

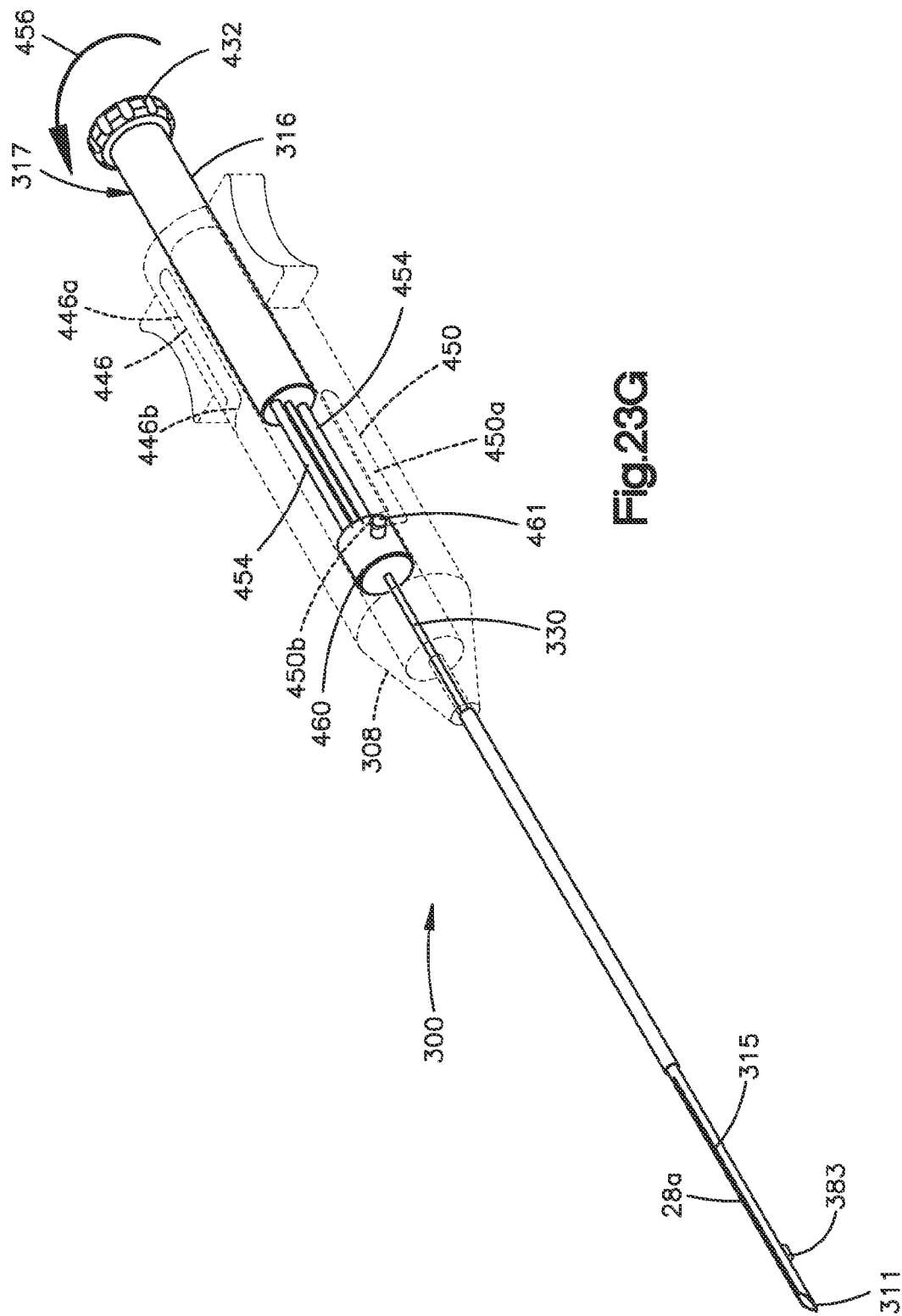

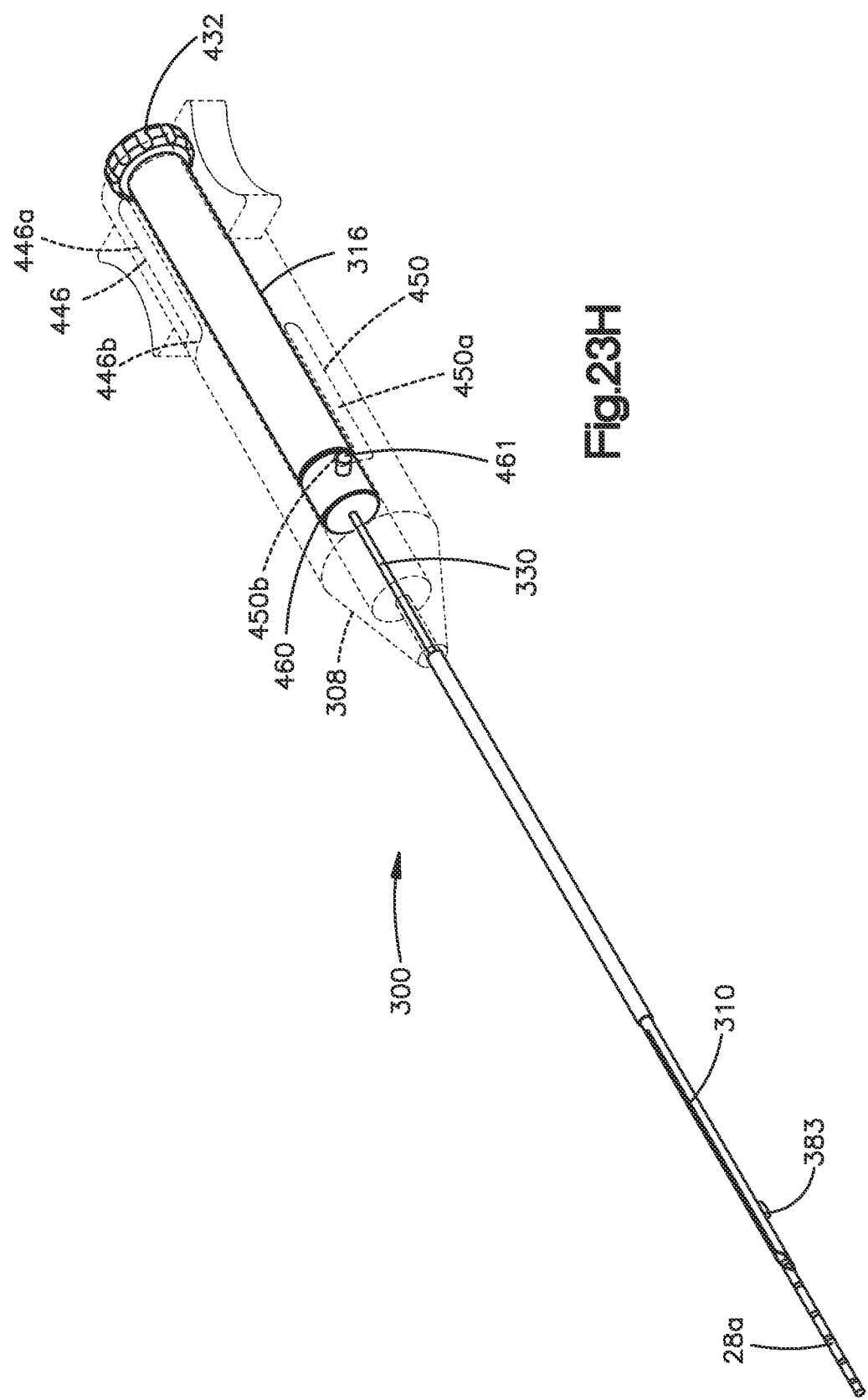

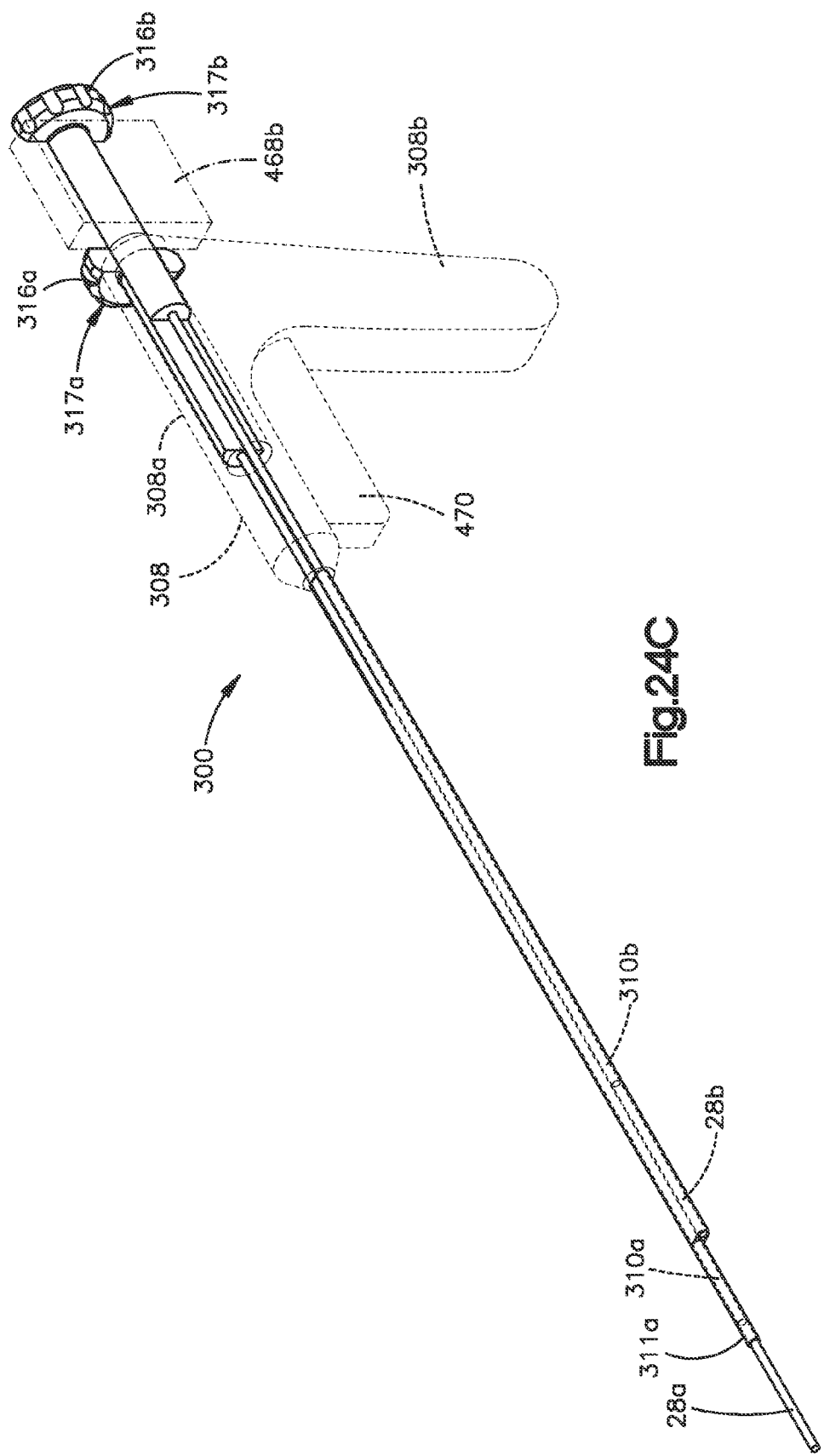

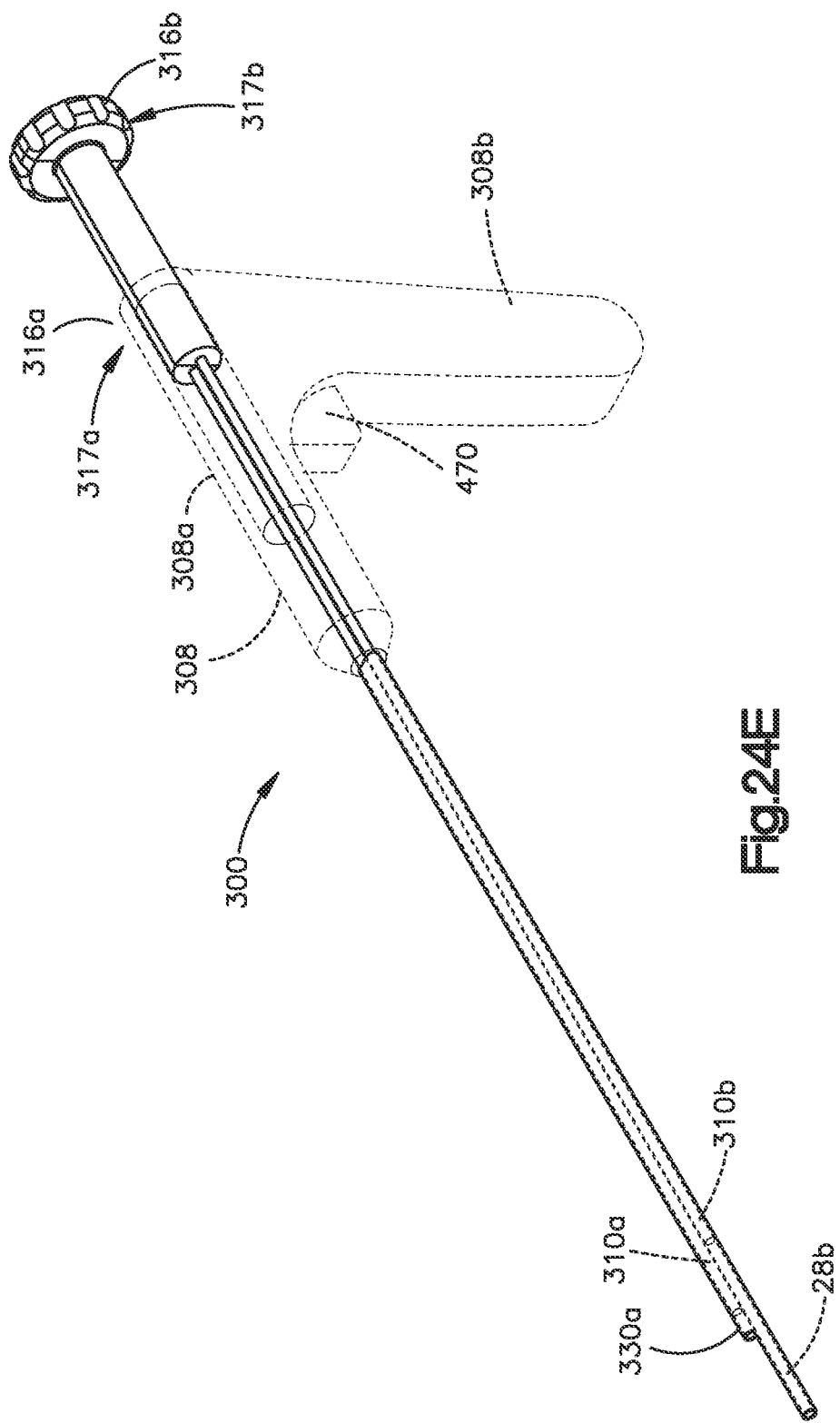

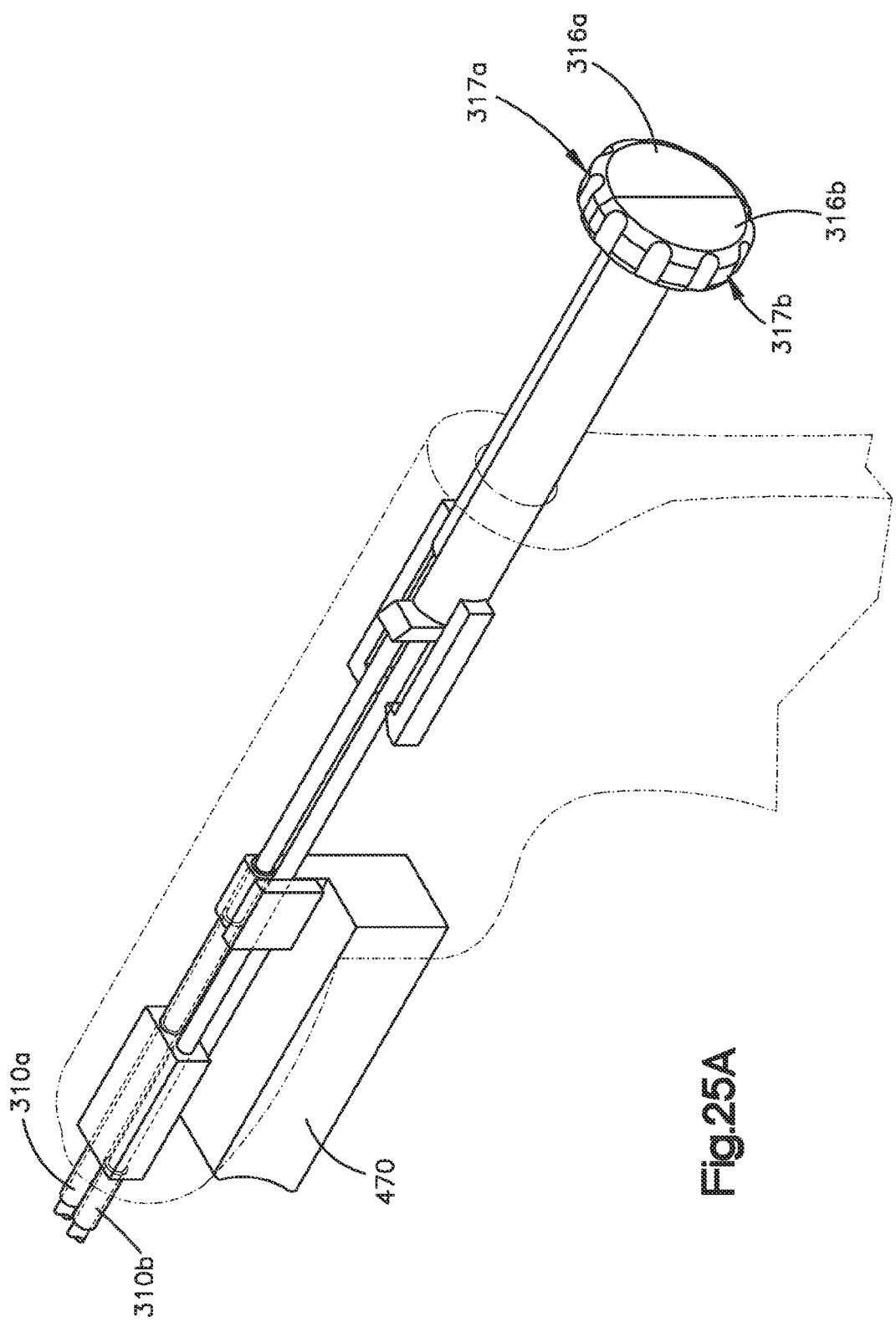

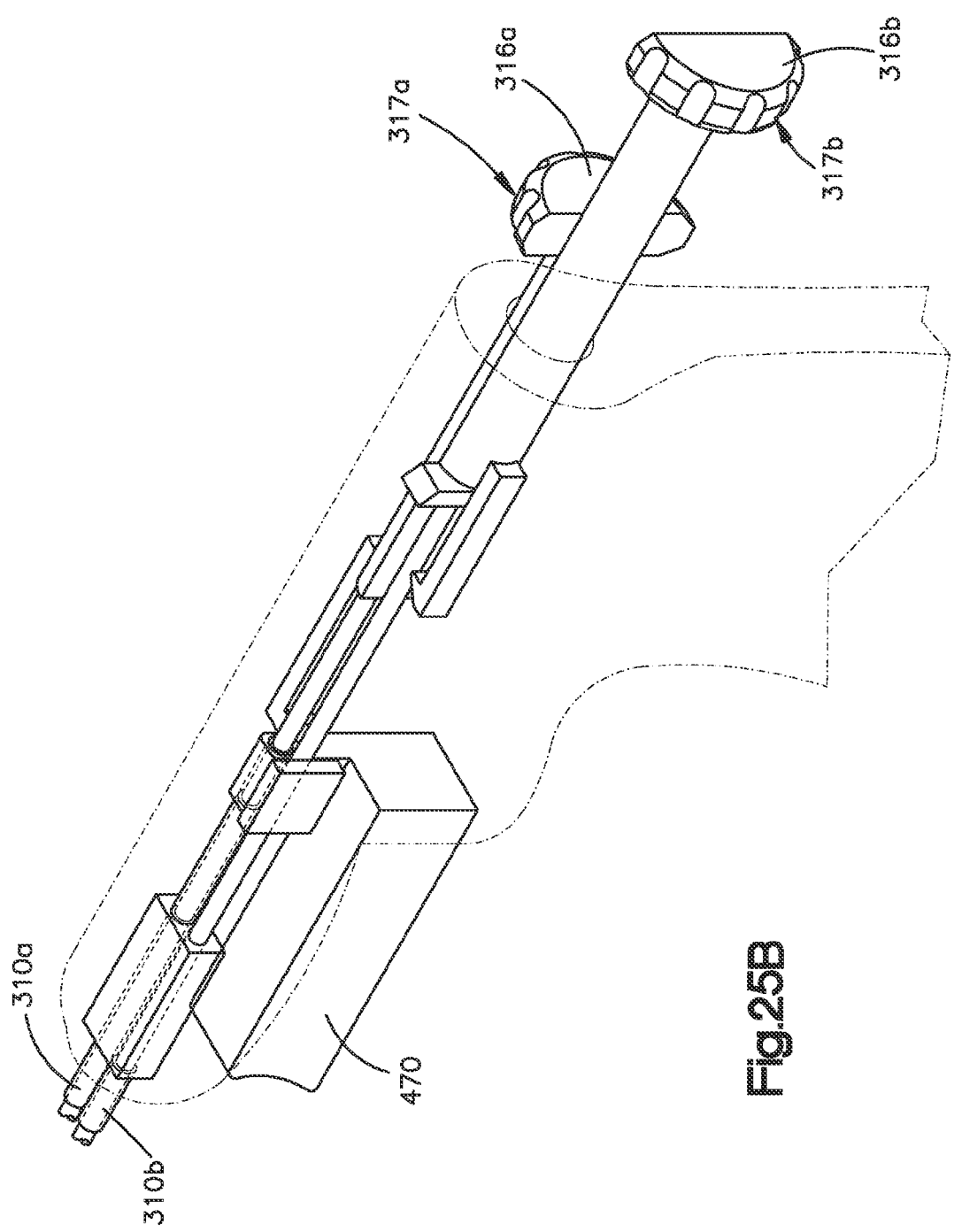

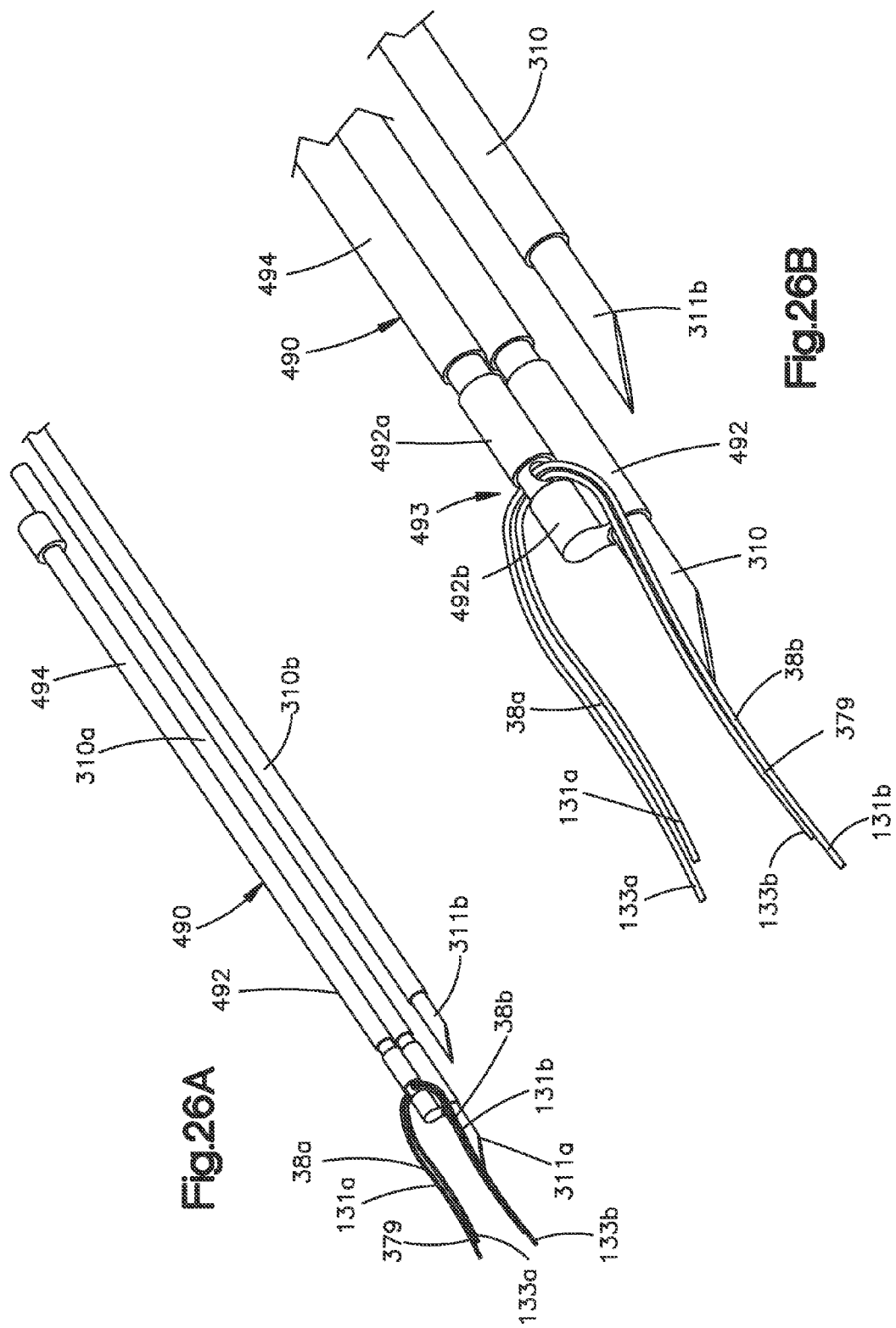

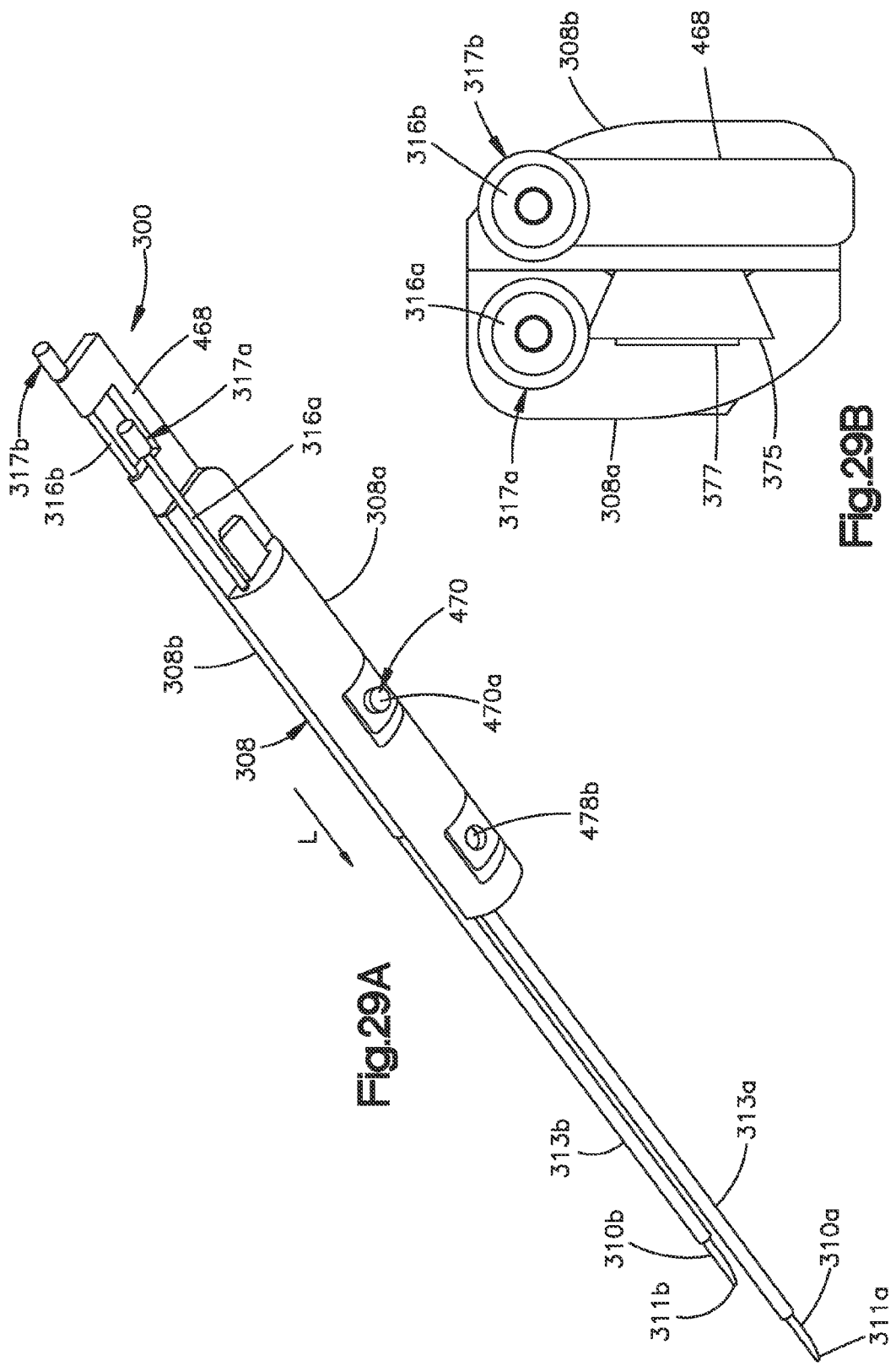

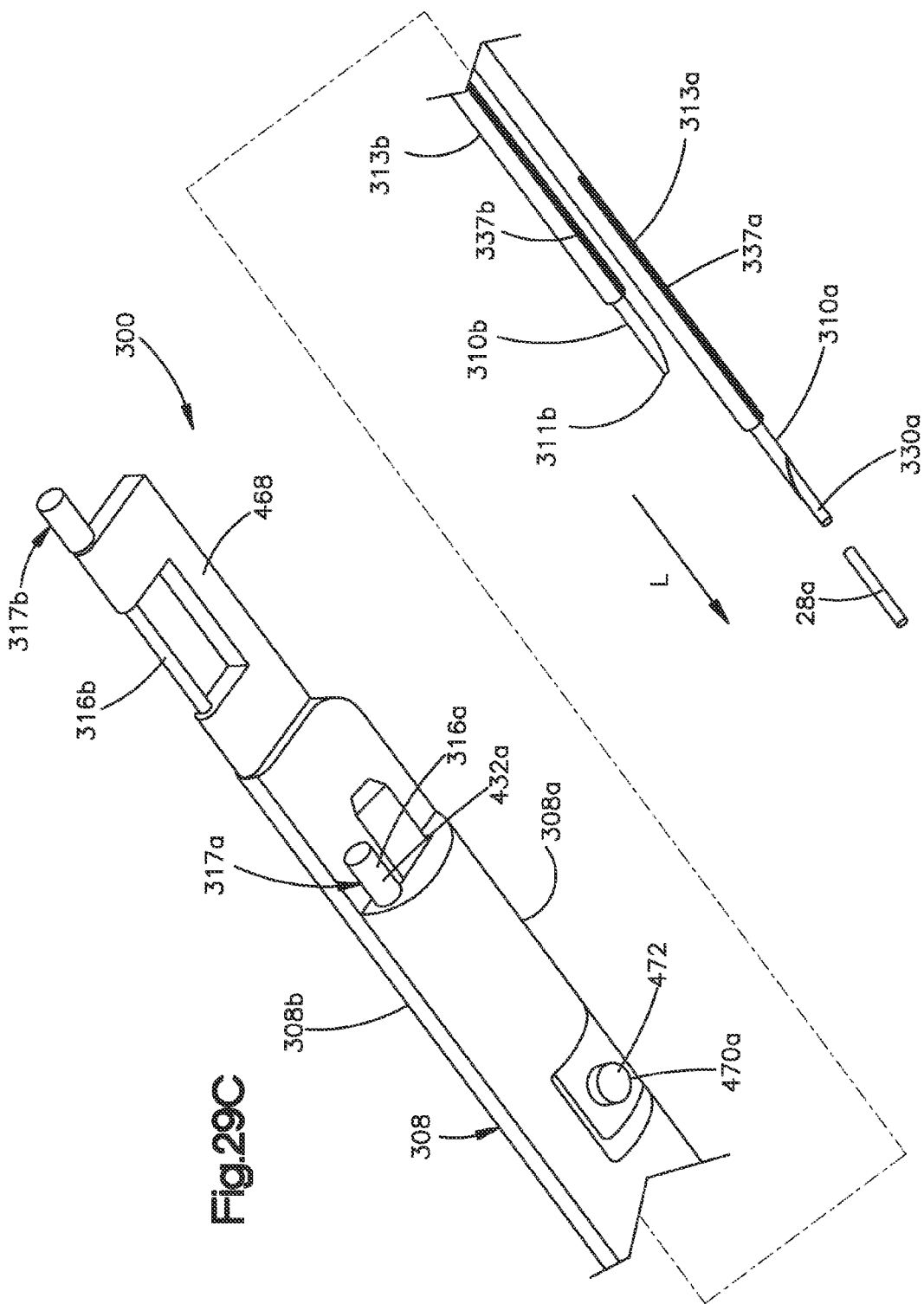

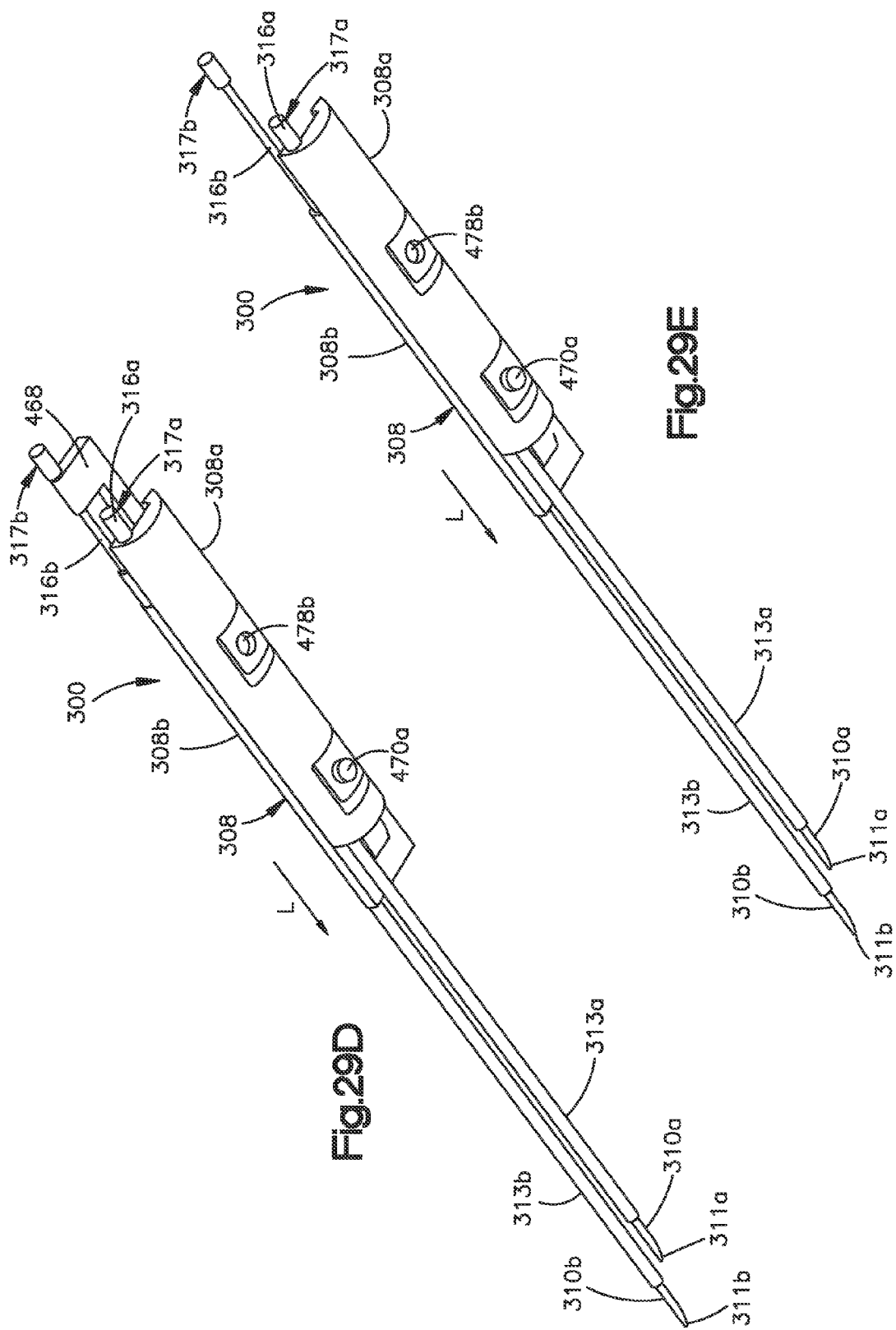

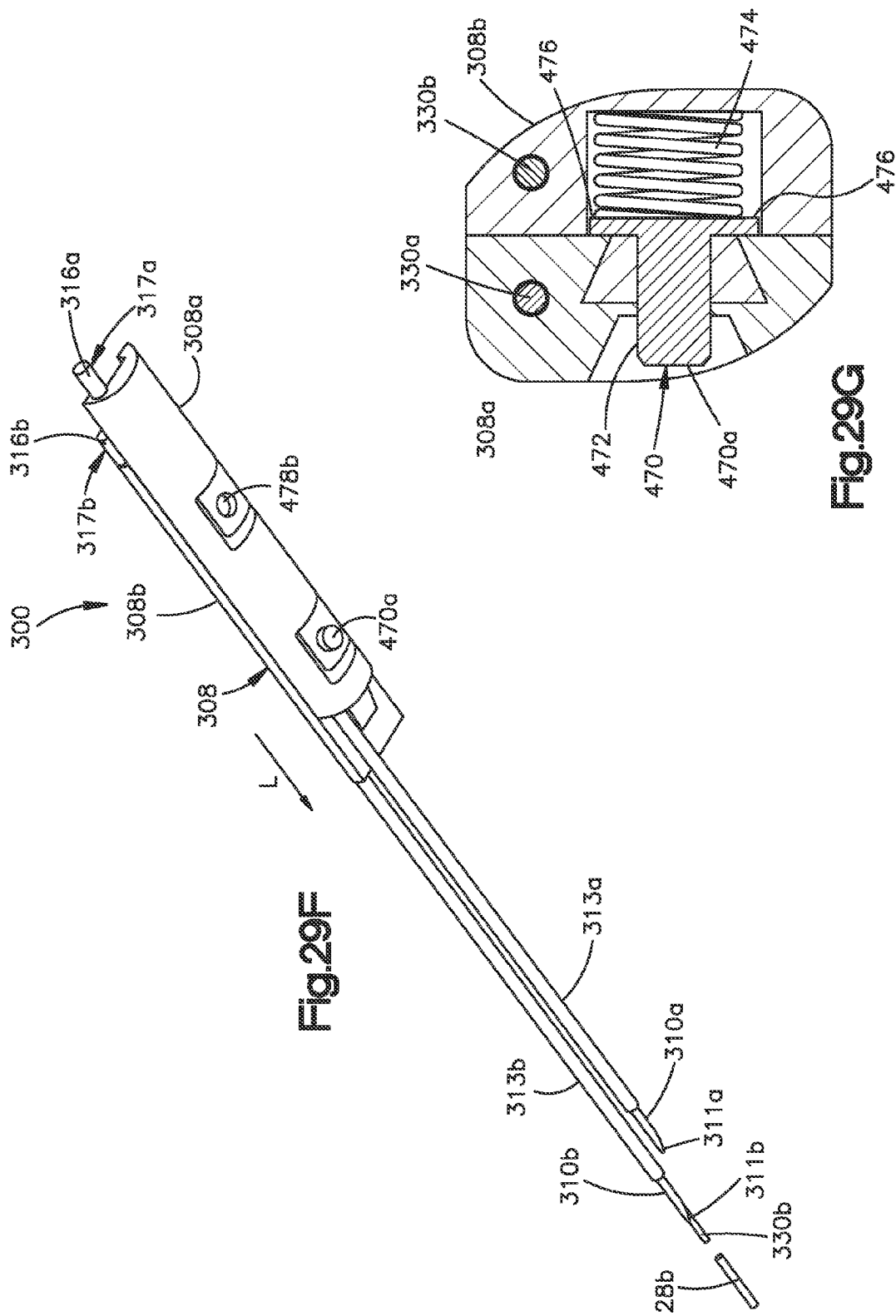

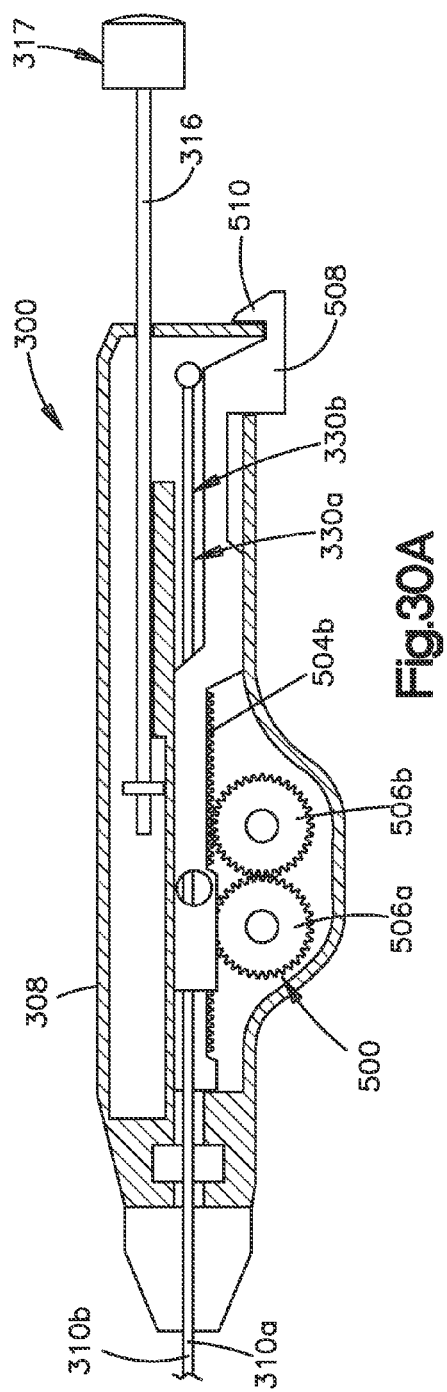
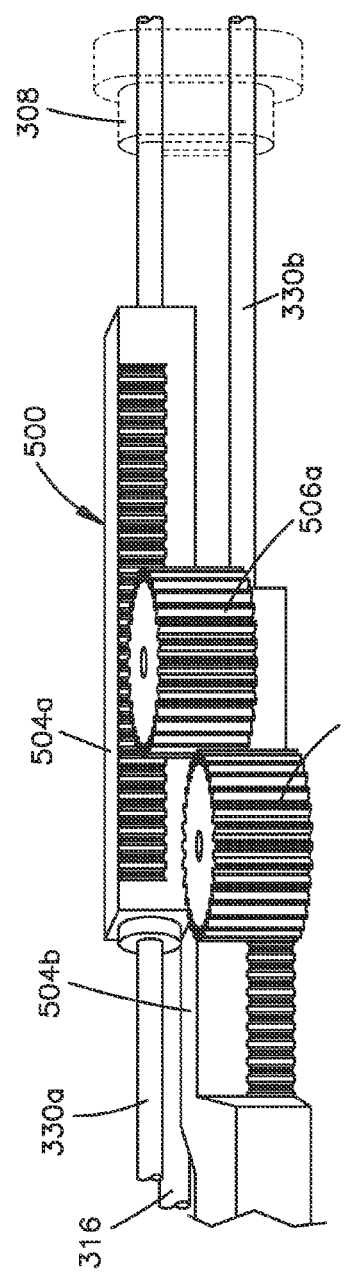
Fig.30A
Fig.30B

INSERTION INSTRUMENT FOR ANCHOR ASSEMBLY

CROSS-REFERENCE TO RELATED APPLICATIONS

This application is a continuation-in-part of U.S. patent application Ser. No. 13/095,192, which claims the benefit of U.S. Patent Application Ser. No. 61/328,251 filed on Apr. 27, 2010 (Overes), the disclose or each of which is hereby incorporated by reference as if set forth in its entirety herein. This application claims the benefit of U.S. Patent Application Ser. No. 61/398,699 filed on Jun. 29, 2010 (Overes, et al.), U.S. Patent Application Ser. No. 61/432,755 filed on Jan. 14, 2011 (Henrichsen, et al.), U.S. Patent Application Ser. No. 61/461,490 filed on Jan. 18, 2011 (Henrichsen, et al.), and U.S. Patent Application Ser. No. 61/443,142 filed on Feb. 15, 2011 (Overes), the disclosure of each of which is hereby incorporated by reference as if set forth in its entirety herein.

BACKGROUND

Orthopaedic surgical procedures often involve the use of a fixation device. Usually an access hole is produced in a bone or soft tissue wherein a suitable fixation device can be fastened. Apart from screws, expandable fixations devices can be used which are inserted into the hole in a collapsed state and transformed into an expanded state once being correctly positioned.

In one example orthopaedic surgical procedure, such as a lumbar microdiscectomy, radiculopathy is treated by surgically removing the herniated nucleus pulposus to achieve neural decompression. The lumbar microdiscectomy is one of the most common spinal surgeries performed today. Many patients find relief with this procedure, but for others, the disc could re-herniate through the opening in the annulus resulting in continuing pain and potentially requiring additional surgery. Currently, the standard microdiscectomy technique does not involve closing the annular defect and presents the surgeon with a dilemma. The surgeon may elect to remove the herniated portion of the nucleus impinging on the nerves, which treats radiculopathy, but may increase the risk of post-operative reherniation of the remaining nucleus through the existing defect of the annulus. Alternately, the surgeon may elect to perform extensive debulking, in which most of the remaining nucleus material is removed in addition to the herniated portion to minimize the risk of post-operative reherniation. However, the risk of post-operative disc height collapse and subsequent progression to lower back pain increases.

Conventional expandable implants include a sleeve with an expandable portion having plurality of fingers or expandable parts formed by intermediate slots or holes in the peripheral wall of the sleeve and a compression element extending through the central bore of the sleeve. The compression element can be coupled to the front end of the sleeve so that upon pulling said compression element towards the rear end of the sleeve said fingers or expandable parts are bent radially outwards so as to transform said expandable portion from its collapsed state to its expanded state.

SUMMARY

In accordance with one embodiment, an insertion instrument is configured to eject at least one anchor at a target location. The anchor includes an anchor body that has a substrate that extends substantially along a direction of elongation. The substrate defines a plurality of openings spaced along the direction of elongation. The anchor further includes an actuation member that is woven through at least two of the openings. The insertion instrument includes a cannula that defines an elongate opening sized to receive the anchor body. The insertion instrument further includes a pusher member insertable into the cannula and configured to be depressed in the elongate opening so as to eject the anchor body from the cannula and into the target location. When a tensile force is applied to the actuation member along a direction substantially along the direction of elongation, the anchor body collapses along the direction of elongation and expands along a second perpendicular with respect to the direction of elongation.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and instrumentalities shown. In the drawings:

FIG. 4A is a sectional elevation view of a fixation kit constructed in accordance with an alternative embodiment, shown in a first rotative state;

FIG. 4B is a sectional side elevation view of the kit illustrated in FIG. 4A, taken along line 4B-4B;

FIG. 4C is a sectional side elevation view of the fixation kit as illustrated in FIG. 4A, but shown in a second rotative state whereby a pair of apertures is aligned;

FIG. 4D-sectional side elevation view of the fixation kit illustrated in FIG. 4C, taken along line 4D-4D;

FIG. 5A is a sectional side elevation view of an insertion instrument during assembly;

FIG. 5B is a sectional side elevation view of the insertion instrument illustrated in FIG. 5A, but shown assembled;

FIG. 5C is a sectional side elevation view of a handle of the insertion instrument illustrated in FIG. 5B;

FIG. 5D is a perspective view of the handle illustrated in FIG. 5C;

FIG. 7A is a perspective view of a fixation kit including an insertion instrument constructed in accordance with an alternative embodiment including a casing and a cannula extending from the casing, the instrument shown in a first configuration with first and second anchor bodies loaded in the insertion instrument;

FIG. 7B is an enlarged perspective view of the cannula of the insertion instrument illustrated in FIG. 7A;

FIG. 7C is a sectional side elevation view of the casing of the insertion instrument illustrated in FIG. 7A;

FIG. 7D is an enlarged sectional side elevation view of the cannula of the insertion instrument illustrated in FIG. 7A;

FIG. 8A is a perspective view of the fixation kit illustrated in FIG. 7A, showing the insertion instrument in the second position so as to eject the second anchor body from the insertion instrument, the second anchor body shown in a first configuration FIG. 8B is an enlarged perspective view of the cannula of the insertion instrument illustrated in FIG. 8A;

FIG. 8C is a sectional side elevation view of the casing illustrated in FIG. 8A;

FIG. 8D is a sectional side elevation view of the cannula illustrated in FIG. 8A;

FIG. 9A is a perspective view of the fixation kit illustrated in FIG. 8A, showing the insertion instrument in an offset position;

FIG. 9B is an enlarged perspective view of the cannula of the insertion instrument illustrated in FIG. 9A FIG. 9C is a sectional side elevation view of the casing of the insertion instrument illustrated in FIG. 9A;

FIG. 9D is a sectional side elevation view of the cannula of the insertion instrument illustrated in FIG. 9A;

FIG. 9E is a perspective view of the fixation kit illustrated in FIG. 9A, showing the second anchor body in an expanded configuration;

FIG. 10A is a perspective view of the fixation kit illustrated in FIG. 9A, showing the insertion instrument in an intermediate position upon completion of an intermediate stroke;

FIG. 10B is an enlarged perspective view of the cannula of the insertion instrument illustrated in FIG. 10A;

FIG. 11A is a perspective view of the fixation kit illustrated in FIG. 10A, showing the insertion instrument upon completion of a first portion of a second stroke after the intermediate stroke;

FIG. 11B is an enlarged perspective view of the cannula of the insertion instrument illustrated in FIG. 11A FIG. 11C is a sectional side elevation view of the casing of the insertion instrument illustrated in FIG. 11A;

FIG. 11D is a sectional side elevation view of the cannula of the insertion instrument illustrated in FIG. 11A;

FIG. 12A perspective view of the fixation kit illustrated in FIG. 11A, showing the insertion instrument in a third position upon completion of a second portion of the second stroke, ejecting a first anchor body from the insertion instrument, the first anchor body shown in a first configuration;

FIG. 12B is an enlarged perspective view of the cannula of the insertion instrument illustrated in FIG. 12A;

FIG. 12C is a sectional side elevation view of the casing of the insertion instrument illustrated in FIG. 12A;

FIG. 12D is a sectional side elevation view of the cannula of the insertion instrument illustrated in FIG. 12A;

FIG. 12E is a perspective view of the fixation kit similar to FIG. 12A, but showing the first anchor body in an expanded configuration;

FIG. 13D is a perspective view of the insertion instrument illustrated in FIG. 10A, with portions removed so as to illustrate the guide system when the insertion instrument is in the intermediate position;

FIG. 13G is a perspective view of a guide track of the guide system illustrated in FIG. 13A;

FIG. 14A is a perspective view of a coupling assembly constructed in accordance with one embodiment, FIG. 14B is a sectional side elevation view of the coupling assembly illustrated in FIG. 14A, shown in a first mode of operation;

FIG. 14C is a sectional side elevation view of the coupling assembly illustrated in FIG. 14B, shown in a transition between the first mode of operation and a second mode of operation;

FIG. 14D is a sectional side elevation view of the coupling assembly illustrated in FIG. 14C, shown in the second mode of operation.

FIG. 15A is a sectional side elevation view of the insertion instrument constructed in accordance with another embodiment, showing a coupling assembly disposed in a first mode of operation;

FIG. 15B is a sectional end elevation view of the coupling assembly illustrated in FIG. 15A, taken along line 15B-15B;

FIG. 15C is a sectional side elevation view of the insertion instrument illustrated in FIG. 15A, but showing the coupling assembly transitioning from the first mode of operation to a second mode of operation;

FIG. 15D is a sectional end elevation view of the coupling assembly illustrated in FIG. 15C, taken along line 15D-15D;

FIG. 15E is a sectional side elevation view of the insertion instrument illustrated in FIG. 15C, but showing the coupling assembly in the second mode of operation;

FIG. 16A is a schematic side elevation view of the anchor assembly as illustrated in FIG. 1G, including a tensioning strand in accordance with an alternative embodiment, showing on of the anchor bodies implanted in the first configuration;

FIG. 16B is a schematic side elevation view of the anchor assembly as illustrated in FIG. 16A, but showing the implanted anchor body in the expanded configuration;

FIG. 16C is a schematic side elevation view of the anchor assembly as illustrated in FIG. 16B, showing the other anchor body implanted in the first configuration;

FIG. 16D is a schematic side elevation view of the anchor assembly as illustrated in FIG. 16C, showing the other anchor body in the expanded configuration;

FIG. 16E is a schematic side elevation view of the anchor assembly as illustrated in FIG. 16D, showing locking of the locking member;

FIG. 16F is a schematic side elevation view of the anchor assembly as illustrated in FIG. 16E, show in a final assembled configuration;

FIG. 18A is a schematic side elevation view of the anchor assembly as illustrated in FIG. 1G, including a pair of tensioning strands in accordance with an alternative embodiment, showing the anchor bodies in the first configuration;

FIG. 18B is a schematic side elevation view of the anchor assembly as illustrated in FIG. 18A, but showing the anchor bodies in the expanded configuration;

FIG. 18C is a schematic side elevation view of the anchor assembly as illustrated in FIG. 18B, showing actuation of a locking member and approximation of an anatomical gap;

FIG. 18D is a schematic side elevation view of the anchor assembly as illustrated in FIG. 18C, showing locking of the locking member;

FIG. 18E is a schematic side elevation view of the anchor assembly as illustrated in FIG. 18D, show in a final assembled configuration;

FIG. 20A is a sectional side elevation view of the insertion instrument including a cutting assembly in accordance with another embodiment, showing the cutting assembly in a disengaged position;

FIG. 20B is a sectional side elevation view of the insertion instrument as illustrated in FIG. 20A, but showing the cutting assembly in an engaged position;

FIG. 21A is a sectional side elevation view of the insertion instrument as illustrated in FIG. 20A, but including a cutting assembly constructed in accordance with another embodiment, shown in a disengaged position;

FIG. 21B is a sectional side elevation view of the insertion instrument as illustrated in FIG. 21A, but showing the cutting assembly in an engaged position;

FIG. 22A is a perspective view of the insertion instrument illustrated in FIG. 7A, but constructed in accordance with an alternative embodiment, shown in the first position;

FIG. 22B is a side elevation view of the insertion instrument as illustrated in FIG. 22A;

FIG. 22C is a side elevation view of the insertion instrument illustrated in FIG. 22B, but shown in a second position;

FIG. 22D is a side elevation view of the insertion instrument illustrated in FIG. 22C, but shown in a third position;

FIG. 23B is a perspective view of a plunger of the insertion instrument illustrated in FIG. 23A;

FIG. 23C is a perspective view of a distal end of the insertion instrument illustrated in FIG. 23A;

FIG. 23D is a perspective view of various components of the insertion instrument illustrated in FIG. 23A, including the plunger illustrated in FIG. 23B, a push rod, and a pair of first coupling members;

FIG. 23E is a perspective view of a second coupling member configured to engage the first coupling members illustrated in FIG. 23D;

FIG. 23F is a perspective view of the insertion instrument illustrated in FIG. 23A, shown in a second position;

FIG. 23G is a perspective view of the insertion instrument illustrated in FIG. 23F, shown in an intermediate position;

FIG. 23H is a perspective view of the insertion instrument illustrated in FIG. 23G, shown in a third position;

FIG. 24C is a perspective view of the insertion instrument illustrated in FIG. 24B, after actuation of the first pusher assembly to a second position;

FIG. 24E is a perspective view of the insertion instrument illustrated in FIG. 24D, after actuation of a swap actuator;

FIG. 25A is a perspective view of components of the insertion instrument illustrated in FIG. 24A, showing each of the first and second pusher assemblies in the first position;

FIG. 25B is a perspective view of the components of the insertion instrument illustrated in FIG. 25A, after the first pusher assembly has been actuated to the second position;

FIG. 26A is a perspective view of a retention assembly constructed in accordance with one embodiment;

FIG. 26B is an enlarged perspective view of a portion of the retention assembly illustrated in FIG. 26A;

FIG. 29A is a perspective view of an insertion instrument constructed in accordance with another embodiment, the insertion instrument including first and second pusher assemblies disposed in a side-by-side relationship, showing each of the pusher assemblies in a first position;

FIG. 29B is an end elevation view of the insertion instrument illustrated in FIG. 29A;

FIG. 29C is a perspective view of the insertion instrument illustrated in FIG. 29A, showing the first pusher assembly in a second position;

FIG. 29D is a perspective view of the insertion instrument illustrated in FIG. 29C, after actuation of a swap actuator from a first position to a second position;

FIG. 29E is a perspective view of the insertion instrument illustrated in FIG. 29D, after removal of a lockout tab from the second pusher assembly;

FIG. 29F is a perspective view of the insertion instrument illustrated in FIG. 29E, showing the second pusher assembly in a second position;

FIG. 29G is a schematic sectional end elevation view of the insertion instrument illustrated in FIG. 29D, showing a portion of the swap actuator;

FIG. 30A is a perspective view of an insertion instrument constructed in accordance with another embodiment, the insertion instrument including first and second reciprocally movable cannulas, the drawing showing a portion of the casing cut away so as to expose internal components of the insertion instrument;

FIG. 30B is a perspective view of a reciprocal motion assembly of the insertion instrument illustrated in FIG. 30A, the reciprocal motion assembly configured to reciprocally drive the first and second cannulas;

FIG. 30C is a perspective view of a drive member of the reciprocal motion assembly illustrated in FIG. 30B;

FIG. 30D is a perspective view of a selective plunger engagement assembly configured to selectively move the plunger between operably communication with the first and second cannulas; and FIG. 31 is a perspective view of an insertion instrument, wherein the cannula defines a side ejection port in accordance with another embodiment.

DETAILED DESCRIPTION

Figure 1A:
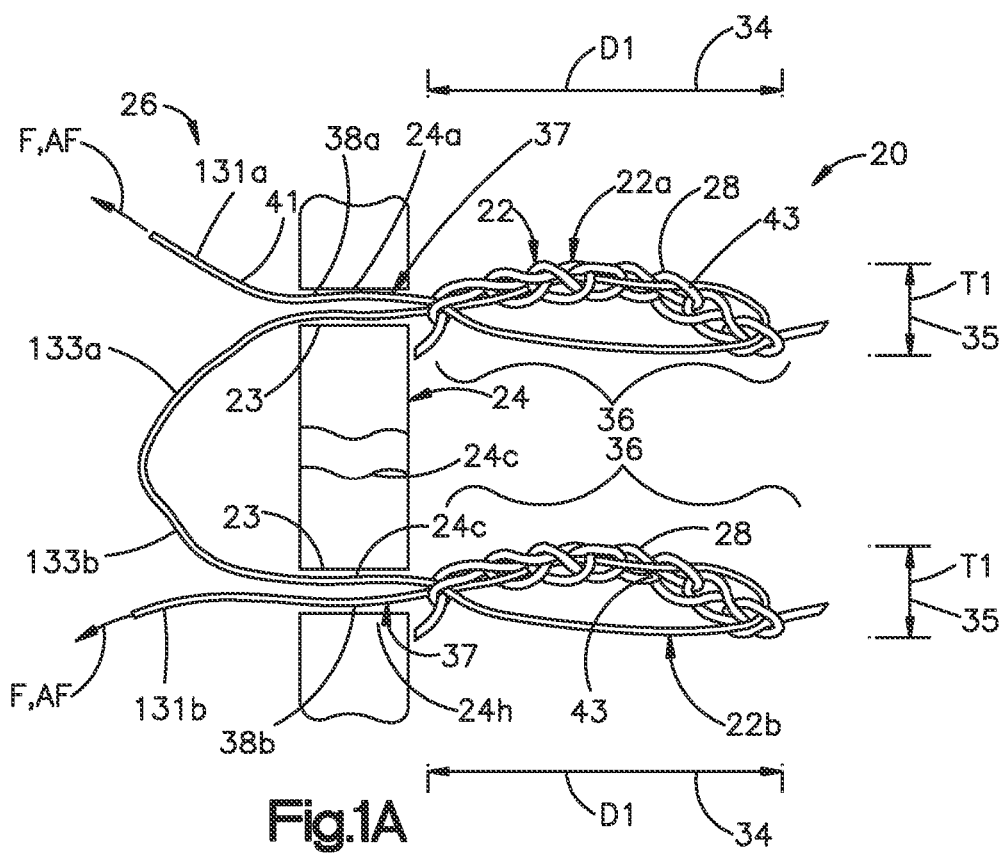
FIG. 1A is a schematic side elevation view of an anchor assembly including a pair of anchor bodies implanted across an anatomical defect and shown in a first configuration.
Figure 1B:
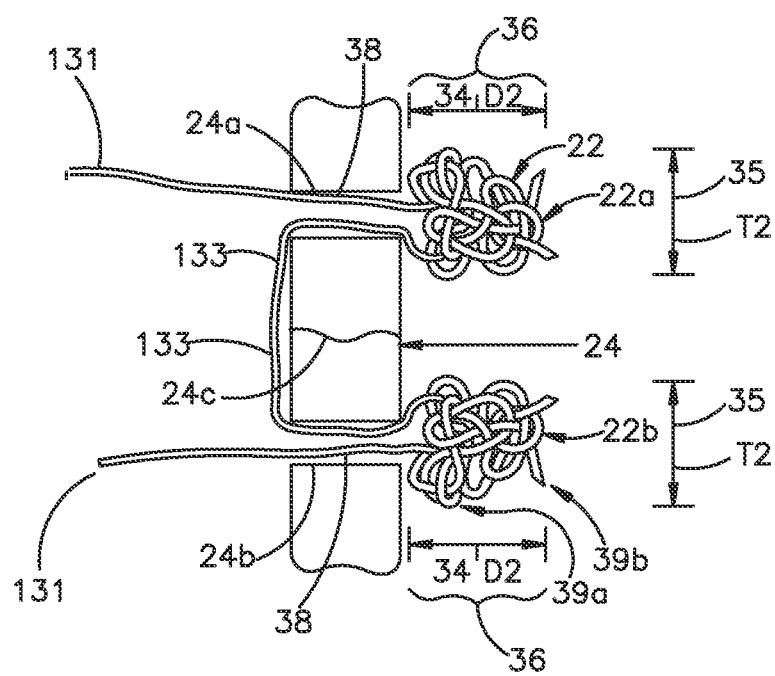
FIG. 1B is a schematic side elevation view of the anchor assembly illustrated in FIG. 1A, showing the anchor bodies in an expanded configuration and in an approximated position.

Referring initially to FIGS. 1A-B, an anchor assembly 20 can include at least one expandable anchor 22 such as a first expandable anchor 22a and a second expandable anchor 22b that, in turn, include respective anchor bodies 28a and 28b that are configured to be secured to an anatomical location, which can be defined by at least one anatomical structure 24. The anatomical structure 24 can be defined by, for instance, anatomy of a human or other animal, or an implant that is secured or configured to be secured to anatomy of a human or other animal. The anatomy can be defined by tissue that can include at least one of bone and soft tissue such as a tendon, a ligament, cartilage, the annulus of an intervertebral disc, or the like.

In accordance with one embodiment, the at least one anatomical structure 24 can define first and second target anatomical locations 24a and 24b on opposite sides of a gap, such as a gap 24c. Thus, the gap 24c can be disposed in an anatomical structure, and can for instance define an anatomical defect, or can be disposed between different anatomical structures. First and second anchors 22a and 22b can be injected or otherwise driven or inserted into the respective first and second target anatomical locations 24a and 24b on opposite sides of the gap 24c, and subsequently drawn toward each other so as to approximate the gap 24c. Alternatively or additionally still, the anchor assembly 20 can be configured to secure an auxiliary structure to the anatomical structure. In this regard, it should be further appreciated that the anchor assembly 20 can include any number of anchors 22 as desired.

Each anchor body 28a and 28b can include a respective expandable portion 36a and 36b, and an actuation member 37a and 37b, such as an actuation strand 38a and 38b, that is configured to actuate the respective expandable portion 36a and 36b, and thus the respective anchor body 28a and 28b, from a first configuration illustrated in FIG. 1A, whereby the anchor body 28a and 28b is initially placed at the target anatomical location, to an expanded configuration illustrated in FIG. 1B, whereby the respective anchor body 28a and 28b can be secured to the anatomical structure 24. Thus, the anchor bodies 28a and 28b of the anchors 22a and 22b can be inserted through an opening 23 at the respective target anatomical locations 24a and 24b that can be created, for example, when delivering the anchor bodies 28a and 28b to the respective target anatomical locations 24a and 24b, for instance by injecting the anchor bodies 28a and 28b to the respective target anatomical locations 24a and 24b.

The expandable portion 36 of the anchor body 28 extends along the direction of elongation 34 so as to define an initial distance D1 as measured from the proximal end 39a to the distal end 39b along the direction of elongation 34 when in the first configuration. The initial distance D1 can be any length as desired, such within a range having a lower end that can be defined by approximately 5 mm, alternatively approximately 10 mm, alternatively still approximately 20 mm, and alternatively still approximately 24.5 mm, and having an upper end that can be defined by approximately 50 mm, alternatively approximately 40 mm, alternatively still approximately 30 mm, and alternatively still approximately 25.5 mm.

Furthermore, when in the first configuration, the expandable portion 36 defines an initial maximum thickness T1 that extends in a second direction 35 that is substantially perpendicular, with respect to the direction of elongation 34. The initial maximum thickness T1 can be sized as desired. As illustrated in FIG. 1B, when the expandable portion 36 in the expanded configuration, the expandable portion 36 is collapsed, for instance compressed or tangled, along the direction of elongation 34 to a second distance D2 as measured from the proximal end 39a to the distal end 39b along the direction of elongation 34. The second distance D2 can be less than the initial distance D1. As the expandable portion 36 collapses along the direction of elongation, for instance as it is actuated from the first configuration to the expanded configuration, the expandable portion 36 expands along the second direction 35 to a second maximum thickness T2 that is greater than the initial maximum thickness T1. The second maximum thickness T2 extends along the second direction 35 which is substantially perpendicular to the direction of elongation 34.

The maximum thicknesses T1 and T2 in the second direction 35 can be defined such the anchor body 28 does not define a thickness in the second direction 35 that is greater than the maximum thicknesses T1 and T2, respectively. It should be appreciated that the proximal and distal ends 39a and 39b can change locations on the expandable portion 36 as the expandable portion 36 actuates to the expanded configuration, for instance due to configuration of the expandable portion 36 when in the expanded configuration. However, when the expandable portion 36 is in the expanded configuration, the proximal and distal ends 39a and 39b continue to define the proximal-most and distal-most ends of the expandable portion 36, such that the distance D2 along the direction of elongation 34 is defined linearly between the proximal and distal ends 39a and 39b of the expandable portion 36 when the expandable portion 36 is in the expanded configuration.

Each of the actuation strands 38 of the first and second anchors 22a and 22b can be attached to each other. For instance, the actuation strand 38 of the first anchor 22a can be integral with the actuation strand 38 of the second anchor 22b. Alternatively, as will be described in more detail below with reference to FIGS. 2A-C, the actuation strand 38 of the first anchor 22a can be separate from the actuation strand 38 of the second anchor 22a, such that the actuation strands 38 of the first and second anchors 22a and 22b are subsequently attached, directly or indirectly, using any suitable connector member 63. The connector member 63 can be integral with either or both of the actuation strands 38a and 38b or can be separately attached to each of the actuation strands 38a and 38b. In accordance with one embodiment, the actuation strands 38a and 38b of each of the first and second anchors 22a and 22b defines at least one respective actuation portion 131a and 131b and can further include at least one respective attachment portion 133a and 133b. The actuation portions 131a and 131b are each configured to receive an actuation force that causes the respective anchor 22a and 22b to actuate from the first configuration to the expanded configuration.

In accordance with the illustrated embodiment, the attachment portions 133a and 133b of the actuation strands 38a and 38b of the first and second anchors are configured to be attached to each other so as to span across the gap 24c and attach the first anchor body 28a to the second anchor body 28b. The attachment portions 133a and 133b can be integral with each other, or attached to each other using any suitable connector member. Furthermore, in accordance with the illustrated embodiment, the actuation portions 131a and 131b can also define attachment portions that are configured to be attached to each other in any suitable manner, either before or after the actuation force F is applied to the actuation portions 131a and 131b. Thus, the attachment portion 133a and 133b of a respective anchor 22a and 22b is configured to attach the respective anchor to another anchor, such as an attachment portion of the other anchor. Furthermore, the actuation portion 131a of the first anchor 22a is configured to attach the respective anchor 22a to the second anchor 22b. In accordance with the illustrated embodiment, the attachment portion 133a of the actuation strand 38a of the first anchor 22a is integral with the attachment portion 133b of the actuation strand 38b of the second anchor 22b, though it should be appreciated that the attachment portions 133a-b of the first and second anchors 22a-b can be separate from each other and attached to each other, as described in more detail below.

With continuing reference to FIGS. 1A-B, once the expandable portions 36a-b of the anchors 22a-b have actuated to the expanded configuration, the actuation strands 38a-b can be placed in tension. For instance, in accordance with one embodiment, an approximation Force AF can be applied to either or both of the actuation portion 131a-b of the actuation strands 38a-b of the first and second anchors 22a-b, thereby inducing a tension in the actuation strands 38a-b of the first and second anchors 22a-b so as to apply a biasing force that draws the first and second anchors 22a and 22b toward each other. Accordingly, if a gap 24c is disposed between the first and second anchors 22a and 22b, movement of the anchors 22a and 22b toward each other in response to the biasing force approximates the gap 24c which, in certain embodiments, can be an anatomical defect, such as a tissue defect as described above.

Furthermore, when the actuation strands 38a-b are maintained in tension after the defect 24 has been approximated, the anchor bodies 28a-b are prevented from backing out from the anatomy through the respective target locations 24a-b, which could allow the gap 24c to open. Thus, once the gap 24c has been approximated, the actuation strand 38a of the first anchor 22a can be attached to the actuation strand 38b of the second anchor 22b so as to maintain tension between the first and second anchors 22a and 22b and prevent the first and second anchors 22a and 22b from separating.

The anchor bodies 28a and 28b can be constructed by weaving any suitable substrate, such as a strand, for instance a strand of suture, in any manner desired so as to produce a plurality of openings 43 that extend through the respective anchor bodies 28a and 28b. The first and second actuation strands 38a and 38b can be woven through at least two of the openings 43 along the direction of elongation 34 of the anchor bodies 28a and 28b.

In accordance with the embodiment illustrated in FIGS. 1A-1F, the first and second actuation strands 38a and 38b are integral with the respective first and second anchor bodies 28a and 28b. In accordance with other embodiments, the first and second actuation strands 38a and 38b are illustrated as separate from and attached to the respective first and second anchor bodies 28a and 28b (see FIG. 2C). In accordance with still other embodiments, one of the first and second actuation strands 38a and 38b is integral with the respective anchor body and the other of the first and second actuation strands 38a and 38b is separate from and attached to the respective anchor body. In accordance with embodiments whereby the first and second actuation strands 38a and 38b are illustrated and described as integral with the respective first and second anchor bodies 28a and 28b, it should be appreciated that the first and second actuation strands 38a and 38b can alternatively be separate from and attached to the respective first and second anchor bodies 28a and 28b, unless otherwise indicated. Furthermore, in accordance with embodiments whereby the first and second actuation strands 38a and 38b are illustrated and described as separate from and attached to the respective first and second anchor bodies 28a and 28b, it should be appreciated that the first and second actuation strands 38a and 38b can alternatively be integral with the respective first and second anchor bodies 28a and 28b, unless otherwise indicated.

Referring to FIGS. 1C-1F, the anchor assembly 20 can include at least one connector member 63 that is configured to join the anchors 22 and allow a biasing force to be applied to at least one of the anchors 22a and 22b that draws the anchors 22a and 22b together, thereby approximating the anatomical defect 24. The connector member 63 can be integral with one or both of the first and second anchors 22a and 22b, for instance integral with one or both of the first and second actuation strands 38a and 38b, can be integral with one or both of the first and second anchor bodies, or can be separate from and attached (directly or indirectly) to one or both of the first and second anchors 22a and 22b. For instance, the connector member 63 can be separate from and attached between the first and second anchors 22a and 22b, as will be described in more detail below. While connector members 63 are described herein in accordance with various embodiments, it should be appreciated that the anchor assembly 20 can alternatively include any suitable connector member configured to attach the first anchor 22a to the second anchor 22b.

Figure 2A:
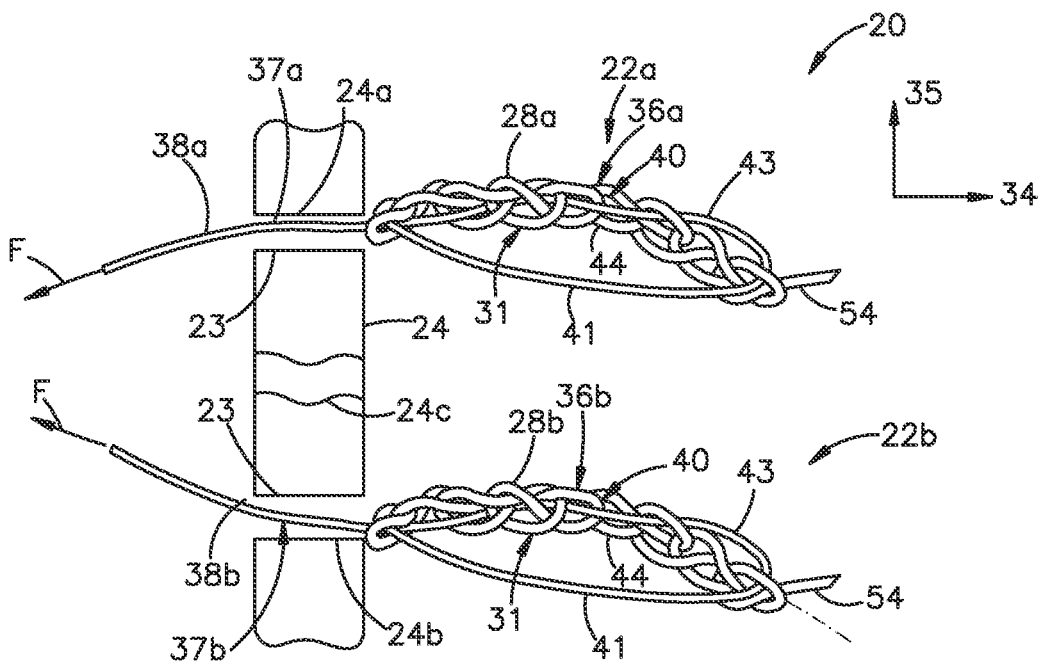
FIG. 2A is a side elevation view of an anchor assembly including first and second anchors implanted in an anatomical structure on opposed sides of an anatomical defect and shown in a first configuration.

The anchor assembly 20 can include a connector member 63 that is integral with the corresponding actuation strands 38a and 38b. As described above, each of the first and second anchor bodies 28a and 28b can be implanted at respective first and target anatomical locations 24a and 24b that are disposed on opposite sides of a gap 24c as illustrated in FIG. 2A. Each of the first and second actuation strands 38a and 38b can receive an actuation force F substantially along the direction of elongation 34 that causes the respective first and second anchor bodies 28a and 28b, and in particular the respective expandable portions 36a and 36b, to actuate from the first configuration to the expanded configuration so as to fix the first and second anchor bodies 28a and 28b at the respective first and second target anatomical locations 24a and 24b. The actuation force F applied to each of the actuation strands 38a and 38b can be in the form of different actuation forces, or can be the same actuation force.

Figure 1C:
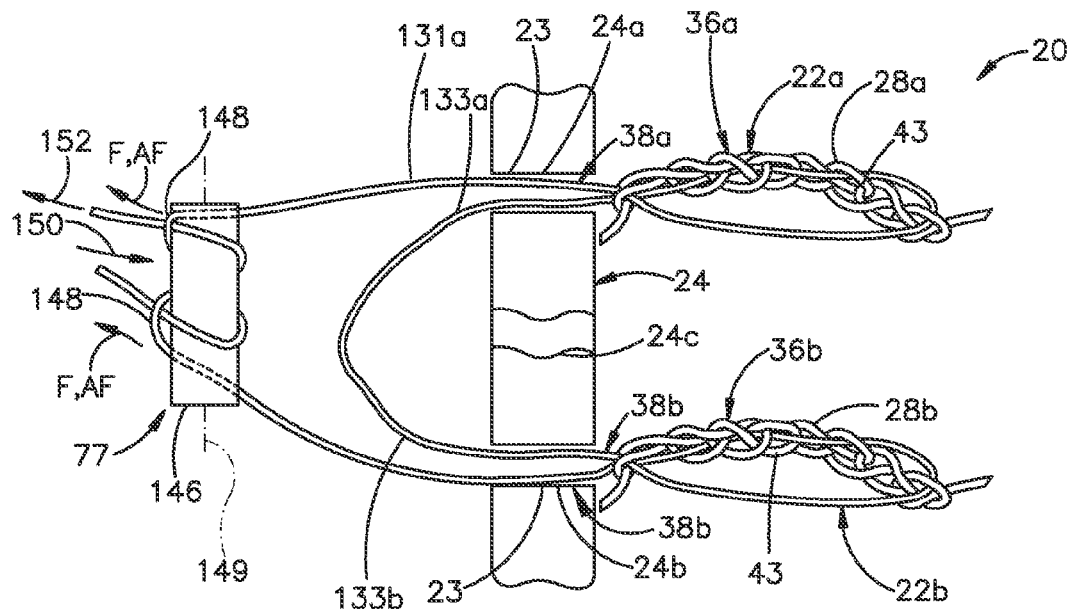
FIG. 1C is a side elevation view of an anchor assembly including the anchor bodies illustrated in FIG. 1A and a connector member configured to attach actuation portions of the anchor bodies, showing the anchor bodies in the first configuration.
Figure 1D:
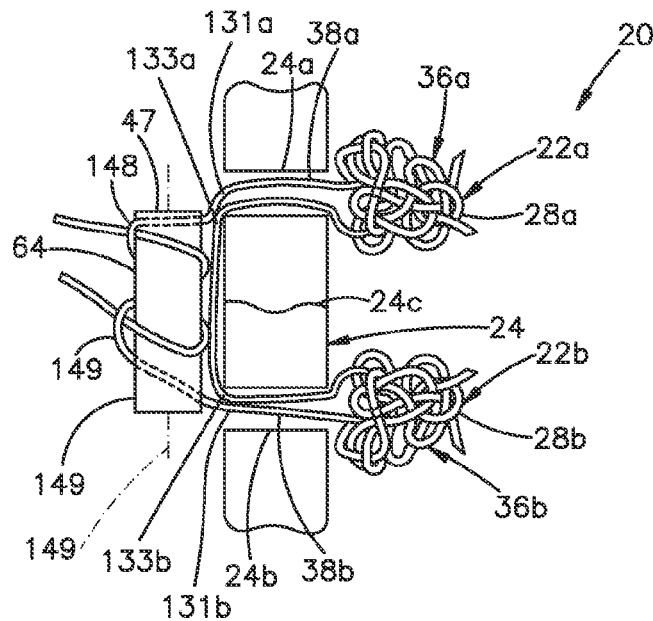
FIG. 1D is a side elevation view of the anchor assembly illustrated in FIG. 1C, showing the connector member tightened with the anchor bodies in the expanded configuration.

For instance, referring to FIGS. 1C-1D, the connector member 63 can be configured as an auxiliary connector member 77, that is a connector member that is separate from one or both of the first and second actuation strands 38a and 38b and configured to attach to the first and second actuation strands 38a and 38b to each other. For instance, the auxiliary connector member 77 can be made from any suitable metal, plastic, or any alternative biocompatible material, and can be configured as a body 146, which can be flexible or rigid, that is configured to attach to either or both of the first actuation strands 38a and 38b, and in particular to the actuation portions 131a-b, at a location between the anchors 22a and 22b. For instance, each of the first and second actuation portions 131a-b can be stitched through the body 146 and tied about the body 146 so as to define a knot 148 that can be actuated from an unlocked configuration to a locked configuration. The first and second actuation portions 131a-b are slidable with respect to the body 146 when the knots 148 are in the unlocked configuration, and fixed with respect to sliding movement relative to the body 146 when the knots 148 are in the locked configuration. The body 146 can define any shape as desired, such as substantially cylindrical, and can be flexible or substantially rigid as desired.

During operation, the actuation portions 131a-b can be stitched through the body 146 along a direction away from the anatomical structure 24 and tied about the body 146 such that the respective knots 148 are in the unlocked configuration. The body 146 can be oriented such that its long axis 149 is oriented substantially parallel to the anatomical structure 24. The body 146 can be translated along the first and second actuation strands 38a and 38b along the direction of Arrow 150 toward the anatomical structure 24 while the actuation strands 38a and 38b are under tension, which causes the actuation strands 38a and 38b to translate relative to the body 146 along an opposite direction indicated by Arrow 152. As the body 146 translates along the actuation strands 38a and 38b toward the gap 24c, the body 146 applies the actuation force F to the actuation strands 38a and 38b, thereby causing the anchors 22a and 22b to actuate from the first configuration to the expanded configuration.

As the body 146 further translates toward the gap 24c after the anchors 22a and 22b have been actuated to their expanded configuration, the body 146 applies the approximation force AF to at least one or both of the actuation strands 38a and 38b that draws at least one or both of the anchors 22a and 22b inward toward the other, thereby approximating the gap 24c. In this regard, it should be appreciated that the approximation force AF can be a continuation of the actuation force F. Alternatively, the actuation force F can be applied to the actuation strands 38a and 38b at a location upstream of the body 146, or prior to attaching the actuation strands 38a and 38b to the body 146. The knot 148 can then be tightened so as to secure the first and second actuation strands 38a and 38b to the body 146, and therefore also to each other so as to prevent separation of the first and second anchors 22a and 22b. Once the gap 24c has been approximated, the body 146, and thus the knots 148, can be disposed along the outer surface of the anatomical structure 24. Alternatively, the body 146 can be sized such that a portion of the body 146, and thus the knots 148, is disposed in the opening 23 that receives the anchor bodies 28a and 28b once the gap 24c has been approximated. Accordingly, the knots 148 can be disposed behind the anatomical structure 24, or can be embedded in the anatomical structure 24.

The body 146 can thus define a sliding member 47 that allows one of the first and second actuation strands 38*a* and 38*b* to slide with respect to the other of the first and second actuation strands 38*a* and 38*b* so as to approximate the gap 24*c*, and can further define a locking member 64 that secures the first and second actuation strands 38*a* and 38*b* to each other, for example with respect with respect to relative movement that would allow the first and second anchor bodies 28*a* and 28*b* to separate.

Figure 1E:
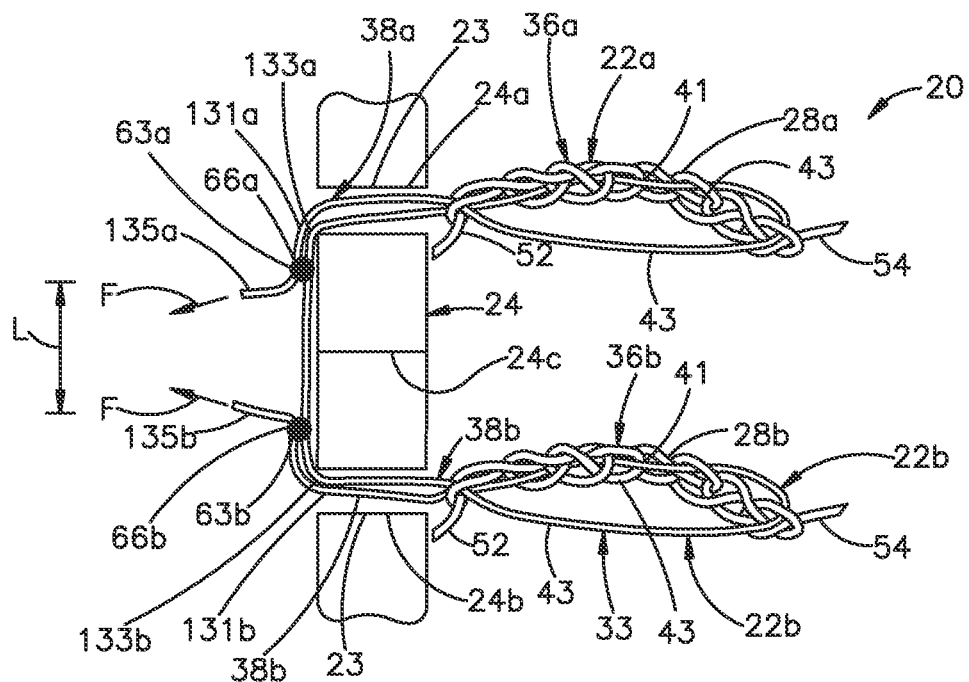
FIG. 1E is a side elevation view of an anchor assembly similar to FIG. 1C, but including an integral connector member.
Figure 1F:
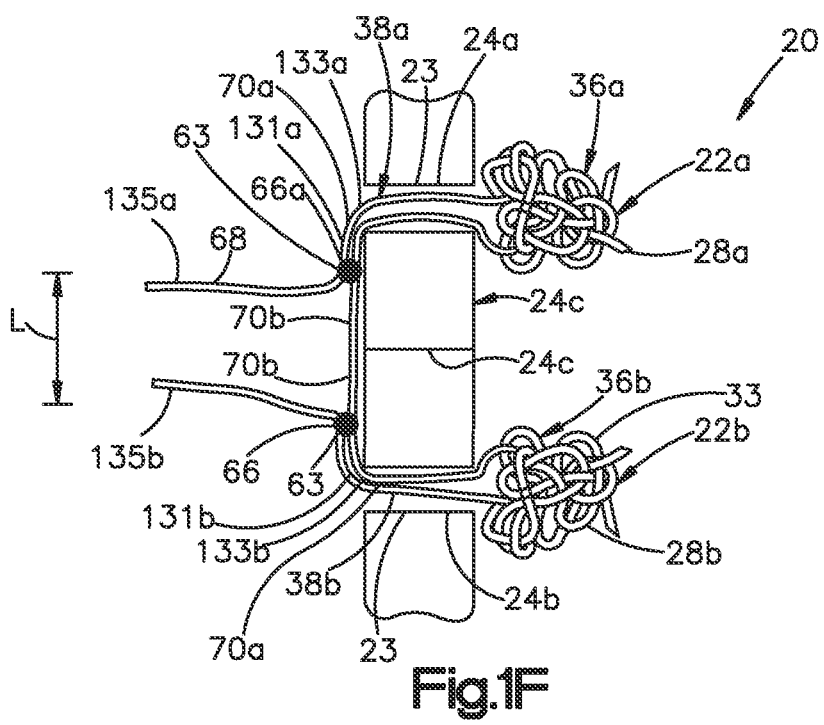
FIG. 1F is a side elevation view of the anchor assembly illustrated in FIG. 1E, showing the connector member tightened with the anchor bodies in the expanded configuration.

Referring now to FIGS. 1E-1F, the anchor assembly 20 can include a pair of connector members 63*a* and 63*b* configured to attach at least one or both of the actuation portions 131*a* and 131*b* to the respective attachment portions 133*a* and 133*b*. In accordance with the illustrated embodiment, the actuation strands 38*a* and 38*b* are defined by a common actuation member, such as a common strand, which can be an auxiliary strand 33 that is separate from, and woven through, at least one such as a pair or a plurality of openings of both the first and second anchor bodies 28*a-b*, such that the respective attachment portions 133*a* and 133*b* are integral with each other. Thus, in accordance with the illustrated embodiment, the first and second actuation strands 38*a* and 38*b* are integral with each other. The anchor assembly 20 can include first and second connector members 63*a* and 63*b* that are defined by the actuation strands 38*a* and 38*b*, and are configured to attach the actuation portions 131*a* and 131*b* to other locations of the common strand, and thus to each other. In accordance with the illustrated embodiment, the first and connector member 63*a* can attach the corresponding first actuation portion 131*a* to another location of the auxiliary strand 33 that is spaced from the first actuation portion 131*a*. Likewise, the second and connector member 63*b* can attach the corresponding second first actuation portion 131*b* to another location of the auxiliary strand 33 that is spaced from the second first actuation portion 131*b*. For instance, in accordance with the illustrated embodiment, the first connector member 63*a* attaches the first actuation portion 131*a* to the first attachment portion 133*a*, and the second connector member 63*b* attaches the second actuation portion 131*b* to the second attachment portion 133*b*.

Thus, it can be said that at least one connector member, such as the first and second connector members 63*a* and 63*b*, can attach the first and second actuation portions 131*a* and 131*b* to respective other locations of the auxiliary strand 33 so as to attach the first and second actuation portions 131*a* and 131*b* to each other, for instance indirectly through at least one or both of the attachment portions 133*a* and 133*b*. It can further be said that the first connector member 63*a* operably attaches one portion of the first actuation strand 38*a* to another location of the actuation strand 38*a*, and the second connector member 63*b* operably attaches one portion of the second actuation strand 38*b* to another location of the second actuation strand 38*b*. Alternatively, it should be appreciated that the first and second connector members 63*a* and 63*b* can attach the respective first and second actuation portions 131*a* and 131*b* to the anchor body 28, such as at respective first and second end portions 52 and 54. While the actuation strands 38*a* and 38*b* are illustrated as separate from each other, the actuation strands 38*a* and 38*b* can alternatively be attached to each other, for instance via any suitable connector member 63 of the type described herein, so as to define an outer connector strand.

In accordance with the illustrated embodiment, each of the first and second connector members 63*a* and 63*b* can be configured as respective knots 66*a* and 66*b* that are defined by the auxiliary strand 33. In accordance with the illustrated embodiment, the first knot 66*a* includes a post end 68, which can be defined by the actuation portion 131*a* of the first actuation strand 38*a*, and a free end, which can include a static portion 70*a* that is defined by a first end 137*a* of the first attachment portion 133*a* and a free portion 70*b* that is defined by a second end 139*a* of the first attachment portion 133*a*. The first end 137*a* can be disposed between the knot 66*a* and the first anchor body 28*a*, and the second end 139*a* can be disposed between the knot 66*a* and the second connector member 63*b*. Alternatively, the free portion 70*b* can be defined by the attachment portion 133*b* of the second actuation strand 38*b*.

In accordance with one embodiment, the second knot 66*a* includes a post end 68, which can be defined by the actuation portion 131*b* of the second actuation strand 38*b*, and a free end, which can include a static portion 70*a* that is defined by a first end 137*b* of the second attachment portion 133*b* and a free portion 70*b* that is defined by a second end 139*b* of the second attachment portion 133*b*. The first end 137*b* can be disposed between the knot 66*b* and the second anchor body 28*b*, and the second end 139*b* can be disposed between the knot 66*b* and the first connector member 63*a*. Alternatively, the free portion 70*b* can be defined by the attachment portion 133*a* of the first actuation strand 38*a*. The attachment portions 133*a* and 133*b* are illustrated as being integral with each other, though it should be appreciated that the attachment portions 133*a* and 133*b* can be separate and attached to each other as desired.

Each of the first and second knots 66*a* and 66*b* can define respective sliding members 47 that allow the respective post ends 68 to translate therethrough relative to the free ends. Thus, the sliding members 47 allow the first and second actuation portions 131*a* and 131*b* to translate relative to the first and second attachment portions 133*a* and 133*b*, for instance in response to the applied actuation force F when the knots 66*a* and 66*b* are in unlocked configurations, thereby actuating the respective anchor body 28*a* and 28*b* from the first configuration to the expanded configuration. Each knot 66 further defines a locking member 64 that can be actuated to a locked configuration so as to secure the at least one or both of the anchors 22*a* and 22*b* in their respective biased positions. For instance, a tensile locking force can be applied to the free portions 70*b* of the free ends of the knots 66*a* and 66*b* so as to prevent the actuation portions 131*a* and 131*b* from translating through the knots 66*a* and 66*b* relative to the attachment portions 133*a* and 133*b*.

The first and second knots 66*a* and 66*b* can be spaced apart a fixed distance L along the auxiliary strand 33, such that the gap 24*c* is maintained approximated when the anchor bodies 22*a* and 22*b* are inserted into the respective target anatomical locations 24*a* and 24*b*. For instance, the gap 24*c* can be approximated prior to injecting the knots 66*a* and 66*b* into the respective target anatomical locations 24*a* and 24*b*. During operation, once the first and second anchors 22*a* and 22*b* are implanted at the respective first and second target anatomical locations 24*a* and 24*b*, the knots 66*a-b* can be in an unlocked configuration such that application of the actuation force F to the respective actuation strands 38*a-b*, for instance the actuation portions 131*a-b*, causes the respective anchor bodies 28*a-b* to actuate from the first configuration to the expanded configuration. Next, a tensile locking force can be applied to the respective attachment portions 133*a-b* against the corresponding knots 66*a-b*, so as to actuate the knots 66*a-b* to their locked configurations and maintain the anchor 22*a-b* in their expanded configurations.

The distance L between the first and second knots 66a and 66b can be substantially equal to or less than the distance between the target anatomical locations 24a and 24b, such that the gap 24c is approximated when the first and second anchors 22a and 22b are expanded behind the anatomy and joined by the auxiliary strand 33, such that tension induced in the actuation strands 38a and 38b maintains the approximation of the gap 24c. While the first and second connector members 63a-b can be configured as respective knots 66, it should be appreciated that either or both of the first and second connector members 63a and 63b can be alternatively configured as any suitable locking member 63 of any type described herein or any suitable alternatively constructed locking member. For instance, at least one or both of the connector members 63a-b can define a splice, whereby the respective actuation strands 38a-b can be spliced through the other of the actuation strands 38a-b or itself, and the connector strand is placed in tension after actuation of the anchors 22a and 22b so as to apply a compressive force that prevents translation of the anchor strands 38a-b.

It should be appreciated that the anchor bodies 28a and 28b can be constructed in accordance with any suitable embodiment as desired. For instance, referring now to FIGS. 1G-1H, each of the anchor bodies 28a and 28b can include an eyelet 90 that extends from a distal end of the respective expandable portions 36a and 36b. The actuation strand 38 can be configured as an auxiliary strand 33 that is separate from the anchor bodies 28. The actuation strand can be woven through the anchor bodies 28a and 28b, and can extend through the respective eyelets 90a and 90b so as to define a path for the eyelets 90a and 90b to travel through the respective anchor bodies 28a and 28b when the anchor bodies 28a and 28b are actuated from the first configuration to the expanded configuration. The auxiliary strand 33 can thus attach the first anchor body 28a to the second anchor body 28b, and can further be configured to receive the actuation force F that cases the anchor bodies 28a and 28b to actuate from the first configuration to the expanded configuration once implanted in the respective target anatomical locations 24a and 24b.

As described above, the anchor assembly 20 can include any suitable connector member 63 that can be configured to attach to the first and second actuation portions 131a and 131b, thereby attaching the first and second actuation strands 38a and 38b to each other, and also attaching the anchors 22a and 22b to each other. The first and second actuation strands 38a and 38b are illustrated as integral with each other, and thus define a common actuation strand. Alternatively, the first and second actuation strands 38a and 38b can be separate from each other and attached to each other in any manner desired.

Figure 1G:
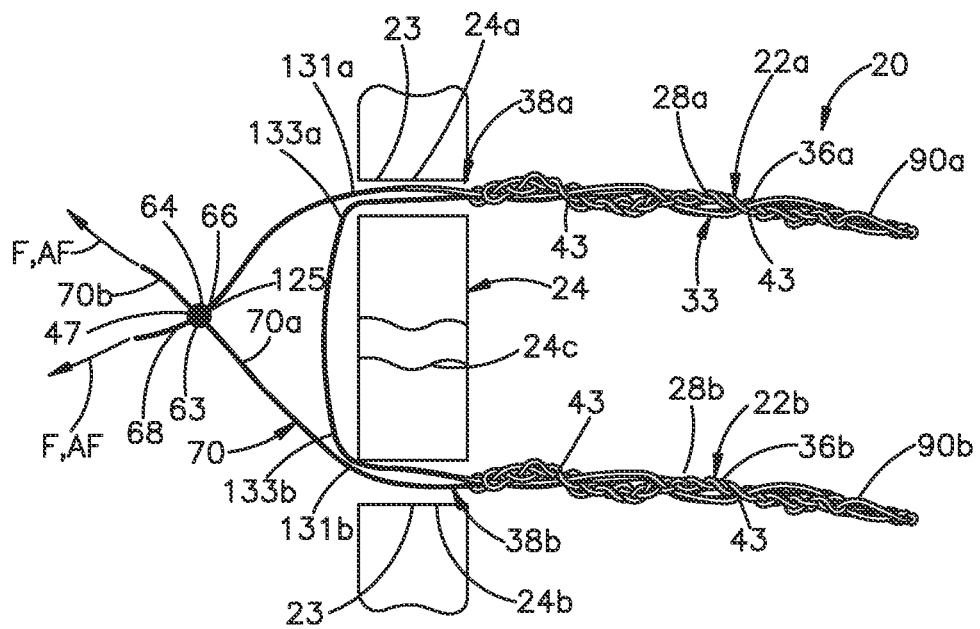
FIG. 1G is a schematic side elevation view of an anchor assembly including a pair of anchor bodies constructed in accordance with an alternative embodiment, shown implanted across an anatomical defect and shown in a first configuration.
Figure 1H:
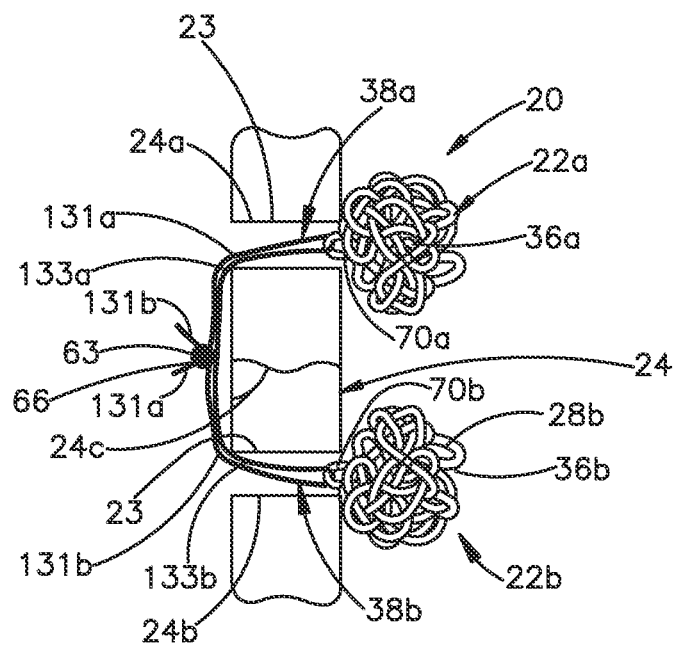
FIG. 1H is a schematic side elevation view of the anchor assembly illustrated in FIG. 1G, showing the anchor bodies in an expanded configuration and in an approximated position.

In accordance with the embodiment illustrated in FIGS. 1G-H, the connector member 63 is defined by and integral with the first and second actuation strands 38a and 38b. Thus, the actuation portions 131a and 131b of the actuation strands 38a and 38b are attached directly to each other. The connector member 63 can define a sliding member 47 and a locking member 64 at a junction 125. For instance, the connector member 63 can define a knot 66 that can be constructed as desired, and can be defined by one or both of the actuation strands 38a and 38b. Thus, at least a portion of the connector member 63 can be integral with at least one or both of the actuation strands 38a and 38b.

One of the first and second actuation strands 38a and 38b can define the post end 68 of the knot 66, and the other of the first and second actuation strands 38a and 38b can define the free end 70 of the knot 66. In accordance with the illustrated embodiment, the first actuation strand, such as the first actuation portion 131a, defines the post end 68 and the second actuation strand 38b, such as the second actuation portion 131b, defines the free end 70.

The first and second actuation strands 38a and 38b can be tied into the knot 66 prior to applying tension to the actuation strands 38a and 38b that biases the first and second anchors 22a and 22b toward each other and approximates the gap 24c. Once the knot 66 is formed, and when the knot 66 is in an unlocked configuration, the actuation force F can be applied to the actuation strands 38a and 38b, and in particular to the actuation portions 131a-b, so as to actuate the respective expandable portions 36 from the first configuration to the expanded configuration. Next, the approximation force AF can be applied to the terminal portion 135a of the first actuation strand 38a, which defines the post strand 68, thereby causing the post end 68 to slide through the knot 66 and draw the respective anchor, such as the first anchor 22a, toward the other anchor, such as the second anchor 22b. Once the gap 24c has been approximated, the free strand 70b of the free end 70, for instance defined by the terminal portion 135b of the second actuation strand 38b, can be placed in tension so as to lock knot 66 and prevent the first actuation strand 38a from translating through the knot 66, thereby fixing the actuation strands 38a and 38b in tension. While the connector member 63 can be configured as the knot 66, it should be appreciated that the connector member 63 can alternatively be configured in accordance with any embodiment described herein or any suitable alternative connector as desired.

Figure 2B:
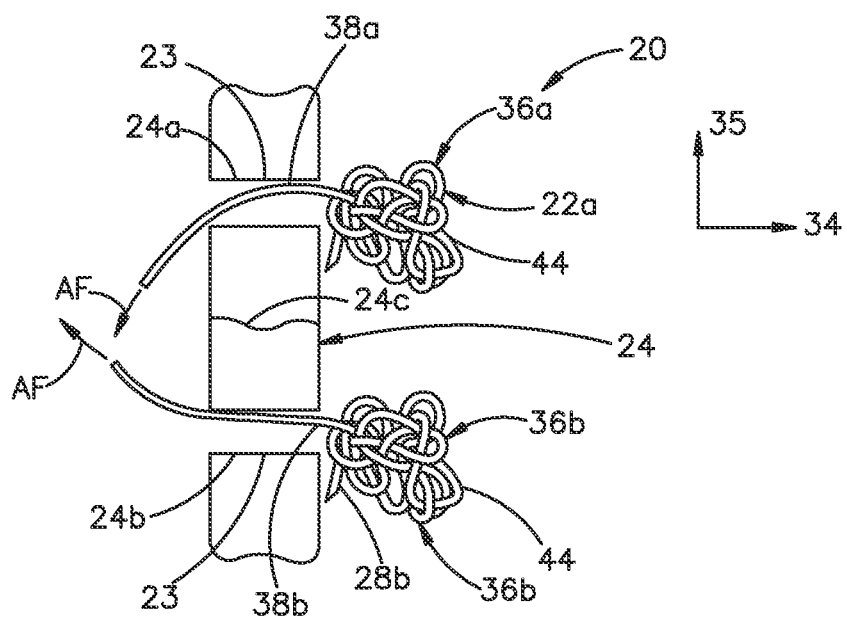
FIG. 2B is a side elevation view of the anchor assembly illustrated in FIG. 2A, showing the first and second anchors in respective expanded configurations.
Figure 2C:
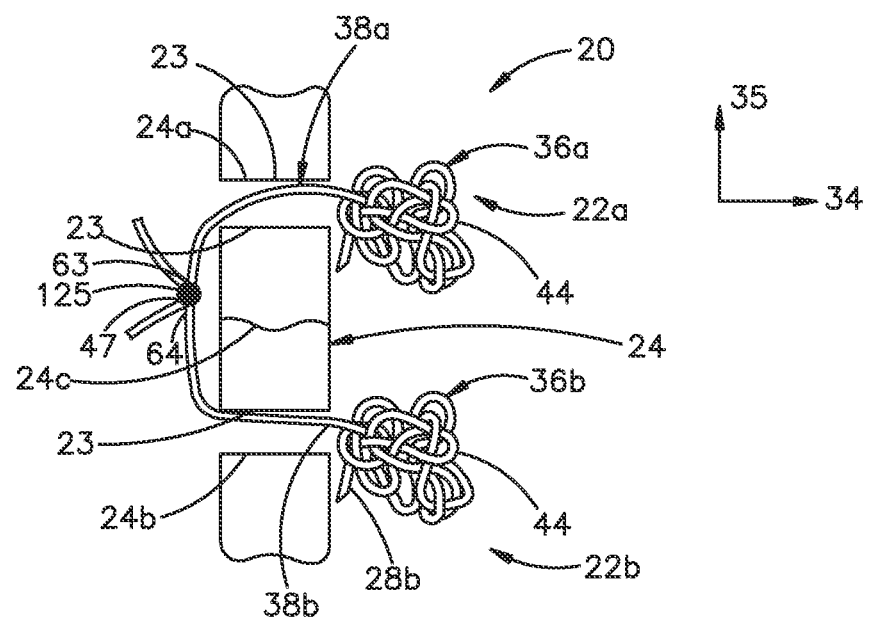
FIG. 2C is a side elevation view of the anchor assembly illustrated in FIG. 2A, including a connector member that attaches the first anchor to the second anchor.

Referring now to FIGS. 2A-C, and as generally described above with respect to FIGS. 1A-B, the anchor assembly 20 can include first and second anchors 22a and 22b. The first anchor 22a includes a first anchor body 28a that extends substantially along the direction of elongation 34 and defines a first plurality of openings 40a that extend through the first anchor body 28a. The first anchor 22a further includes a first actuation strand 38a that extends through at least one of the openings 40a, such as a plurality of the openings, and is configured to receive an actuation force F that causes the first anchor body 28a to actuate from the first configuration to the expanded configuration in the manner described above. The first actuation strand 38a can be separate from and attached to, for instance woven through openings of, the first anchor body 28a, or can be integral with the first anchor body 28a and extend through openings of the first anchor body 28a.

The second anchor 22b includes a second anchor body 28b that extends substantially along the direction of elongation 34 and defines a second plurality of openings 40b that extend through the second anchor body 28b. The second anchor 22b further includes a second actuation strand 38b that extends through at least one of the openings 40b, such as a plurality of the openings, and is configured to receive an actuation force F that causes the second anchor body 28b to actuate from the first configuration to the expanded configuration in the manner described above. The second actuation strand 38b can be separate from and attached to, for instance woven through openings of, the second anchor body 28b, or can be integral with the second anchor body 28b and extend through openings of the second anchor body 28b.

In accordance with the embodiment illustrated in FIGS. 2A-B, the first and second actuation strands 38a and 38b are integral with the respective first and second anchor bodies 28a and 28b. In accordance with other embodiments, the first and second actuation strands 38a and 38b are illustrated as separate from and attached to the respective first and second anchor bodies 28a and 28b. In accordance with still other embodiments, one of the first and second actuation strands 38a and 38b is integral with the respective anchor body and the other of the first and second actuation strands 38a and 38b is separate from and attached to the respective anchor body. In accordance with embodiments whereby the first and second actuation strands 38a and 38b are illustrated and described as integral with the respective first and second anchor bodies 28a and 28b, it should be appreciated that the first and second actuation strands 38a and 38b can alternatively be separate from and attached to the respective first and second anchor bodies 28a and 28b, unless otherwise indicated. Furthermore, in accordance with embodiments whereby the first and second actuation strands 38a and 38b are illustrated and described as separate from and attached to the respective first and second anchor bodies 28a and 28b, it should be appreciated that the first and second actuation strands 38a and 38b can alternatively be integral with the respective first and second anchor bodies 28a and 28b, unless otherwise indicated.

With continuing reference to FIG. 2C, the anchor assembly 20 can include at least one connector member 63 that is configured to join the anchors 22 and allow a biasing force to be applied to at least one of the anchors 22a and 22b that draws the anchors 22a and 22b together, thereby approximating the anatomical defect 24. The connector member 63 can be integral with one or both of the first and second anchors 22a and 22b, for instance integral with one or both of the first and second actuation strands 38a and 38b, can be integral with one or both of the first and second anchor bodies, or can be separate from and attached (directly or indirectly) to one or both of the first and second anchors 22a and 22b. For instance, the connector member 63 can be separate from and attached between the first and second anchors 22a and 22b, as will be described in more detail below. While connector members 63 are described herein in accordance with various embodiments, it should be appreciated that the anchor assembly 20 can alternatively include any suitable connector member configured to attach the first anchor 22a to the second anchor 22b. At least one or both of the actuation strands 38a-b can be configured to receive an approximation force AF that biases at least one of the first and second anchors 22a and 22b toward the other so as to approximate the gap 24c.

The anchor assembly 20 can include a connector member 63 that is integral with the corresponding actuation strands 38a and 38b. As described above, each of the first and second anchor bodies 28a and 28b can be implanted at respective first and target anatomical locations 24a and 24b that are disposed on opposite sides of a gap 24c as illustrated in FIG. 2A. Each of the first and second actuation strands 38a and 38b can receive an actuation force F substantially along the direction of elongation 34 that causes the respective first and second anchor bodies 28a and 28b, and in particular the respective expandable portions 36a and 36b, to actuate from the first configuration to the expanded configuration so as to fix the first and second anchor bodies 28a and 28b at the respective first and second target anatomical locations 24a and 24b. The actuation force F applied to each of the actuation strands 38a and 38b can be in the form of different actuation forces, or, as is described in more detail below, can be the same actuation force.

Referring now to FIG. 2B, once the first and second anchor bodies 28a and 28b are secured to the respective first and second target anatomical locations 24a and 24b, an approximation force AF can be applied to at least one or both of the first and second actuation segments 38a and 38b substantially along a direction toward the other of the respective first and second anchor bodies 28a and 28b, which can also be toward the respective gap 24c. Thus the approximation force AF can have a directional component that is toward the other of the respective first and second anchor bodies 28a and 28b, for instance can be directed purely toward the other of the first and second anchor bodies 28a and 28b. Likewise, the approximation force AF can have a directional component that is directed toward the gap 24c, for instance directed purely toward the gap 24c. Accordingly, the approximation force AF biases at least one or both of the anchor bodies 28a and 28b toward the other of the anchor bodies 28a and 28b to respective biased positions that to approximate the gap 24c.

Referring again to FIG. 2C, the connector member 63 that can define at least one or both of a sliding member 47 and a locking member 64 that attaches the first and second connector actuation strands 38a and 38b together, for instance at a junction 125. Thus, it should be appreciated that the at least one of the sliding member 47 and locking member 64 can likewise attach the first actuation strand 38a to the second actuation strand 38b. In accordance with one embodiment, the connector member 63 can attach the first and second actuation strands 38a and 38b after the first and second actuation strands 38a and 38b have been put under tension so as to maintain the gap 24c in an approximated state. The member 63 can be actuated to the locked configuration so as to prevent or resist separation of the first and second anchors 22a and 22b that would cause the gap 24c to open from the approximated state. Alternatively or additionally, the connector member 63 can attach the first and second actuation strands 38a and 38b to each other prior to applying the approximation force AF to the actuation strands 38a and 38b, and placing the actuation strands 38a and 38b under tension, and therefore prior to approximating the gap 24c.

In accordance with certain embodiments, the connector member 63 is defined by, and integral with, the first and second actuation strands 38a and 38b, and can be configured as a sliding and locking knot that can iterate from an unlocked configuration, whereby one of the actuation strands 38a and 38b to slide relative to the other so as to approximate the gap 24c, and a locked configuration, whereby the actuation strands 38a and 38b are prevented from sliding relative to each other through the knot. The connector member 63 defines the at least one of the sliding member 47 and the locking member 64 at the junction 125. Thus, it can be said that the connector member 63 can directly or indirectly attach the first and second actuation strands 38a and 38b together.

Figure 3A:
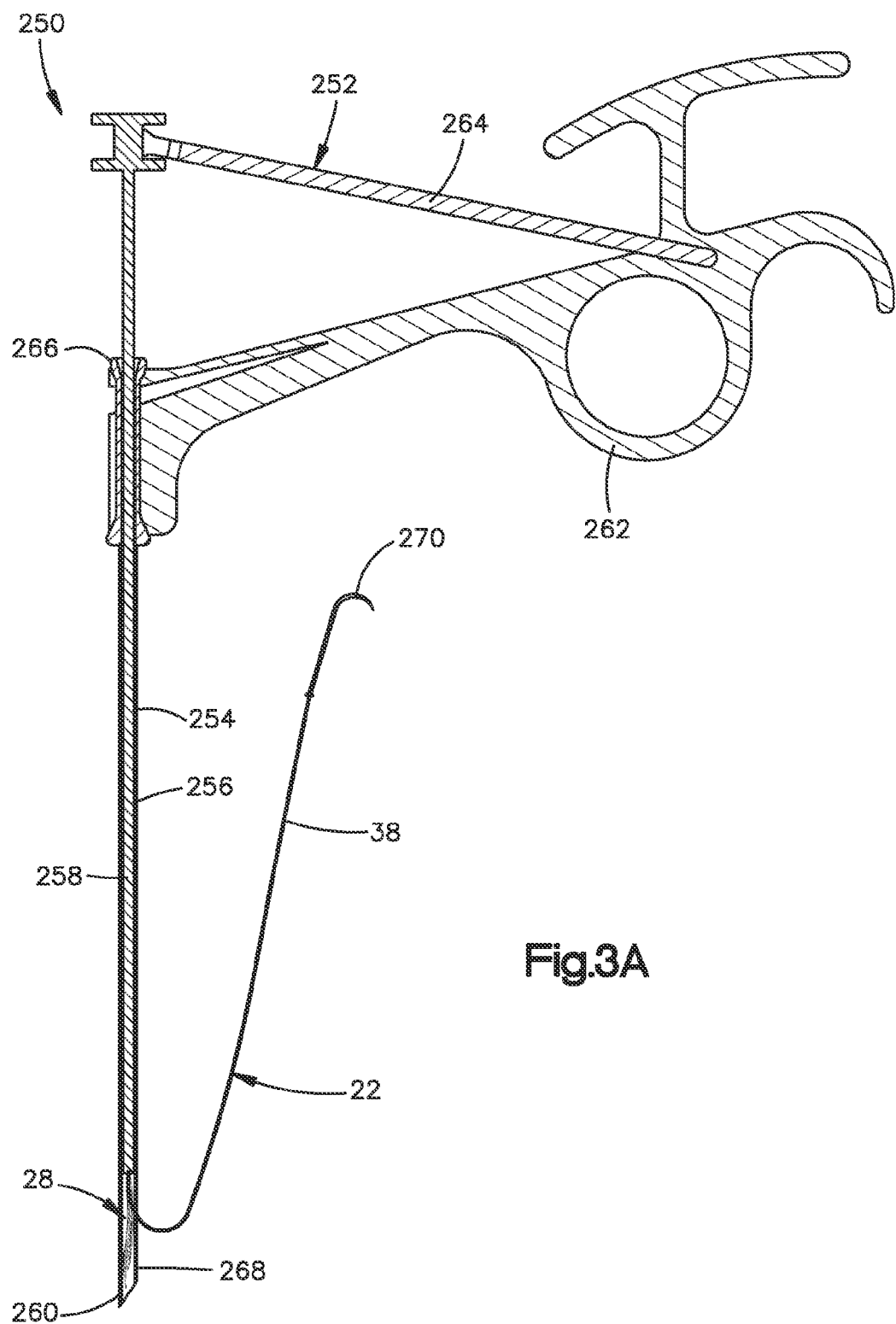
FIG. 3A is a side elevation view of a fixation kit including at least one anchor and an insertion instrument.

Referring now to FIG. 3A, a fixation assembly 250 can include the anchor assembly 20, such as at least one anchor 22, and an insertion instrument 252 configured to inject the anchor 22 in the anatomical structure 24 as illustrated in FIGS. 1A-B. It should be appreciated that the fixation kit 250 can include at least one or more up to all of the anchors 22 described herein alone, attached to each other, or configured to be attached to each other in accordance with any of the embodiments describer herein. The insertion instrument 252 can include a cannula 254 with a central opening 256 and a first pusher member such as a plunger or push rod 258 which is coaxially insertable into the central opening 256. the cannula 254 has an acuminated tip 260 and a slot 268 extending axially from the tip 260. The cannula 254 can extends substantially straight as illustrated, or can be curved or define any suitable shape as desired so as to eject an anchor body 28.

Further, the insertion instrument 252 comprises a handle 262 with an operating lever 264. One end of the handle 262 is detachably attached to the cannula 254 and the operating lever 264 is detachably attached to the plunger 258. The outer diameter of the plunger 258 corresponds to the inner diameter of the central opening 256 of the cannula 254. At the rear end the central opening of the cannula 254 is conically configured in such a manner that it enlarges towards the rear end of the cannula 254 at an inlet 266. Thus, the anchor body 28 of the anchor 22 can be inserted in its first configuration through the conical inlet 266 and into the central opening 256 of the cannula 254, such that the anchor body 28 can be compressed.

When the anchor body 28 is pressed out of the cannula 254 by pressing the plunger 258 forward the anchor body 28 can radially expand, for instance in the second direction 35 (see FIGS. 1A-B) in such a manner that it can be retained by the front face of the cannula 254 when a tensile force is exerted onto the actuation strand 38 in order to tighten the anchor body 28. the actuation strand 38 is led through the slot 268 so that it can be led alongside the cannula 254 when the cannula 254 is inserted into the anatomical structure 24. At the free end of the actuation strand 38 a needle 270 is attached that can be used for finishing a surgical procedure when the anchor body 28 of the anchor 22 has been actuated to the expanded configuration and secured to the anatomical structure 24.

Figure 3B:
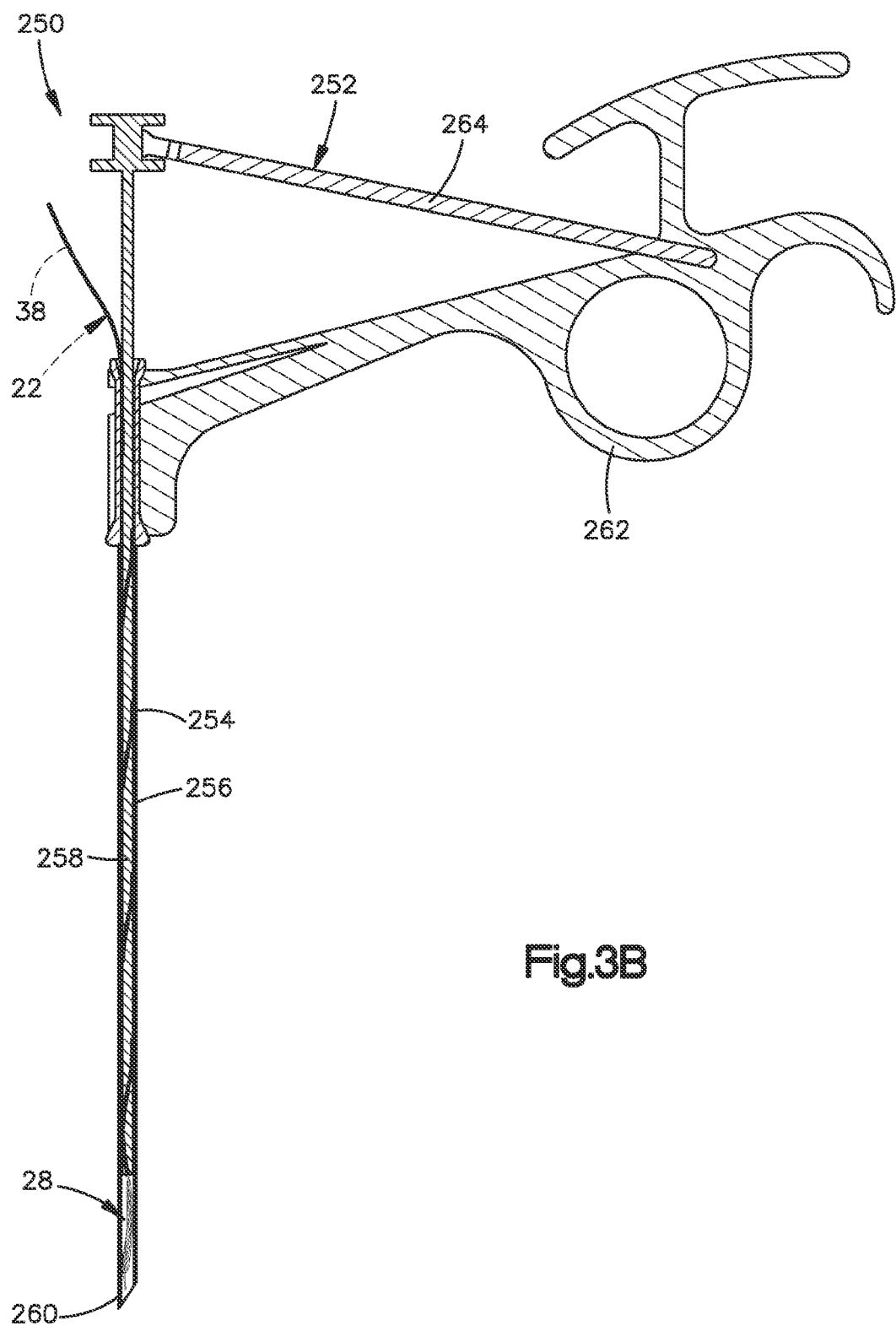
FIG. 3B is a sectional side elevation view of the fixation kit illustrated in FIG. 3A.

Referring to FIG. 3B, the plunger 258 can have an outer diameter or alternative cross-sectional dimension that is less than the inner diameter or cross-sectional dimension of the central opening 256 of the cannula 254. The actuation strand 38 of the anchor 22 can thus be led through the central opening 256 of the cannula 254 when the plunger 258 is inserted in the central opening 256 of the cannula 254. By actuating the operating lever 264 at the handle 262, the plunger 258 can push the anchor 22 forward in the cannula 254 as far as the anchor body 28 exits from the central opening 256 at the tip 260 of the cannula 254. Once the anchor body 28 is positioned in the central opening 256 the actuation strand 38 can be pulled backward at the rear end of the cannula 254 so that the anchor body 28 can be actuated in the cavity 256 to its expanded configuration.

Referring to FIGS. 4A-D, the plunger 258 can define a central bore 272 where the actuation strand 38 of the anchor 22 can be led through. Further, the cannula 254 has a first longitudinal aperture 274 extending between the tip 260 and the rear end of the cannula 254 so that the cannula 254 is slotted over its entire length. A second longitudinal aperture 276 extends on the plunger 258 between the front end and the rear end of the plunger 258 so that the plunger 258 is slotted over its entire length as well. As shown in FIG. 4B when the cannula 254 is in a first rotative position relative to the plunger 258 the first longitudinal aperture 274 of the cannula 254 is diametrically opposite to the second longitudinal aperture 276 of the plunger 258. In the first rotative position of the cannula 254 the actuation strand 38 of the anchor 22 is retained by the central bore 272. Once the anchor body 28 of the anchor 22 has been fixed in a cavity of a patient's body by pulling the actuation strand 38 of the anchor 22 backward the cannula 254 can be rotated into a second rotative position relative to the plunger 258 (FIG. 4D). In this second rotative position of the cannula 254 the first longitudinal aperture 274 of the cannula 254 is aligned with the second longitudinal aperture 276 of the plunger 258 and the insertion instrument 252 can be released from the actuation strand 38 of the anchor 22.

FIGS. 5A-D illustrate the handle 262 and the attachment of the cannula 254 to the handle 262 of an embodiment of the insertion instrument 252 of FIGS. 3A to 4D. The upper end portion of the handle 262 comprises a groove 278 into which the cannula 254 can be inserted and a spring member such as a leaf spring 279 so as to provide a releasable snap lock configured to releasably attach the cannula 254 to the handle 262. The rear end of the plunger 258 can be snapped into a resilient fork 280 arranged at the upper end of the operating lever 264.

Figure 6:
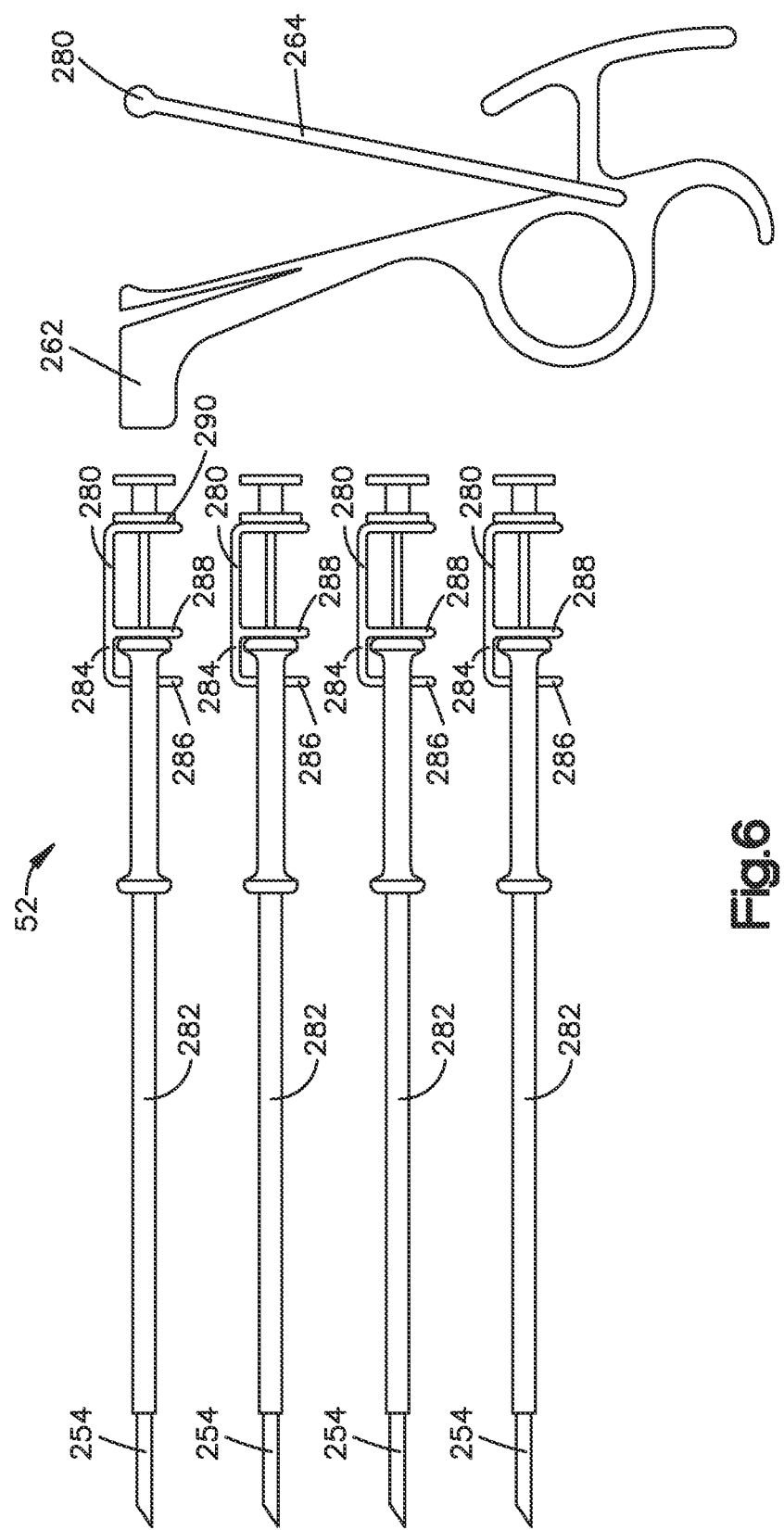
FIG. 6 is a side elevation view of the fixation kit constructed in accordance with another embodiment.
Figure 10C:
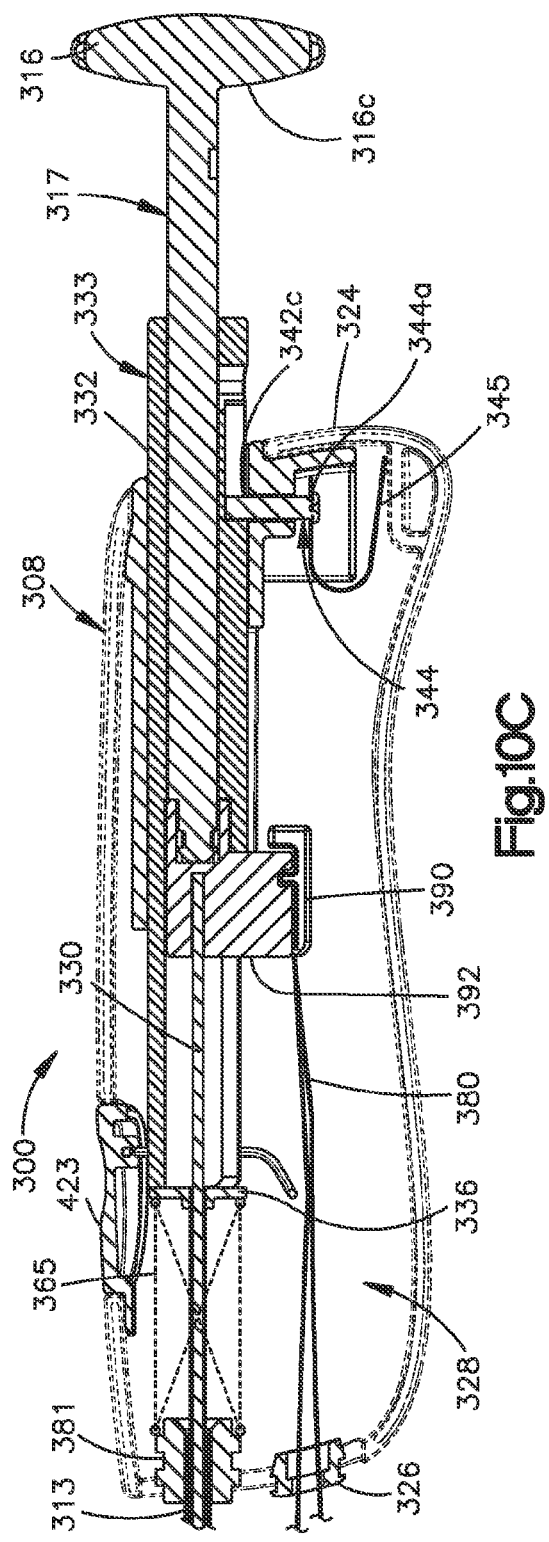
FIG. 10C is a sectional side elevation view of the casing of the insertion instrument illustrated in FIG. 10A.
Figure 10D:
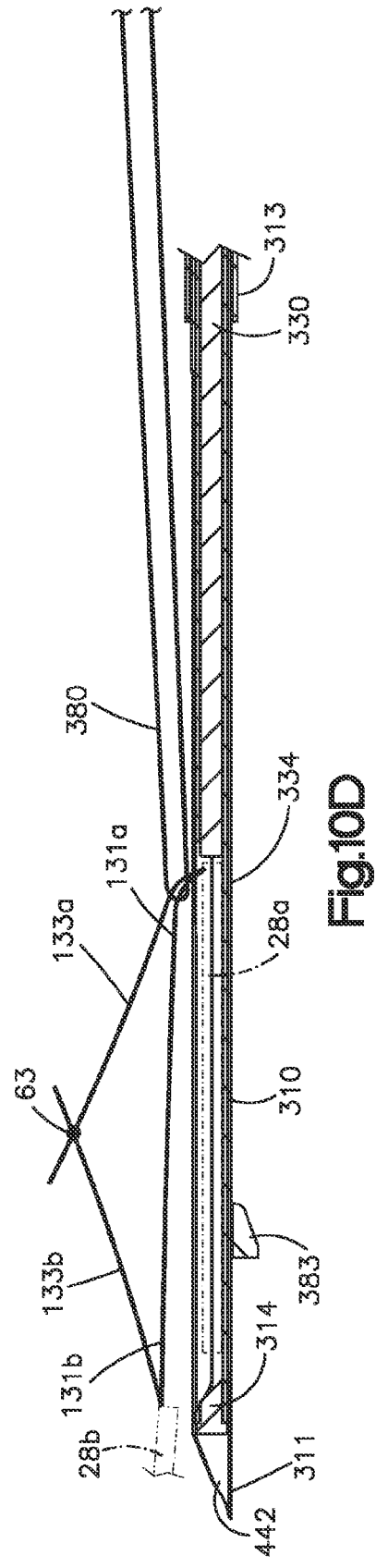
FIG. 10D is a sectional side elevation view of the cannula of the insertion instrument illustrated in FIG. 10A

Referring to FIG. 6, the insertion instrument 52 can include a depth control tube 282 slid over the cannula 254 and a clamping element 284. The insertion instrument 52 is pre-operatively prepared by inserting the anchor 22 into the cannula 254 and inserting the plunger 258. Once the anchor 22 and the plunger 258 have been inserted any one of a plurality of clamping elements 284 is attached to the rear end of the insertion instrument 252 by snapping a first tab 286 onto the rear portion of the cannula 254. To prevent an unintended displacement of the plunger 258 relative to the cannula 254 the clamping element 284 comprises a second tab 288 which abuts the rear end of the cannula 254 and a third tab 290 which abuts an enlarged portion at the rear end of the plunger 258. Before using the insertion instrument 252, the clamping element 284 is removed from the cannula 254 and the handle 262 is attached to the cannula 254, and the insertion instrument 252 can be operated in the manner described herein.

Referring now to FIGS. 1A and 7A-D, an insertion instrument 300 constructed in accordance with an alternative embodiment is configured to deliver at least one anchor knot, such as the first and second anchor knots 22a and 22b, to a respective target location, such as target locations 24a and 24b (FIG. 1A). The insertion instrument 300 is illustrated as elongate along a longitudinal axis 302 that extends substantially along a longitudinal direction L, and defines a proximal end 304 and an opposed distal end 306 that is spaced from the proximal end 304 along the longitudinal axis 302. Thus, it should be appreciated that the terms "distal" and "proximal" and derivatives thereof refer to a spatial orientation closer to the distal end 306 and the proximal end 304, respectively. Furthermore, the directional term "downstream" and "upstream" and derivatives thereof refer to a direction that extends from the proximal end 304 toward the distal end 306, and a direction that extends from the distal end 306 toward the proximal end 304, respectively. The insertion instrument 300 further extends along a lateral direction A that is substantially perpendicular to the longitudinal direction L, and a transverse direction T that is substantially perpendicular to the longitudinal direction L and the lateral direction A. It can also be said that the lateral and transverse directions A and T extend radially with respect to the longitudinal axis 302. Thus, the terms "radially outward" and "radially inward" and derivatives thereof refer to a direction away from and toward the longitudinal axis 302, respectively, and can be used synonymously with laterally and transversely as desired.

The insertion instrument 300 includes a casing 308 that can provide a handle, and a cannula 310 that is supported by the casing 308 and extends distally out from the casing 308 along a central axis 309. The cannula 310 can be fixed to the casing 308 with respect to translation. The central axis 309 can extend longitudinally and can thus be inline with the longitudinal axis 302 of the insertion instrument 300, or can be offset with respect to the longitudinal axis 302 of the insertion instrument 300. The cannula 310 extends substantially straight as illustrated, but can alternatively be curved or define any suitable alternative shape as desired. The cannula 310 defines an elongate opening 312, which can be elongate longitudinally or along any other direction or combination of directions as desired, that is sized to receive the at least one anchor knot, such as the first and second anchor knots 22a and 22b. The insertion instrument 300 can further include a biasing member such as a plug 314 that is disposed in the elongate opening 312, such that the first knot anchor body 28a is disposed in the cannula 310 at a location upstream of the plug 314, and the second knot anchor 28b is disposed in the cannula 310 at a location downstream of the plug 314. Thus, the plug 314 can further provide a divider that separates the first anchor body 28a from the second anchor body 28b along the longitudinal direction. The first and second anchor bodies 28a and 28b are stacked in the instrument 300 along the longitudinal axis 302. The cannula 310 defines a distal tip 311 that is configured to pierce tissue at a target location so as to deliver at least one anchor to the target location.

The insertion instrument 300 further includes a plunger 316 that is supported by the casing 308, and extends proximally out from the casing 308. The plunger 316 is configured to translate distally from an initial or first position illustrated in FIGS. 7A-D along a first stroke to a second position illustrated in FIGS. 8A-D, thereby causing the plug 314 to bias the second anchor 22b distally so as to eject the second anchor 22b out the cannula 310, for instance out a distal ejection port 442 that extends substantially longitudinally through the tip 311.

Figure 12F:
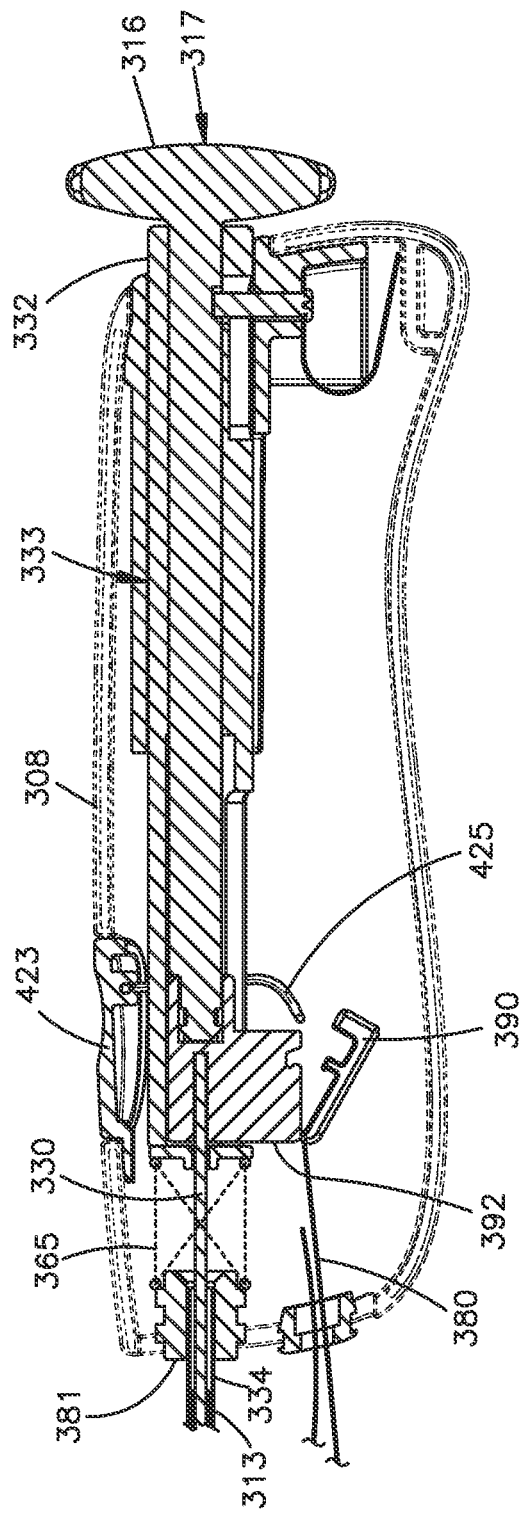
FIG. 12F is a sectional side elevation view of the casing of the insertion instrument illustrated in FIG. 12A, after release of a strand retention mechanism.

Once the second anchor 22b has been ejected out the ejection port 442, the plunger 316 is configured to translate further distally along a first portion of a second stroke illustrated in FIGS. 11A-C, and along a second portion of the second stroke illustrated in FIGS. 12A-C, such that a push rod 330 (see FIG. 7C) biases the first anchor body 28a distally so as to eject the first anchor 22a out the cannula 310, for instance out the ejection port 442, into the first target anatomical location 22a. Alternatively, as described in more detail below, the cannula 310 can define a side ejection port 318 (described below with reference to FIG. 31) that is configured to eject the first and second anchor bodies 28a and 28b out the cannula 310 along a direction angularly offset with respect to the central axis 309.

The insertion instrument 300 can be configured such that the plunger 316 moves distally from the second position to an offset position as illustrated in FIGS. 9A-D before moving along an intermediate stroke from the offset position to an intermediate position as illustrated in FIGS. 10A-D. Accordingly, the plunger 316 can move from the second position, to the offset position, to the intermediate position, and finally to the third position illustrated in FIGS. 12A-D. In accordance with the illustrated embodiment, the plunger 316 is rotated from the second position to the intermediate position prior to translating along the second stroke to the third position. For instance, the plunger 316 can move along a first portion of the second stroke as illustrated in FIGS. 11A-D prior to moving along a second portion of the second stroke as illustrated in FIGS. 12A-D. An actuation force can be applied to the actuation portion 131a and 131b of the first and second anchors 22a and 22b, respectively, after each anchor has been ejected, or can alternatively be applied after both anchors 22a and 22b have been ejected. The anchors 22a and 22b can be attached to each other in any manner as desired, for instance across the gap 24c.

Referring now to FIGS. 7A-C in particular, the casing 308 defines a body 320 that defines at least one radially outer side wall 322, such as a plurality of joined walls that can be of any size and shape, and further defines a proximal wall 324 and an opposed distal wall 326. The at least one outer wall 322, the proximal wall 324, and the distal wall 326 at least partially define an interior 328 that can be in fluid communication with the elongate opening 312 of the cannula 310. The cannula 310 is attached to the distal wall 326 of the casing 308 and is thus fixed to the casing 308. The cannula 310 extends distally from the casing 308 to the tip 311. The tip 311 can be tapered distally, such that the cannula 310 defines a tapered distal end. For instance, the tip 311 can be conical, that is the tip 311 can define a portion that is conical, and can define the shape of a cone or any suitable alternative shape as desired. The insertion instrument 300 can further include a support sleeve 313 that at least partially surrounds the cannula 310 at the interface with the casing 308, and extends distally along a portion of the length of the cannula 310. The support sleeve 313 provides structural support and rigidity to the cannula 310.

The plunger 316 defines a distal end 316a that is disposed in the interior 328, a body portion 316b that extends proximally from the distal end 316a and out the proximal wall 324 of the casing 308, and a proximal end 316c that can define a grip that is disposed outside the casing 308. The insertion instrument 300 further includes a first pusher assembly 317 that can include the plunger 316 and a first pusher member, such as a push rod 330 that is attached, directly or indirectly, to the distal end 316a of the plunger 316. The push rod 330 can be attached to the plunger 316 (for instance integral with the plunger 316 or separately attached to the plunger 316 via any suitable fastener or intermediate apparatus as desired). For instance, in accordance with the illustrated embodiment, the distal end 316a of the plunger is attached to a retention housing 392 as is described in more detail below with reference to FIG. 17. The push rod 330 is attached to the retention housing 392, and is thus attached to the plunger 316. The push rod 330 can extend distally from the plunger 316 into the opening 312 of the cannula 310 and out the distal wall 326 of the casing 308. It should be appreciated that reference to at least one or both of the plunger 316 and the push rod 330 can be applicable to the first pusher assembly 317. For instance, description with respect to the structure that is fixed or coupled to at least one or both of the plunger 316 and the push rod 330 can be said to be fixed or coupled, respectively, to the first pusher assembly 317.

Because the push rod 330 is translatably fixed to the plunger 316, movement of the plunger 316 proximally and distally causes the push rod 330 to likewise move proximally and distally. The push rod 330 defines a distal end 330a disposed in the opening 312 of the cannula 310. Accordingly, the distal end 330a of the push rod 330 is configured to brace against the first anchor 22a when the insertion instrument 300 is in the first position as illustrated in FIGS. 7A-D. The distal end 330a of the push rod 330 is configured to brace against the first anchor 22a when the insertion instrument 300 is in the first position, and also as the plunger 316, and thus the push rod 330, translates distally from the first position to the second position, such that the push rod 330 ejects the first anchor 22a out the insertion instrument 300 and into the respective target location 24a. When a tensile force is applied to the respective actuation member 37a substantially along the direction of elongation of the anchor body 28a after the first anchor body 28a has been ejected and is braced against the anatomical structure 24, the anchor body 28a expands along the second direction 35 that is perpendicular with respect to the direction of elongation 34 of the anchor body 28a (see, for instance, FIGS. 1A-B).

The insertion instrument 300 can further includes a second pusher assembly 333 that includes an attachment member 331, such as a collar 332 that extends about the plunger 316 and can at least partially surround the plunger 316, and a second pusher member, such as a push tube 334 that extends distally from the collar 332 and at least partially surrounds the push rod 330. The push tube 334 can be attached to the collar 332 (for instance integral with the collar 332 or separately attached to the collar 332 via any suitable fastener as desired). Accordingly, description of at least one or both of the push tube and the collar 332 can be applicable to the second pusher assembly 333. For instance, description with respect to the structure that is fixed or coupled to at least one or both of the push tube 334 and the collar 332 can be said to be fixed or coupled, respectively, to the second pusher assembly 333.

The push tube 334 can include the plug 314 that can define the distal end of the push tube 334. The push tube 334 can be cannulated in accordance with the illustrated embodiment so as to define a longitudinally elongate opening 335, and the push rod 330 has an outer diameter that is less than that of the opening 335, such that the push rod 330 is disposed inside the elongate opening 335 of the push tube 334. It should be appreciated that structures described herein as defining a diameter can alternatively define any suitably configured cross section, which can be circular or alternatively shaped, and thus can define any cross-sectional dimension which can be a diameter or not. The cannula 310 can contain both the first and second anchor bodies 28a and 28b. For instance, the push tube 334 can contain the first anchor body 28a at a location upstream of the plug 314, and the cannula 310 can contain the second anchor body 28b at a location distal to the plug 314, and thus distal to the first anchor body 28a.

The insertion instrument 300 can include a force transfer member 336 that can extend radially inward from the distal end of the collar 332, such that the push rod 330 extends distally through or from force transfer member 336. The force transfer member 336 can abut the collar 332, or can be fixed to the distal end of the collar 332. The force transfer member 336 can further abut or be fixed to the proximal end of the push tube 334. If the force transfer member 336 abuts one or both of the collar 332 and the push tube 334, then 1) distal movement of the collar 332 biases the force transfer member 336 distally, which in turn biases the push tube 334, including the plug 314, distally, and 2) proximal movement of the collar 332 does not bias the push tube 334 proximally. If the force transfer member 336 is attached to the collar 332 and the push tube 334, then 1) distal movement of the collar 332 biases the force transfer member 336 distally, which in turn biases the push tube 334, including the plug 314, distally, and 2) proximal movement of the collar 332 biases the force transfer member 336 distally, which in turn biases the push tube 334, including the plug 314, distally. Whether the force transfer member 336 abuts or is fixed to the collar 332 and the push tube 334, it can be said that the collar 332 is translatably coupled to the push tube 334, such that distal translation of the collar 332 causes the push tube 334 to translate distally.

The collar 332, and thus the push tube 334, including the plug 314, is configured to be selectively coupled to and decoupled from the first pusher assembly 317 with respect to translation, and configured to be selectively coupled to and decoupled from the casing 308 with respect to translation.

For instance, in a first configuration, the collar 332 is translatably fixed to the plunger 316, and thus also to the push rod 330. Furthermore, in the first configuration, the collar 332 is translatably decoupled from the casing 308 and thus also translatably decoupled from the cannula 310. Accordingly, in the first configuration, proximal and distal movement of the plunger 316 and push rod 330 relative to the casing 308 and cannula 310 causes the collar 332 to correspondingly move proximally and distally relative to the casing 308 and cannula 310. It should be appreciated that in the first configuration, the push rod 330 is translatably coupled to the push tube 334, such that the push rod 330 and the push tube 334 translate in tandem, for instance during the first stroke, thereby causing the push tube 334 to eject the second anchor body 28b out the cannula 310, as will be described in more detail below. As described above, when a tensile force is applied to the respective actuation member 37b substantially along the direction of elongation of the second anchor body 28b after the second anchor body 28b has been ejected, the second anchor body 28b expands along the second direction 35 that is perpendicular with respect to the direction of elongation 34 of the anchor body 28b (see, for instance, FIGS. 1A-B).

In a second configuration, the collar 332 is translatably decoupled from the plunger 316, and thus the push rod 330, and is translatably coupled to the casing 308, and thus the cannula 310. Accordingly, in the second configuration, the plunger 316 and push rod 330 move proximally and distally relative to the collar 332 and the casing 308 and the cannula 310. It should be appreciated that in the second configuration, after the first stroke, the push rod 330 is translatably decoupled from the push tube 334, such that the push rod 330 translates distally relative to the push tube 334 and thus the plug 314, for instance during at least a portion of the second stroke, thereby causing the push rod 330 to eject the first anchor body 28a out the cannula 310, as will be described in more detail below.

Referring now to FIGS. 13A-G, the insertion instrument 300 includes a guide system 329 that operably couples the casing 308 and the push tube 334 so as to guide relative movement between the casing 308 and the push rod 330. In accordance with the illustrated embodiment, the guide system 329 includes complementary first and second guide members 338 and 340, respectively, that are coupled between the casing 308 and the collar 332. In accordance with the illustrated embodiment, during the first stroke and a first portion of the second stroke, the first and second guide members 338 and 340 cooperate to guide the movement of the plunger 316 (and push rod 330) and collar 332 (and push tube 334) in tandem relative to the casing 308. In that regard, it should be appreciated that the first and second guide members 338 and 340 are operably coupled between the plunger 316 and the collar 332 during the first stroke and a first portion of the second stroke. In accordance with the illustrated embodiment, during a second portion of the second stroke, the first and second guide members 338 and 340 cooperate to guide the movement of the plunger 316 and push rod 330 relative to both the collar 332 (and push tube 334) and the casing 308. In that regard, it should be appreciated that the first and second guide members 338 and 340 are operably coupled between the casing 308 and the collar 332 during the second portion of the second stroke.

In accordance with the illustrated embodiment, one of the first and second guide members 338 and 340 is provided as a guide track 342 that extends into one of the collar 332 and the casing 308, and the other of the guide members 338 and 340 is provided as a guide pin 344 that extends into the guide track 342, such that the guide pin 344 rides in the guide track 342, thereby operably coupling the collar 332 to the casing 308. In accordance with the illustrated embodiment, the first guide member 338 is provided as the guide track 342 that is carried, and defined, by the collar 332, and the second guide member 340 is provided as the guide pin 344 that is translatably fixed to the casing 308 and extends into the guide track 342. For instance, the guide pin 344 extends radially into or through the side wall 322 of the casing 308 and into the guide track 342. It should be appreciated in accordance with an alternative embodiment that the guide track 342 can be carried, and defined, by the casing 308 and the guide pin 344 can be translatably fixed to the collar 332.

In accordance with the embodiment illustrated in FIG. 13G, the track 342 defines a slot 339 that extends radially into the collar 332 but not through the collar 332, and a base 341 of the collar 332 that is located at the radially inner end of the slot 339. The guide track 342 defines a first guide portion such as a first track portion 342a, a second guide portion such as a second track portion 342b that is offset, for instance radially, with respect to the first track portion 342a, and an angled intermediate guide portion such as an angled intermediate track portion 342c that connects the first track portion 342a to the second track portion 342a. Accordingly, the guide pin 344 is configured to travel along the first track portion 342a during the first stroke as the plunger 316 is translated from the first position to the second position. In particular, the second track portion 342a defines a first or distal end 342a' an opposed second or proximal end 342a", and an offset position 342a''' between the distal end 342a and the proximal end 342a". The offset position 342a''' is aligned with an intermediate track portion 342c that extends between the first track portion 342a and the second track portion 342b. Once the guide pin 344 has translated from the proximal end 342a" to the offset position 342a''', the guide pin 344 can travel along the intermediate track portion 342c toward the second track portion 342b as the plunger 316 is rotated to the intermediate position. The guide pin 344 can subsequently travel distally along the second track portion 342b as the plunger 316 is further translated toward the third position.

Figure 13A:
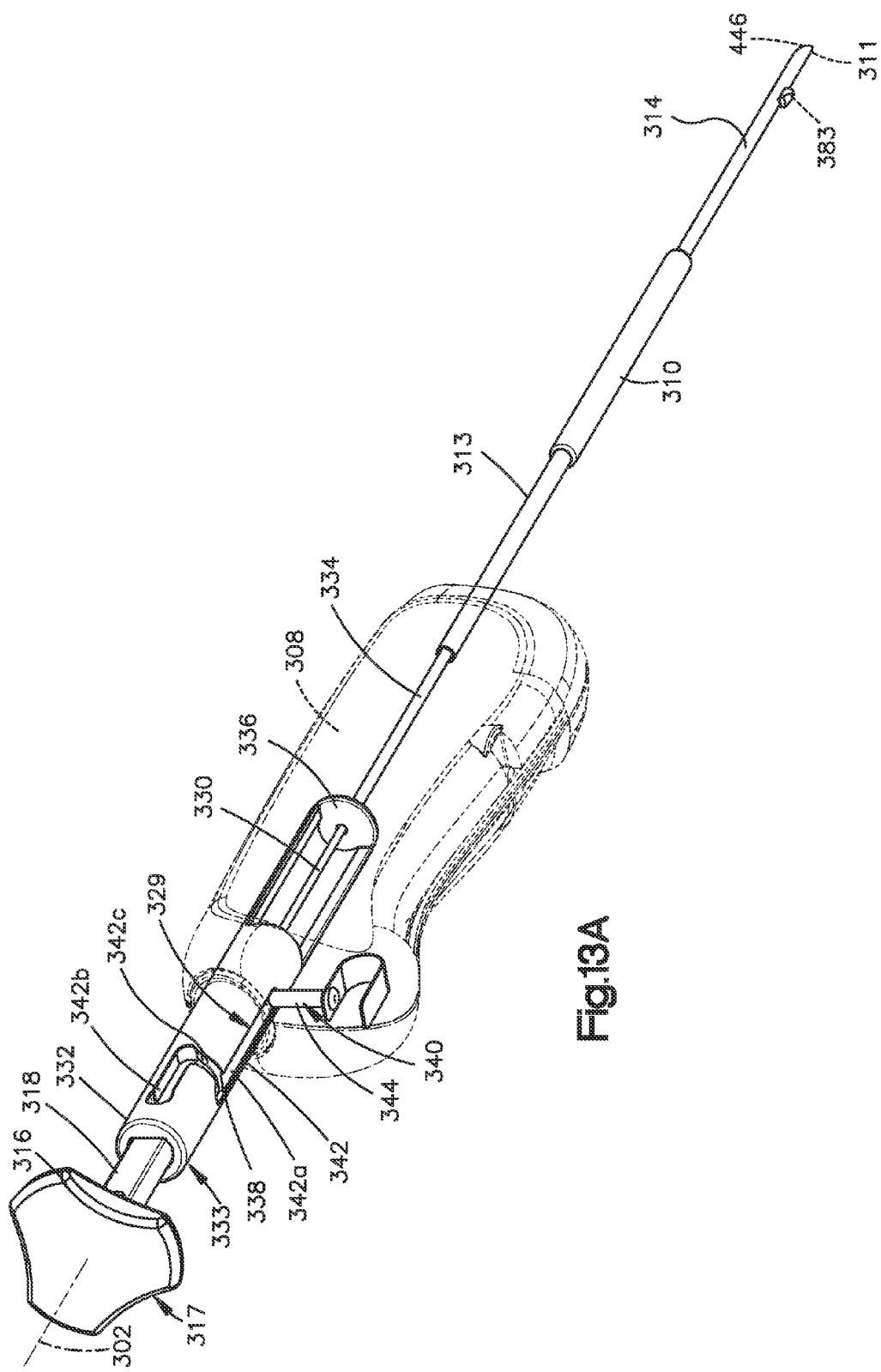
FIG. 13A is a perspective view of the insertion instrument illustrated in FIG. 7A, with portions removed so as to illustrate a guide system when the instrument is in the first position.
Figure 13B:
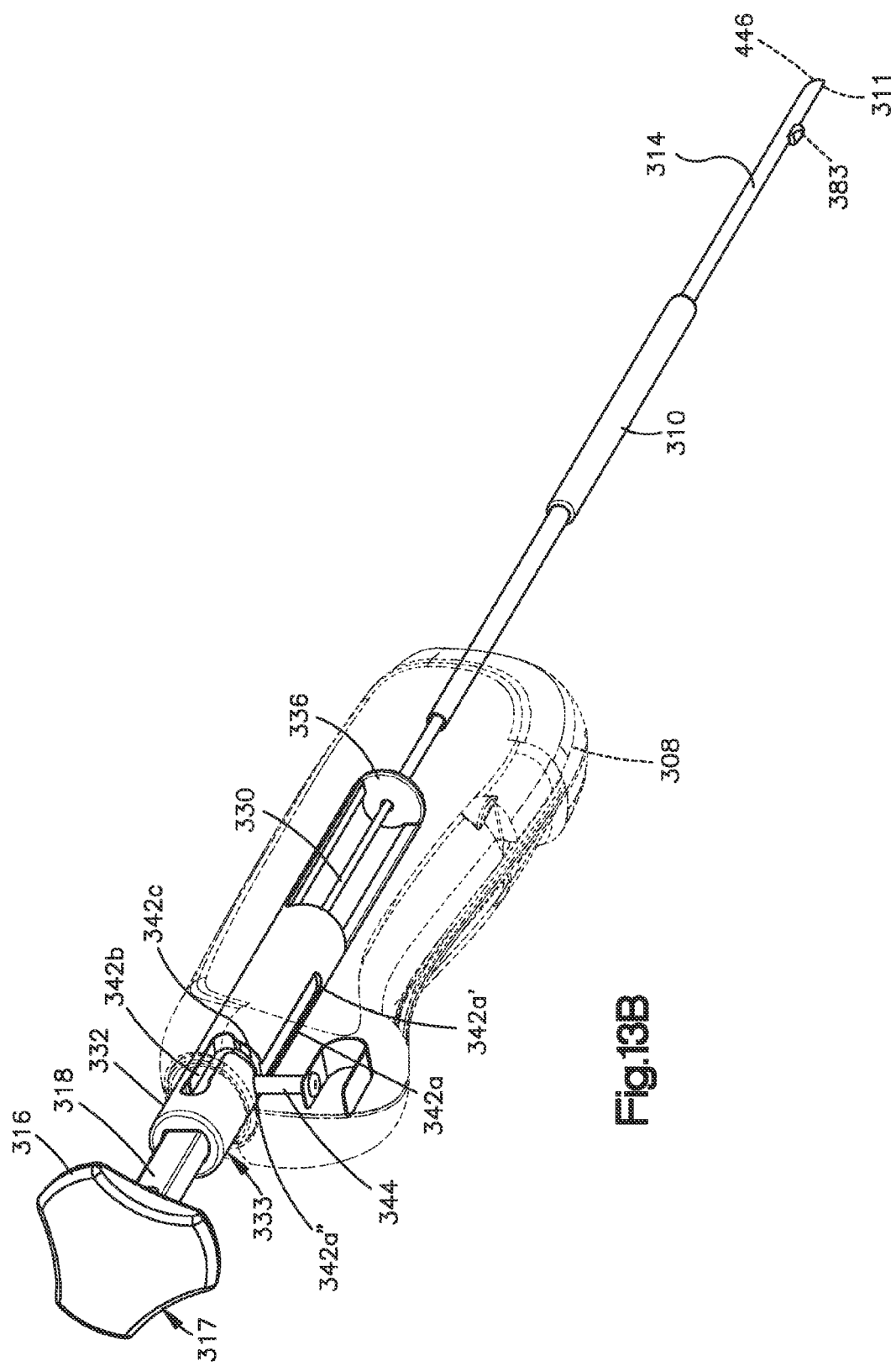
FIG. 13B is a perspective view of the insertion instrument illustrated in FIG. 8A, showing the guide system when the instrument is in the second position.

The first and second guide track portions 342a and 342b extend substantially longitudinally, such that distal translation of the collar 332 relative to the casing 308 during the first stroke causes the guide pin 344 and the guide track 342 to translate relative to each other. In accordance with the illustrated embodiment as shown in FIGS. 13A-B, the guide track 342 translates distally with respect to the guide pin 344, thereby causing the guide pin 344 to translate proximally along the first guide track portion 342a during the first stroke of the plunger 316 and the collar 332. Once the first stroke is completed, and the second anchor body 28b has been ejected from the cannula 310, the guide pin 344 is disposed at the proximal end 342a" of the first track portion 342a. The collar 332 defines a stop member at the proximal end of the first track portion 342a. Thus, the guide pin 344 interferes with the collar 332, thereby preventing the plunger 316 and collar 332 from further translating distally relative to the casing 308. Accordingly, the user is prevented from inadvertently ejecting the first anchor body 308a by continued distal translation of the plunger 316 after the second anchor body 28b has been ejected.

It should be appreciated during the first stroke that the guide pin 344 translates from the distal position 342a' (illustrated in FIG. 13A), past the offset position 342a''' (illustrated in FIG. 13C), to the proximal end 342a" (illustrated in FIG. 13B). When the guide pin 344 is at the offset position 342a''', the push tube 344 is slightly recessed proximally with respect to the distal ejection port 442 (see FIG. 9D). As the guide pin 344 moves to the proximal end 342a", the push tube 344 translates distally with respect to the ejection port 442 (see FIG. 8D). As further illustrated in FIGS. 8A and 9A, the insertion instrument 300 includes a spring member 365, which can be a coil spring, that extends between a spring seat 381 that is secured to the casing 308, for instance at the distal wall 326 of the casing 308, and the force transfer member 336. Thus, the spring member 365 is operably coupled between the casing 308 and the second pusher assembly 333. When the second pusher assembly 333 is coupled to the first pusher assembly 317 with respect to translation, the spring member 365 is operably coupled between the casing 308 and the first pusher assembly 317.

The spring member 365 provides a force that biases the collar 332, and thus the plunger 316, proximally as the plunger 316 translates distally along the first stroke. Accordingly, referring to FIGS. 13B-C, once the guide pin 344 is in the second position at the proximal end 342a" of the first track portion 342a, the spring force biases the collar 332 to move such that the guide pin 344 translates distally from the proximal end 342a" of the first track portion 342a toward the distal end 342a' of the first track portion 342a. However, as is described in more detail below, the track 342 includes a base 341 that interferes with movement of the guide pin 344 along a distal direction from the offset position 342a'''. When the guide pin 344 is in the offset position 342a''', the plug 314 of the push tube 334 is recessed proximally with respect to, or substantially aligned with, the distal ejection port 442 (see FIG. 9D) such that the plug 314 does not extend distally beyond the distal ejection port 442.

Figure 13C:
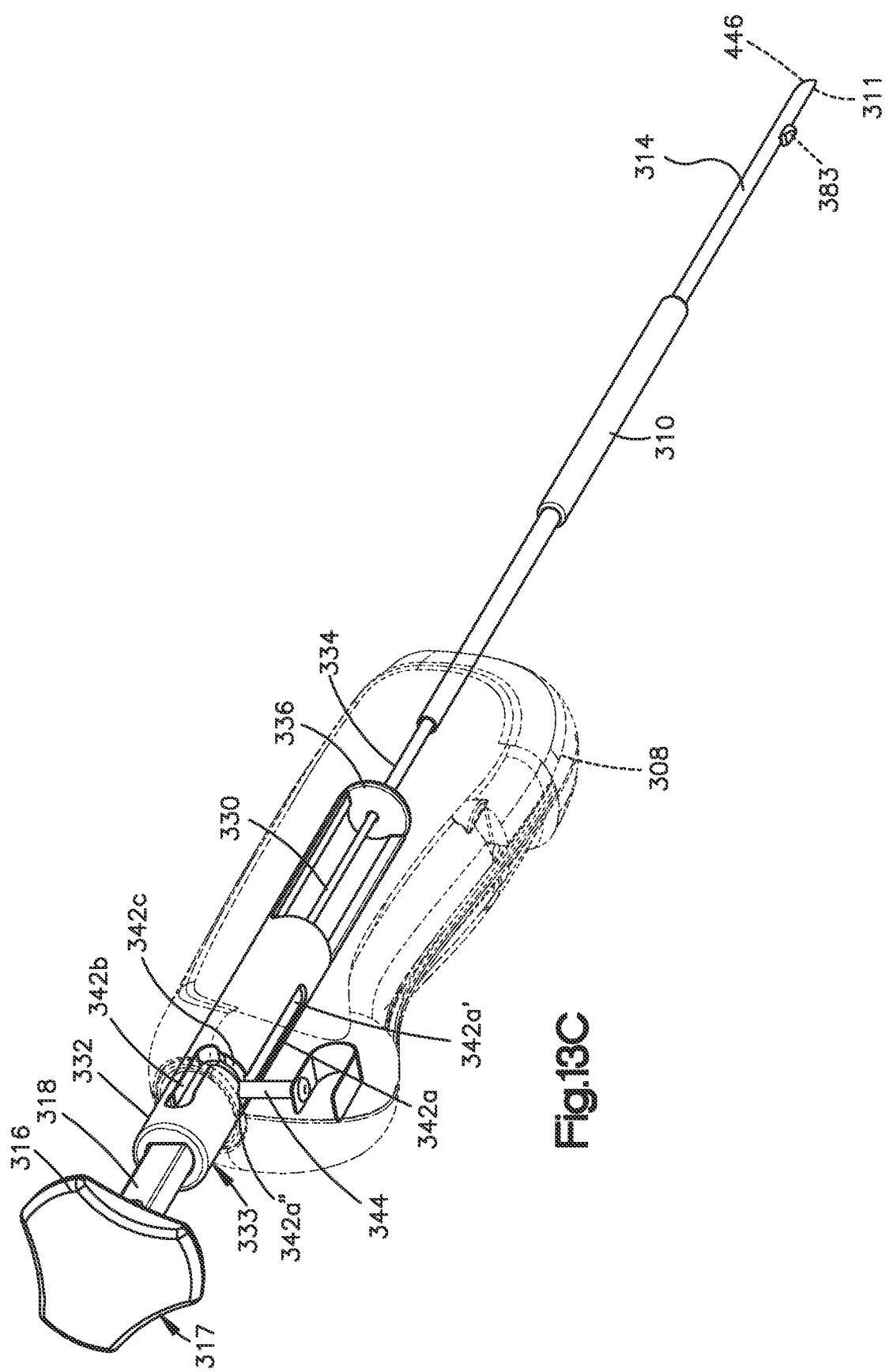
FIG. 13C is a perspective view of the insertion instrument illustrated in FIG. 9A, with portions removed so as to illustrate the guide system when the insertion instrument is in the offset position.
Figure 13E:
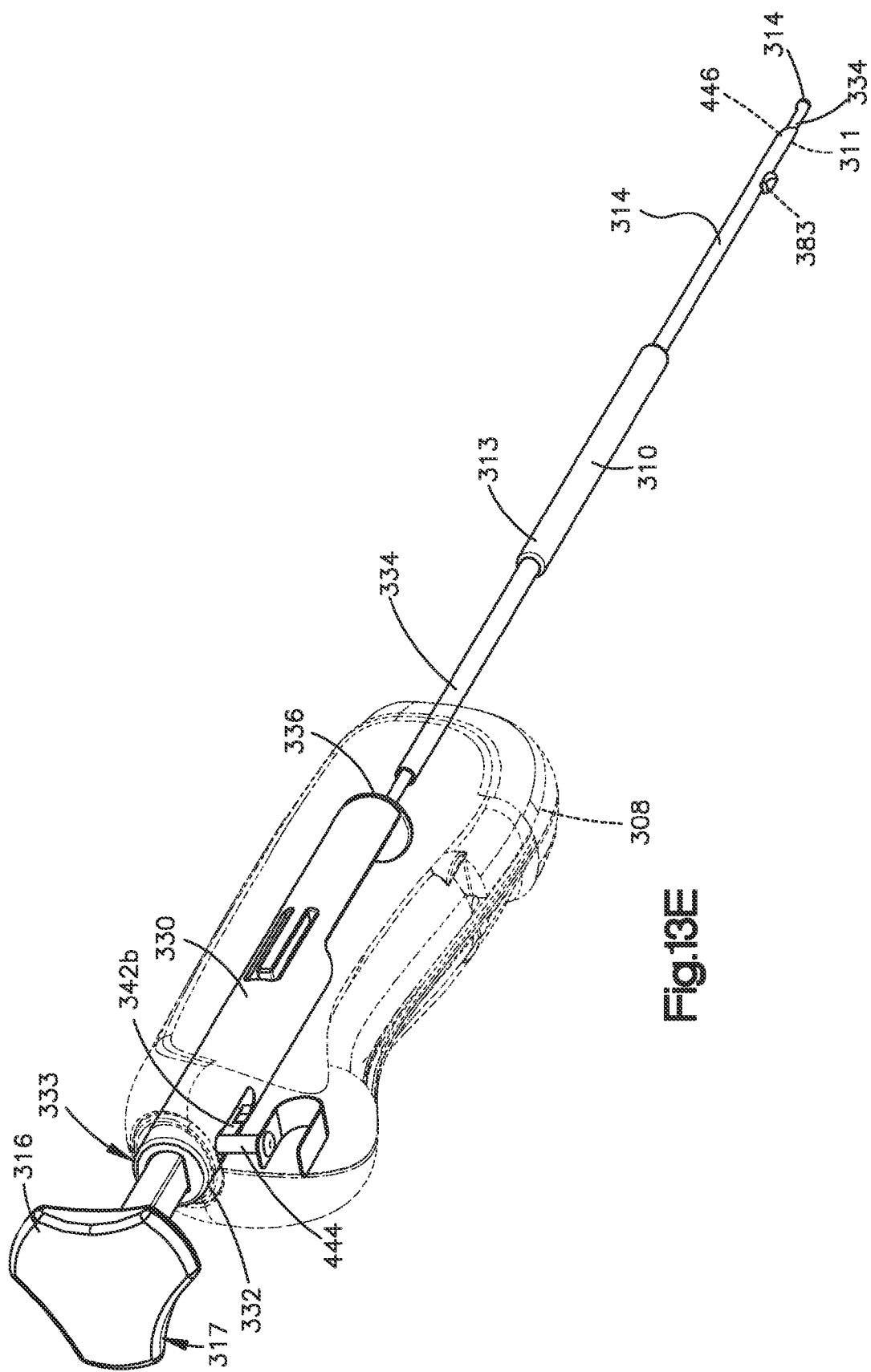
FIG. 13E is a perspective view of the insertion instrument illustrated in FIG. 11A, with portions removed so as to illustrate the guide system when the insertion instrument has completed the first portion of the second stroke.

Referring now to FIGS. 13C-D, the plunger 316 can be rotated along the direction of Arrow A as it travels along the intermediate stroke. The insertion instrument 300 defines a key 318 that rotatably couples the plunger 316 and the collar 332. In accordance with the illustrated embodiment, the key 318 is provided as complementary flat surfaces of the plunger 316 and the collar 332 that prevents defines the plunger 316 from rotating with respect to the collar 332. As a result, rotation of the plunger 316 along the direction of Arrow A causes the collar 332 to likewise rotate along the direction of Arrow A. Accordingly, upon completion of the first stroke, rotation of the plunger 316 causes the guide pin 344 to travel along the intermediate stroke from the first track portion 342a, along intermediate track portion 342c, and to the distal end of the second track portion 342b. Referring now to FIGS. 13D-E, once the guide pin 344 is disposed in the second track portion 342b, further translation of the plunger 316 and the collar 332 along a first portion of the second stroke causes the guide pin 344 to translate distally relative to the casing 308 until the guide pin 344 has traveled to the proximal end of the second track portion 342b. The collar 332 defines a stop member at the proximal end of the second track portion 342b that prevents the collar 332 from continuing to move distally with respect to the casing 308. It can be said that the collar 332 defines a stop member at the terminal ends of the first and second track portions 342a and 342b.

Figure 13F:
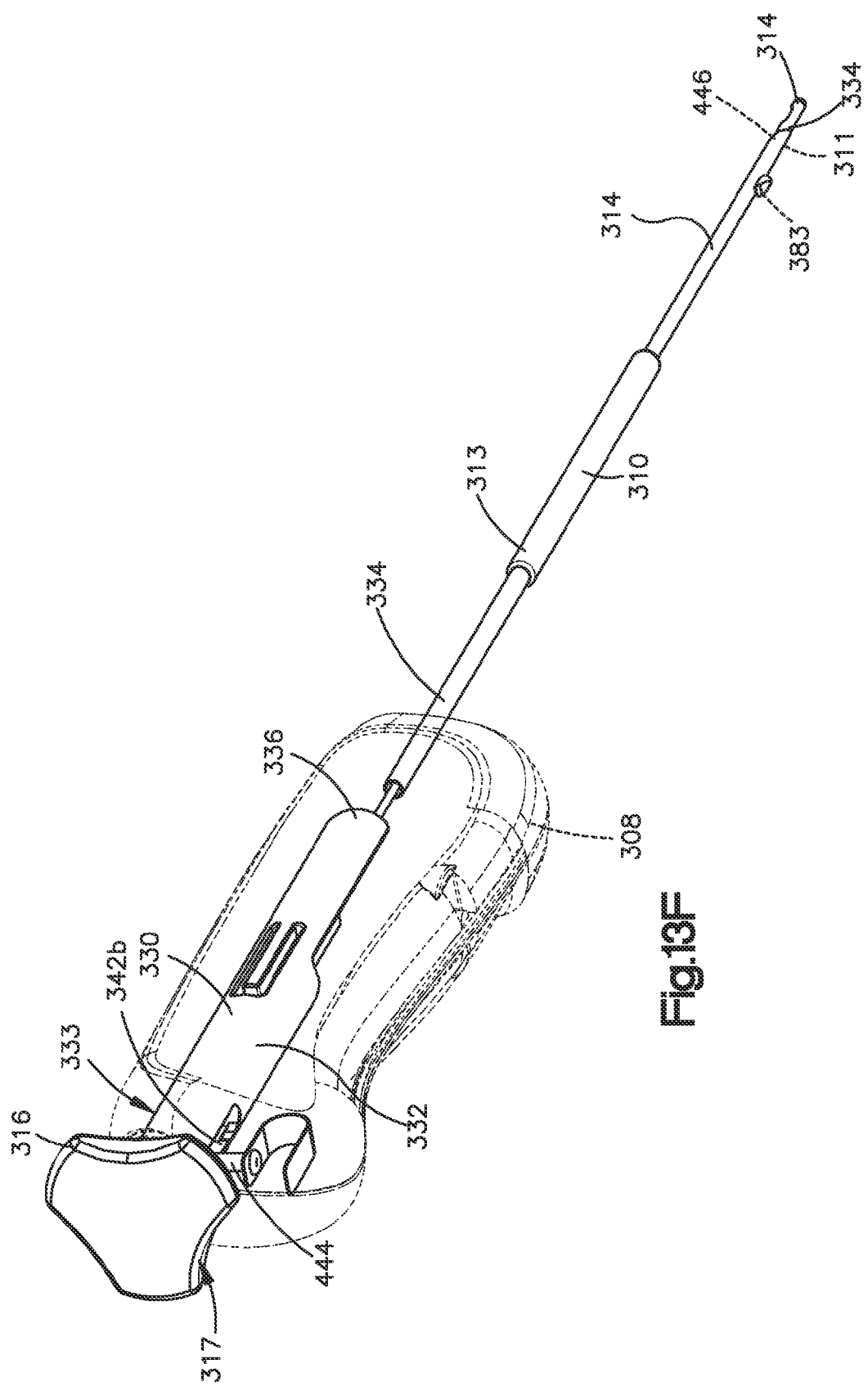
FIG. 13F is a perspective view of the insertion instrument illustrated in FIG. 12A, with portions removed so as to illustrate the guide system when the insertion instrument has completed the second portion of the second stroke.

Referring now to FIGS. 13E-F, and as is described in more detail below, once the guide pin 344 has traveled to the proximal end of the second track portion 342b, further distal translation of the plunger 316 along a second portion of the second stroke is decoupled from the collar 332, such that the plunger 316 and push rod 330 translate relative to the collar 332, the push tube 334, and the casing 308. The plunger 316 is configured to translate distally relative to the collar 332 and casing 308 during the second portion of the second stroke until the distal end 316c of the plunger abuts the casing 308, for instance at the proximal wall 324, thereby completing the second stroke and ejecting the second anchor body 28b out the cannula, as illustrated in FIGS. 12A-C.

Referring now to FIG. 13G in particular, the base 341 of the track 342 defines a first base portion 341a at the first track portion 342a, a second base portion 341b at the second track portion 342b, and an intermediate base portion 341c at the intermediate track portion 342c. The base 341 has portions that are deeper than others such that as the guide pin 344 rides along the track, at least one or both of audible and tactile feedback can be detected by the user to indicate that the collar 332, and in some instances the plunger 316, have completed a stroke or a portion of a stroke. The base 341 can further provide a stop that prevents the guide pin 344 from moving proximally along portions of the track 342. For instance, the first base portion 341a defines a first or distal first base portion 341a' and a second or proximal first base portion 341a'' that is deeper than the distal first base portion 341a'. The first base portion 341a defines an edge 346a that is disposed between the proximal first base portion 341a' and the distal first base portion 341a''. The edge 346a can extend radially, or along a direction having a radial component that extends toward the longitudinal axis 302.

The guide pin 344 can define a post 344a and a spring member 345 that is connected between the casing 308 and the post 344a, and biases the post 344a into the track 342 and against the base 341. Thus, as the guide pin 344 moves proximally relative to the first track portion 342a when the collar 332 and the plunger 316 move along the first stroke, the distal portion 344b of the guide pin 344 moves along the distal first base portion 341a' and over the edge 346a as the guide pin 344 travels to the distal first base portion 341a''. As the guide pin 344 travels over the edge 346a and is biased against the track 341 by a spring force of the spring member 345, at least one of a tactile and an audible feedback can be communicated to the user that the plunger 316 and the collar 332 have completed the first stroke. The edge 346a can be disposed at the offset position 342a''' of the first track portion, such that once the guide pin 344 has traveled along the first base portion 341a to the proximal end 342a'' of the first track portion 342a, the edge 346a prevents the force of the spring member 365 from causing the guide pin 344 to translate proximal with respect to the offset position 342a''' of the first track portion 342a. Rather, because the guide pin 344 abuts the edge 346a, the biasing force of the spring member 365 brings the guide pin 344 into alignment with the intermediate track portion 342c, and in position to be moved or rotated along the intermediate stroke.

With continuing reference to FIG. 13G, the intermediate base portion 341c defines a first or proximal intermediate base portion 341c' and a second or distal intermediate base portion 341c'' that is deeper than the proximal intermediate base portion 341c'. The distal intermediate base portion 341c'' can be aligned with the second base portion 341b. The intermediate base portion 341c defines an edge 346c that is disposed between the proximal intermediate base portion 341a' and the distal intermediate base portion 341a''. Alternatively, the intermediate base portion 341c can be devoid of the distal portion, such that the edge 346c is disposed between the intermediate base portion 341c and the second base portion 341b. The edge 346c can extend radially, or along a direction having a radial component that extends toward the longitudinal axis 302. As the distal portion 344b of the guide pin 344 travels over the edge 346c during a transition between the intermediate stroke and the second stroke, and is aligned with the second track portion 342b, at least one of a tactile and an audible feedback can be communicated to the user that the plunger 316 and the collar 332 have completed the intermediate stroke, and are in position to be moved along the first portion of the second stroke. Furthermore, the edge 346c prevents the plunger 316 from being rotated along a direction opposite the direction of Arrow A (FIG. 13C) once the guide pin 344 is positioned in the second track portion 342b.

The second base portion 341b defines a first or proximal second base portion 341b' and a second or distal second base portion 341b'' that is deeper than the proximal second base portion 341b'. The distal second base portion 341b'' can be disposed at the terminal distal end of the second track portion 342b. The second base portion 341b defines an edge 346b that is disposed between the proximal second base portion 341b' and the distal second base portion 341b''. The edge 346b can extend radially, or along a direction having a radial component that extends toward the longitudinal axis 302. As the distal portion 344b of the guide pin 344 travels over the edge 346b, at least one of a tactile and an audible feedback can be communicated to the user that the plunger 316 and the collar 332 have completed the first portion of the second stroke. The feedback can indicate that the plunger 316 is decoupled from the collar 332, and can translate along the second portion of the second stroke independent of the collar 332, as will now be described. Furthermore, the edge 346b prevents the guide pin 344 from moving proximally along the second track portion 342b once the plunger 316 and the collar 332 have been decoupled.

Referring now to FIG. 7C and FIGS. 14A-D, the insertion instrument 300 includes a coupling assembly 350 that is configured to iterate between a first mode of operation and a second mode of operation. In the first mode of operation, the coupling assembly 350 translatably fixes the first pusher member, illustrated as the push rod 330, and the second pusher member, illustrated as the push tube 334 with respect to translation during the first stroke. In the first mode of operation, the coupling assembly 350 releasably translatably fixes the push rod 330 to the push tube 334, such that in a second mode of operation, the coupling assembly 350 decouples the push rod 330 from the push tube 334 such that the push rod 330 can translate distally relative to the push tube 334 after the first stroke, for instance during the second stroke. Furthermore, in the second mode of operation, the coupling assembly 350 can translatably fix the push tube 334 to the casing 308, such that a distal translation force applied to the plunger 316 causes the plunger 316, and thus the push rod 330, to translate distally relative to the push tube 334, and thus the collar 332. In accordance with the illustrated embodiment, the coupling assembly 350 is in the first mode of operation during the first stroke of the first pusher assembly 317, the intermediate stroke of the first pusher assembly 317, and the first portion of the second stroke of the first pusher assembly 317. In accordance with the illustrated embodiment, the coupling assembly 350 transitions to the second mode of operation, as the first pusher assembly 317 transitions between the first portion of the second stroke and the second portion of the second stroke. In accordance with the illustrated embodiment, the coupling assembly 350 is in the second mode of operation when the first pusher assembly 317 translates along the second portion of the second stroke and the second portion of the second stroke.

The coupling assembly 350 can include at least one first coupling member 352 illustrated as a first recess 354 that extends radially into the first pusher assembly 317, such as the plunger 316, in accordance with the illustrated embodiment. The coupling assembly 350 can further include at least one second coupling member 356 illustrated as a channel 358, that extends radially through the second pusher assembly 333, such as the collar 332, in accordance with the illustrated embodiment. The coupling assembly 350 can further include at least one third coupling member 360 illustrated as a second recess 362 that is carried by the casing 308. For instance, the insertion instrument 300 can include an inner housing 325 that is carried by the casing 308, for instance by the proximal wall 324 of the casing 308. The second recess 362 extends radially outward into the inner housing 325 in accordance with the illustrated embodiment. Alternatively, the second recess 362 could extend radially outward into the casing 308.

Furthermore, in accordance with the illustrated embodiment, the second recess 362 is disposed distal with respect to the channel 358 when the plunger 316 is in the first position illustrated in FIGS. 7C and 14B. The second recess 362 can further be radially offset with respect to the channel 358 when the plunger 316 is in the first position illustrated in FIGS. 7A and 13A. Alternatively, the second recess 362 can be radially aligned with respect to the second recess 362 (for instance if the track 342 does not include the intermediate track portion 342c, and can alternatively still be annular so as to circumscribe the radially inner surface of the casing 308 if desired.

The coupling assembly 350 can further include at least one fourth coupling member 368 illustrated as a latch 370 that is sized to partially fit in each of the first recess 354, the second recess 362. In accordance with the illustrated embodiment, the latch 370 is carried by the collar 332, and is configured as a leaf spring 371 that is disposed in the channel 358, which can be provided as a substantially U-shaped aperture or cut-out of the collar 332 so as to define the leaf spring 371. The leaf spring 371 carries a radially inward projection 373 that is sized to fit into the first recess of the plunger 316. The latch 370 can be further sized to be disposed in the channel 358, and is flexible radially inward and outward. Accordingly, the latch 370 can travel along the channel 358 between the first recess 354 (FIG. 14B) and the second recess 362 (FIG. 14D).

In accordance with the illustrated embodiment, the coupling assembly 350 is in the first mode of operation when the guide pin 344 is in the first track portion 342a, and remains in the first mode of operation when the guide pin 344 travels from the first track portion 342a to the intermediate track portion 342c, and further remains in the first mode of operation when the guide pin 344 travels along part of the second track portion 342b. In particular, the first recess 354 and the channel 358, and the projection 371 of the latch 370, can be positioned so as to be radially aligned when the guide pin 344 extends into the any of, and all of as illustrated, the first track portion 342a, the intermediate track portion 342c, and the portion of the second track portion 342b.

Accordingly, in the first mode of operation, the latch 370 is partially disposed in the first recess 354 of the plunger 316, and extends into the channel 358 of the collar 332. The latch projection 373 can be sized so as to be captured in the first recess 354, so as to couple the plunger 316 to the collar 332 with respect to translational movement. As a result, when the latch 370 is coupled to the plunger 316, the plunger 316 and the collar 332, and thus the first and second pusher assemblies 317 and 333, are coupled with respect to movement or translation along the longitudinal direction.

Referring now to FIGS. 14C-D, because the second recess 362 is sized to receive the latch 370 in accordance with the illustrated embodiment, when the latch 370 moves from the first recess 354 into the second recess 362, the latch 370 decouples the first pusher assembly 317 from the second pusher assembly 333, and couples the second pusher assembly 333, and in particular the collar 332, to the casing 308 with respect to at least translation and can also couple the collar 332 to the casing 308 with respect to rotation. As described above, the casing 308 is fixed to the cannula 310 with respect to at least translation, and can further be fixed to the cannula 310 with respect to translation. In accordance with the illustrated embodiment, when the plunger 316 is rotated from the second position to the intermediate position such that the guide pin 344 travels along the intermediate track portion 342c (see FIGS. 13C-D), the first recess 354 and the channel 358 are brought into longitudinal alignment with the second recess 362.

During the first portion of the second stroke (see FIG. 13E), the plunger 316 and the collar 332 translate longitudinally until the first recess 354 and the channel 358 are aligned with the second recess 362 of the casing 308. During the transition between the first and second portions of the second stroke (see also FIG. 13F), the latch 370 is driven (for instance cams) out of the first recess 352 and thus moves from the first recess 352 into the second recess 362, as illustrated in FIGS. 14C-D. In accordance with an alternative embodiment, the plunger 316 can include a spring member that biases the latch 370 radially outward from the first recess 352 and into the second recess 362. Alternatively still, the insertion instrument 300 can be configured such that the latch 370 can cam out of the first recess 352 and move from the first recess into the second recess 362 the as the plunger 316 and the collar 332 rotate past the second recess 362 of the casing 308. Once the latch 370 has moved out of the first recess 354 and into the second recess 362 while remaining attached to the collar 332, the plunger 316 can continue to translate distally relative to the collar 332 during the second portion of the second stroke (see FIG. 13F), which causes the push rod 330 to translate distally relative to the push tube 334.

Operation of the insertion instrument 300 will now be described with initial reference to FIGS. 7A-D, 13A, and FIGS. 14A-D. In particular, the insertion instrument 300 can be constructed such that when the plunger 316, and thus the push rod 330, is in the first position, the first and second anchor bodies 28a and 28b are disposed in the cannula 310. In accordance with the illustrated embodiment, the first anchor body 28a is disposed longitudinally between the ejection port 442 and the plug 314 of the push tube 334. When the first pusher assembly 317, including the plunger 316 and the push rod 330, and the second pusher assembly 333, including the collar 332 and the push tube 334, are in the first position, the coupling assembly releasably couples the first pusher assembly 317 and the second pusher assembly 333 with respect to longitudinal movement and rotational movement. In particular, the latch 370 extends in both the first recess 354 and the channel 358, thereby releasably coupling the plunger 316 and the collar 332 with respect to longitudinal movement and rotational movement.

Referring now to FIGS. 8A-D, 13A-B, and 14B in particular, the tip 311 can be injected into the anatomical structure 24, for instance at the second target anatomical location 24b, until at least a portion (such as a distal portion) of the ejection port 442 extends distal of, or behind, the anatomical structure 24. In accordance with the illustrated embodiment, the insertion instrument can include a depth stop 383 that extends radially out from the cannula 310, and is configured to abut the anatomical structure 24 and provides resistance to further insertion of the cannula 310 into the anatomical structure 24 once the cannula 310 has been injected to a desired depth, for instance such that the ejection port 442 is disposed behind the anatomical structure 24. In this regard, the depth stop 383 can provide tactile feedback to the user that the cannula 310 has been injected into the target structure 24 at the desired depth. When a distal force is applied to the plunger 316 while the casing 308 remains stationary, for instance when a user grips the casing 308 relatively stationary while applying a distal force to the plunger 316, the first and second pusher assemblies 317 and 333 translate distally with respect to the casing 308 along the first stroke. As the first and second pusher assemblies 317 and 333 travel distally relative to the casing 308, the guide pin 344 travels proximally along the first track portion 342a of the collar 332 until the guide pin 344 reaches the proximal end 342a" of the first track portion 342a. As the second pusher assembly 333 travels distally, the plug 314 biases the second anchor body 28a to translate distally toward the tip 311. Furthermore, because the first pusher assembly 317 translates distally with the second pusher assembly 333 relative to the casing 308, and thus also the cannula 310, the pusher rod 330 biases the first anchor body 28b downstream toward the tip 311 during the first stroke.

Once the guide pin 344 has reached the proximal end 342a" of the first guide track portion 342a, the plug 314 has translated distal with respect to the proximal end of the ejection port 442, and thus has biased the second anchor body 28b out the ejection port 442 to a location behind the anatomical structure 24, for instance at the second target anatomical location 24b (see FIG. 1A) along the direction of Arrow B. Thus, the first track portion 342a has a longitudinal length sufficient such that movement of the guide pin 344 along the first track portion 342a causes the push tube 334 to eject the second anchor body 28b from the insertion instrument 300. Once the plunger 316 and the collar 332 have completed the first stroke, the plug 314 can be spaced proximally from the tip 311. It should be appreciated that the collar 332 defines a stop at the proximal end 342a" of the first track portion 342a that prevents further distal translation of the collar 332, and thus of the push tube 334 and the push rod 330, before the latch 370 is coupled to the casing 308, as described above with respect to FIG. 14C.

Next, referring to FIGS. 9A-D, once the second anchor body 28b has been ejected out the insertion instrument 300, the distal force can be removed from the plunger 316, which causes the spring member 365 to bias the second pusher assembly 333, for instance the collar 332, and thus also the first pusher assembly 317, proximally until the guide pin 344 is aligned with the offset position 342a''' of the first track portion 342a, as described above. Once the guide pin is in the offset position 342a''', the guide pin 344 is aligned with the intermediate track portion 342c, and the plunger 316 can be rotated to the second track portion 342b.

At any time after completion of the first stroke and prior to ejection of the first anchor body 28a, the second anchor body 28b can be actuated to the expanded configuration illustrated in FIG. 1B. For instance, referring to FIG. 9E, the second anchor body 28b can be actuated by removing the insertion instrument from the target anatomy 24. As illustrated at FIG. 9B, and as described in more detail below with respect to, the insertion instrument 300 includes a strand retention assembly 390 that retains, for instance releaseably retains, at least one tensioning strand 380 that is operably coupled to the actuation portions 131a and 131b of the first and second anchor bodies 28a and 28b, extends proximally into the interior 328 of the casing 308 and is releasably connected to the retention assembly 390. The at least one tensioning strand 380 can be sized and positioned along the actuation strand 131 such that when tension is applied to the tensioning strand 380, for instance when removing the insertion instrument 300 proximally out of the anatomical structure 24, and in some embodiments translating the insertion instrument 310 further proximally after removal from the anatomical structure 24, the tensioning strand 380 communicates the tension to the actuation strand 131b, thereby actuating the second anchor body 28b to its expanded configuration. Alternatively still, a user can manually apply the actuation force to the respective actuation portion 131b as desired. The insertion instrument 300 can further define an elongate side slot 315 that extends through one radial side of the cannula 310 at a location proximal with respect to the ejection port 442. For instance, the slot 315 can extend from the ejection port 442 and proximally a sufficient distance and sized sufficiently such that the actuation portions 131a-b and attachment portions 133 can extends through the slot 315 and attach to the tensioning strand 380, which extends proximally into the casing 308. Alternatively, the at least one tensioning strand 380 can be attached to the actuation portions 131a-b inside the cannula 310, and can extend out the slot 315. Thus, the slot 315 can define a circumferential width that is greater than the thickness of the actuation strands 38a-b and the at least one tensioning strand 380, but less than the thickness of the anchor bodies 28a and 28b when the anchor bodies 28a and 28b are in their respective first configurations inside the cannula 310.

Referring now to FIGS. 10A-D, 13C-D, and FIGS. 14A-D, once the second anchor body 28b has been ejected and the guide pin 344 is at the offset position 342a''' of the first track portion 342a, and the insertion instrument 300 has been removed from the anatomical structure 24, the tip 311 of the insertion instrument 300 can be injected into the anatomical structure 24 at the first target anatomical location 24a in the manner described above with respect to the second target anatomical location 24b. The plunger 316 can be rotated along the direction of Arrow A before or after the tip 311 has been injected at the first target anatomical location 24a so as to travel along the intermediate stroke, which causes the guide pin 344 to translate along the intermediate track portion 342c toward the second track portion 342b. The plunger 316 can be rotated along the direction of Arrow A until the plunger 316 is in the intermediate position, whereby the guide pin 344 is longitudinally aligned with the second track portion 342b. Once the plunger 316 and collar 332 have rotated to the intermediate position, the plunger 316 and the collar 332 are again able to translate distally with respect to the casing 308, and the latch 370 is longitudinally aligned with the second recess 362.

Referring now to FIGS. 11A-D, 13D-E, and 14D, if the insertion instrument 300 was not injected into the first target anatomical location 24a prior to driving the plunger 316 to travel along the intermediate stroke, the insertion instrument 300 can be injected into the first target anatomical location 24a after driving the plunger 316 to travel along the intermediate stroke, but before driving the plunger 316 to translate along the second stroke. As the plunger 316 and the collar 332 are further driven distally with respect to the casing 308, the first and second pusher assemblies 317 and 333 translate distally with respect to the casing 308 along a first portion of the second stroke. Translation of the plunger 316 along the first portion of the second stroke causes the guide pin 344 to translate proximally from the intermediate portion to a location between the proximal and distal ends of the second track portion 342b.

As the plunger 316 translates distally with respect to the casing 308, the coupling assembly 350 causes the collar 332, and thus the push tube 334 including the plug 314, to correspondingly translate distally with respect to the casing 308 and cannula 310 until the first recess 354 becomes radially aligned with the second recess 362. Thus, it can be said that movement of the guide pin 344 along the second track portion 342b causes the latch 370 to move in alignment with the second recess 362. The second recess 362 can be positioned such that the latch 370 is radially aligned with the second recess 362 once the plug 314 has translated to a position distal with respect to the tip 311, and thus distal with respect to the ejection port 442, which can occur once the plunger 316 has translated along the first portion of the second stroke. Because the plug 314 has translated distal to the ejection port 442, the plug 314 is removed from interference with the first anchor body 28a as the first anchor body 28a is ejected out the cannula 310. Furthermore, because the push rod 330 and the push tube 334 translate together along the first portion of the second stroke, the push rod 330 continues to bias the first anchor body 28b downstream in the elongate opening 312 of the cannula 310 toward the tip 311. As the first and second recesses 354 and 362 become radially aligned at the transition between the first and second portions of the second stroke, the latch 370 is driven from the first recess 354 into the second recess 362.

Referring now to FIGS. 12A-D, 13E-F, and 14D, once the latch 370 is disposed in second recess 352, the second pusher assembly 333 becomes coupled to the casing 308 with respect to translation. Because the latch 370 is removed from the first recess 354, the first pusher assembly 317 is decoupled from the second pusher assembly 333 with respect to translation. Accordingly, the first pusher assembly 317 can translate with respect to the second pusher assembly 333 and the casing 308, and thus also with respect to the cannula 310. Thus, it can be said that the latch 370 moves into the second recess 362 so as to translatably decouple the push rod 330 and the push tube 334, such that the push rod 330 is translatable independently of the push tube 344 so as to eject the first anchor body 28a from the insertion instrument 330.

In accordance with the illustrated embodiment, as the first pusher assembly 317 is further biased distally with respect to the second pusher assembly 333 during the second portion of the second stroke, the plunger 316 and the push rod 330 translate distally with respect to the casing 308, and thus also the cannula 310. As a result, the push rod 330, for instance at its distal end, biases the second anchor body 28b to move distally relative to the plug 314. The plug 314 can define a ramp 376 at its proximal end. The ramp 376 can thus be disposed distal of the ejection port 442 and positioned along the longitudinal axis 302, and thus aligned with the first anchor body 28a as the pusher rod 330 translates along the longitudinal direction and ejects the first anchor body 28a out the cannula 310 along the longitudinal direction. The ramp 376 can define a tapered ejection surface 378 that is angled radially outward as it extends distally. Accordingly, as the pusher rod 330 biases the first anchor body 28a to translate distally from the ejection port 442 onto the ejection surface 378 as the pusher rod 330 translates relative to the plug 314, the first anchor body 28a rides along the ejection surface 378, which directs the first anchor body 28a away from the insertion instrument 300 at the first target anatomical location 24a. Thus, the second track portion 342b has a longitudinal length so as to allow the plug 314 to translate to a location distal of the tip 311, such that distal translation of the push rod 330 ejects the first anchor body 28a out the insertion instrument.

While the coupling assembly 350 is configured such that the collar 332 moves along the first stroke with the plunger 316, moves along the intermediate stroke with the plunger 316, and moves along a first portion of the second stroke with the plunger 316, it should be appreciated in accordance with alternative embodiments that the coupling assembly 350 can be configured such that the collar 332 translatably decouples from the plunger 316 after or during the first stroke, or after or during the intermediate stroke.

Referring now to FIG. 12E, once the first anchor body 28a has been injected to the first target location 24a at a location behind the anatomical structure 24, the first anchor body 28a can be actuated to its expanded configuration. For instance, the first anchor body 28a can be manually expanded by the user applying the actuation force F (FIG. 1A) to the respective actuation portion 131a. In accordance with the illustrated embodiment, the actuation strands 38a and 38b of the first and second anchor bodies 28a and 28b, respectively, can be a common strand. Accordingly, the actuation portion 131a is integral with the actuation portion 131b, and proximal translation of the insertion instrument 300, for instance upon removal of the insertion instrument 300 from the anatomical structure 24, can cause the insertion instrument 300 to apply a proximal tensile force onto the tensioning strand 380, which communicates the tensile force to the second anchor body 28b, thereby actuating the second anchor body 28 to its expanded configuration.

Referring now to FIGS. 15A-E, the coupling assembly 350 can be constructed in accordance with another embodiment, and can include at least one first coupling member 352 illustrated as a first recess 354 that extends radially into the first pusher assembly 317, such as the plunger 316, in accordance with the illustrated embodiment. The coupling assembly 350 can further include at least one second coupling member 356 illustrated as a channel 358, that extends radially through the second pusher assembly 333, such as the collar 332, in accordance with the illustrated embodiment. The coupling assembly 350 can further include at least one third coupling member 360 illustrated as a second recess 362 (FIG. 15C), that extends radially outward into the casing 308 in accordance with the illustrated embodiment. Furthermore, in accordance with the illustrated embodiment, the second recess 362 is disposed distal with respect to the channel 358 when the plunger 316 is in the first position illustrated in FIGS. 7A and 13A. The second recess 362 can further be radially offset with respect to the channel 358 when the plunger 316 is in the first position illustrated in FIGS. 7A and 13A. Alternatively, the second recess 362 can be radially aligned with respect to the second recess 362 (for instance if the track 342 does not include the intermediate track portion 342c, and can alternatively still be annular so as to circumscribe the radially inner surface of the casing 308 if desired.

The coupling assembly 350 can further include at least one fourth coupling member 368 illustrated as a latch 370 that is sized to partially fit in each of the first recess 354, the second recess 362. In accordance with the illustrated embodiment, the latch 370 is substantially spherical, and each of the first recess 354 and the second recess 362 can be substantially partially spherical, though it should be appreciated that the latch 370 and each of the first recess 354 and the second recess 362 can define any suitable shape as desired. The latch 370 can be further sized to be disposed in the channel 358, which can be in the form of a slot that is defined by a longitudinal dimension substantially equal to that of the latch 370, and is further defined by a radial dimension that is substantially equal to that of the latch 370. Accordingly, the latch 370 can travel along the channel 358 between the first recess 354 (FIGS. 15A-B) and the second recess 362 (FIGS. 15D-E).

In accordance with the illustrated embodiment, the coupling assembly 350 is in the first mode of operation when the guide pin 344 is in the first track portion 342a, and remains in the first mode of operation when the guide pin 344 travels from the first track portion 342a to the intermediate track portion 342c, and further remains in the first mode of operation when the guide pin 344 travels along part of the second track portion 342b. In particular, the first recess 354 and the channel 358 can be positioned so as to be radially aligned when the guide pin 344 extends into the any of, and all of as illustrated, the first track portion 342a, the intermediate track portion 342c, and the portion of the second track portion 342b. Further, the latch 370 defines a radial dimension substantially equal to that of the first recess 354 and the channel 358 combined, which is substantially equal to that of the channel 358 and the second recess 362, combined. Thus, the radial dimension of the latch 370 is also substantially equal to that of the channel 358 and the second recess 362 combined. It should also therefore be appreciated that the first recess 354 and the second recess 362 can define substantially the same radial dimension.

Accordingly, in the first mode of operation, the latch 370 is partially disposed in the first recess 354 of the plunger 316, and extends into the channel 358 of the collar 332. The latch 370 can be sized so as to be captured between the casing 308 and the plunger 316, and to extend through the collar 332 in the channel 358. Because the first recess 354 is shaped substantially equal to a portion of the latch 370 in the longitudinal and circumferential directions, longitudinal and rotational motion of the plunger 316 correspondingly causes the latch 370 to move longitudinally and rotationally, respectively, along with the plunger 316 when the latch 370 is disposed in the first recess 354. Furthermore, because the channel 358 is dimensioned substantially equal to that of the latch 370 in both the longitudinal and circumferential directions, longitudinal and rotational motion of the latch 370 correspondingly causes the collar 332 to move longitudinally and rotationally, respectively. As a result, when the latch 370 is disposed in the first recess 354 and the channel 358, the plunger 316 and the collar 332, and thus the first and second pusher assemblies 317 and 333, are coupled with respect to movement or translation along the longitudinal direction, and are further coupled with respect to rotation or movement in the radial direction.

Referring now to FIGS. 15C-E, because the second recess 362 is shaped substantially equal to a portion of the latch 370 in accordance with the illustrated embodiment, when the latch 370 moves from the first recess 354 into the second recess 362, the latch 370 decouples the first pusher assembly 317 from the second pusher assembly 333, and couples the second pusher assembly 333, and in particular the collar 332, to the casing 308 with respect to at least translation and can also couple the collar 332 to the casing 308 with respect to rotation. As described above, the casing 308 is fixed to the cannula 310 with respect to at least translation, and can further be fixed to the cannula 310 with respect to translation. In accordance with the illustrated embodiment, when the plunger 316 is rotated from the second position to the intermediate position such that the guide pin 344 travels along the intermediate track portion 342c (see FIGS. 13C-D), the first recess 354 and the channel 358 are brought into longitudinal alignment with the second recess 362.

During the first portion of the second stroke (see FIG. 13E), the plunger 316 and the collar 332 translate longitudinally until the first recess 354 and the channel 358 are aligned with the second recess 362 of the casing 308. During the transition between the first and second portions of the second stroke (see also FIG. 13F), the latch 370 is driven (for instance cams) out of the first recess 352 and thus moves from the first recess 352 into the second recess 362. In accordance with an alternative embodiment, the plunger 316 can include a spring member that biases the latch 370 radially outward from the first recess 352 and into the second recess 362. Alternatively still, the insertion instrument 300 can be configured such that the latch 370 can cam out of the first recess 352 and move from the first recess into the second recess 362 the as the plunger 316 and the collar 332 translate past the second recess 362 of the casing 308. Once the latch 370 has moved out of the first recess 354 and into the second recess 362 while remaining disposed in the channel 358 of the collar 332, the plunger 316 can continue to translate distally relative to the collar 332 during the second portion of the second stroke (see FIG. 13F), which causes the push rod 330 to translate distally relative to the push tube 334.

Referring now to FIGS. 16A-17D, the anchor assembly 20 can include at least one tensioning member, such as a tensioning strand 380 that can be stitched through the first and second actuation strands 38a and 38b, respectively, of the first and second anchor bodies 28a and 28b. The anchor assembly 20 can include as many tensioning strands as desired that extend through one or both of the first and second actuation strands 38a and 38b. The tensioning strand 380 defines a first end 380', a second end 380", and a middle portion 380''' that extends between the first and second ends 380' and 380".

The tensioning strand 380 can be stitched through the first actuation strand of at least one of the anchor bodies 28a and 28b. In accordance with the illustrated embodiment, the tensioning strand 380 is stitched through the first actuation strand, and in particular through the first actuation portion 131a and the first attachment portion 133a of the first anchor body 28a. For instance, the first tensioning stand 380a can be threaded onto a needle, which is driven through the first actuation strand 38a, so as to insert the tensioning strand 380 through the actuation strand 38a, such that the tensioning strand 380 is connected to the actuation strand 38a at a location closer to the first anchor body 28a than the second anchor body 28b.

Referring now to FIGS. 7C and 17A-D the insertion instrument 300 can include a retention assembly, such as a strand retention assembly 390, that is configured to retain the at least one tensioning strand 380, and in particular the first and second ends 380a' and 380" of the tensioning strand 380. In accordance with one embodiment, the retention assembly releasably retains the tensioning strands 380. As will now be described, the retention assembly 390 is translatably fixed to the first pusher assembly 317, and thus moves proximally and distally along the longitudinal direction L along with the plunger 316. Accordingly, the tensioning strand 308 provides sufficient slack for the implantation of the first and second anchor bodies 28a and 28b in the respective target anatomical locations 24a and 24b. After the second anchor body 28b has been ejected from the cannula 310, proximal movement of the insertion instrument 300, for instance when removing the instrument from the anatomical structure 24, causes the retention assembly 390 to move in the proximal direction, thereby applying the tensile actuation force to the second tensioning strand 380, which communicates the actuation force to the second actuation portion 131b of the second actuation strand 38b, and causes the second anchor body 28b to expand. Similarly, after the first anchor body 28a has been ejected from the cannula 310, proximal movement of the insertion instrument 300, for instance when removing the instrument from the anatomical structure 24, causes the retention assembly 390 to move in the proximal direction, thereby applying the tensile actuation force to the tensioning strand 380, which communicates the actuation force to the first actuation portion 131a of the first actuation strand 38a, and causes the first anchor body 28a to expand.

The retention assembly 390 includes a retention housing 392 having a housing body 394 that is supported, directly or indirectly, by the plunger 316 is coupled to the distal end 316a of the plunger 316 in accordance with the illustrated embodiment. The housing body 394 is further coupled to the push rod 330, which extends distally from the retention assembly 390. The retention housing 392 includes a first locking member 400 and a second locking member 402 that extend from opposite, for instance laterally opposite, ends of the housing body 394. The first and second locking members 400 and 402 are configured to retain the respective first and second opposed ends 380' and 380" of the tensioning strand 380. The first locking member 400 is configured to be disengaged so as to release the first end 380'. The second locking member 402 is configured to retain the second end 380" of the tensioning strand 380 when the first locking member 400 is released.

In accordance with the illustrated embodiment, the first locking member 400 includes a locking body 407, and a clip 409 that is configured to be removably secured to the locking body 407. For instance, the clip 409 can be hingeably attached to the locking body 407, or otherwise movably attached to the locking body 407 as desired. The retention housing 392 can define a retention channel 411 disposed between the locking body 407 and the clip 409. The retention channel 411 can have any suitable shape as desired, and defines a serpentine shape in accordance with the illustrated embodiment. When the clip 409 is secured to the locking body 407, the retention channel 411 has a thickness less than that of the first end 380' of the tensioning strand 380. The clip 409 includes an outwardly projecting release tab 413 that is configured to receive a release force so as to release the clip 409 from the locking body 407, thereby freeing the first end 380' of the retention strand 380 from the retention assembly 39, as is described in more detail below.

In accordance with the illustrated embodiment, the second locking member 402 includes a second locking body 415, and a second clip 417 that is configured to be secured to the second locking body 415. The retention housing 392 can define a second retention channel 419 disposed between the second locking body 415 and the second clip 417. The second retention channel 419 can have any suitable shape as desired, and defines a serpentine shape in accordance with the illustrated embodiment. When the second clip 417 is secured to the second locking body 415, the second retention channel 419 has a thickness less than that of the second end 380" of the tensioning strand 380.

Thus, during operation, the first end 380' of the tensioning strand 380 can extend through the first retention channel 411 and the clip 409 can be secured to the locking body 407, thereby releasably locking the first end 380' of the tensioning strand 380 in the first locking member 400. Similarly, the second end 380" of the tensioning strand 380 can extend through the second retention channel 419 and the second clip 417 can be secured to the second locking body 415, thereby releasably locking the second end 380" of the tensioning strand 380 in the second locking member 402. When the first and second ends 380' and 380" are secured to the retention assembly, the insertion instrument can translate proximally once the first and second anchors 28a and 28b have been implanted to thereby deliver the tensile actuation force to the tensioning strand 380, which communicates the tensile actuation force to the respective actuation portions of the anchor bodies, thereby causing the anchor bodies to expand in the manner described above.

The retention assembly 490 further includes an actuator assembly 421 that is configured to release the first locking member 400. In particular, the actuator assembly 421 can include an actuator or button 423 that is carried by the casing 308 (see FIG. 7C), and at least one biasing member, such as a pair of arms 425 that extend into the interior 328 of the casing 308 from the button 423. It is recognized that the first anchor body 28a is ejected from the instrument 300 once the plunger 316 has completed the second stroke. Accordingly, the actuator assembly 421 is positioned such that the arms contact the retention housing 492 once the plunger 316 has reached the end of the second stroke.

Figure 17A:
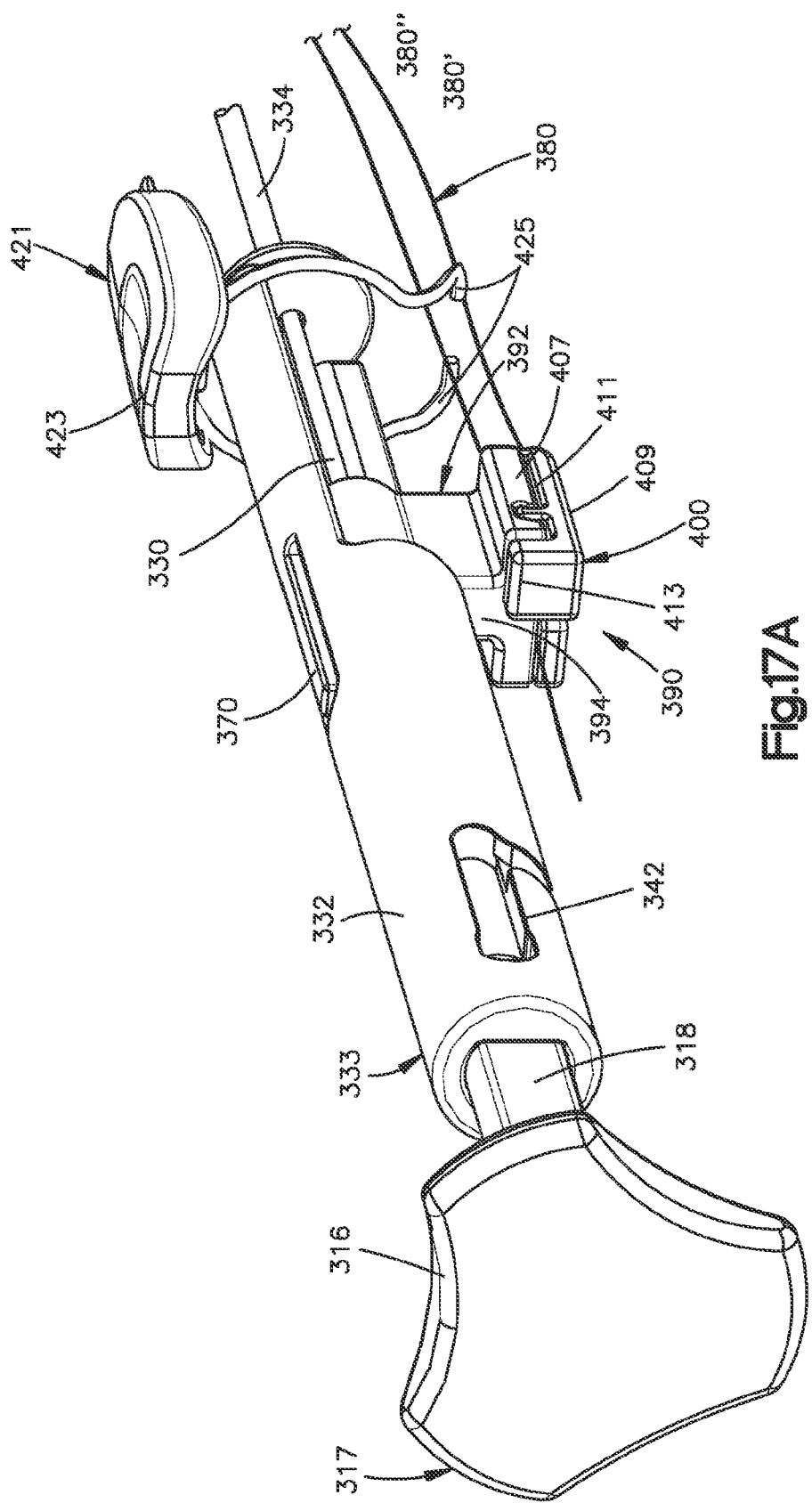
FIG. 17A is a perspective view of a strand retention assembly constructed in accordance with one embodiment, showing a releasable locking member.
Figure 17B:
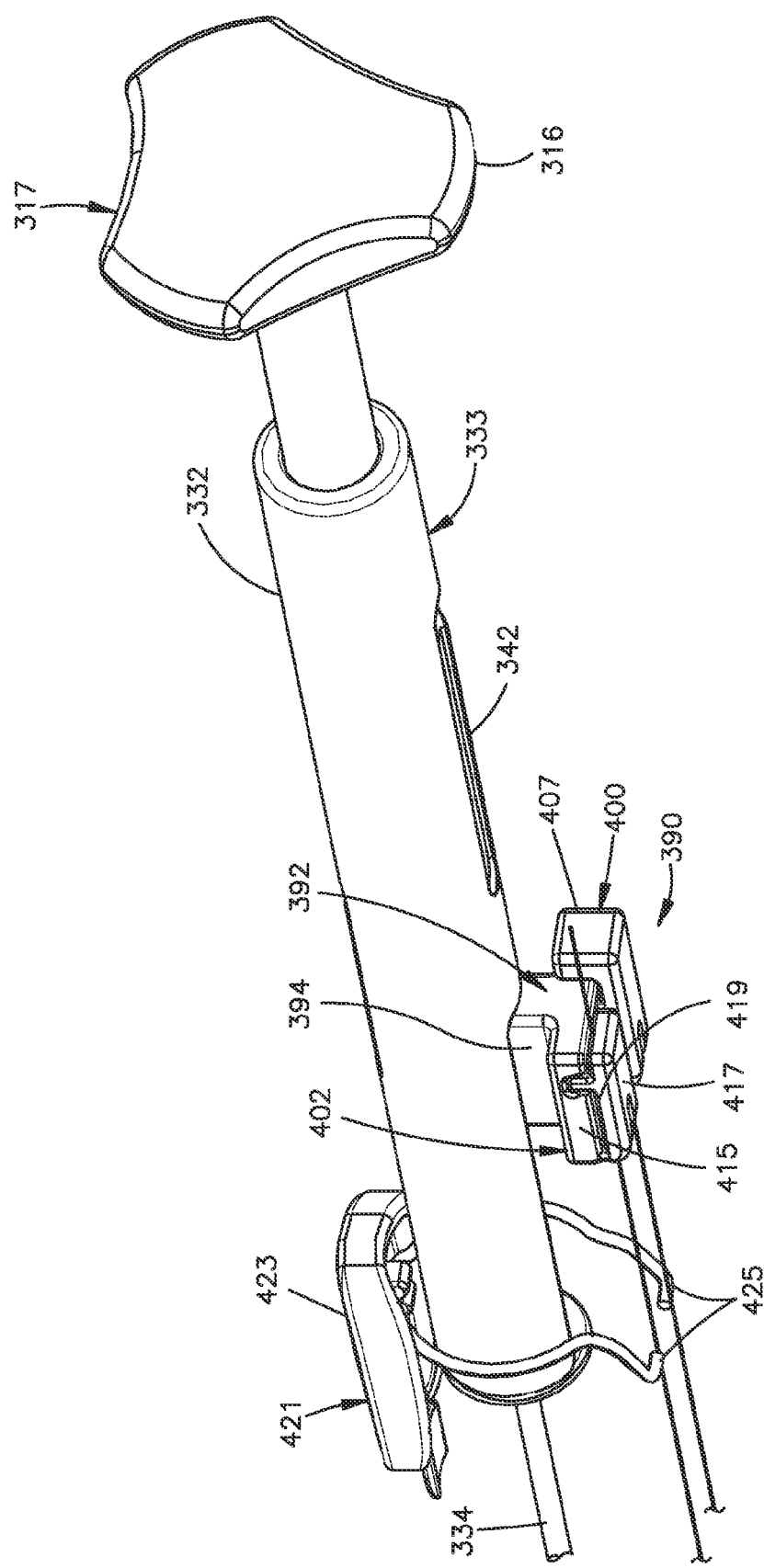
FIG. 17B is a perspective view of the strand retention assembly illustrated in FIG. 17A, showing a fixed locking member.
Figure 17C:
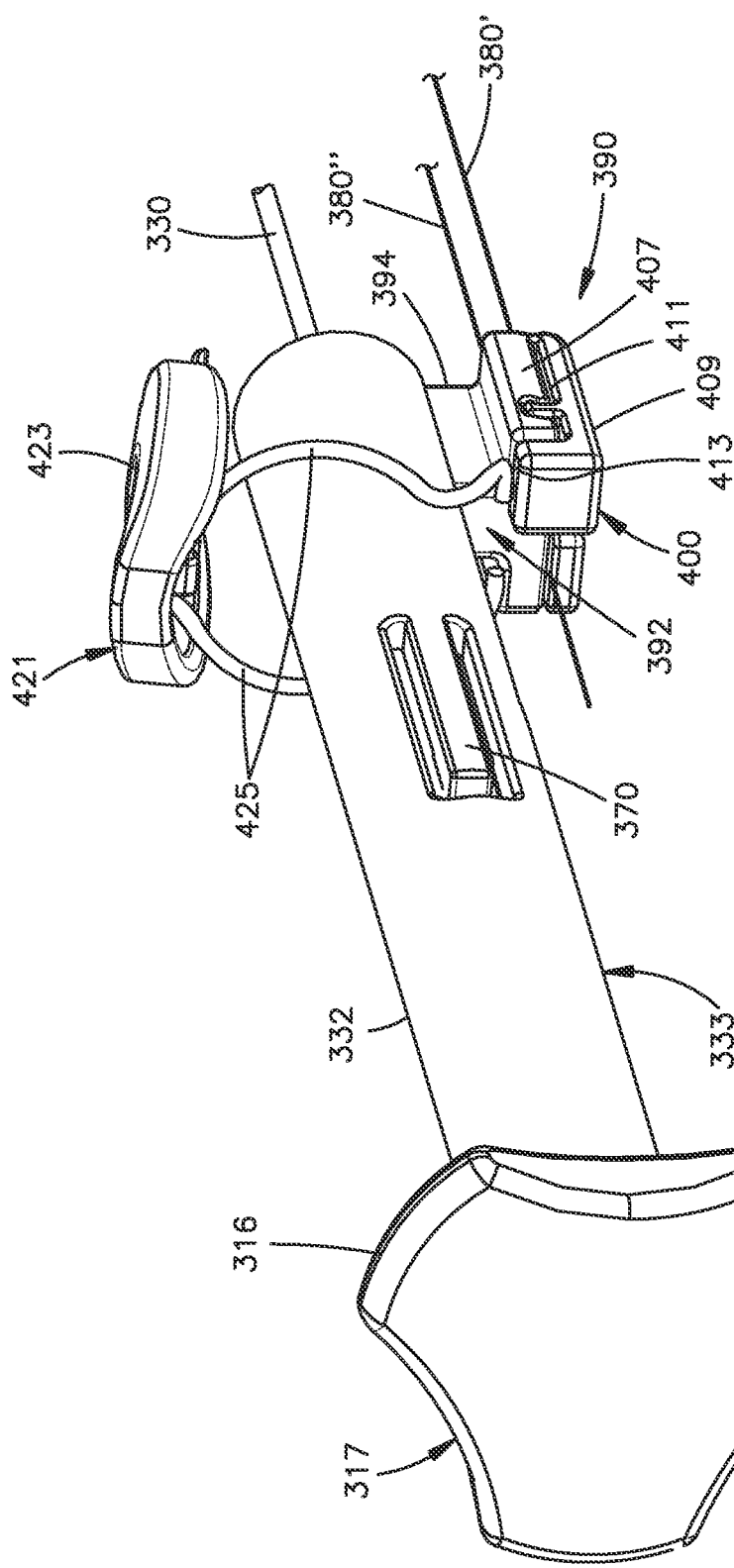
FIG. 17C is a perspective view of the strand retention assembly illustrated in FIG. 17A, operably coupled to an actuator.
Figure 17D:
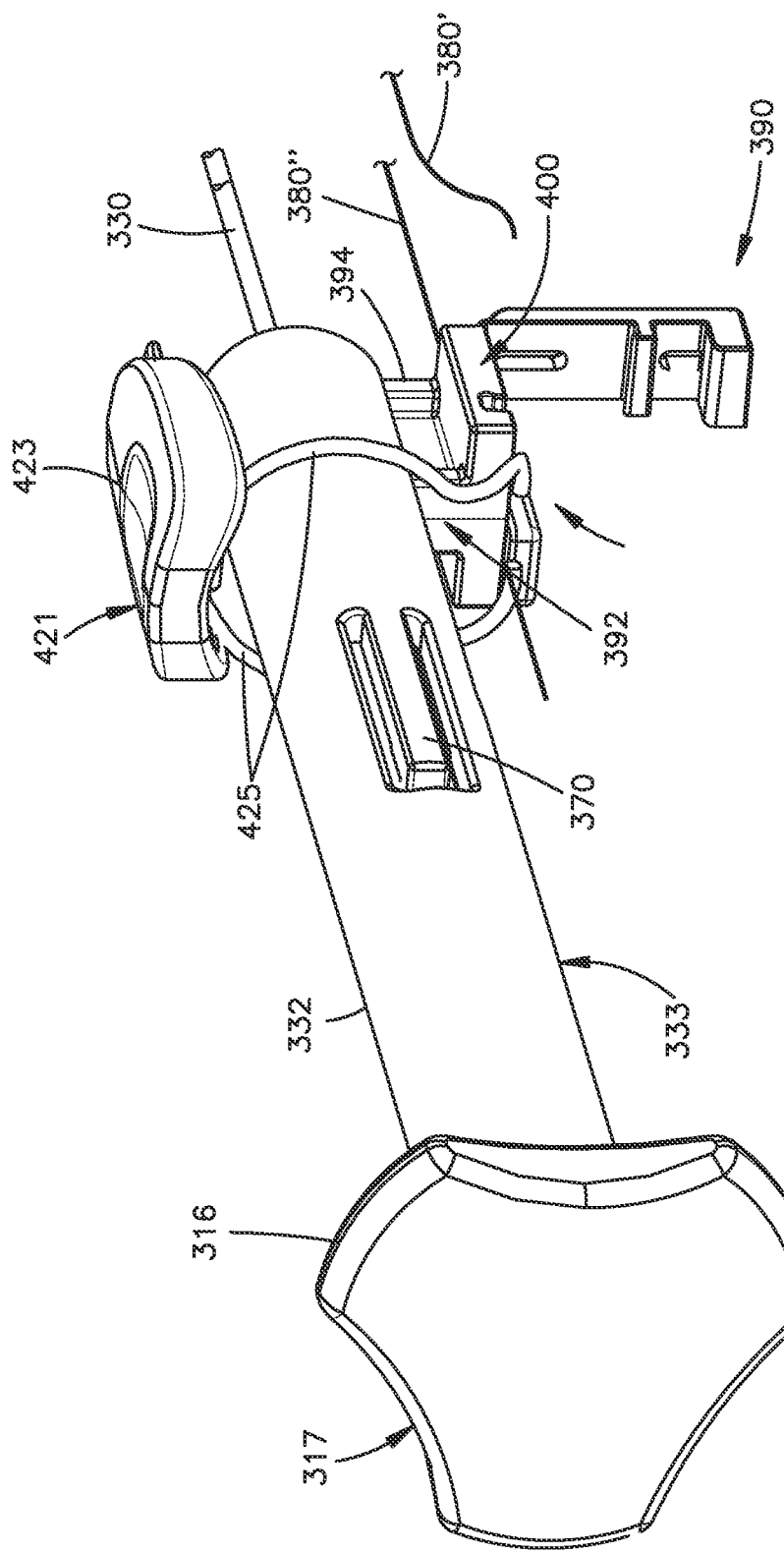
FIG. 17D is a perspective view of the strand retention assembly illustrated in FIG. 17C, shown in a released position.

Referring to FIGS. 12C and 17C, As the plunger 316 reaches the end of the second stroke, the arms 425 ride along outer surfaces of the first and second locking bodies 407 and 415, respectively, which causes the button 423 to raise radially outwardly from an unloaded position to a loaded position. Once the plunger 316 has reached the end of the second stroke, one of the arms is aligned with the release tab 413. Accordingly, the button 423 can be depressed, which causes one of the arms 425 to drive the release tab 413 away from the first locking body 407, which causes the clip 409 to move into an unlocked position whereby the clip 409 is removed from the locking body 407 a sufficient amount such that the retention channel 411 is thicker than the first end 380' of the tensioning strand 380. As a result, the first end 380' becomes unlocked from the retention assembly 390, and the instrument can be moved proximally so as to draw the tensioning strand 380 through the actuation strands of the anchor bodies.

Referring now to FIG. 18A, the anchor assembly 20 can alternatively include a pair of tensioning members, such as a first tensioning strand 380a and a second tensioning strand 380b that can be stitched through the first and second actuation strands 38a and 38b, respectively, of the first and second anchor bodies 28a and 28b. The anchor assembly 20 can include as many tensioning strands as desired that extend through one or both of the first and second actuation strands 38a and 38b. The first tensioning strand 380a defines a first end 380a', a second end 380a", and a middle portion 380a'" that extends between the first and second ends 380a' and 380a". Similarly, the second tensioning strand 380b defines a first end 380b', a second end 380b", and a middle portion 380b'" that extends between the first and second ends 380b' and 380b".

The first tensioning strand 380a can be stitched through the first actuation strand 38a, for instance through opposed ends of the first actuation strand 38a. For instance, the first tensioning stand 380a can be threaded onto a needle, which is driven through the first actuation strand 38a, so as to insert the first tensioning strand 380a through the first actuation strand 38a. The first tensioning strand 380a can extend through the first attachment portion 133a and the first actuation portion 131a of the first actuation strand 38a, and can loop back through the first actuation portion 131a and the first attachment portion 133a, at a location between the first and second anchor bodies 28a and 28b.

Similarly, the second tensioning strand 380b can be stitched through the second actuation strand 38b, for instance through opposed ends of the second actuation strand 380b. For instance, the second tensioning stand 380b can be threaded onto a needle, which is driven through the second actuation strand 38b so as to insert the second tensioning strand 380b through the second actuation strand 38b. The second tensioning strand 380b can extend through the first attachment portion 133b and the actuation portion 131b of the second actuation strand 38b, and can loop back through the second attachment portion 133b and the second actuation portion 131b at a location between the first and second anchor bodies 28a and 28b.

Figure 19A:
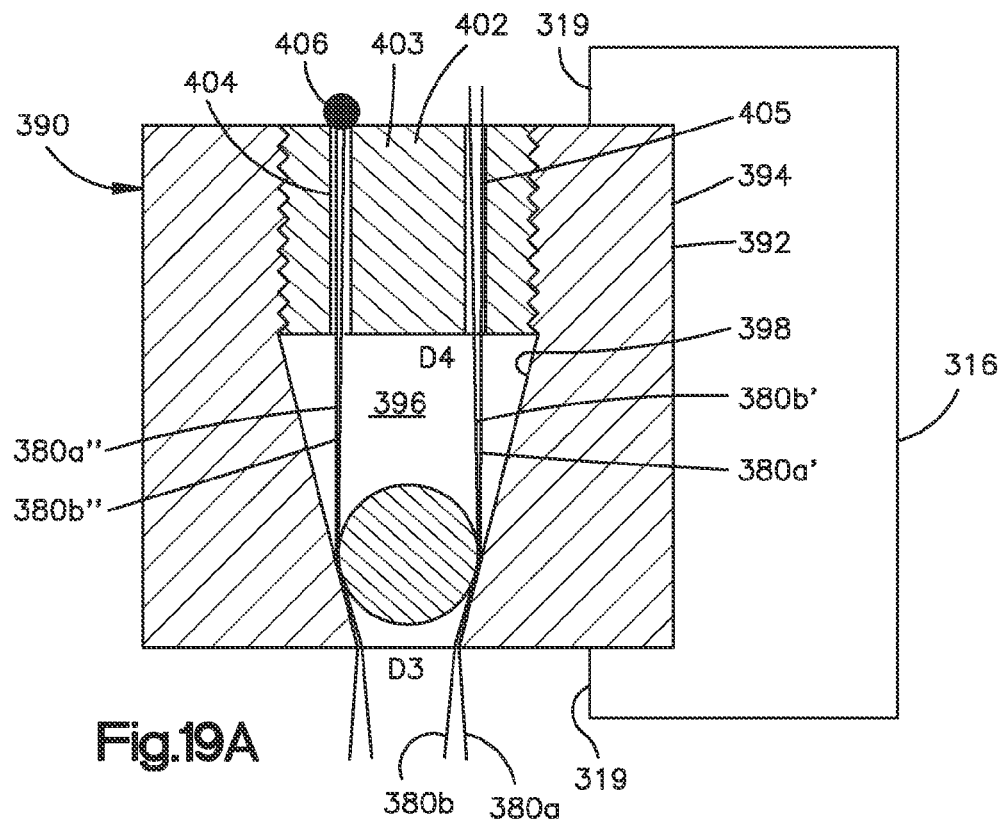
FIG. 19A is a schematic sectional side elevation view of a retention assembly of the insertion instrument constructed in accordance with another embodiment, shown in a locked configuration.
Figure 19B:
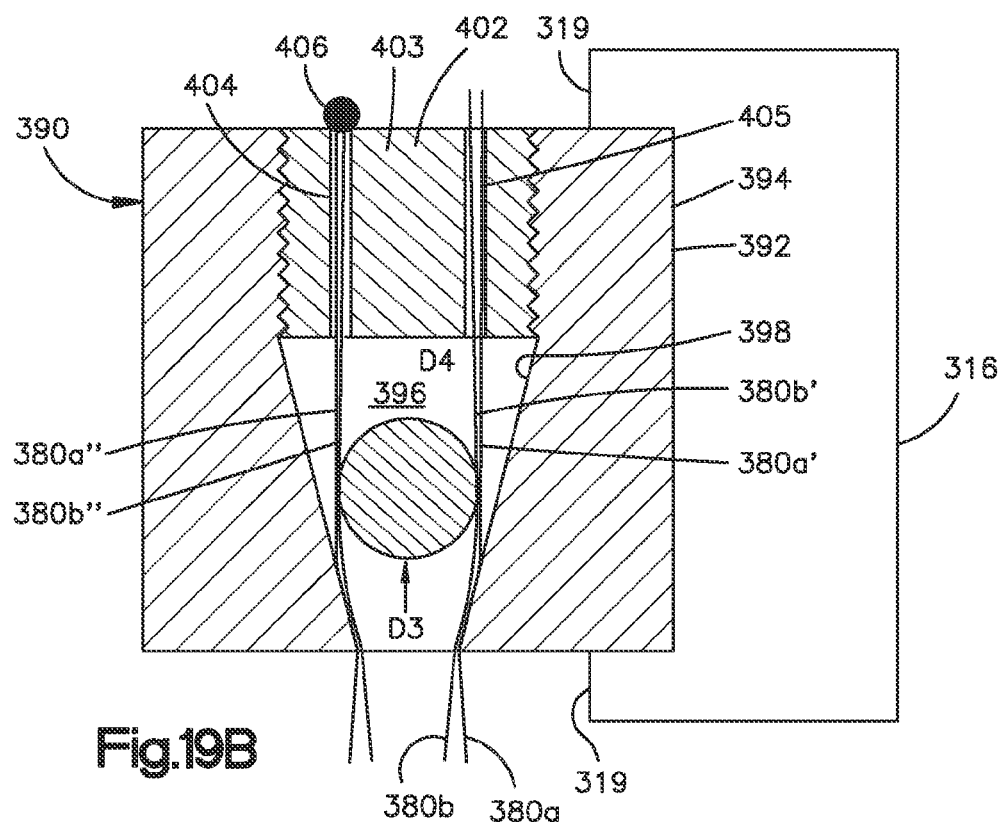
FIG. 19B is a schematic sectional side elevation view of a retention assembly of the insertion instrument illustrated in FIG. 19A, shown in an unlocked configuration.

Referring now to FIGS. 19A-B, the strand retention assembly 390 can be constructed in accordance with an alternative embodiment to releasably retain the at least one tensioning strand 380. Thus, while the strand retention assembly 390 illustrated in FIGS. 19A-B are illustrated as retaining the pair of first and second tensioning strands 380a and 380b, the retention assembly 390 can alternatively releasably retain a single tensioning strand, for instance as described above with respect to FIGS. 16-17. In accordance with the embodiment illustrated in FIGS. 19A-B, the retention assembly 390 retains the first and second ends 380a' and 380" and 380b' and 380b" of the first and second tensioning strands 380a and 380b. In accordance with one embodiment, the retention assembly 390 releasably retains the first and second tensioning strands 380a and 380b. As will now be described, the retention assembly 390 is translatably fixed to the first pusher assembly 317, and thus moves proximally and distally along the longitudinal direction L along with the plunger 316. Accordingly, after the second anchor body 28b has been ejected from the cannula 310, movement of the plunger 316 and the push rod 330 in the proximal direction causes the retention assembly 390 to move in the proximal direction, thereby applying the tensile actuation force to the second tensioning strand 380b, which communicates the actuation force to the second actuation portion 131b of the second actuation strand 38b, and causes the second anchor body 28b to expand. Similarly, after the first anchor body 28a has been ejected from the cannula 310, movement of the plunger 316 and the push rod 330 in the proximal direction causes the retention assembly 390 to move in the proximal direction, thereby applying the tensile actuation force to the first tensioning strand 380a, which communicates the actuation force to the first actuation portion 131a of the first actuation strand 38a, and causes the first anchor body 28a to expand.

The retention assembly 390 includes a retention housing 392 having a housing body 394 that is supported, directly or indirectly, by the casing 308. In accordance with the illustrated embodiment, the retention housing 392 is disposed in the interior 328 of the casing 308, though the retention housing 392 can alternatively be carried external of the casing 308, and can be attached to the plunger 316 or any suitable alternative structure of the insertion instrument 300 as desired. The retention housing 392 defines a bore 396 that extends longitudinally into the housing body 394 along the proximal direction. In accordance with the illustrated embodiment, the bore 396 extends longitudinally through the housing body 394. The housing body 394 can define at least one interior surface 398 that defines a perimeter of the bore 396. The interior surface 398 can slope (for instance linearly, curvilinearly, or along any suitable alternative shape) radially outward as it travels proximally along a direction from a distal end of the housing body 394 to a proximal end of the housing body 394. Thus, the bore 396 can define a first cross-sectional dimension D3 along a direction substantially perpendicular to the longitudinal axis 302 at its first or proximal end, and a second cross-sectional dimension D4 along a direction substantially perpendicular to the longitudinal axis 302 at its second or distal end. Because the bore 396 can be tapered, the first cross-sectional dimension D3 can be less than the second cross-sectional dimension D4. The bore 396 can be tapered, for instance linearly, curvilinearly, or along any suitable alternatively shape as desired.

The retention assembly 390 can further include a first locking member 400 that is disposed inside the bore 396. The first locking member 400 has a cross-sectional dimension D5, for instance along a direction substantially perpendicular to the longitudinal axis 302, that is between the first cross-sectional dimension D3 and the second cross-sectional dimension D4. The first locking member 400 can be substantially spherical as illustrated, or can alternatively define any shape as desired. The retention assembly 390 is configured to retain at least one strand between the first locking member 400 and the interior surface 398 of the housing body 394. For instance, the first end of at least one or both of the tensioning strands 380a' and 380b' can extend between the first locking member 400 and the interior surface 398. The first locking member 400 is configured to bear against the interior surface 398 during operation of the instrument, thereby capturing the first ends 380a' and 380b' between the first locking member 400 and the interior surface 398 of the housing body 394, and preventing relative movement between each of the first ends 380a' and 380b' and the retention housing 392. Thus, the first locking member 400 can present a first locking surface, and the interior surface 398 can present a second locking surface that cooperates with the first locking surface so as to retain the first ends 380a' and 380b' of the first and second retention strands 380a and 380b in the retention assembly 390.

The retention assembly 390 can further include a second locking member 402 that is configured to be attached to the first locking member 400. In particular, the second locking member 402 can include a threaded plug 403 that is threadedly inserted into the proximal end of the housing body 394. Accordingly, the second locking member 402 can be disposed adjacent the tapered inner surface 398, and can close the proximal end of the tapered bore 396. Alternatively, the second locking member 402 can be integral with the housing body 394. The second locking member 402 defines at least one opening, such as a longitudinal opening 404, that is configured to receive the end of the one or more tensioning strands that are opposite the end of the tensioning strands that are captured between the first locking member 400 and the interior surface 398 of the housing body 394. Accordingly, the second locking member 402 is configured to receive each of the second ends 380a" and 380b" of the first and second tensioning strands 380a and 380b. The second locking member 402 can thus be aligned with the tapered bore 396, such that the second end 380a" and 380b" of each of the first and second strands 380a and 380b extends through the tapered bore 396 and is attached to the second locking member 402.

In accordance with the illustrated embodiment, the longitudinal opening 404 extends longitudinally between the bore 396 and the exterior of the plug 403, which can be the interior 328 of the casing 308. Each or both of the second ends 380a" and 380b" can be tied in a knot 406 at the proximal end of the longitudinal opening 404, such that the knot 406 abuts the proximal end of the second locking member 402. Thus, the retention assembly 390 is configured to fix the first and second ends 380a' and 380a" of the first tensioning strand 380a, and is further configured to fix the first and second ends 380b' and 380b" of the second tensioning strand 380b. The second ends 380a" and 380b" can alternatively or additionally extend between the first locking member 400 and the interior surface 398, and can be captured between the first locking member 400 and the interior surface 398 as desired so as to retain the second ends 380a" and 380b" in the retention assembly 390. The second locking member 402 can further include a second longitudinal opening 405 that is spaced from the longitudinal opening 404. The second longitudinal opening 405 is configured to receive the remainder of the first ends 380a' and 380b' that are captured between the first locking member 400 and the interior surface 398.

Figure 19C:
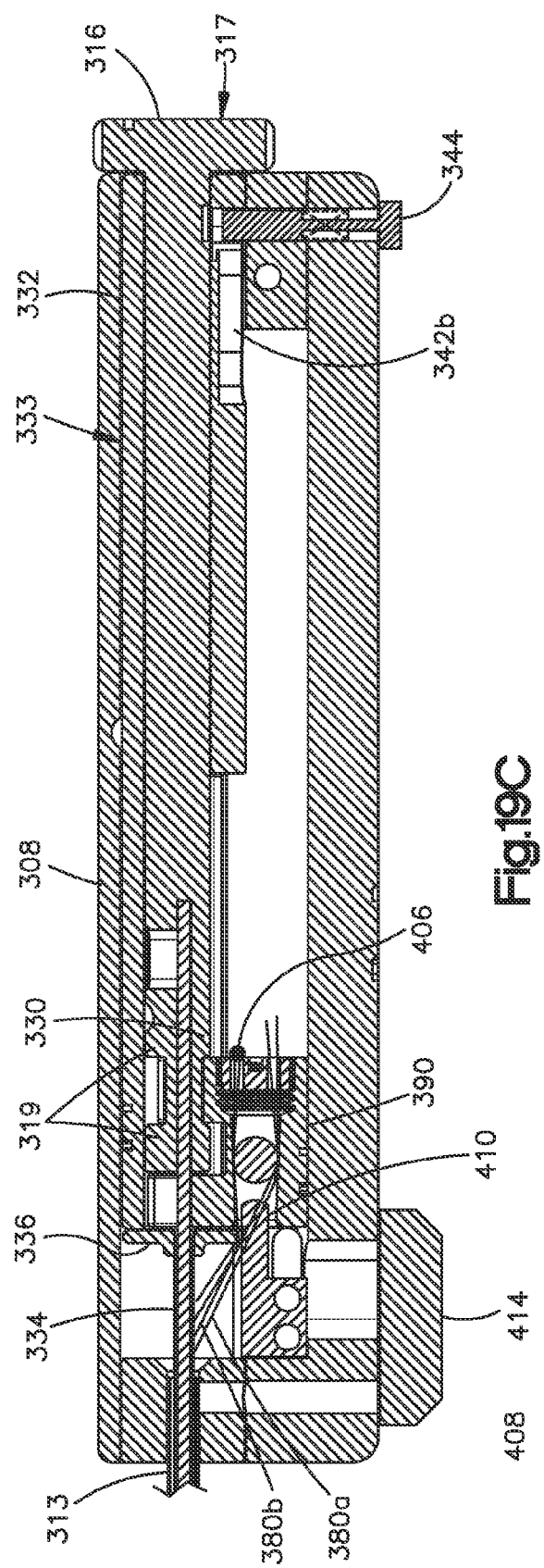
FIG. 19C is a sectional side elevation view of the casing of an insertion instrument similar to the insertion instrument as illustrated in FIG. 12C, but including a retention assembly constructed in accordance with an alternative embodiment.

Referring to FIG. 19C, the first pusher assembly 317 can include a pair of flanges 319 that project out from the plunger 316 so as to define a gap 321 that extends between the flanges 319. The gap 321 can be sized to receive the housing body 394, such that each of the flanges 319 abuts the proximal and distal ends of the housing body 394, respectively. Accordingly, proximal movement of the plunger 316 causes the distal one of the flanges 319 to bias the housing body 394 and thus the retention assembly 390, to move proximally along with the plunger 316, and therefore also along with the push rod 330. Similarly, distal movement of the plunger 316 causes the proximal one of the flanges 319 to bias the housing body 394 and thus the retention assembly 390, to move distally along with the plunger 316, and therefore also along with the push rod 330.

During operation, because the plunger 316 and the push rod 330 move distally in tandem along the first stroke and the second stroke, and because the first and second anchor bodies 28a and 28b move distally along with the push rod 330, the retention assembly 390 likewise moves distally along with the first and second anchor bodies 28a and 28b. Accordingly, the retention assembly 290 can operate so as to not induce tension in either of the first and second tensioning strands 380a and 380b, and thus in the respective first and second actuation strands 38a and 38b, before the first and second anchor bodies 28a and 28b have been ejected from the cannula 310. However, as will now be described, the insertion instrument 300, and in particular the plunger 316, can be actuated so as to apply the respective first and second actuation forces to the first and second anchor bodies 28a and 28b after the first and second anchor bodies have been ejected from the cannula 310.

For instance, referring now to FIGS. 8A-D and FIGS. 19A-B, once the plunger 316 has traveled along the first stroke, thereby ejecting the second bone anchor 28b from the cannula 310 at a location behind the anatomical structure 24 and the second anatomical location 24b, the plunger 316 can be translated proximally such that the guide pin 344 rides along the first track portion 342a along the distal direction until contacting the collar 332, which provides stop surface at the distal end of the first track portion 342a, thereby preventing further proximal translation of the plunger. Because contact between the anatomical structure 24 and the second anchor body 28b prevents the second anchor body 28b from translating proximally along with the retention assembly 390, the retention assembly 390 applies a tensile force to the tensioning strand 380b, which is communicated to the second actuation strand 38b as the actuation force that causes the second anchor body 28b to move from the first configuration illustrated in FIG. 9A to the expanded configuration illustrated in FIG. 9E.

For instance, referring now to FIGS. 9A-E and FIGS. 19A-B, once the plunger 316 has traveled along the first stroke, thereby ejecting the second bone anchor 28b from the cannula 310 at a location behind the anatomical structure 24 at the second anatomical location 24b, the insertion instrument 300 can be translated proximally as it is removed from the anatomical tissue 24 as described above. Because contact between the anatomical structure 24 and the second anchor body 28b prevents the second anchor body 28b from translating proximally along with the insertion instrument 300, the retention assembly 390 applies a tensile force to the tensioning strand 380b, which is communicated to the second actuation strand 38b as the actuation force that causes the second anchor body 28b to move from the first configuration illustrated in FIG. 9A to the expanded configuration illustrated in FIG. 9E.

Similarly, referring now to FIGS. 18A-E and FIGS. 19A-B, once the plunger 316 has traveled along the second portion of the second stroke, thereby ejecting the first bone anchor 28a from the cannula 310 at a location behind the anatomical structure 24 at the first anatomical location 24a, the insertion instrument 300 can be translated proximally as it is removed from the anatomical tissue 24. Because contact between the anatomical structure 24 and the first anchor body 28a prevents the first anchor body 28a from translating proximally along with the retention assembly 390, the retention assembly 390 applies a tensile force to the first tensioning strand 380a, which is communicated to the first actuation strand 38a as the actuation force that causes the first anchor body 28a to move from the first configuration illustrated in FIG. 12A to the expanded configuration illustrated in FIG. 12E.

Once the first and second anchor bodies 28a and 28b have been actuated to their expanded configurations, the tensioning strands 380a and 380b can be released from the retention assembly 390. For instance, as will now be described, the retention assembly 390 can configured to release at one of the ends of the tensioning strands 380a and 380b. Alternatively, as described in more detail below, the insertion instrument 300 can include a cutting blade that is configured to sever the first and second tensioning strands 380a and 380b. Referring to FIG. 19C, the insertion instrument 300 can include a release member 408 that is coupled to the retention assembly 390 and is configured to iterate the retention assembly 390 to an unlocked configuration. The release member 480 can include any suitable linkage 410 that can be aligned with the first locking member 400. The release member 408 can include an actuator 414 that is carried by the casing 308 and coupled to the linkage 410, such that a user can manipulate the actuator 414, for instance slide the actuator proximally, so as to cause the linkage 410 to contact the first locking member 400 and bias the first locking member 400 proximally along the direction of Arrow 401 to an unlocked configuration, which creates a gap 412 between the first locking member 400 and the interior surface 398, as illustrated in FIG. 19B. The gap can be greater than a cross-sectional dimension of the tensioning strands 380a and 380b.

When the second ends 380a" and 380b" are tied at the second locking member 402, proximal translation of the insertion instrument 300 relative to the implanted anchor bodies 28a and 28b, causes the first ends 380a' and 380b' of the first and second tensioning strands 380a and 380b to travel out the retention assembly 390 through the gap, and further draws the respective first and second tensioning strands 380a and 380b through the respective actuation strands 38a and 38b, thereby removing the first and second tensioning strands 380a and 380b from the actuation strands 38a and 38b as illustrated in FIGS. 18C-18D. Alternatively, if the first and second ends 380a" and 380b" are retained by the first locking member 400 and not the second locking member 402, proximal translation of the insertion instrument 300 relative to the implanted anchor bodies 28a and 28b removes the tensioning strands 380a and 380b from the insertion instrument 300. The user can then manually draw the tensioning strands 380a and 380b through the respective actuation strands 38a and 38b so as to remove the first and second tensioning strands 380a and 380b from the actuation strands 38a and 38b.

Referring now to FIG. 18D, once the tensioning strands 380a and 380b have been removed from the actuation strands 38a and 38b, the user can draw the connector 63 toward the anatomical structure. It should be appreciated that the connector 63 can be attached to the actuation strands 38a and 38b when the first and second anchor bodies 28a and 28b are loaded in the insertion instrument 300. Alternatively, the user can connect the actuation strands 38a and 38b after the first and second anchor bodies 28a and 28b have been ejected. While the connector member 63 illustrated in FIGS. 18C-E is configured as a knot of the type described above, the connector member 63 can be alternatively configured as desired. In accordance with the embodiment illustrated in FIGS. 18C-E, a tensile force can be applied to the free end 70, which causes the connector member to translate toward the anatomical structure, thereby applying an approximation force to the actuation strands 38a and 38b, thereby approximating the tissue gap 24c. The portion of the actuation strands 38a and 38b that extend out from the connector member 63 can then be severed as desired.

Referring now to FIGS. 20A-B, and as described above, the insertion instrument 300 can include a cutting assembly 416 that includes a cutting blade 418, and is movable between a disengaged position whereby the cutting blade 418 is spaced from one of the ends, such as the first ends 380a' and 380b' of the tensioning strands 380a and 380b that are retained by the retention assembly 390, and an engaged position whereby the cutting blade severs the first ends 380a' and 380b' of the tensioning strands 380. It should be appreciated that the retention assembly 390 illustrated in FIGS. 20A-B can be configured as illustrated in FIG. 17, and that the retention assembly 390 can be attached to a single tensioning strand, such that the cutting blade 418 is configured to cut a first end of the single tensioning strand, such that removal of the insertion instrument 300 from the anchor bodies 28a and 28b draws the tensioning strand through and away from actuation strands 38a and 38b.

The cutting assembly 416 can include a longitudinally elongate shaft 420, and a switch 422 that is pivotally coupled between the elongate shaft 420 and the cutting blade 418, thereby coupling the elongate shaft 420 to the cutting blade 418. The cutting blade 418 can be carried by a blade housing 424, such that the elongate shaft 420 and the switch 422 are indirectly coupled to the cutting blade 418. The proximal end of the longitudinally elongate shaft 420 can extend proximally out of the casing 408, and the longitudinal shaft can extend in a side wall of the casing 408. The shaft 420 is movable longitudinally in the distal direction from a disengaged position to an engaged position. Distal movement of the shaft 420 causes the switch to pivot, thereby driving the cutting blade 418 to translate proximally and into the first ends 380a' and 380b' of the first and second tensioning strands 380a and 380b, thereby severing the first ends 380a' and 380b'. Once the tensioning strands 380a and 380b have been severed, the instrument can be translated proximally with respect to the ejected anchor bodies 28a and 28b so as to remove the tensioning strands 380a and 380b from the respective actuation strands 38a and 38b in the manner described above.

Referring now to FIGS. 21A and 21B, it should be appreciated that the cutting assembly 416 can be constructed in accordance with any alternative embodiment as desired. For instance, the cutting assembly 416 can include an actuator 426 that extends laterally out the side wall of the casing 408 along a direction angularly offset with respect to the longitudinal direction L, and is movable radially inward from the disengaged position to the engaged position. The actuator 426 can carry the cutting blade 418. Accordingly, as the actuator 426 moves radially inward, the cutting blade 418 severs the first and second ends 380a' and 380b' of the actuation strands 380a and 380b. The insertion instrument 300 can include a divider wall 428 that separates the first and second ends of the actuation strands 380a and 380b and is aligned with the cutting blade 418. Accordingly, the cutting blade 418 drives into the divider wall 428 and does not sever the second ends of the first and second actuation strands 380a and 380b. Of course, it should be appreciated that a single tensioning strand can be coupled to the actuation strand 38 of the anchor assembly 20 as described above, such that the cutting blade 418 can cut one of the first and second ends of the single tensioning strand.

Referring now to FIGS. 22A-D generally, the insertion instrument 300 can be constructed substantially as described above with respect to FIG. 7A-21B, but can include the guide system 329 that operably couples the casing 308 and the push rod 330 so as to guide relative movement between the casing 308 and the push rod 330 in accordance with another embodiment. For instance, the guide track 342 can be defined in the collar 332 as described above, but extends substantially linearly along the longitudinal direction L. Accordingly, as the plunger translates distally along the first and second strokes, the guide track 342 translates linearly with respect to the guide pin 344. It should be appreciated in the embodiment illustrated in FIGS. 22A-D, the second recess 362 illustrated in FIGS. 13C-E can be longitudinally aligned with the first recess 354, such that the latch 370 moves from the first recess 354 into the second recess 362 so as to decouple the plunger 316 from the collar 332 without rotating the plunger 316. The plunger 316 can include a shaft portion 430 that defines a portion of the key 318 as described above, and a distal end cap that can define a grip portion 432 that extends radially out from the proximal end of the shaft portion 430. The collar 332 can extend at least partially around the shaft portion 430, and can extend radially out from the shaft portion 430 in accordance with the illustrated embodiment.

The insertion instrument 300 can further include a clip 434 that has a longitudinal length substantially equal to the longitudinal distance between the grip portion 432 of the plunger 316 and the proximal end of the collar 332 when the plunger 316 is in the first position. The clip 434 can be removably secured to the shaft portion 430 of the plunger 316. Thus, as the plunger 316 translates distally, the grip portion 432 biases the clip 434 against the collar 332, which causes the collar 332 to translate along with the plunger 316. It should therefore be appreciated that the clip 434 couples the plunger 316 and the collar 332 with respect to distal translation along the longitudinal direction L. Accordingly, during operation, the plunger 316 and collar 332 can be translated distally from the first position to the second position in tandem along the first stroke in the manner described above. As the plunger 316 and collar 332 move along the first stroke, the guide pin 344 translates proximally within the entire guide track 342. The plunger 316 and collar 332 reach the second position when the clip 434 abuts the casing 308, at which point the latch member 370 moves from the first recess 354 into the second recess 358 as described above with respect to FIGS. 14C-D. Next, the clip 434 can be removed from the plunger 316, and the plunger 316 can translate distally with respect to the collar 332 along the second stroke. It should be appreciated that the plunger 316 can translate along the entire second stroke independent of the collar 332.

Accordingly, the push tube 334 ejects the second anchor body 38*b* as described above with respect to FIGS. 9A-E after the plunger and collar 332 have moved along the first stroke from the first position to the second position. Thus, the plunger 316 can be depressed a first distance that causes the second anchor body 28*b* to be ejected from the insertion instrument, and the clip 434 abuts the casing 308 once the plunger 316 has been depressed the first distance so as to prevent the plunger 316 from being depressed a second distance greater than the first distance until the collar 434 is removed from the plunger 316. The push rod 330 can then eject the first anchor body 28*a* after the plunger 136 has moved from the second position to the third position along the second stroke in the manner described above with respect to FIGS. 12A-E. The guide pin 344 can abut the proximal end of the guide track 342 when the second stroke has been completed. Furthermore, the grip portion 432 of the plunger 316 can abut the casing 308 once the plunger 316 has completed the second stroke and has moved to the third position. It should be appreciated in the embodiment illustrated in FIGS. 22A-D that because the plunger 316 is rotatably keyed to the collar 332 and thus rotatably fixed to the collar 332, and because the latch 370 (described above) rotatably couples the collar 332 to the casing 308, the plunger 316 is unable to rotate with respect to the casing 308 as the plunger 316 translates along the second stroke. Alternatively, the insertion instrument can be configured to allow the plunger 316 to rotate as desired so as to align the latch 370 with the second recess 362, as described above.

Figure 23A:
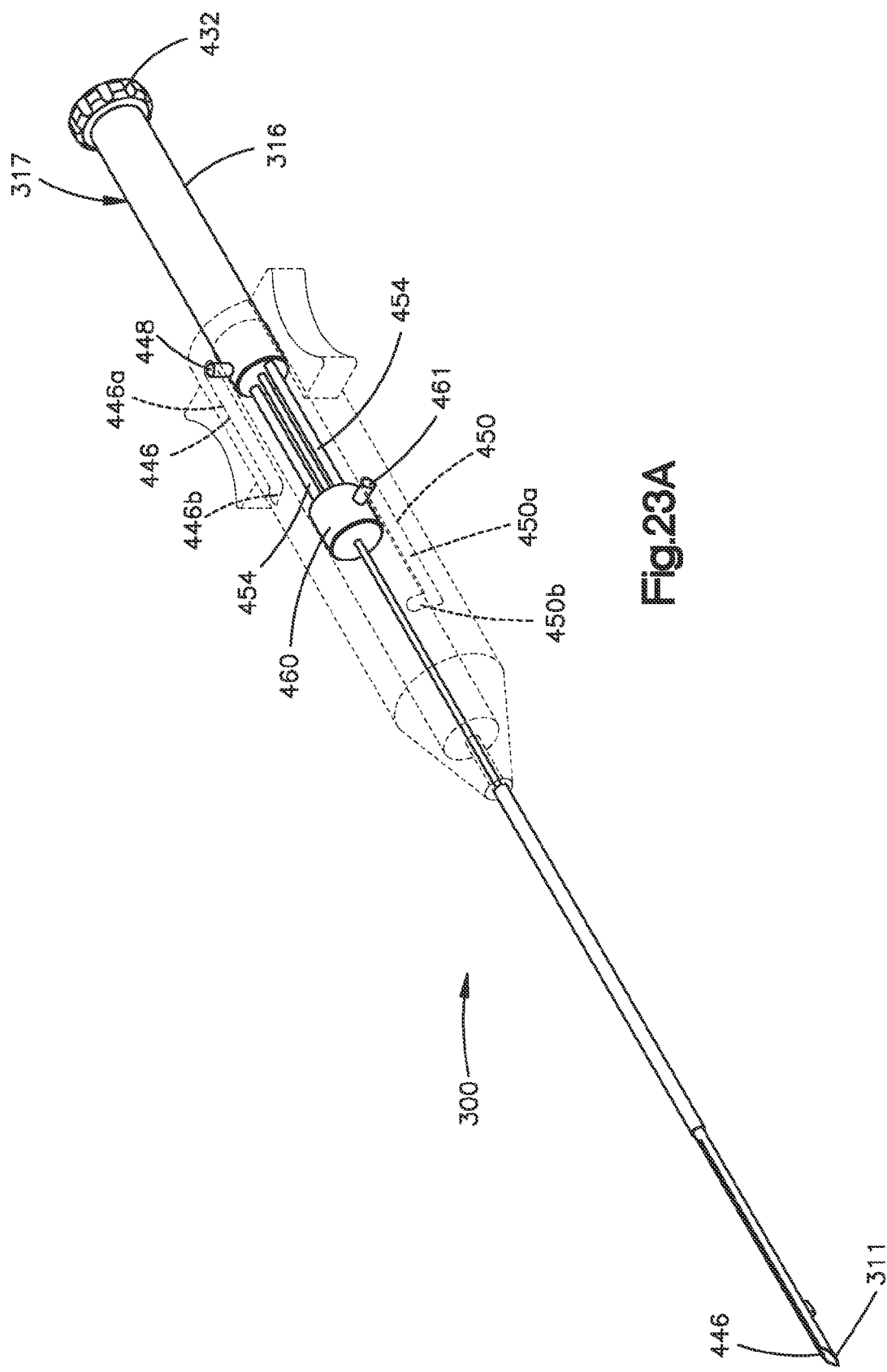
FIG. 23A is a perspective view of an insertion instrument constructed similar to the insertion instrument illustrated in FIG. 7A, but constructed in accordance with another embodiment, and shown in a first position.

As described above with respect to the insertion instrument illustrated in FIGS. 7A-13G, the guide track 342 can be carried by the casing 308, and the guide pin 344 can be carried by one of the pusher assemblies. Referring now to FIG. 23A, the insertion instrument 300 includes at least one guide track, such as a first guide track 446 that is carried by the casing 308, and at least a one guide member such as a first guide pin 448 carried by the pusher assembly 317, and in particular carried by the plunger 316, that rides in the first guide track 342.

As illustrated in FIG. 23B, the shaft portion 430 of the plunger 316 defines a distal surface 431, and further defines a first central aperture 440 that extends longitudinally into, or distally into, the distal surface 431. The shaft portion 430 of the plunger 316 further defines a radial aperture 435 that receives the guide pin 448. The first aperture 440 receives the push rod 330, such that the plunger 316 and the push rod 330 are coupled to each other with respect to both longitudinal translation and rotation. As illustrated in FIG. 23D, the push rod 330 extends from the plunger 316 and into the cannula 310, which is fixed to the casing 308 with respect to translation and rotation. Referring also to FIG. 23C, the tip 311 can be cannulated so as to define a distal ejection port 442 that is substantially aligned with the longitudinal axis 302, and thus also substantially aligned with the elongate opening 312 of the cannula 310. The push rod 330 is movable longitudinally inside the channel 312 in the manner described above. It should be appreciated that the insertion instrument 300 can alternatively define a side ejection port constructed substantially as described below. The cannula 310 can define a longitudinal slot 337, such that the attachment portions 133*a* and 133*b* of the actuation strands 38*a* and 38*b* (see FIG. 1A) that attach the first anchor body 28*a* to the second anchor body 28*b* can extend out the slot 337.

Referring now also to FIGS. 23D-E, the insertion instrument includes a guide system 444 that is configured to operably couple the casing 308 to the push rod 330 so as to guide relative movement between the casing 308 and the push rod 330. For instance, the guide system 444 includes the first guide member in the form of the first guide track 446 that is carried by the casing 308, and the second guide member illustrated as the first guide pin 448 that extends from the pusher assembly 317. The first guide track 446 can be configured as a slot that extends radially outward into the radially inner surface of the casing 308. Furthermore, in accordance with the illustrated embodiment, the first guide pin 448 extends radially out from the shaft portion 430 of the plunger 316, and rides within the first guide track 448. The first guide track 446 defines a first track portion 446*a* that extends substantially longitudinally, and an intermediate track portion 446*b* that extends circumferentially from the distal end of the first track portion 446*a*.

With continuing reference to FIG. 23E, the guide system 444 further includes a third guide member configured as a second guide track 450 that is carried by the casing 308, and is configured as a slot that extends radially outward into the inner surface of the casing 308. The second guide track 450 defines a first track portion 450*a* that extends substantially longitudinally, and an intermediate track portion 450*b* that extends circumferentially from the distal end of the second guide track 450*b*. The intermediate track portion 450*b* extends from the first track portion 450*a* the same direction that the intermediate track portion 446*b* extends from the first track portion 446*a*.

The first track portions 446*a* and 450*a* define a first stroke of movement for the plunger 316 that causes the push rod 330 to eject the second anchor out the ejection port 442. The intermediate track portions 446*ba* and 450*b* are configured such that the plunger is rotated so as to align a fifth guide member with a second track portion that is radially offset from the first track portions 446*a* and 450*a*. In particular, as illustrated in FIG. 23B, the insertion instrument 330 further includes a pair of apertures 452 that are disposed adjacent the central aperture 440 and extend longitudinally into the distal surface 431 of the shaft portion 430 of the plunger 416. The apertures 452 are each configured to receive respective fifth guide members configured as guide posts 454 (FIG. 23D) that extend distally from the plunger 416, and a sixth guide member illustrated as a guide housing 460 (FIG. 23E) that is disposed in the interior 328 of the casing 308 and fixed to the casing 308 with respect to translation. The guide housing 460 defines a seventh guide member configured as a radially outwardly extending second guide pin 461 that is configured to ride in the second guide track 450. The guide housing 460 further defines a guide member in the form of at least one aperture such as a pair of apertures that extend longitudinally through the guide housing 460 and define second track portions 462. The second track portions 462 are sized to receive the guide posts 454. The proximal end of the guide housing 460 can define a pair of recesses 464 that extend longitudinally into, but not through, the guide housing 460 at a location adjacent the second track portions 462. The recesses 464 can be arcuate shaped or alternatively shaped as desired.

Referring now to FIGS. 23A and 23F, a distal biasing force can be applied to the plunger 316, which causes the plunger 316 and the push rod 330 to translate distally along the first stroke with respect to the casing 308 and thus the cannula 310 and the guide housing 460. The plunger 316 translates from the first position illustrated in FIG. 23A to the second position illustrated in FIG. 23F. As the plunger 316 translates distally from the first position to the second position, the first guide pin 448 translates distally along the first track portion 446a of the first guide track 446 until the first guide pin 448 is aligned with the intermediate track portion 446b of the first guide track 446. Likewise, as the plunger 316 translates distally from the first position to the second position, the second guide pin 461 translates distally in the first track portion 450a of the second guide track 450 until the second guide pin 461 is aligned with the intermediate track portion 450b of the second guide track 450. Once the plunger 316 has translated to the second position, the guide posts 454 are circumferentially offset from the respective second track portions 462, and abut the guide housing 460, for instance in the recesses 464.

Referring now to FIG. 23G, the plunger 316 can be rotated along the direction of Arrow 456, which causes the first and second guide pins 448 and 461 to travel in the respective intermediate track portions 446b and 450b, until reaching the end of the intermediate track portions 446b and 450b, which define respective stops that prevent the plunger 316 from continuing to rotate relative to the casing 308, and further prevents the guide posts 454 from rotating relative to the guide housing 460. Once the plunger 316 has finished rotating, the guide posts 454 are aligned with the second track portions 462. Accordingly, as illustrated in FIG. 23H, the plunger 316 can be further translated distally along the second stroke from the second position to a third position, at which point the plunger 316 abuts the guide housing 460 and is prevented from traveling distally further. Thus, the guide housing 460 defines a stop that prevents the plunger 316 from translating distally beyond the third position.

As the plunger 316 translates along the second stroke, the push rod 330 translates distally within the channel 312 of the cannula 310, and ejects the first anchor body 28a out the ejection port 442. After each anchor body 28a and 28b has been ejected from the instrument to a location behind the anatomical structure 24 (see FIG. 1A), an actuation force can be applied to each anchor body 28a and 28b. For instance, the insertion instrument 330 can include a retention assembly of the type described above, such as the retention assembly 390 or any suitable alternatively constructed retention assembly. Alternatively, the user can manually apply the actuation force to the respective actuation strands 131a and 131b. A connector member can then attach the actuation strands 131a and 131b together in the manner described above.

Referring now to FIGS. 24A-25D generally, it should be appreciated that an insertion instrument can be configured having a first and second cannulas supported by the casing in a side-by-side orientation that retain first and second anchor bodies, and first and second pusher assemblies operatively associated with the first and second cannulas, respectively, so as to eject the first and second anchor bodies out the respective first and second cannulas. It can be desirable to ensure that a desired cannula from which the anchor body is to be ejected is distally disposed with respect to the other cannula, such that the desired cannula can be inserted into the underlying tissue without also inserting the other cannula.

Figure 24A:
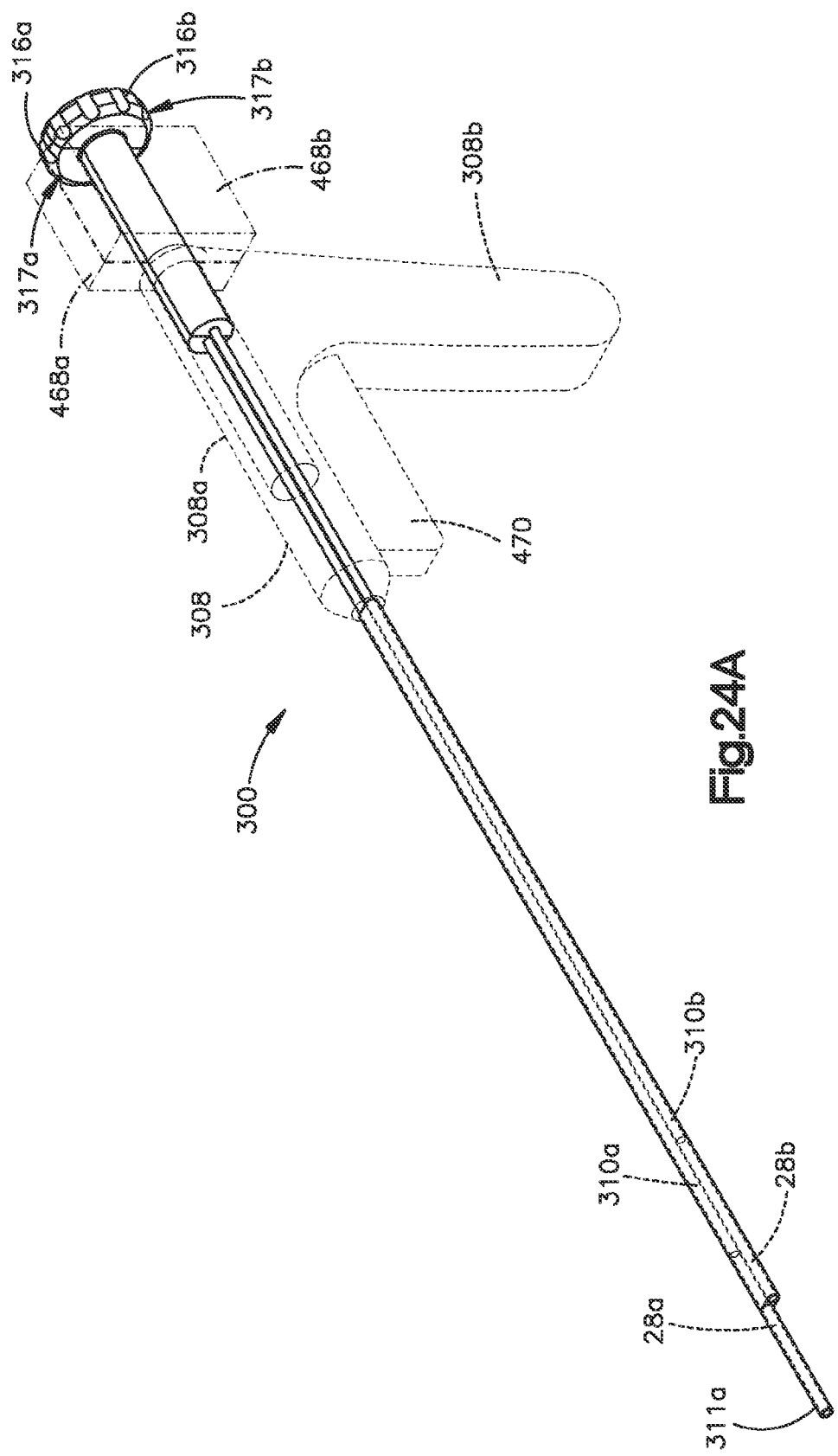
FIG. 24A is a perspective view of an insertion instrument including first and second pusher assemblies disposed in a side-by-side relationship, showing each of the pusher assemblies in a first position.

As illustrated in FIG. 24A, an insertion instrument 300 includes a casing 308 that includes a body portion 308a and a handle portion 308b that extends out from the body portion 308a. The insertion instrument 300 further includes a first cannula 310a that extends distally from the casing 308, and in particular from the body portion 308a, and a second cannula 310b that extends distally from the casing 308, and in particular from the body portion 308a, at a location adjacent the first cannula 310a. The first and second cannulas 310a and 310b can extend substantially parallel to each other as illustrated. Accordingly, the first and second cannulas 310a and 310b can be described as being in a side-by-side relationship. The first and second cannulas 310a and 310b can define respective longitudinally elongate channels 312a and 312b that retain respective first and second anchor bodies 28a and 28b.

The insertion instrument 300 can further include first and second pusher assemblies 317a and 317b operatively associated with the first and second cannulas 310a and 310b, respectively. Thus, the first pusher assembly 317a is configured to eject the first anchor body 28a out the first cannula 310a, and the second pusher assembly 317b is configured to eject the second anchor body 28b out the second cannula 310b. The first and second cannulas 310a and 310b can define respective first and second tapered tips 311a and 311b, and first and second distal ejection ports that extend longitudinally through the respective tips 311a and 311b.

Each of the first and second pusher assemblies 317a and 317b includes first and second plungers 316a and 316b, respectively, and first and second pusher rods 330a and 330b, respectively, that extend distally from the corresponding plungers 316a and 316b. Each of the plungers 316a and 316b define respective shaft portions 430a and 430b and respective end caps that can define first and second grip portion 432a and 432b that extends radially out from the proximal end of the corresponding shaft portions 430 and 430b. When the first and second plungers 316a and 316b are in their respective first positions, the first and second grip portions 432a and 432b are proximally spaced from the casing 308. The insertion instrument 300 can further include first and second lock-out tabs 468a and 468b that are removably attached to the first and second plungers 316a and 316b. For instance, in accordance with the illustrated embodiment, the first and second lock-out tabs 468a and 468b are attached to the respective first and second shaft portions 430a and 430b at a location longitudinally between the corresponding grip portions 432a and 432b and the casing 308. Accordingly, the first and second lock-out tabs 468a and 468b interfere with the respective grip portions 432a and 432b, and prevent the plungers 316 from translating distally relative to the casing 308 to a depth that would eject the respective first and second anchor bodies 28a and 28b.

The insertion instrument 330 can further include a swap actuator 470 in the form of a trigger that extends partially into the casing 308, and can extend out from the handle portion 308b. The swap actuator 470 is configured to be moved from a first position to an actuated position so as to reverse a relative position of the fist and second tips 311a and 311b. The swap actuator 470 can be coupled to the first pusher assembly 317a, such that proximal translation of the actuator 470 causes the first pusher assembly 317a, including the first plunger 316a and the first cannula 310a, to translate proximally. As illustrated in FIG. 24A, the first tip 311a of the first cannula 310a is disposed distally with respect to the second tip 311b of the second cannula 310b. Furthermore, the distal end of the second push rod 330b can extend slightly out from the respective second tip 311b, such that the longitudinal distance between the distal end of the second push rod 330b and the distal end of the first tip 311a defines an insertion depth into underlying tissue. Otherwise stated, the second push rod 330b can define a depth stop for insertion of the first tip 311a into underlying tissue. It should thus be appreciated that the first tip 311a can be injected into underlying tissue, for instance at the first target anatomical location 24a (see FIG. 1A) without causing the second tip 311b to inject into the underlying tissue. As is described in more detail below, actuation of the swap actuator 470 from a first position to a second position causes the first tip 311a to move proximally with respect to the casing 308 and the second tip 311b, such that the second tip 311b can be injected into the underlying tissue, for instance at the second target anatomical location 24b (see FIG. 1B) without causing the first tip 311a to inject into the underlying tissue.

Figure 24B:
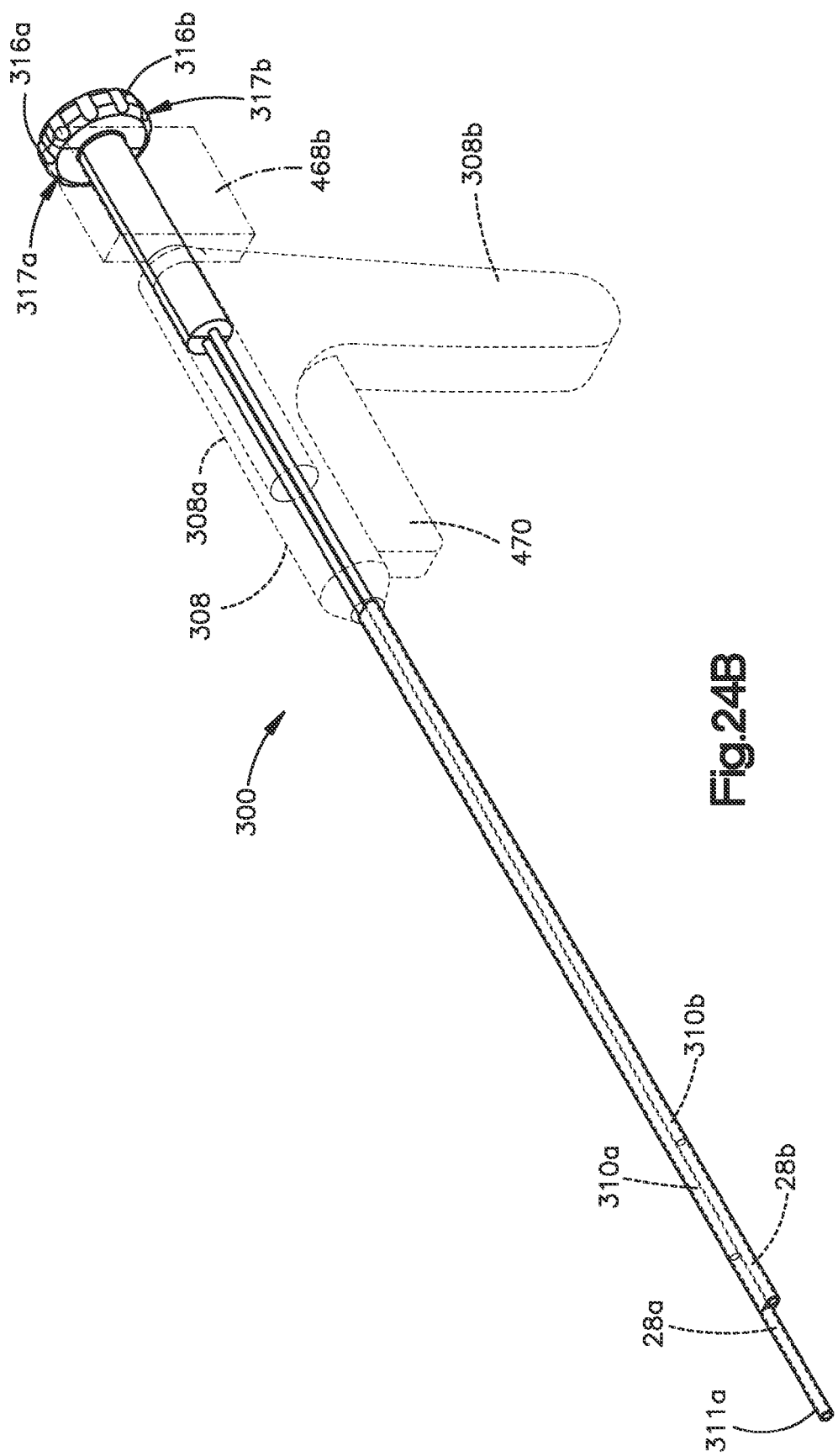
FIG. 24B is a perspective view of the insertion instrument illustrated in FIG. 24A, after removal of a first lockout tab from the first pusher assembly.

During operation, referring to FIG. 24B, the first lock-out tab 468a can be removed from the first plunger 316a, such that the first plunger 316a can travel distally with respect to the casing 308 from the first position illustrated in FIG. 24A to a second position as illustrated in FIG. 24C, whereby the first grip portion 432a abuts the casing 308. Because the first push rod 330a is translatably fixed to the first plunger 316a, distal translation of the first plunger 316a causes the first push rod 330a to likewise translate in the first cannula 310a. The first push rod 330a abuts the first anchor body 28a, such that distal translation of the first push rod 330a ejects the first anchor body 28a out the first ejection port, for instance into the first target anatomical location.

Figure 24D:
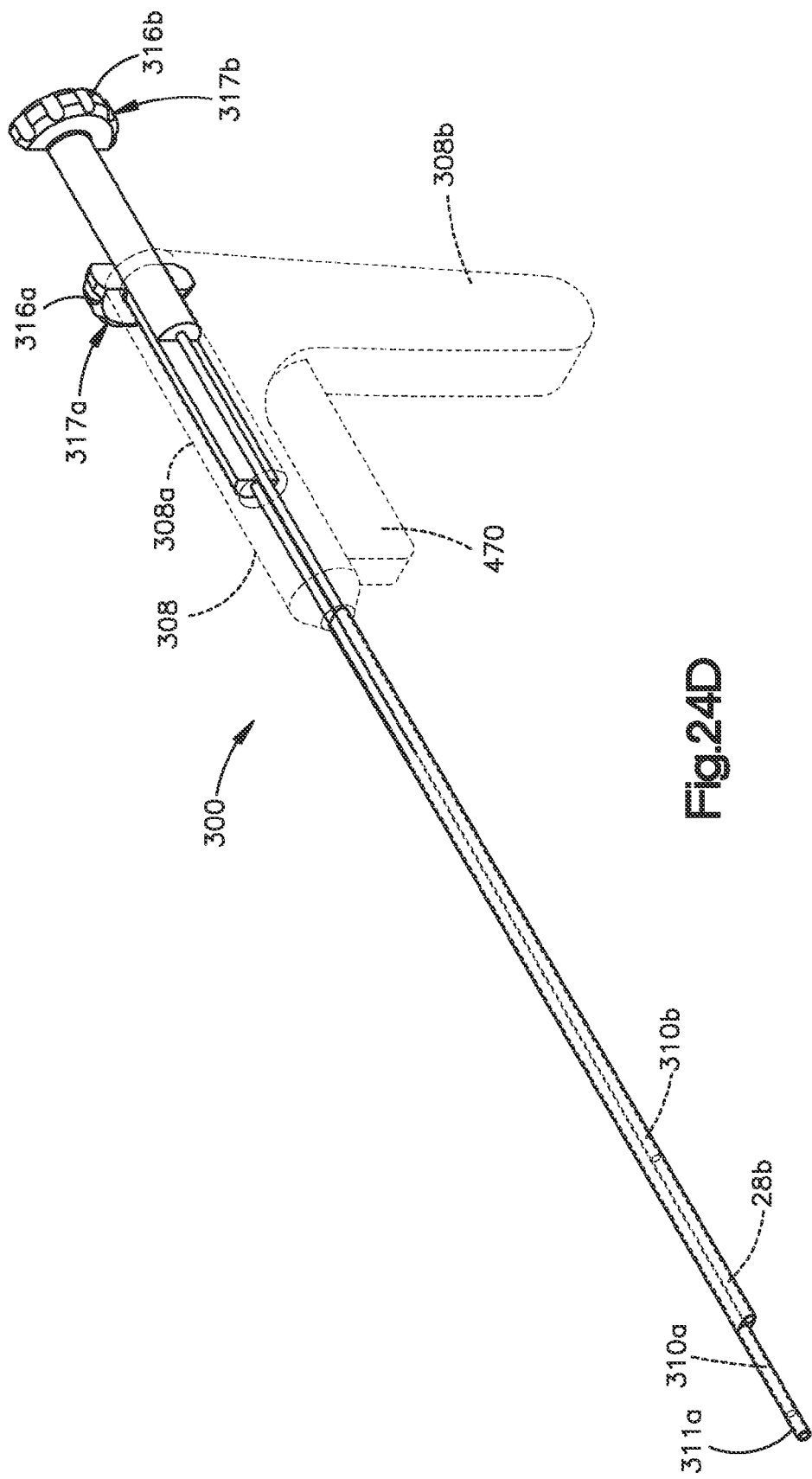
FIG. 24D is a perspective view of the insertion instrument illustrated in FIG. 24C, after removal of a second lockout tab from the second pusher assembly.

Next, referring to FIG. 24D, the second lock-out tab 468b can be removed from the second plunger 316b, as illustrated in FIG. 24D. Referring to FIG. 24E, the swap actuator 470 can be actuated, for instance can be moved proximally, to retract the first tip 311a proximally with respect to the second cannula 310b until the first tip 311a is disposed proximally with respect to the second tip 311b. Furthermore, the distal end of the first push rod 330a can extend slightly out from the respective first tip 311a, such that the longitudinal distance between the distal end of the first push rod 330a and the distal end of the second tip 311b defines an insertion depth of the second tip 311b into the underlying anatomical structure. Otherwise stated, the first push rod 330a can define a depth stop for insertion of the second tip 311a into underlying tissue. It should thus be appreciated that the second tip 311b can be injected into underlying tissue, for instance at the second target anatomical location 24b (see FIG. 1A) without causing the first tip 311a to inject into the underlying tissue. In accordance with the illustrated embodiment, actuation of the swap actuator 470 further causes the first plunger 316a to translate proximally to the first position illustrated in FIG. 24A.

Figure 24F:
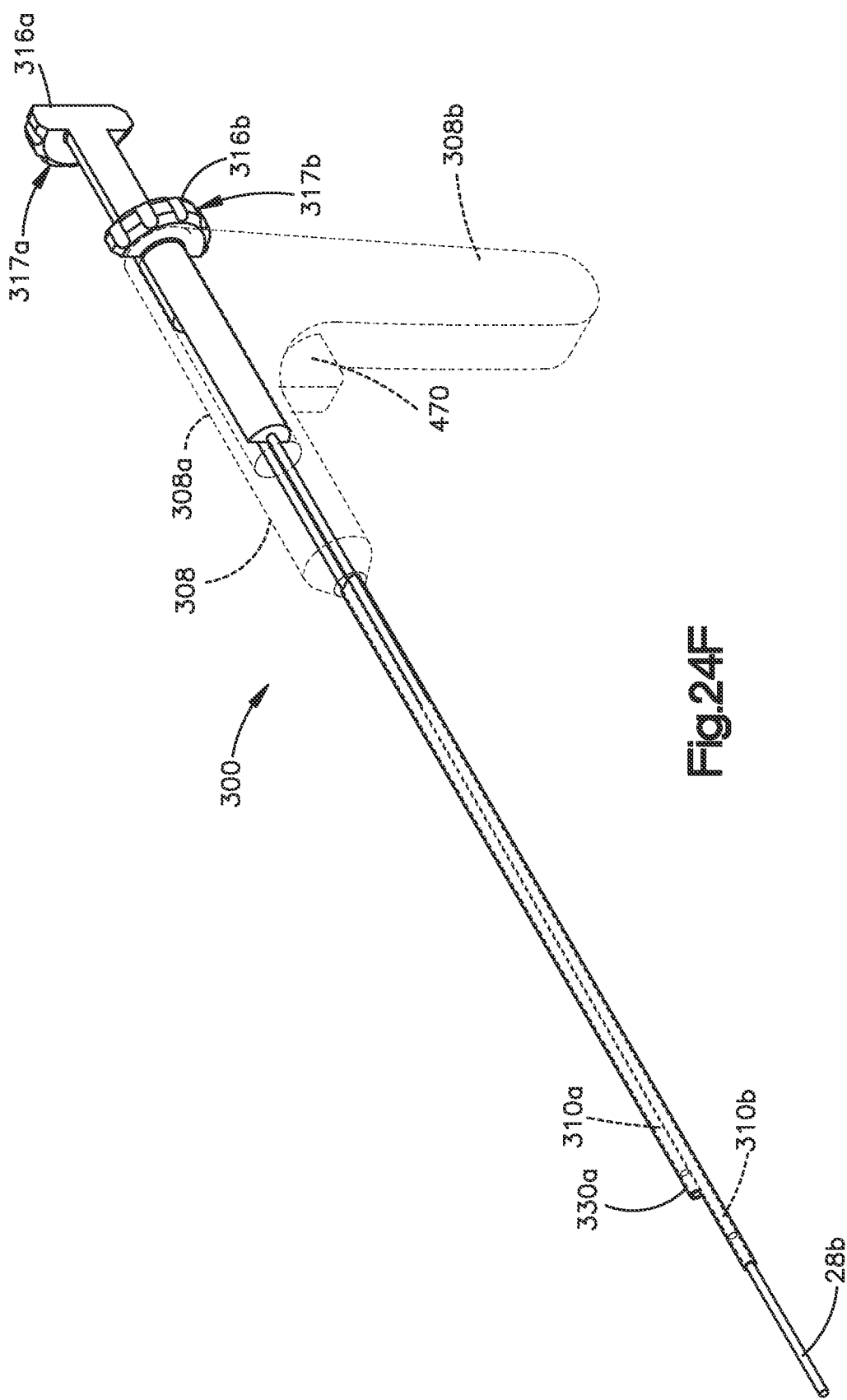
FIG. 24F is a perspective view of the insertion instrument illustrated in FIG. 24E, after actuation of the second pusher assembly to a second position.
Figure 25C:
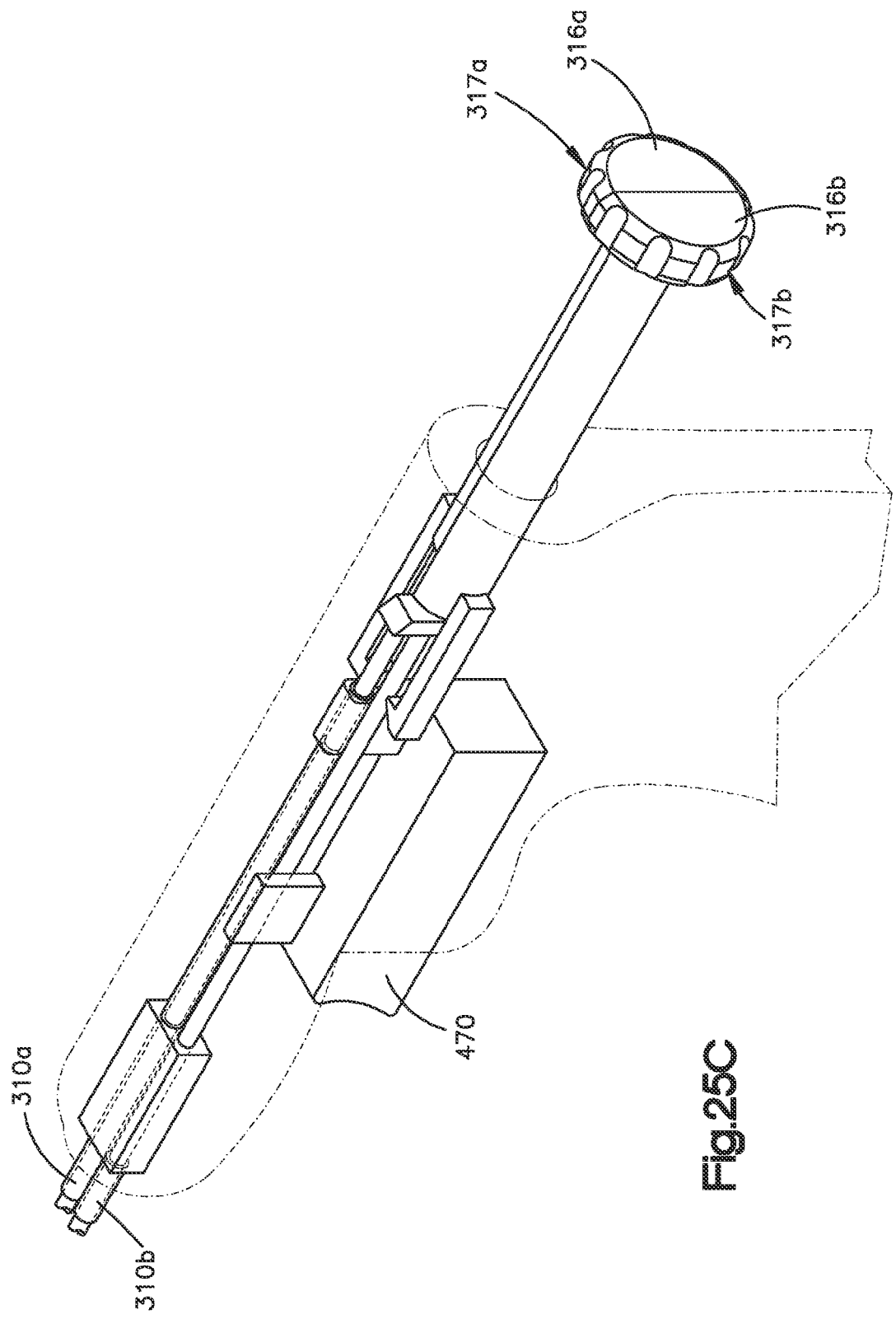
FIG. 25C is a perspective view of the components of the insertion instrument illustrated in FIG. 25B, after actuation of the swap actuator.
Figure 25D:
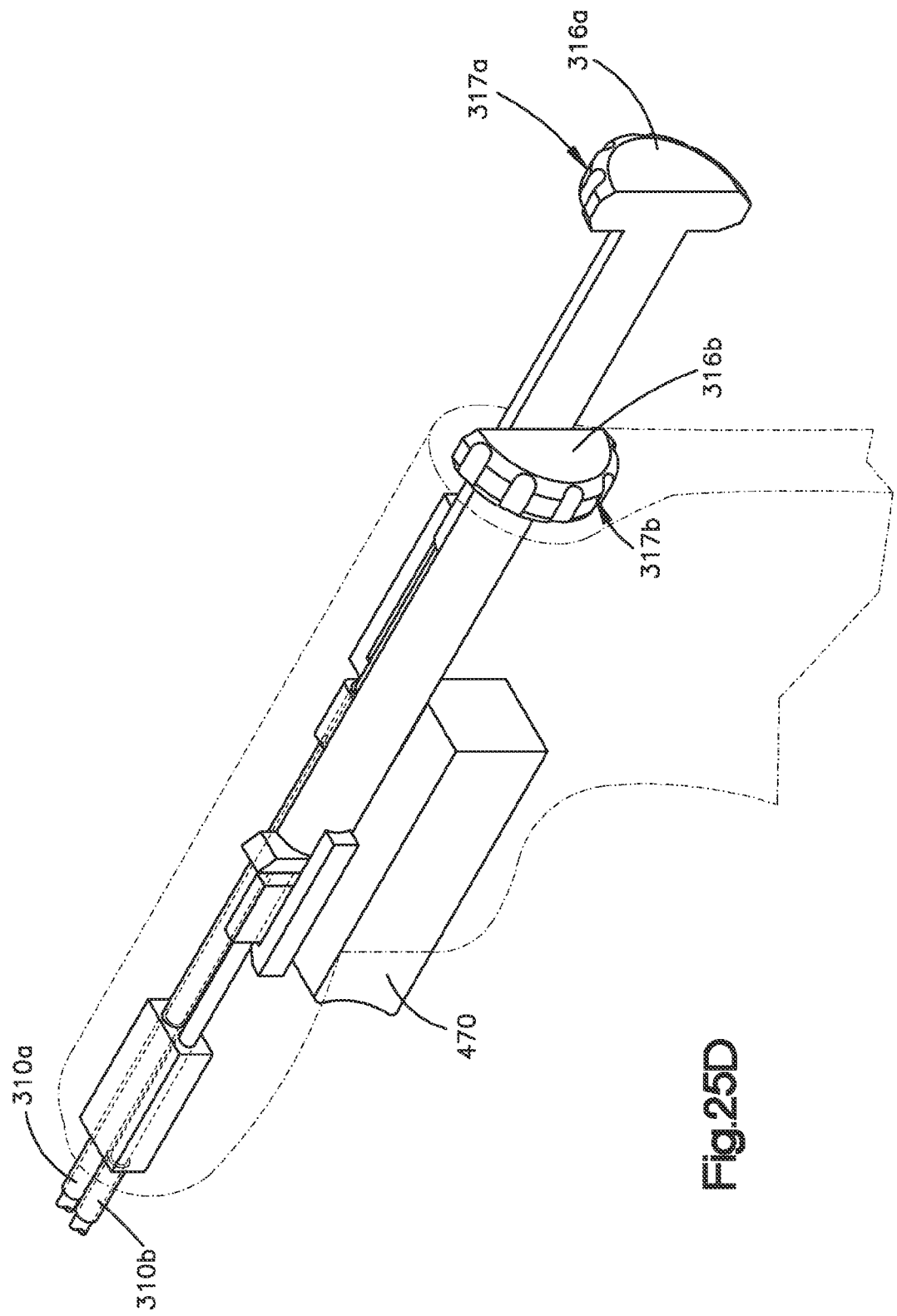
FIG. 25D is a perspective view of the components of the insertion instrument illustrated in FIG. 25C, after the second pusher assembly has been actuated to the second position.

Referring now to FIG. 24F, the second plunger 316b can travel distally with respect to the casing 308 from the first position illustrated in FIG. 24E to a second position as illustrated in FIG. 24F whereby the second grip portion 432b abuts the casing 308. Because the second push rod 330b is translatably fixed to the second plunger 316b, distal translation of the second plunger 316b causes the second push rod 330b to likewise translate in the second cannula 310b, thereby ejecting the second anchor body 28b out the second ejection port 442b and into the second target anatomical location.

Operation of the insertion instrument 300 illustrated in FIGS. 24A-25D will now be further described with particular reference to FIGS. 25A-D. In particular, the insertion instrument 300 includes at least one latch assembly such as a first latch assembly 305a, a second latch assembly 305b, and a third latch assembly 305c. The first latch assembly 305a is configured to lock the swap actuator 470 in its proximal position once it has been moved proximally from a first position illustrated in FIG. 24D to a second recessed position illustrated in FIG. 24E. For instance, the first latch assembly 305 can include a latch member 307 that is supported by the casing 308 extends proximally toward a proximal abutment surface 307a configured to abut the swap actuator 470 once the swap actuator 470 is in its second proximal position, thereby interfering with distal movement of the swap actuator 470 relative to the casing 308. As the swap actuator 470 moves proximally, the latch member 307 can deflect inwardly away from the swap actuator 470 so as to allow proximal translation of the swap member 470 relative to the latch member 307. Once the swap actuator 470 has been moved from its first initial position to its second proximal position relative to the casing 308, the latch member 307 moves outward under its spring force such that the proximal abutment surface 307a abuts the swap actuator 470 and prevents the swap actuator 407 from moving distally from its second position with respect to the casing 308.

The second latch assembly 305b includes a first latch member 347 carried by the swap actuator 470 and movable with the swap actuator 470, and a second latch member 349 that is carried by the first plunger 316a, and is movable with the first plunger 316a. The first latch member 347 is attached to the first cannula 310a, such that the first latch member 347 causes the first cannula 310a to translate with the swap actuator 470. The second latch member 349 includes a body 349a, a first attachment portion such as a hook at the distal end of the body 349a, and a second attachment portion such as an abutment surface at the proximal end of the body (the second latch member 349 can be constructed as the mirror image of the second latch member 353 of the third latch assembly 305c described below). Accordingly, as the first plunger 316a is translated from its first position illustrated in FIG. 24A to its second position illustrated in FIG. 24B, the hook deflects inwardly away from the first latch member and rides along and past the first latch member 347. Once the first plunger 316a is in its second position illustrated in FIG. 24B such that the first anchor body 28a has been ejected, the hook of the second latch member 349 moves outward under its spring force such that the hook is disposed distal of the first latch member 347, and the abutment surface of the second latch member is disposed proximal of the first latch member 347. Accordingly, the first latch member 347 is captured between the hook of the second latch member 349 and the abutment surface of the second latch member 349. Thus, the first and second latch members 349 are coupled with respect to translation.

Accordingly, once the first anchor body 28a has been ejected from the first cannula 310a, the second latch member 349 is attached to the first latch member 347, which translatably couples the first plunger 316a to the swap actuator 470 with respect to translation. Furthermore, because the first latch member 347 is carried by the swap actuator 470 and is further attached to the first cannula 310a, movement of the swap actuator 470 proximally causes both the first cannula 310a and the first plunger 316 to move proximally to a position whereby the first tip 311a and the first push rod 330a are disposed proximal with respect to the second tip 311b, while the first push rod 330a remains disposed distal of the first tip 311a. Furthermore, because the first plunger 316a is coupled to the swap actuator 470 with respect to relative translation both proximally and distally, and because the swap actuator 470 is coupled to the casing 308 with respect to at least proximal translation, the first plunger 316 is prevented from translating proximally with respect to the casing 308 once the first anchor body 28a has been ejected. The first push rod 330a can thus provide an insertion depth stop for the second tip 311b as described above.

The third latch assembly 305c includes a first latch member 351 carried by the casing 308, and a second latch member 353 carried by the second plunger 316b. The second latch member 353 includes a body 353a, a first attachment portion 353b such as a hook at the distal end of the body 353a, and a second attachment portion 353c such as an abutment surface disposed at the proximal end of the body 353a. When the second plunger 316b is translated distally from its first position illustrated in FIG. 24E to its second distal position illustrated in FIG. 24F, for instance when ejecting the second anchor body 28b, the hook can deflect inwardly, away from the first latch member 351 and ride along and move past the first latch member 351. Once the second plunger 316b is in its second position illustrated in FIG. 24F such that the second anchor body 28b has been ejected, the hook of the second latch member 353 moves outwardly under its spring force at a location distal of the first latch member 351, and the abutment surface of the second latch member 353 is disposed proximal of the first latch member 351. The first latch member 351 is thus captured between the hook of the second latch member 353 and the abutment surface of the second latch member 353. As a result, the second plunger 316b is prevented from moving proximally or distally with respect to the casing 308 once the second anchor body 28b has been ejected, and the blunt distal end of the second push rod 330b remains distal to the second tip 311b.

Once the anchor bodies 28a and 28b have been ejected, a tensile force can be applied to the actuation portions 131a and 131b (see FIG. 1A) so as to expand the anchor bodies 28a and 28b in the manner described above. For instance, first and second tensioning strands 380a and 380b (see FIGS. 18A-18B) can be attached between the respective actuation portions 131a and 131b, and the respective lock-out tabs 468a and 468b. Accordingly, after the lock-out tabs 468a and 468b have been removed from the respective plungers 316a and 316b and the respective first and second anchor bodies 28a and 28b have been ejected, proximal movement of the lock-out tabs 468a and 468b with respect to the anchor bodies 28a and 28b causes the tensile force to be applied to the corresponding tensioning strands 380a and 380b, which communicates the tensile force to the actuation portions 131a and 131b so as to expand the anchor bodies 28a and 28b. Alternatively, the tensioning strands 380a and 380b can be secured in the casing 308 in any manner described above.

Referring now to FIGS. 26A-B, the insertion instrument 300 can include a retention assembly 490 constructed in accordance with an alternative embodiment that is configured to apply an actuation force to the first and second actuation strands 38a and 38b (see FIG. 1A). For instance, the retention assembly 490 can retain the first and second actuation strands 38a and 38b directly. In accordance with the illustrated embodiment, the retention assembly 490 retains both the actuation portions 131a and 131b and the attachment portions 133a and 133b of the first and second anchor bodies 28a and 28b, respectively, for instance when the attachment portions 133a and 133b are not attached when loaded in the insertion instrument 300. Alternatively, if the attachment portions 133a and 133b are pre-attached to each other when loaded in the insertion instrument 300, the retention assembly can retain only the actuation portions 131a and 131b. Alternatively still, as described above, at least one tensioning strand can be stitched through the first and second actuation strands 38 and 38b, respectively, and can further be retained in the retention assembly 490. Regardless of the configuration, the retention assembly can be configured to apply an actuation force to the actuation strands 38a and 38b that causes the respective anchor bodies 28a and 28b to move to their expanded configurations.

In accordance with the illustrated embodiment, the retention assembly 490 can be mounted to either or both of the cannulas, such as the first cannula 310a as shown in FIG. 26A. The retention assembly 490 can include a first locking member such as a retention housing 492 that is mounted to the first cannula 310a and defines a lateral strand-receiving gap 493 extending therein. In particular, the retention housing includes a first or proximal housing portion 492a and a second or distal housing portion 492b, such that the gap 493 is disposed between the first and second housing portions 492a and 492b. The retention assembly 490 can further include a second locking member such as a pincher 494 that can be threadedly mounted to the retention housing 492, for instance to the first housing portion 492a at a location is aligned with the gap 493. Rotation of the pincher 494 relative to the retention housing 492 in a first direction causes the pincher 494 to translate into the gap 493 toward the second housing portion 492b. Rotation of the pincher 494 relative to the retention housing 492 in a second direction opposite the first direction causes the pincher 494 to translate out of the gap 493 and away from the second housing portion 492b.

Accordingly, during operation, one or more target strands 379, such as the actuation strand or strands 38a and 38b or at least one tensioning strand can be loaded into the gap 493, and the pincher 494 can be rotated in the first direction until the retention assembly 490 captures the target strands 379 between a distal end of the pincher 494 and the second housing portion 492b. Once the first and second anchor bodies 28a and 28b have been ejected into the respective first and second target anatomical locations (see FIG. 1A), the insertion instrument can be translated proximally away from the anatomical location, thereby applying the actuation force, either directly or indirectly, to the first and second actuation strands 38a and 38b, thereby actuating the anchor bodies 28a and 28b to their expanded configurations. The pincer 494 can then be rotated along the second direction so as to increase the gap 493 until the insertion instrument 300 can be pulled free from the target strands 379. Alternatively or additionally, for instance when the target strands 379 are provided as tensioning strands, the tensioning strands can be cut while captured in the retention assembly 490. Because the cannulas 310a and 310b can define longitudinal slots that extend through one side of the cannulas 310a and 310b, the actuation strands 38a and 38b can be freed from the respective cannula, for instance out the longitudinal slot, when the corresponding anchor bodies 28a and 28b are ejected from the cannula.

Referring now to FIGS. 27A-28B generally, the insertion instrument 300 can be configured having a first and second cannulas 310a and 310b supported by the casing 308 in a side-by-side orientation that retain first and second anchor bodies 28a and 28b, and first and second pusher assemblies 317a and 317b operatively associated with the first and second cannulas 310a and 310b, respectively, so as to eject the first and second anchor bodies 28a and 28b out the respective first and second cannulas 310a and 310b. Furthermore, as described above, it can be desirable to ensure that a desired cannula from which the anchor body is to be ejected is distally disposed with respect to the other cannula, such that the desired cannula can be inserted into the underlying tissue without also inserting the other cannula.

Figure 27A:
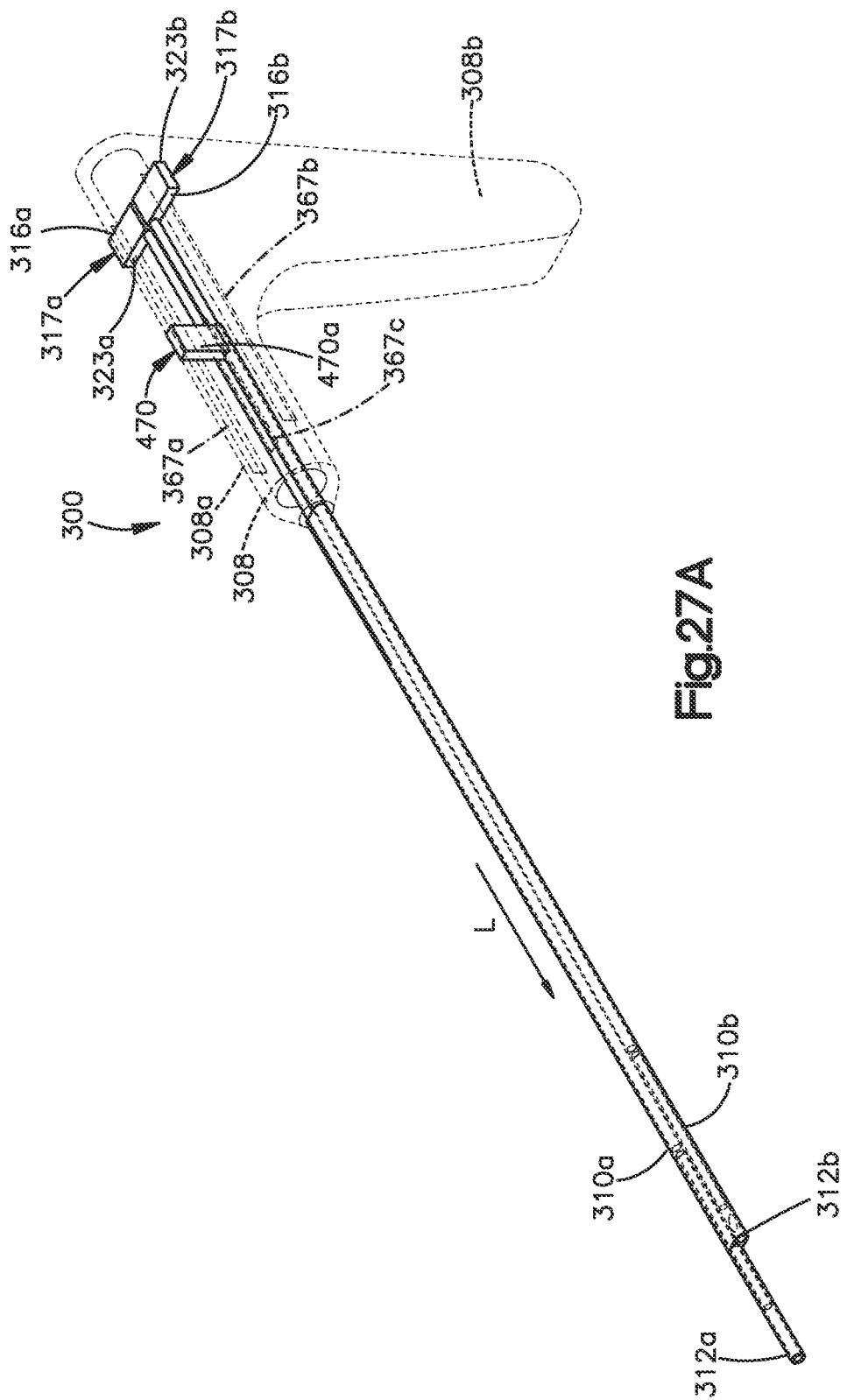
FIG. 27A is a perspective view of an insertion instrument constructed in accordance with another embodiment, the insertion instrument including first and second pusher assemblies disposed in a side-by-side relationship, showing each of the pusher assemblies in a first position.

As illustrated in FIG. 27A, the insertion instrument 300 includes a casing 308 that includes a body portion 308a and a handle portion 308b that extends out from the body portion 308a. The insertion instrument 300 further includes a first cannula 310a that extends distally from the casing 308, and in particular from the body portion 308a, and a second cannula 310b that extends distally from the casing 308, and in particular from the body portion 308a, at a location adjacent the first cannula 310a. The first and second cannulas 310a and 310b can extend substantially parallel to each other as illustrated. Accordingly, the first and second cannulas 310a and 310b can be described as being in a side-by-side relationship. The first and second cannulas 310a and 310b can define respective longitudinally elongate channels 312a and 312b that retain respective first and second anchor bodies 28a and 28b.

The insertion instrument 300 can further include first and second pusher assemblies 317a and 317b operatively associated with the first and second cannulas 310a and 310b, respectively. Thus, the first pusher assembly 317a is configured to eject the first anchor body 28a out the first cannula 310a, and the second pusher assembly 317b is configured to eject the second anchor body 28b out the second cannula 310b. The first and second cannulas 310a and 310b can define respective first and second tapered tips 311a and 311b, and first and second distal ejection ports 442a and 442b that extend longitudinally through the respective tips 311a and 311b.

Each of the first and second pusher assemblies 317a and 317b includes first and second plungers 316a and 316b, respectively, that extends out the casing 308, such as the body portion 308a of the casing 308. The first and second plungers 316a and 316b can extend proximally out the casing 308 as described above with respect to FIGS. 24A-F, or can extend out the casing along a direction angularly offset with respect to the longitudinal direction L so as to present respective tabs 323a and 323b that project out the casing 308. Each of the first and second pusher assemblies 317a and 317b can further include first and second pusher rods 330a and 330b, respectively, that extend distally from the corresponding plungers 316a and 316b. When the first and second plungers 316a and 316b are in their respective first positions (FIG. 27A), the first and second anchor bodies 28a and 28b are disposed in the respective cannulas 310a and 310b. The plungers 316a and 316b can be moved to respective second positions (FIG. 27D) so as to eject the respective first and second anchor bodies 28a and 28b out the respective cannulas 310a and 310b.

The insertion instrument 330 can further include a swap actuator 470 that can include a swap tab 470a that extends out from the casing 308, and can extend out from the body portion 308a at a location between the first and second tabs 323a and 323b. The casing 308 can defines slots 367a-c that extend through the upper end of the body portion 308 and are longitudinally elongate, and positioned such that the first and second tabs 323a and 323b extend out the first and second slots 367a and 367b, and the swap tab 470a extends out the third slot 367c at a location between the first and second tabs 323a and 323b. The slots 367a-c can thus provide tracks that define the longitudinal movement of the first and second pusher assemblies 317a and 317b and the swap actuator 470 as the tabs 323a-b and 470a ride in the respective slots 367a-c. The swap actuator 470 is configured to be moved from a first position to an actuated position so as to reverse a relative position of the fist and second tips 311a and 311b. For instance, as illustrated in FIG. 27A, the first tip 311a of the first cannula 310a is disposed distally with respect to the second tip 311b of the second cannula 310b. It should thus be appreciated that the first tip 311a can be injected into underlying tissue, for instance at the first target anatomical location 24a (see FIG. 1A) without causing the second tip 311b to inject into the underlying tissue. As is described in more detail below, actuation of the swap actuator 470 from a first position (FIG. 27A) to a second position along the direction of Arrow 355 (FIG. 27C) causes the second tip 311b to move distally with respect to the first tip 311a, such that the second tip 311b can be injected into the underlying tissue, for instance at the second target anatomical location 24b (see FIG. 1B) without causing the first tip 311a to inject into the underlying tissue.

Figure 27B:
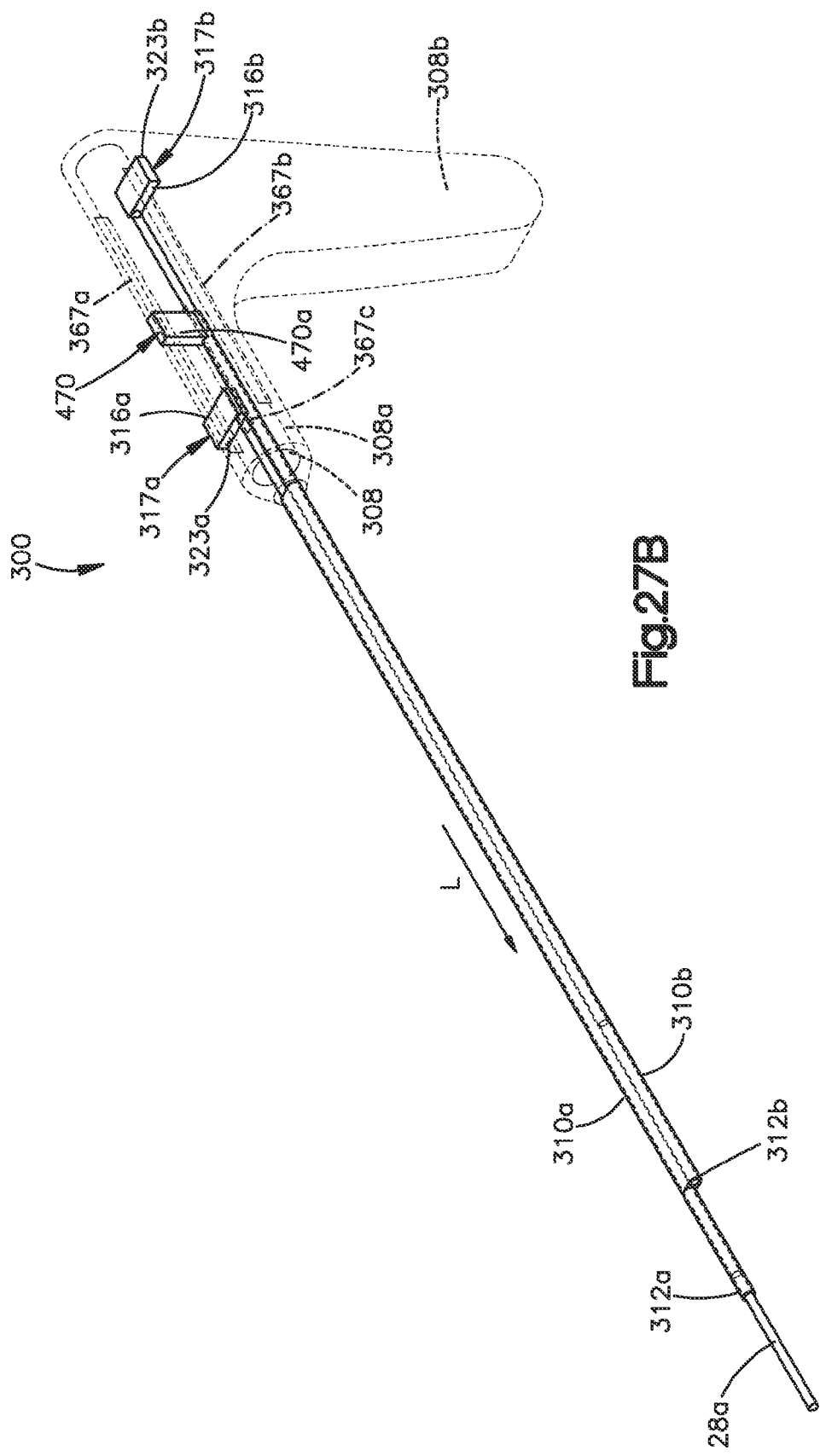
FIG. 27B is a perspective view of the insertion instrument illustrated in FIG. 27A, after actuation of the first pusher assembly to a position configuration.

During operation, referring to FIGS. 27A-B, the first plunger 316a can be translated distally along the direction of Arrow 357 from the first position to the second position, which causes the first push rod 330a to likewise translate distally in the first cannula 310a. The first push rod 330a abuts the first anchor body 28a, such that the first push rod 330a ejects the first anchor body 28a out the first cannula 310a, for instance into the first target anatomical location, as the first push rod 300a translates distally to the second position. The first plunger tab 323a abuts the casing 308 at the distal end of the first slot 367a when the first pusher assembly 317a is in the second position, whereby the first anchor body 28a has been ejected. Thus, when the first plunger tab 323a is in the second position, the plunger 316a is prevented from further distal translation. Thus, the user is provided with tactile feedback that the first anchor body 28a has been ejected.

Figure 27C:
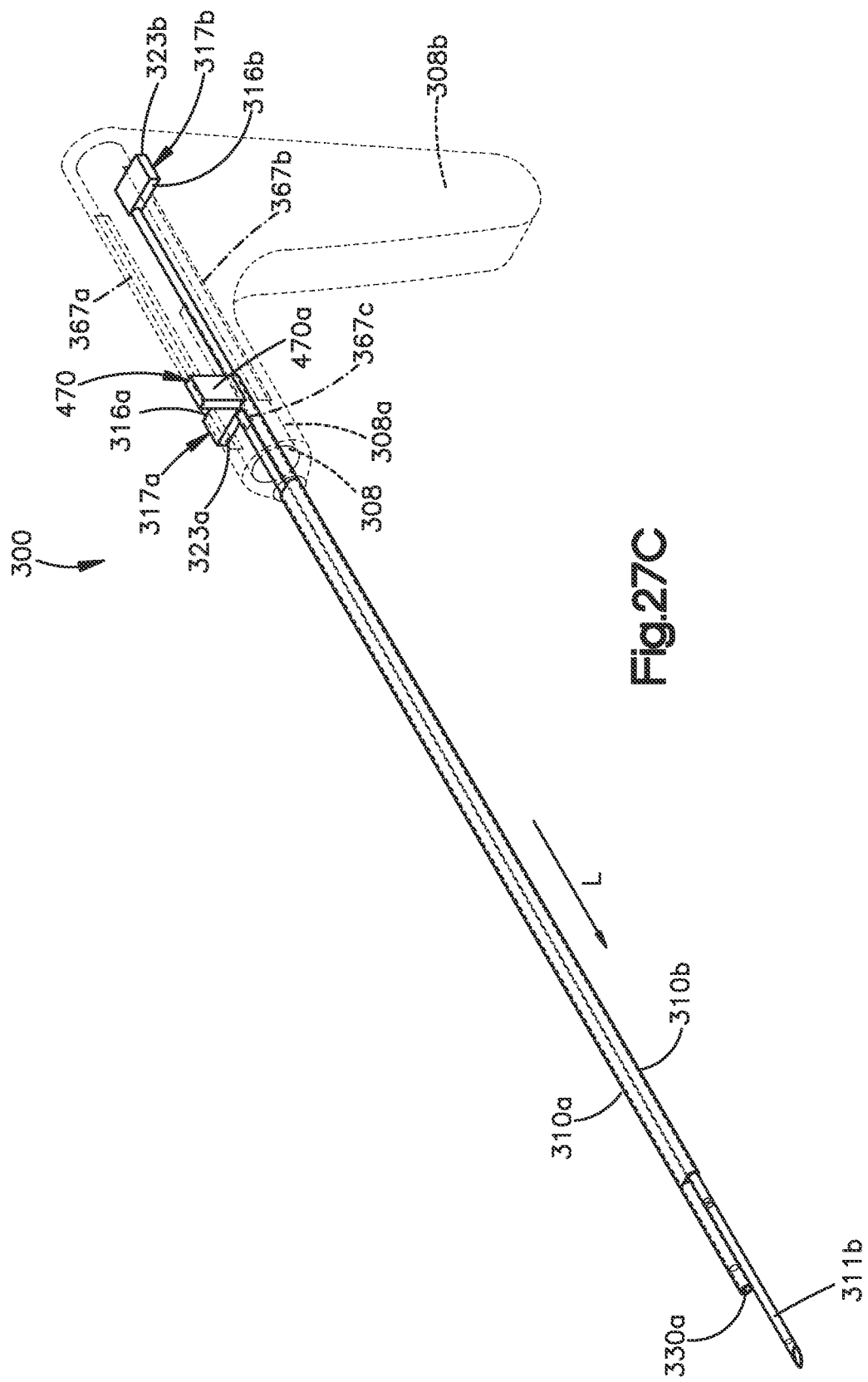
FIG. 27C is a perspective view of the components of the insertion instrument illustrated in FIG. 27B, after actuation of the swap actuator from a first position to an actuated position.

Next, referring to FIG. 27C, the swap actuator 470 can be actuated, for instance can be moved distally along the direction of Arrow 355, from the first position to the actuated position, which causes the second tip 311b to advance, or translate distally, with respect to the casing 308 and the first cannula 310a until the second tip 311b is disposed distally with respect to the first tip 311a. It should thus be appreciated that the second tip 311b can be injected into underlying tissue, for instance at the second target anatomical location 24b (see FIG. 1A) without causing the first tip 311a to inject into the underlying tissue. For instance, the distal end of the first push rod 330a, which is disposed distal with respect to the first tip 311a, can provide a depth stop for the insertion of the second tip 311b into the second target anatomical location. Thus, the second tip 311b can be injected until the first push rod 330a abuts the anatomical structure. In accordance with the illustrated embodiment, actuation of the swap actuator 470 further causes the second plunger 316b, and thus the second push rod 330b, to translate distally as illustrated in FIG. 27C. The swap tab 470a abuts the casing 308 at the distal end of the third slot 367c once the swap actuator 470 has been moved to the actuated position, such that the swap actuator 470 is prevented from further distal translation. Thus, the user is provided with tactile feedback that the swap actuator 470 has been actuated.

Figure 27D:
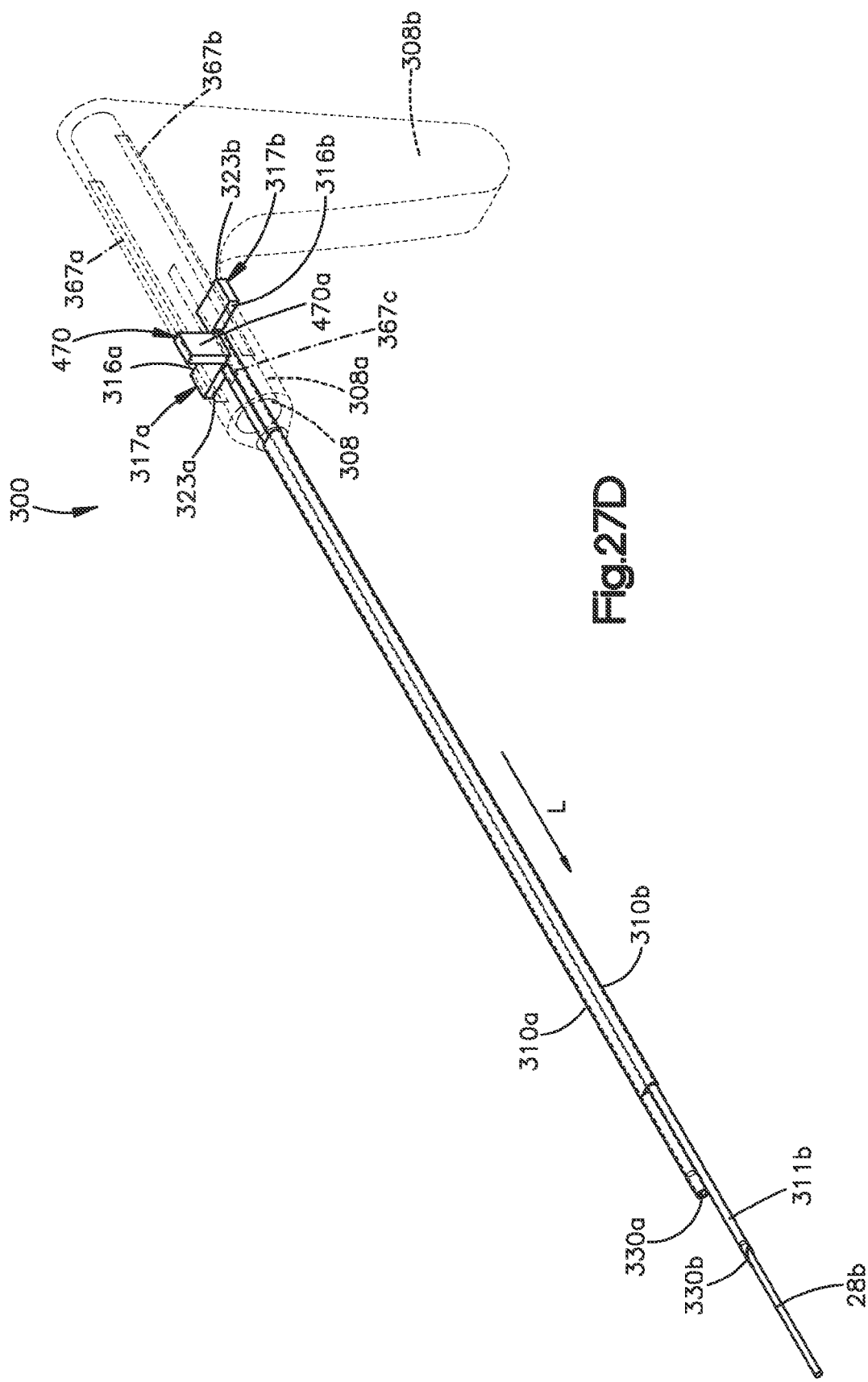
FIG. 27D is a perspective view of the insertion instrument illustrated in FIG. 27C, after actuation of the second pusher assembly to a second position.

Referring now to FIG. 27D, the second plunger 316b can be translated distally along the direction of Arrow 359 from the first position to the second position, which causes the second push rod 330b to likewise translate distally in the second cannula 310*b*. The second push rod 330*b* abuts the second anchor body 28*b*, such that the second push rod 330*b* ejects the second anchor body 28*b* out the second cannula 330*b*, for instance into the second target anatomical location, as the second push rod 300*b* translates distally to the second position. The second plunger tab 323*b* abuts the casing 308 at the distal end of the second slot 367*b* when the second pusher assembly 317*b* is in the second position, whereby the second anchor body 28*b* has been ejected. Thus, when the plunger tab 323*b* is in the second position, the plunger 316*b* is prevented from further distal translation. Thus, the user is provided with tactile feedback that the second anchor body 28*b* has been ejected.

Figure 28A:
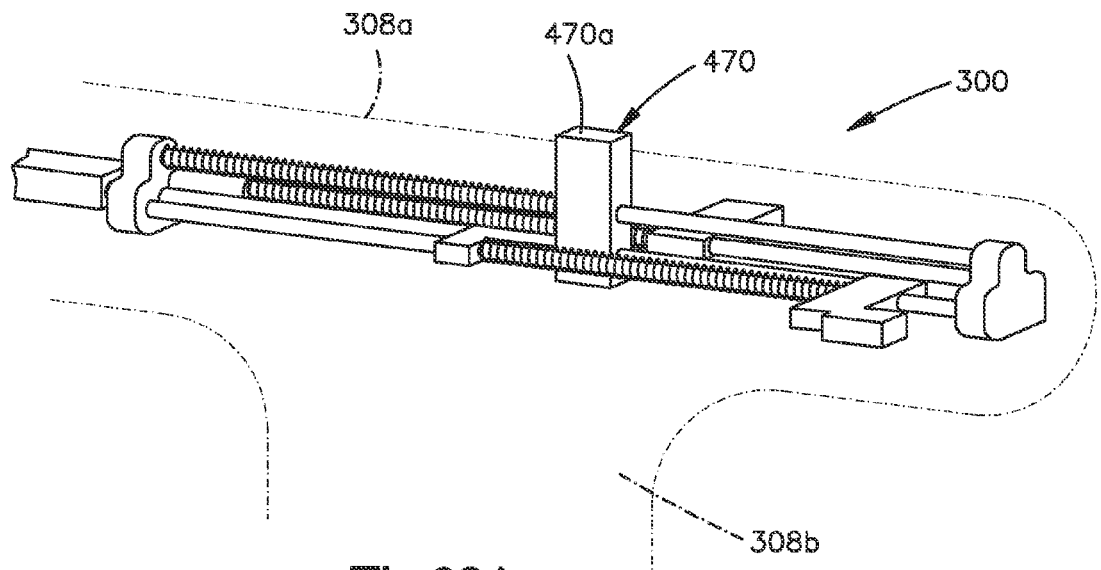
FIG. 28A is a perspective view of components of the insertion instrument illustrated in FIG. 27A, shown with the swap actuator in the first position.
Figure 28B:
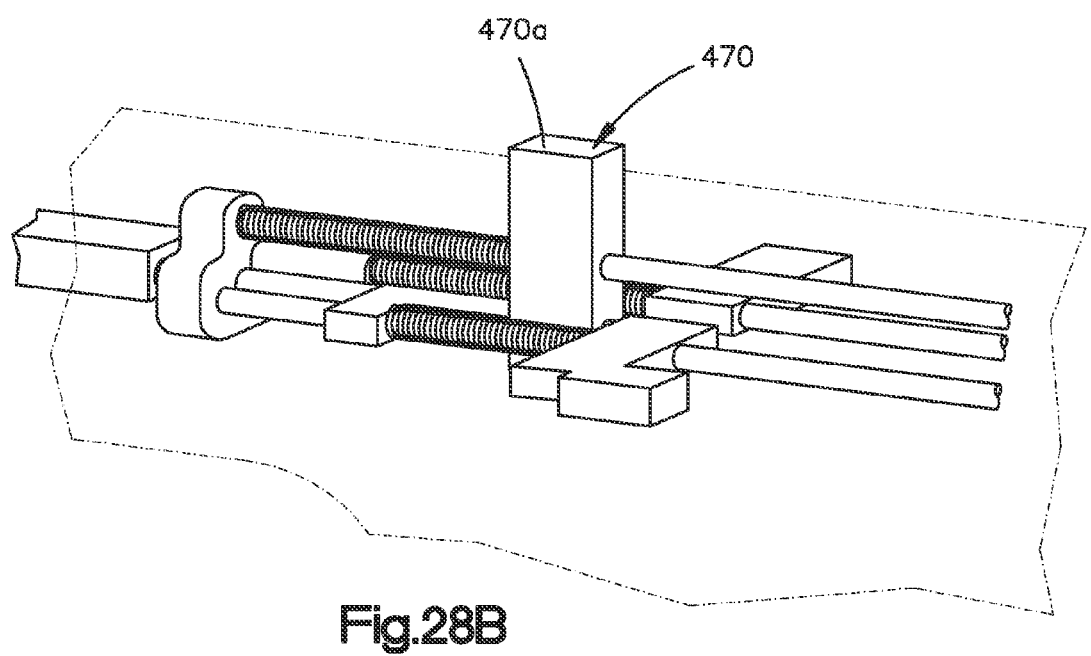
FIG. 28B is a perspective view of components of the insertion instrument illustrated in FIG. 28A, shown with the swap actuator in the second position.

Operation of the insertion instrument 300 illustrated in FIGS. 27A-28B will now be further described with particular reference to FIGS. 28A-B. In particular, the insertion instrument 300 includes at least one latch assembly such as a first latch assembly 482, a second latch assembly 484, and a third latch assembly 486. The first latch assembly 482 is configured to lock the swap actuator 470 in its distal position once it has been moved distally from a first position illustrated in FIG. 27B to a second recessed position illustrated in FIG. 27C. For instance, the first latch assembly 482 can include a latch member 488 that is supported by the casing 308 and configured to latch onto the swap actuator 470 so as to be coupled to the swap actuator 470 with respect to translation. The latch member 488 defines a body 488*a*, a first attachment portion 488*b* in the form of a hook carried by the body 488*a*, and a second attachment portion 488*c* in the form of an abutment surface carried by the body 488*a* disposed distal of the first attachment portion 488*b*. As the swap actuator 470 moves distally, the first attachment portion 488*a* can deflect inwardly away from the swap actuator 470 so as to allow distal translation of the swap member 470 relative to the latch member 488, such as an outwardly projecting tab 470*a* of the swap actuator 470. Once the swap actuator 470 has been moved from its first initial position to its second distal position relative to the casing 308, the swap actuator 470 contacts the abutment surface and the hook can deflect outward under the spring force of the body 488*a*, such that the swap actuator 470, for instance the tab 470*a*, becomes captured between the first and second attachment portions 488*b* and 488*c*. Accordingly, the latch member 488 prevents the swap actuator 470 from moving proximally and distally relative to the casing once the swap actuator 470 has been moved to its proximal position that advances the second pusher assembly 317*b* distally with respect to the first pusher assembly 316*a*.

The insertion instrument 300 can further include at least one first guide member 483*a* such as a guide wire that is translatably fixed to the casing 308. For instance, the insertion instrument 300 can include a mount 485 that is supported by the casing 308 and is attached to the first guide member 483*a*. The first guide member 483 can extend through the swap actuator 470 so as to guide the swap actuator to translate distally.

The second latch assembly 484 is configured to lock the first plunger 316*a*, and thus the first pusher assembly 317*a*, in its proximal position proximal position once it has been moved distally from a first position illustrated in FIG. 27A to a second distal position illustrated in FIG. 27B that causes the first push rod 330*a* to eject the first anchor body 28*a*. For instance, the second latch assembly 484 can include a latch member 489 that is supported by the casing 308 and configured to latch onto the first plunger 316*a* so as to be coupled to the first plunger 316*a* with respect to translation. The second latch member 489 can be constructed substantially identically with respect to the first latch member 488, and thus defines a body, a first attachment portion in the form of a hook carried by the body, and a second attachment portion in the form of an abutment surface carried by the body and disposed distal of the hook. As the first plunger 316*a* moves distally, the first attachment portion can deflect inwardly away from the first plunger 316*a* so as to allow distal translation of the first plunger 316*a* relative to the second latch member 489, such as an outwardly projecting tab 316*c* of the first plunger 316*a*. Once the first plunger 316*a* has been moved from its first initial position to its second distal position relative to the casing 308, the first plunger 316*a* contacts the abutment surface and the hook can deflect outward under the spring force of the body of the latch member 489, such that the first plunger 316*a*, for instance the tab 316*c*, becomes captured between the first and second attachment portions of the latch member 489. Accordingly, the latch member 489 prevents the first plunger 316*a* from moving proximally and distally relative to the casing 308 once the first plunger 316 has been moved to its distal position that ejects the first anchor body 28*a* from the first cannula 310*a*.

The insertion instrument 300 can further include at least one second guide member 483*b* such as a guide wire that is translatably fixed to the casing 308. For instance, the mount 485 can be attached to the second guide member 483*b*, which can extend distally through the first plunger 316*a* so as to guide the first plunger 316*a* to translate distally.

The third latch assembly 486 is configured to lock the second plunger 316*b*, and thus the second pusher assembly 317*b*, in its distal position proximal position once it has been moved distally from a first position illustrated in FIG. 27C to a second distal position illustrated in FIG. 27D that causes the second push rod 330*b* to eject the second anchor body 28*b*. For instance, the third latch assembly 486 can include a third latch member 495 that is supported by the casing 308 and configured to latch onto the second plunger 316*b* so as to be coupled to the second plunger 316*b* with respect to translation. The third latch member 495 can be constructed substantially identically with respect to the first and second latch members 488 and 489, and thus defines a body 495*a*, a first attachment portion 495*b* in the form of a hook carried by the body 495*a*, and a second attachment portion 495*c* in the form of an abutment surface carried by the body 495*a* at a location distal of the hook. As the second plunger 316*b* moves distally, the first attachment portion 495*b* can deflect inwardly away from the second plunger 316*b* so as to allow proximal translation of the second plunger 316*b* relative to the third latch member 495, such as an outwardly projecting tab 316*d* of the second plunger 316*b*. Once the second plunger 316*b* has been moved from its first initial position to its second proximal position relative to the casing 308, the second plunger 316*b*, for instance at the tab 316*d*, contacts the abutment surface 495*c* and the hook 495*b* can deflect outward under the spring force of the latch member body 495*a*, such that the second plunger 316*b* becomes captured between the first and second attachment portions of the latch member 495. Accordingly, the latch member 495 prevents the second plunger 316*b* from moving proximally and distally relative to the casing 308 once the second plunger 316*b* has been moved to its distal position that ejects the second anchor body 28*b* from the second cannula 310*b*.

The insertion instrument 300 can further include at least one third guide member 483*c* such as a guide wire that is translatably fixed to the casing 308. For instance, the mount 485 can be attached to the third guide member 483*c*, which can extend distally through the second plunger 316*b* so as to guide the second plunger 316b to translate distally. Furthermore, the insertion instrument 300 can include an attachment member 496 in the form of an attachment wire that attaches the second plunger 316b to the swap actuator 470 with respect to distal translation of the swap actuator 470. For instance, distal translation of the swap actuator 470 causes the second plunger 316b to translate distally along with the swap actuator 470. A distal force applied to the second plunger 316b can allow the second plunger 316b to translate distally relative to the swap actuator 470. In accordance with one embodiment, the attachment member 496 can be translatably fixed to the swap actuator 470, and can be attached to the second plunger 316b so that it interferes with the second plunger 316 with respect to proximal movement 316b of the second plunger 316b relative to the attachment member 493. The swap actuator 470 can include a second tab 470b that is attached to the second cannula 310b with respect to translation, such that distal translation of the swap actuator 470 causes the second cannula 310b to translate distally along with the swap actuator 470. Accordingly, distal translation of the swap actuator 470 causes the attachment member 496 to drag the second plunger 316b, the second cannula 310b, and the second push rod 330b distally until the second tip 311b is disposed distal of the first tip 311a. Because the first pusher rod 330a remains disposed distal of the first tip 311a after the first anchor body 28a has been ejected, the distal end of the first pusher rod 330a can define an insertion depth stop for the second tip 311b in the manner described above.

The attachment member 496 can extend at least partially through the second plunger 496b so as to allow the second plunger 496b to translate distally with respect to the attachment member 496 and therefore also with respect to the swap actuator 470. As a result, once the swap actuator 470 has been translated distally, thereby also translating the second cannula 310b and the second pusher assembly 317b distally, translation of the second plunger 316b causes the second push rod 330b to eject the second anchor body 28b from the second cannula 310b in the manner described above.

Referring now to FIGS. 29A-29G generally, the insertion instrument 300 can be configured having a first and second cannulas 310a and 310b supported by the casing 308 in a side-by-side orientation that retain first and second anchor bodies 28a and 28b, and first and second pusher assemblies 317a and 317b operatively associated with the first and second cannulas 310a and 310b, respectively, so as to eject the first and second anchor bodies 28a and 28b out the respective first and second cannulas 310a and 310b. Furthermore, as described above, it can be desirable to ensure that a desired cannula from which the anchor body is to be ejected is distally disposed with respect to the other cannula, such that the desired cannula can be inserted into the underlying tissue without also inserting the other cannula.

As illustrated in FIG. 29A, the insertion instrument 300 includes a casing 308 that includes a first casing portion 308a and a second casing portion 308b that is disposed adjacent the first casing portion 308b. The insertion instrument 300 further includes a first cannula 310a that extends distally from the first casing portion 308a, and a second cannula 310b that extends distally from the second casing portion 308b. The first and second casing portions 308a and 308b can extend substantially parallel to each other as illustrated. Accordingly, the first and second cannulas 310a and 310b can be described as being in a side-by-side relationship. The first and second cannulas 310a and 310b can define respective longitudinally elongate channels that retain respective first and second anchor bodies 28a and 28b in the manner described above. The first and second cannulas 310a and 310b can further include longitudinally elongate side slots 337a and 337b, respectively, that extend into one side of the cannulas and are in communication with the respective elongate channels. Accordingly, the attachment portions 133a-b of the actuation strands 38a and 38b can extend out the respective side slots 337a and 337b and attach to each other (see FIG. 1A) when the first and second anchor bodies 28a and 28b are loaded in the respective first and second cannulas 310a and 310b.

The insertion instrument 300 can further include first and second pusher assemblies 317a and 317b operatively associated with the first and second cannulas 310a and 310b, respectively. Thus, the first pusher assembly 317a is configured to eject the first anchor body 28a out the first cannula 310a, and the second pusher assembly 317b is configured to eject the second anchor body 28b out the second cannula 310b. The first and second cannulas 310a and 310b can define respective first and second tapered tips 311a and 311b, and first and second distal ejection ports that extend longitudinally through the respective tips 311a and 311b.

Each of the first and second pusher assemblies 317a and 317b includes first and second plungers 316a and 316b, respectively, that are disposed outside the respective first and second casing portions 308a and 308b at a location proximal with respect to the casing portions 308a and 308b as illustrated. Each of the first and second pusher assemblies 317a and 317b can further include first and second pusher rods 330a and 330b, respectively, that extend distally from the corresponding plungers 316a and 316b, through the respective first and second casing portions 308a and 308b, and into the respective first and second cannulas 310a and 310b. When the first and second plungers 316a and 316b are in their respective first positions (FIG. 29A), the first and second anchor bodies 28a and 28b are disposed in the respective cannulas 310a and 310b. The plungers 316a and 316b can be moved to respective second positions (FIG. 29F) so as to eject the respective first and second anchor bodies 28a and 28b out the respective cannulas 310a and 310b.

The insertion instrument 330 can further include a swap actuator 470 that can include a swap button 470a that extends laterally through the first casing portion 308a and into the second casing portion 308b. The swap actuator 470 is configured to selectively couple and decouple the first and second casing portions with respect to relative translation in the longitudinal direction L. For instance, as illustrated in FIGS. 29B and 29G, the first and second casing portions 308a and 308b can be slidably coupled along the longitudinal direction. For instance, one of the casing portions, such as the first casing portion 308a, can define a slot 375 extending along at least a portion of its longitudinal length. The other casing portion, such as the second casing portion 308b, can include a slider member such as a projection 377 that is configured to ride inside the slot so as to guide longitudinal movement of the first and second casing portions 308a and 308b relative to each other. The slot 375 and the projection 377 can flare angularly outward in a dovetail arrangement such that the first and second casing portions 308a and 308b are prevented from separating along a direction angularly offset from the longitudinal direction L. The swap actuator 470 is configured to move the first and second casing portions 308a and 308b relative to each other along the longitudinal direction such that the respective tips 311a and 311b move from a first relative position to a second relative position that is opposite the first relative position.

For instance, as illustrated in FIG. 29A, the first tip 311*a* of the first cannula 310*a* can be initially disposed distally with respect to the second tip 311*b* of the second cannula 310*b*. It should thus be appreciated that the first tip 311*a* can be injected into underlying tissue, for instance at the first target anatomical location 24*a* (see FIG. 1A) without causing the second tip 311*b* to inject into the underlying tissue. As is described in more detail below, actuation of the swap actuator 470 from a first position (FIG. 29D) to a second position causes the second tip 311*b* to move distally with respect to the first tip 311*a* such that the second tip 311*b* is positioned distal of the first tip 311*a*. Accordingly, the second tip 311*b* can be injected into the underlying tissue, for instance at the second target anatomical location 24*b* (see FIG. 1B) without causing the first tip 311*a* to inject into the underlying tissue.

During operation, referring to FIG. 29C, the first plunger 316*a* can be translated distally from the first position to the second position, which causes the first push rod 330*a* to likewise translate distally in the first cannula 310*a*. The first push rod 330*a* abuts the first anchor body 28*a*, such that the first push rod 330*a* ejects the first anchor body 28*a* out the first cannula 310*a*, for instance into the first target anatomical location, as the first push rod 300*a* translates distally to the second position. The first plunger 316*a* can abuts the first casing portion 308*a* when the first pusher assembly 317*a* is in the second position, whereby the first anchor body 28*a* has been ejected. Thus, when the first plunger 316*a* is in the second position, the first plunger 316*a* is prevented from further distal translation. Thus, the user is provided with tactile feedback that the first anchor body 28*a* has been ejected.

Next, referring to FIGS. 29C, 29D, and 29G, the swap actuator 470 can be actuated so as to reverse the relative position of the first and second tips 311*a* and 311*b* in the manner described above. For instance, the swap actuator 470 can include a button 472 that extends laterally through the first casing portion 308*a* and into the second casing portion 308*a*. The second casing portion 308*b* can include a spring member 474 that biases the button 472 outward toward its first position. The button 472 can include at least one flange 476 that abuts a wall of the second casing portion 308*b* so as to prevent the force of the spring member 474 from ejecting the button 472 out the first casing portion 308*a*.

The first casing portion 308*a* can include a pair of apertures 478*a-b* sized to receive the button 472 such that the button 472 extends out the first casing portion 308*a*. The first aperture 478*a* is disposed proximal with respect to the second aperture 478*b*. When the button 472 extends through the first aperture 478*a*, the first tip 311*a* is disposed distal with respect to the second tip 311*b*. Furthermore, interference between the button 472 and the first casing portion 308*a* prevents the first casing portion 308*a* from translating longitudinally relative to the second casing portion 308*b*. When the button 472 is depressed into the slot 375, and thus into the projection 377, interference between the button 472 and the first casing portion 308*a* is removed, such that the first and second casing portions 308*a* and 308*b* are configured to translate longitudinally relative to each other. For instance, the second casing portion 308*b*, and thus the second cannula 310*b*, can slide distally with respect to the first casing portion 308*a*, and thus the first cannula 310*a*, until the button 472 is driven through the second aperture 478*b* as illustrated in FIG. 29D. When the button 472 extends through the second aperture 478*b*, the second tip 311*b* is disposed distal with respect to the first tip 311*a*. It should thus be appreciated that the second tip 311*b* can be injected into underlying tissue, for instance at the second target anatomical location 24*b* (see FIG. 1A) without causing the first tip 311*a* to inject into the underlying tissue.

Referring now to FIGS. 29D-E, the insertion instrument 300 can further include a lock-out tab 468 that is removably attached to the second push rod 330*b* at a location longitudinally between the corresponding plunger 316*b* and the second casing portion 308*b*. Accordingly, the lock-out tab 468 interferes with the distal translation of the plunger 316*b* relative to the second casing portion 308*b* to a depth that would eject the respective second anchor body 28*b*. The lock-out tab 468 can remain attached to the second push rod 330*b* until the first anchor body 28*a* has been ejected and the swap actuator 470 has been actuated. The insertion instrument 300 can further include a lock-out tab operatively associated with the first pusher assembly 317 in the manner described with respect to the second pusher assembly 317*b*.

Referring now to FIGS. 29E-F, once the lock-out tab 468 has been removed from the second push rod 430, the second plunger 316*b* can be translated distally from the first position to the second position, which causes the second push rod 330*b* to likewise translate distally in the second cannula 310*b*. The second push rod 330*b* abuts the second anchor body 28*b*, such that the second push rod 330*b* ejects the second anchor body 28*b* out the second cannula 330*b*, for instance into the second target anatomical location, as the second push rod 300*b* translates distally to the second position. The grip portion 432*b* of the second plunger 416*b* abuts the casing 308 at the distal end after the second anchor body 28*b* has been ejected, thereby providing the user with tactile feedback that the second anchor body 28*b* has been ejected.

Referring now to FIGS. 30A-D generally, the insertion instrument 300 can be configured having a first and second cannulas 310*a* and 310*b* supported by the casing 308 in a side-by-side orientation that retain first and second anchor bodies, respectively. Each of the first and second cannulas 310*a* and 310*b* is supported by the casing 308 so as to be translatably movable with respect to the casing 308. The insertion instrument 300 further includes a reciprocal motion assembly 500 that is configured to drive the first and second cannulas 310*a* and 310*b* in opposite directions. For instance, when the first cannula 310*a* is driven distally with respect to the casing 308, the reciprocal motion assembly 500 drives the second cannula 310*b* proximally with respect to the casing 308. Similarly, when the first cannula 310*a* is driven proximally with respect to the casing 308, the reciprocal motion assembly 500 drives the second cannula 310*b* distally with respect to the casing 308. Similarly, when the second cannula 310*b* is driven distally with respect to the casing 308, the reciprocal motion assembly 500 drives the first cannula 310*a* proximally with respect to the casing 308. Similarly, when the second cannula 310*b* is driven proximally with respect to the casing 308, the reciprocal motion assembly 500 drives the first cannula 310*a* distally with respect to the casing 308.

The insertion instrument 300 can include a pusher assembly 317 having a plunger 316 and first and second pusher members 330*a* and 330*b*. The first pusher member 330*a* extends into the first cannula 330*a* and is configured to eject a first anchor body out the first cannula 330*a* in the manner described above. Similarly, the second pusher member 330*b* extends into the second cannula 330*b* and is configured to eject a second anchor body 28*b* out the second cannula 330*b* in the manner described above. The insertion instrument further can include a selective plunger engagement assembly 502 that is operable so as to selectively engage the plunger between one of the first and second push rods 330a and 330b. Thus, the plunger 316 can be translatably coupled to the first push rod 330a, such that distal translation of the plunger 316 causes the push rod 330a to translate distally and eject the first anchor body 28a out of the respective first cannula 330a. The plunger 316 can be translatably coupled to the second push rod 330b, such that distal translation of the plunger 316 causes the push rod 330b to translate distally and eject the second anchor body 28b out of the respective first cannula 330b.

Figure 30C:
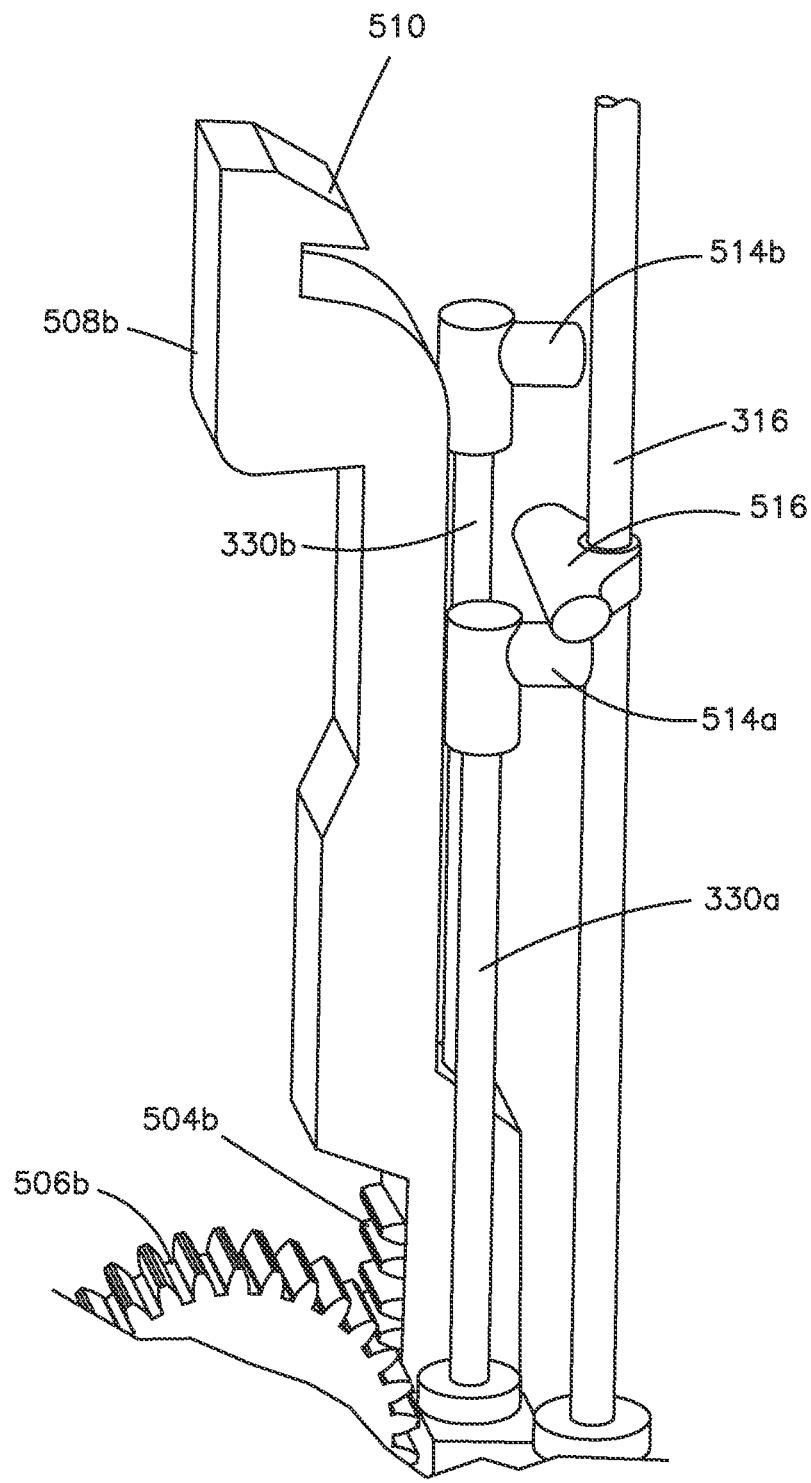

Referring now to FIGS. 30A-C, the reciprocal motion assembly 500 includes a first force transfer member, such as a toothed first rack 504a that is attached to the first cannula 310a and is translatably fixed to the first cannula 310a. The first rack 504a can be integral with the first cannula 310a or discretely attached to the first cannula 310a as desired. In accordance with the illustrated embodiment, the first rack 504a extends proximally from the first cannula 310a. The reciprocal motion assembly 500 can further include a second force transfer member such as a second toothed rack 504b that is attached to the second cannula 310b and is translatably fixed to the second cannula 310b. The second rack 504b can be integral with the second cannula 310b or discretely attached to the second cannula 310b as desired. In accordance with the illustrated embodiment, the second rack 504b extends proximally from the second cannula 310b.

The reciprocal motion assembly 500 can further include a third force transfer member such as a first gear 506a, which can be a spur gear, that mates with the first rack such that rotation of the first gear 506a drives the first rack 504a to translate substantially linearly, for instance proximally or distally. The first cannula 310a translates along with the first rack 504a. The reciprocal motion assembly 500 can further include a fourth force transfer member such as a second gear 506b, which can be a spur gear, that mates with the second rack 504b such that rotation of the second gear 506b drives the first rack 504a to translate substantially linearly, for instance proximally or distally. The second cannula 310b translates along with the second rack 504b. Furthermore, the first and second gears 506a and 506b are mated such that rotation of one of the first and second gears 506a and 506b in a first rotational direction along their respective axes of rotation 508a and 508b drives the other of the first and second gears 506a and 506b to rotate in a second rotational direction opposite the first rotational direction. The first and second gears 506a and 506b can be supported in the casing 308 such that the axes of rotation 508a and 508b remains stationary as the gears 506a and 506b rotate.

The second rack 504b can include a handle 508b that extends out the casing 308. During operation, for instance when the first cannula 310a extends distal with respect to the second cannula 310b, the handle 508b can be driven distally, which causes the second cannula 310b and the second rack 504b to translate distally, thereby rotating the second gear 506b along a direction of rotation. The second gear 506b drives the first gear 506a to rotate along an opposite direction of rotation, which causes the first cannula 310a to translate proximally toward the casing 308. Thus, as the second cannula 310b is driven distally, the reciprocal motion assembly drives the first cannula 310 in an opposite direction, such as proximally as illustrated.

When the second cannula 310b extends distal with respect to the first cannula 310a, the handle 508b can be driven proximally, which causes the second cannula 310b and the second rack 504b to translate proximally, thereby rotating the second gear 506b along a direction of rotation. The second gear 506b drives the first gear 506a to rotate along an opposite direction of rotation, which causes the first cannula 310a to translate distally away from the casing 308. Thus, as the second cannula 310b is driven proximally, the reciprocal motion assembly drives the first cannula 310a in an opposite direction, such as distally as illustrated.

The handle 508b can include a hook 510 that latches onto the casing 308 so as to provide a safety catch that prevents distal translation of the handle 508, and thus also distal translation of the second rack 504b. The hook 510 can be configured to latch onto the casing 308 when the second cannula 310b is retracted, and the first cannula 310a is extended and disposed distal with respect to the second cannula 310b.

Figure 30D:
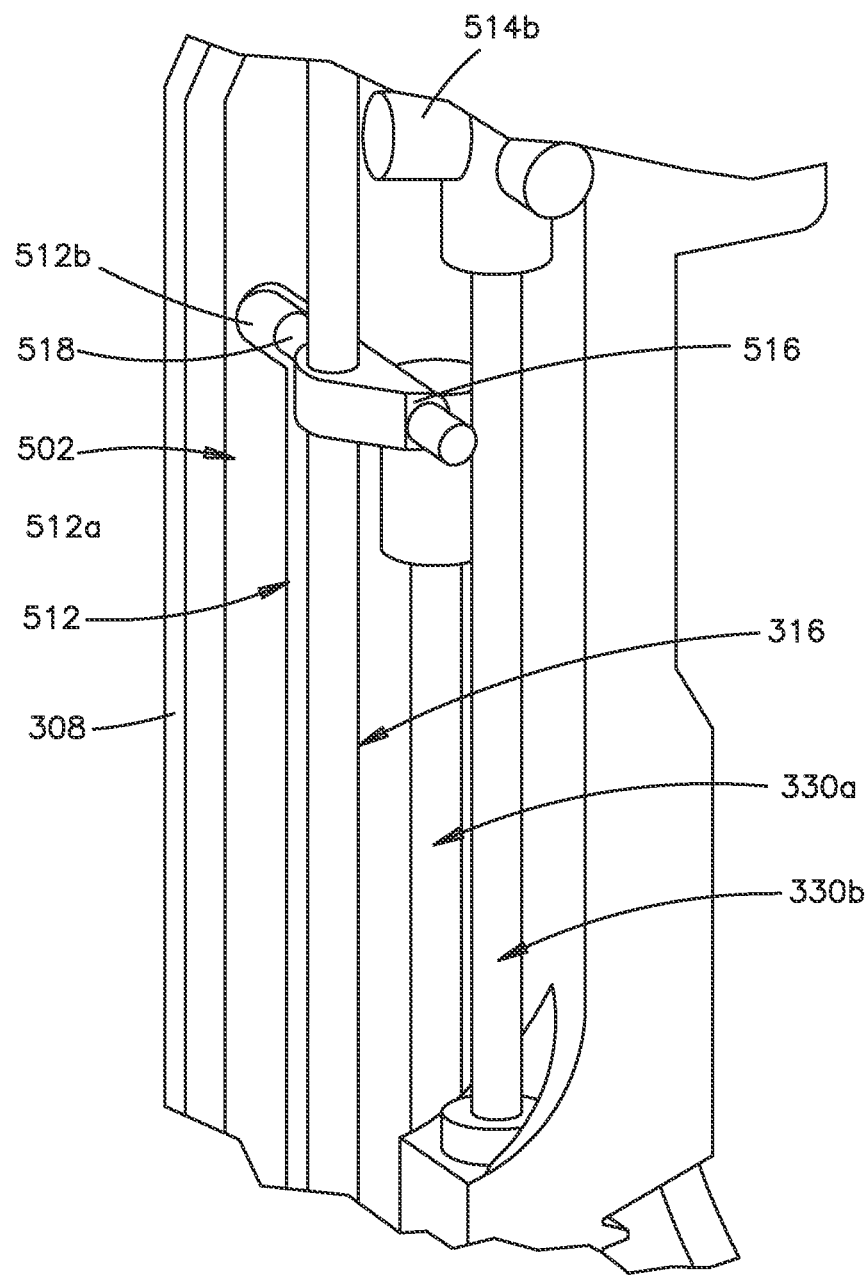

Referring now to FIGS. 30C-D, the selective plunger engagement assembly 502 includes a track 512 carried by the casing 308. The track 512 can extend radially outward into an inner wall of the casing 308. The track includes a first portion 512a that extends substantially longitudinally and parallel to the cannulas 310a and 310b and the push rods 330a and 330b. The track further includes a second portion 512b that extends from the first portion 512a, for instance from the proximal end of the first portion 512a, and extends proximally and outward, such as laterally outward, from the first portion 512b. Thus, it can be said that the second portion 512b is offset with respect to the first portion 512a. In accordance with the illustrated embodiment, the second portion 512b is angularly offset with respect to the first portion 512a.

The plunger 316 is configured to ride in the track 512, and is movable distally along the track 512 so as to drive a select one of the first and second push rods 330a and 330b distally within a respective one of the first and second cannulas 310a and 310b so as to eject the respective one of the first and second anchors out the insertion instrument. In accordance with the illustrated embodiment, the first and second push rods 330a and 330b carry first and second engagement members 514a and 514b. The engagement members 514a and 514b can be spaced from each other so as to provide clearance as the first and second cannulas 310a and 310b are driven reciprocally. It should be appreciated that because the first and second push rods 330a and 330b extend into the respective first and second cannulas 310a and 310b, the push rods 330a and 330b are likewise driven reciprocally during reciprocal movement of the cannulas 310a and 310b.

The plunger 316 carries a biasing member 516 that is longitudinally aligned with each of the engagement members 514a and 514b when the plunger 316 is disposed in the first track portion 512a. The plunger 316 further carries a follower 518 that is sized and shaped so as to ride in the track 512 and guide the travel path of the plunger 316 as the plunger is driven proximally and distally. The plunger 316 can include a proximal end that extends out, for instance proximally out, from the casing 308. Thus, the plunger 316 can be driven distally along the first track portion 512a and proximally along the first track portion 512a. The plunger can further be driven proximally along the second track portion 512b, which causes the biasing member 516 to move out of longitudinal alignment with the engagement members 514a and 514b. Thus, the cannulas 310a and 310b, and the respective push rods 330a and 330b, can move reciprocally without the engagement members 514a and 514b interfering with each other, and further without the engagement members 514a and 514b interfering with the biasing member 516 of the plunger 316.

When it is desired to eject one of the anchor bodies out of the respective cannula, for instance the first cannula 310a, the first push rod 330a can be placed into alignment with the plunger 316. For instance, the reciprocal motion assembly 500 can be actuated as desired so as to position the respective engagement member 514a distal of the proximal end of the first track portion 512a. Accordingly, the plunger 316 can be driven distally along the track 512. Once the plunger 512 travels distally along the first track portion 512a, the biasing member 516 engages the engagement member 514a, and drives the push rod 330a distally in the respective cannula 310a, thereby ejecting the anchor body out the cannula 310a as described above.

Once it is desired to eject the second anchor body from the second cannula 310b, the plunger 316 can be driven proximally onto the second track portion 512b until the biasing member 516 is out of longitudinal alignment with the engagement members 514a and 514b of the first and second push rods 330a and 330b. Next, the reciprocal motion assembly 500 can be actuated so as to drive the second cannula 310b and second push rod 330b distally, which causes the first cannula 310a and the first push rod 330a to translate proximally, until the first engagement member 514a is disposed proximal of the proximal end of the first track portion 512a, and the second engagement member 514b is disposed distal of the proximal end of the first track portion 512a. Thus, the second cannula 310b is disposed distal with respect to the first cannula 310a. Next, the plunger 316 can be driven distally, which causes the biasing member 516 to engage the second engagement member 514b, which drives the second push rod 330b distally in the second cannula 330b so as to eject the second anchor out the insertion instrument.

Figure 31:
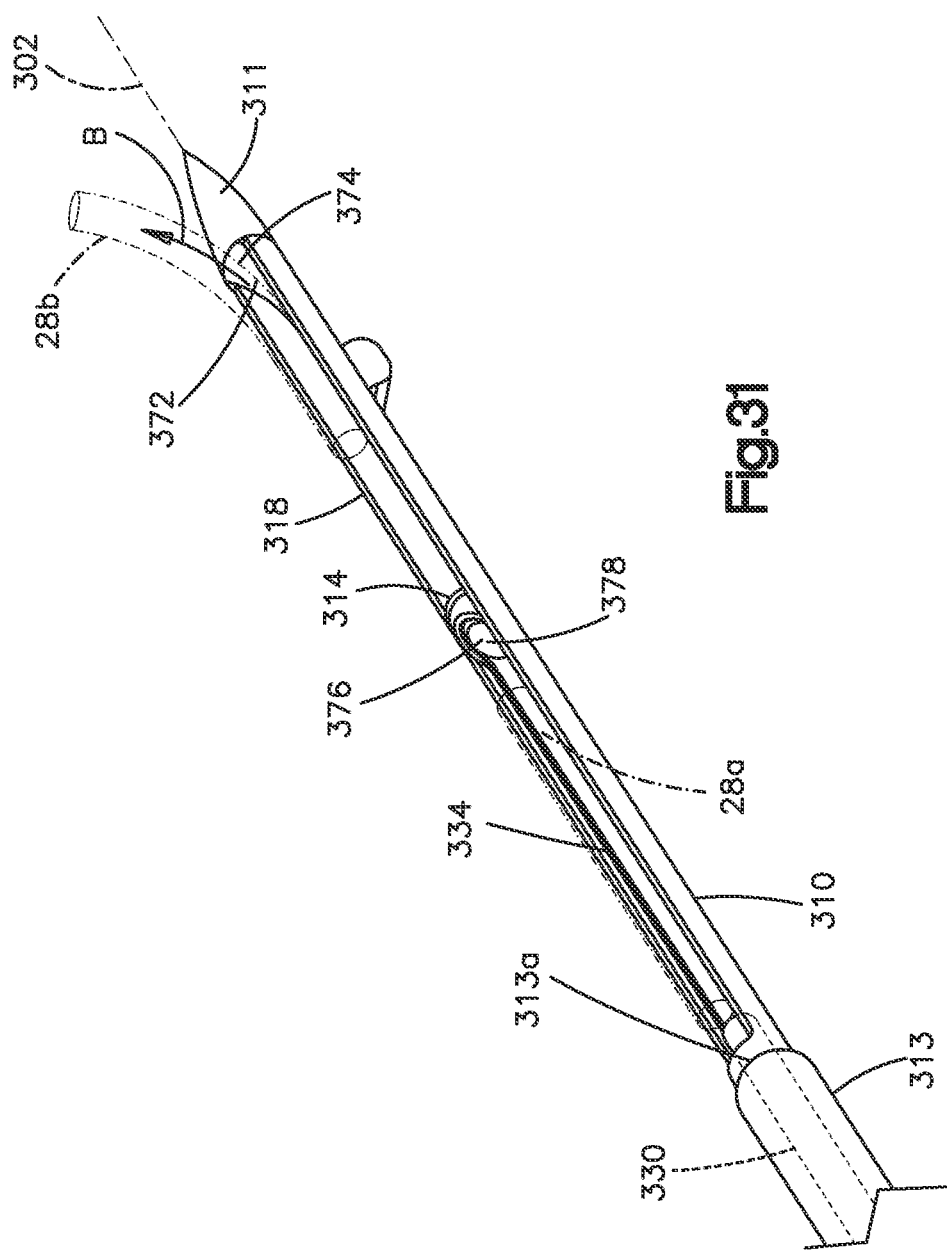

Referring now to FIG. 31, while various insertion instruments 300 have been described as including a distal ejection port 442, the insertion instruments 300 can define a side ejection port 318 as an alternative to the distal ejection port 442. For instance, the side ejection port 318 can be defined as a slot that extends radially through a distal portion of the cannula 310 at a location proximal with respect to the tip 311. The tip 311 can be closed so as to prevent the anchor bodies 28a and 28b from ejecting out the distal ejection port 442 that is defined by the tip 311. The side ejection port 318 can define a circumferential dimension at least substantially equal to or greater than the largest cross-sectional dimension of each of the first and second anchor bodies 28a and 28b, such that the anchor bodies 28a and 28b are sized to travel through the side ejection port 318. Furthermore, the side ejection port 318 can define a longitudinal length that is substantially equal to or greater than the longitudinal length of each of the first and second anchor bodies 28a and 28b. The longitudinal length of the side ejection port 318 can be slightly less than that of each of the first and second anchor bodies 28a and 28b, for instance, if the first and second anchor bodies 28a and 28b are angularly offset with respect to the longitudinal axis 302 as they are ejected out the side ejection port 318.

The tip 311 can define a ramp 372 at its proximal end. The ramp 372 can thus be disposed at the distal end of the side ejection port 318 and substantially aligned with the longitudinal axis 302. The ramp 372 can define a tapered ejection surface 374 that is angled radially outward toward the side ejection port 318 as it extends distally. Accordingly, as the plug 314 biases the second anchor body 28b distally from the elongate opening 312 of the cannula 310 onto the ejection surface 374 as the plunger 316 and push tube 334 collar 332 move from the first position to the second position, second anchor body 28b rides along the ejection surface 374, which directs the second anchor body 28b out the side ejection port 318 along the direction of Arrow B, thereby ejecting the second anchor body 28b out the insertion instrument 300 at the second target anatomical location 24b (see FIG. 1A). When the at least the distal portion of the side ejection port 318 is disposed behind the anatomical structure 24, the second anchor body 28b is ejected from the insertion instrument 300 at a location behind the anatomical structure 24, as further shown in FIG. 1A. The insertion instrument 300 can be configured such that the plug 314 is disposed proximal to and adjacent to the tip 311 when the push rod 330 and the push tube 334 become decoupled. Accordingly, translation of the push rod 330 relative to the push tube 334 causes the push rod to eject the first anchor 28a along the ramp surface 378 of the plug 314 in the manner described above, and out the side ejection port 318.

The embodiments described in connection with the illustrated embodiments have been presented by way of illustration, and the present invention is therefore not intended to be limited to the disclosed embodiments. Furthermore, the various structures, features, and methodologies associated with any embodiment described herein can apply to any other embodiment as described herein, unless otherwise indicated. For instance, unless otherwise indicated, any insertion instrument described herein can include a retention assembly as described herein in accordance with any suitable alternative embodiment, a cutting assembly as described herein or in accordance with any suitable alternatively embodiment, a swap assembly of the type described herein or constructed in accordance with any suitable alternative embodiment, a reciprocal motion assembly of the type described herein or constructed in accordance with any suitable alternative embodiment, and a selective plunger engagement assembly of the type described herein or constructed in accordance with any suitable alternative embodiment. Accordingly, those skilled in the art will realize that the invention is intended to encompass all modifications and alternative arrangements included within the spirit and scope of the invention, for instance as set forth by the appended claims.

We claim:

1. An insertion instrument assembly configured to eject a first anchor and a second anchor at respective target locations, the first and second anchors including respective first and second anchor bodies that extend substantially along a respective direction of elongation, each of the first and second anchors further including a respective actuation member, the insertion instrument assembly comprising:
   a casing;
   a cannula fixed with respect to the casing, the cannula extending out relative to the casing in a distal direction along a cannula axis to a distal end of the cannula, the cannula defining an elongate opening that extends along the cannula axis;
   a first pusher member aligned with the elongate opening of the cannula;
   a second pusher member aligned with the elongate opening of the cannula so as to be movable within the cannula along the cannula axis, wherein 1) the second pusher member contains the first anchor body, 2) the elongate opening of the cannula contains the second anchor body and 3) the first pusher member is configured to be depressed in the elongate opening so as to eject the first and second anchor bodies from the cannula and into the respective target locations;
   a coupling assembly that releasably translatably couples the first pusher member to the second pusher member, such that, in a first mode of operation the first and second pusher members are coupled together and translate together to eject the second anchor body from the cannula, and in a second mode of operation, the first and second pusher members are decoupled from each other so that the first pusher member is translatable with respect to the second pusher member to eject the first anchor body from the second pusher member and out the cannula; and a plunger attached to the first pusher member, the plunger configured for rotational movement with respect to the casing so as to transition the coupling assembly from the first mode of operation to the second mode of operation so as to eject the first and second anchors from the cannula, wherein, when a tensile force is applied to the respective actuation member substantially along the direction of elongation, the respective first and second anchor bodies expand along a respective second direction perpendicular with respect to the respective direction of elongation.

2. The insertion instrument assembly as recited in claim 1, wherein the first pusher member is configured to brace against the first anchor body.

3. The insertion instrument assembly according to claim 1, wherein the cannula defines a slot that receives the respective actuation member, such that the respective actuation member extends out the cannula.

4. The insertion instrument assembly according to claim 1, wherein the first pusher member comprises a push rod that has an outer cross-sectional dimension which is smaller than that of the elongate opening of said cannula such that the respective actuation member extends through said elongate opening of said cannula alongside the push rod.

5. The insertion instrument assembly according to claim 1, wherein said cannula has a conical inlet.

6. The insertion instrument assembly according to claim 1, wherein the second anchor body is spaced from first anchor body along the distal direction.

7. The insertion instrument assembly according to claim 6, wherein the distal end of the cannula defines a needle tip, and depressing the first pusher member causes at least one of the first and second anchor bodies to translate distally out the elongate opening along the distal direction.

8. The insertion instrument assembly according to claim 7, wherein the needle tip is conical.

9. The insertion instrument assembly according to claim 6, wherein the elongate opening terminates at an elongate opening distal end, and the cannula defines a side ejection portal in communication with the elongate opening distal end.

10. The insertion instrument assembly according to claim 9, further comprising a tip that extends from the cannula along the distal direction.

11. The insertion instrument assembly according to claim 10, wherein the tip is conical.

12. The insertion instrument assembly according to claim 11, wherein the tip comprises a cone.

13. The insertion instrument assembly according to claim 6, wherein the cannula defines a tapered distal end.

14. The insertion instrument assembly according to claim 6, wherein the second pusher member defines a plug disposed between the first and second anchor bodies, and translation of the first and second pusher members a sufficient distance to eject the second anchor body causes the plug to translate to a location out the cannula.

15. The insertion instrument assembly according to claim 6, wherein in the first mode of operation, the first pusher member is initially coupled to the second pusher member such that the first pusher member and the second pusher member translate in the distal direction in tandem during a first stroke of the first pusher member.

16. The insertion instrument assembly according to claim 15, wherein the first stroke causes the second pusher member to eject the second anchor body out the cannula.

17. The insertion instrument assembly according to claim 16, wherein in the second mode of operation, the first pusher member is decoupled from the second pusher member after the first stroke such that the first pusher member translates with respect to the second pusher member.

18. The insertion instrument assembly according to claim 15, wherein a second stroke of the first pusher member ejects the first anchor body from the cannula.

19. The insertion instrument according to claim 18, wherein the first and second pusher members are coupled so as to translate in tandem during a first portion of the second stroke.

20. The insertion instrument assembly according to claim 18, further comprising a stop member that is translatably fixed with respect to the cannula, and a clip removably couples the first and second pusher members together.

21. The insertion instrument assembly according to claim 20, wherein the plunger is translatably fixed to the first pusher member, the plunger configured to be depressed so as to depress the first pusher member in the elongate opening.

22. The insertion instrument assembly according to claim 20, wherein the clip is removably attached to the plunger.

23. The insertion instrument assembly according to claim 22, further comprising an attachment member that is translatably fixed to the second pusher member, wherein the clip abuts the attachment member.

24. The insertion instrument assembly according to claim 23, wherein the plunger is depressed a first distance that causes the second anchor body to be ejected from the insertion instrument assembly, and the clip abuts the casing once the plunger has been depressed the first distance so as to prevent the plunger from being depressed a second distance greater than the first distance.

25. The insertion instrument assembly according to claim 24, wherein removal of the clip from the plunger translatably decouples the first and second pusher members, such that depression of the plunger the second distance causes the first pusher member to eject the first anchor body from the insertion instrument assembly.

26. The insertion instrument assembly according to claim 1, wherein the cannula defines a first longitudinal aperture and the first pusher member defines a second longitudinal aperture so that by rotating said first pusher member relative to said cannula said first and second longitudinal apertures can be aligned and said insertion instrument assembly can be released from said respective first and second anchor bodies.

27. The insertion instrument assembly according to claim 1, further comprising complementary first and second guide members that are operably coupled between the casing and the second pusher member so as to guide relative movement between the casing and the second pusher member.

28. The insertion instrument assembly according to claim 27, further comprising an attachment member that is supported by the second pusher member so as to be translatably fixed relative to the second pusher member.

29. The insertion instrument assembly according to claim 28, wherein the plunger is translatably fixed to the first pusher member.

30. The insertion instrument assembly according to claim 29, wherein the first and second guide members are operably coupled between the casing and the attachment member.

31. The insertion instrument assembly according to claim 29, wherein the first and second guide members are configured to translatably couple the first pusher member to the second pusher member.

32. The insertion instrument assembly according to claim 31, wherein the attachment member comprises a collar that extends about the plunger.

33. The insertion instrument assembly according to claim 29, wherein the attachment member is translatably coupled to the plunger.

34. The insertion instrument assembly according to claim 28, wherein the first and second guide members comprise a 1) guide track that extends into at least one of the attachment member and the casing, and 2) a guide pin that is coupled to the other of the attachment member and the casing, such that the guide pin rides in the guide track.

35. The insertion instrument assembly according to claim 34, wherein the guide track extends into the attachment member and the guide pin extends from the casing into the guide track.

36. The insertion instrument assembly according to claim 35, wherein the guide pin is translatably fixed to the casing.

37. The insertion instrument assembly according to claim 35, wherein the guide track defines a first track portion and a second track portion that is offset with respect to the first track portion.

38. The insertion instrument assembly as recited in claim 37, wherein rotation of the plunger causes the guide pin to ride from the first track portion to the second track portion.

39. The insertion instrument assembly as recited in claim 38, wherein the attachment member defines a stop member at terminal ends of the first and second track portions.

40. The insertion instrument assembly as recited in claim 34, wherein the guide pin translates proximally in the guide track as the plunger moves distally relative to the casing so as to eject the first and second anchor bodies from the insertion instrument assembly.

41. The insertion instrument assembly as recited in claim 34, wherein the guide track defines a base having an edge, wherein the guide pin translates along the edge so as to provide at least one of tactile and audio feedback.

42. The insertion instrument assembly according to claim 28, wherein the coupling assembly comprises a coupling member that is carried by the attachment member, the coupling member configured to translatably couple the attachment member relative to the first pusher member.

43. The insertion instrument assembly according to claim 42, wherein the first pusher member defines a first recess, and the coupling member is configured to extend into the first recess so as to translatably couple the first and second pusher members during the first mode of operation.

44. The insertion instrument assembly according to claim 43, wherein the complimentary first and second guide members define a first portion, a second portion that is offset from the first portion, and a stop at one end of the first portion.

45. The insertion instrument assembly according to claim 44, wherein the coupling member is a latch, and the stop of the first portion prevents translation of the second pusher member relative to the first pusher member in the distal direction before the latch is aligned with the second recess.

46. The insertion instrument assembly according to claim 45, wherein the first portion has a length sufficient such that movement of the second guide member along the first portion causes the second pusher member to eject the second anchor body from the insertion instrument.

47. The insertion instrument assembly according to claim 46, wherein the casing carries a second recess that is spaced from the first recess, and wherein movement of the second guide member along the second portion causes the latch to move in alignment with the second recess.

48. The insertion instrument assembly according to claim 47, wherein the latch moves into the second recess so as to translatably decouple the first and second pusher members in the second mode of operation, such that the first pusher member is translatable independently of the second pusher member so as to eject the first anchor body from the insertion instrument assembly.

49. The insertion instrument assembly as recited in claim 48, wherein the cannula defines a distal ejection port, and the first and second anchor bodies are ejected from the instrument through the distal ejection port.

50. The insertion instrument assembly as recited in claim 47, wherein the second pusher member comprises a plug that is disposed such that an ejection port of the cannula extends between the plug and the first pusher member when the latch is in alignment with the second recess, such that the first anchor body can be ejected from the insertion instrument assembly through the ejection port.

51. The insertion instrument assembly as recited in claim 47, wherein when the coupling member moves to a location aligned with the second recess, the coupling member is driven out of the first recess and into the second recess, thereby translatably decoupling the second pusher member from the first pusher member.

52. The insertion instrument assembly according to claim 1, wherein the coupling assembly fixes the first and second pusher members during a first stroke whereby the second anchor body is ejected from the cannula.

53. The insertion instrument assembly according to claim 52, wherein the coupling assembly decouples the first and second pusher members from each other during a second stroke such that the first pusher member is translatable relative to the second pusher member, whereby the first pusher member ejects the first anchor body out the cannula.

54. The insertion instrument assembly according to claim 1, further comprising an attachment member that is translatably fixed to the second pusher member.

55. The insertion instrument assembly according to claim 54, wherein the plunger is translatably fixed to the first pusher member.

56. The insertion instrument assembly according to claim 55, wherein the attachment member is releasably attached to the plunger during translation of the plunger with respect to the casing.

57. The insertion instrument assembly according to claim 56, wherein the coupling assembly comprises a coupling member that is carried by the attachment member, wherein the coupling member is configured to a) extend into a first recess of the plunger so as to translatably couple the attachment member to the plunger prior to rotation of the plunger, and b) be removed from the first recess of the plunger after rotation of the plunger.

58. The insertion instrument assembly according to claim 57, wherein the casing carries a second recess that is spaced from the first recess.

59. The insertion instrument assembly according to claim 58, wherein the casing defines the second recess.

60. The insertion instrument assembly according to claim 59, wherein when the coupling member moves to a location aligned with the second recess, the coupling member is driven out of the first recess and into the second recess, thereby translatably decoupling the attachment member and the plunger.

61. The insertion instrument assembly according to claim 60, wherein the attachment member defines a channel, and the coupling member is configured to move across the channel so as to decouple from the plunger and couple to the casing.

62. The insertion instrument assembly as recited in claim 58, wherein the casing carries an inner housing that carries the second recess.

63. The insertion instrument assembly as recited in claim 62, wherein when the coupling member moves to a location aligned with the second recess, the coupling member is driven out of the first recess and into the second recess, thereby translatably decoupling the attachment member and the plunger.

64. The insertion instrument assembly as recited in claim 63, wherein the coupling member comprises a leaf spring that is attached to the attachment member.

65. The insertion instrument assembly as recited in claim 63, wherein the leaf spring is integral with the attachment member.

66. The insertion instrument assembly according to claim 1, further comprising a depth stop that extends out from the cannula.

67. The insertion instrument assembly according to claim 1, further configured to retain at least one end of a tensioning member that is coupled to the respective actuation members.

68. The insertion instrument assembly according to claim 67, wherein the tensioning member comprises a tensioning strand having first and second ends, and the insertion instrument assembly is configured to retain the first and second ends.

69. The insertion instrument assembly accordingly to claim 68, configured to selectively release one of the first and second ends.

70. The insertion instrument assembly accordingly to claim 69, further comprising a retention assembly that is movable with the first pusher member, and proximal movement of the insertion instrument assembly after the first anchor body has been ejected causes the tensile force to be applied to the respective actuation member of the second anchor.

71. The insertion instrument assembly accordingly to claim 70, wherein the retention assembly is movable with the first pusher member, such that proximal movement of the first pusher member after the first anchor body has been ejected causes the first tensile force to be applied to the respective actuation member of the first anchor, and
the first pusher member is configured to be depressed in the elongate opening so as to eject the second anchor body from the cannula, such that when a second tensile force is applied to the respective actuation member of the second anchor, the second anchor body expands, wherein the retention assembly is movable with the first pusher member, such that proximal movement of the first pusher member after the second anchor body has been ejected causes the second tensile force to be applied to the respective actuation member of the second anchor.

72. The insertion instrument assembly as recited in claim 69, further comprising a tapered inner surface that defines a tapered bore, and a first locking member having a cross-sectional dimension less than a cross-sectional dimension of a first end of the tapered bore and greater than a cross-sectional dimension of a second end of the tapered bore, wherein the first locking member is configured to releasably retain at least one of the first and second ends of the tensioning strand between the locking member and the tapered surface.

73. The insertion instrument assembly according to claim 72, further comprising a second locking member that is configured to attach to the second end of the tensioning strand.

74. The insertion instrument assembly according to claim 73, wherein the plunger is translatably fixed to the first pusher member, wherein the plunger is configured to depress the first pusher member in the elongate opening.

75. The insertion instrument assembly according to claim 74, further comprising a release member in communication with the first locking member, wherein movement of the release member biases the first locking member out to release the tensioning strand.

76. The insertion instrument assembly according to claim 75, wherein the release member pushes the first locking member toward the first end of the tapered bore so as to create a gap between the first locking member and the tapered inner surface.

77. The insertion instrument assembly according to claim 73, wherein the second locking member is threadedly attached at a location adjacent the tapered inner surface.

78. The insertion instrument assembly according to claim 77, wherein the second locking member is aligned with the tapered bore, such that the second end of the tensioning strand extends through the tapered bore and is attached to the second locking member.

79. The insertion instrument assembly according to claim 69, further comprising a retention assembly including a first locking body configured to releasably retain the first end of the tensioning strand, and a second locking body configured to retain the second end of the tensioning strand.

80. The insertion instrument assembly according to claim 79, further comprising an actuator operably coupled to the first locking body so as to release the first locking body from the first end of the tensioning strand.

81. The insertion instrument assembly according to claim 79, wherein the actuator becomes operably coupled to the first locking body once the first and second anchor bodies have been ejected.

82. The insertion instrument assembly according to claim 69, further comprising a cutting assembly having a cutting blade, the cutting assembly movable between a disengaged position whereby the cutting blade is spaced from the tensioning strand and an engaged position whereby the cutting blade severs the tensioning strand.

83. The insertion instrument assembly according to claim 82, wherein the cutting assembly includes a longitudinally elongate shaft that is coupled to the cutting blade, and longitudinal translation of the shaft causes the cutting blade to sever the tensioning strand.

84. The insertion instrument assembly according to claim 83, wherein the cutting assembly further includes a switch pivotally coupled between both the elongate shaft and the cutting blade.

85. The insertion instrument assembly according to claim 82, wherein the cutting assembly includes an actuator that is elongate along a direction angularly offset with respect to the cannula, and movement of the actuator along the direction angularly offset with respect to the cannula severs the tensioning strand.

86. The insertion instrument assembly according to claim 1, wherein the first anchor body defines a first plurality of openings spaced apart with respect to each other along the respective direction of elongation of the first anchor body, the respective actuation member of the first anchor extends through at least three of the first plurality of openings of the first anchor body, such that the respective actuation member of the first anchor is configured to apply the tensile force to the first anchor body so as to expand the first anchor body.

87. The insertion instrument assembly according to claim 86, wherein the second anchor body defines a second plurality of openings spaced apart with respect to each other along the respective direction of elongation of the second anchor body, the respective actuation member of the second anchor extends through at least three of the second plurality of openings of the second anchor body, such that the respective actuation member of the second anchor is configured to apply the tensile force to the second anchor body so as to expand the second anchor body.

88. The insertion instrument assembly according to claim 1, wherein the second pusher member defines a cannulation that extends along the distal direction, wherein the first pusher member is insertable into the cannulation of the second pusher member.

* * * * *